United States Patent
Steurer et al.

(10) Patent No.: US 11,001,570 B2
(45) Date of Patent: May 11, 2021

(54) 6-AMINO-QUINOLINONE COMPOUNDS AND DERIVATIVES AS BCL6 INHIBITORS

(71) Applicants: Boehringer Ingelheim International GmbH, Ingelheim am Rhein (DE); Felix Paul Kerres

(72) Inventors: Steffen Steurer, Vienna (AT); Georg Dahmann, Biberach (DE); Nina Kerres, Vienna (AT); Manfred Koegl, Moedling (AT)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 0 days.

(21) Appl. No.: 16/469,071

(22) PCT Filed: Dec. 7, 2017

(86) PCT No.: PCT/EP2017/081899
§ 371 (c)(1),
(2) Date: Jun. 12, 2019

(87) PCT Pub. No.: WO2018/108704
PCT Pub. Date: Jun. 21, 2018

(65) Prior Publication Data
US 2020/0071297 A1 Mar. 5, 2020

(30) Foreign Application Priority Data
Dec. 13, 2016 (EP) .................... 16203746

(51) Int. Cl.
*C07D 401/12* (2006.01)
*A61K 31/415* (2006.01)
*C07D 401/14* (2006.01)
*A61P 35/00* (2006.01)
*C07D 413/14* (2006.01)
*C07D 417/14* (2006.01)
*C07D 471/04* (2006.01)
*C07D 491/113* (2006.01)
*C07D 498/08* (2006.01)

(52) U.S. Cl.
CPC ............ *C07D 401/14* (2013.01); *A61P 35/00* (2018.01); *C07D 413/14* (2013.01); *C07D 417/14* (2013.01); *C07D 471/04* (2013.01); *C07D 491/113* (2013.01); *C07D 498/08* (2013.01)

(58) Field of Classification Search
CPC .. C07D 471/04; C07D 401/12; C07D 401/14; C07D 403/12; C07D 403/14; C07D 413/14; C07D 417/14; A61K 31/415
See application file for complete search history.

(56) References Cited

FOREIGN PATENT DOCUMENTS

| CN | 105037265 A | 11/2015 | | |
|---|---|---|---|---|
| WO | 2007070359 A2 | 6/2007 | | |
| WO | 2007136592 A2 | 11/2007 | | |
| WO | 2008066887 A2 | 6/2008 | | |
| WO | WO-2019119138 A1 | * | 6/2019 | ............ A61P 35/00 |
| WO | WO-2019119144 A1 | * | 6/2019 | ........... C07D 401/14 |

OTHER PUBLICATIONS

N. Kerres et al., 20 Cell Reports (2017) (Year: 2017).*
P. Wu et al., 36 Trends in Pharmacological Sciences, 422-439 (2015) (Year: 2015).*
Z. Wang et al., 19 Drug Discovery Today, 145-150 (2014) (Year: 2014).*
U.K. Marelli et al., 3 Frontiers in Oncology, 1-12 (2013) (Year: 2013).*
K. Hatzi et al., 20 Trends in Molecular Medicine (2014) (Year: 2014).*
M. Cardenas et al., 126 the Journal of Clinical Investigation (2016) (Year: 2016).*
P. Sena et al., 31 Oncology Reports (2014) (Year: 2014).*
M. Xie et al., European Journal of Immunology, 1136-1141 (2017) (Year: 2017).*
Abstract in English for CN105037265, Nov. 11, 2015.
International Search Report and Written Opinion for corresponding application, PCT/EP2017/081899, dated Feb. 5, 2018.
Kerres et al., "Chemically induced Degradation of the Oncogenic Transcription Factor BCL6", Cell Reports, 2017, vol. 20, pp. 1860-1875.

* cited by examiner

Primary Examiner — Bruck Kifle
(74) Attorney, Agent, or Firm — Philip I. Datlow

(57) ABSTRACT

The present invention encompasses compounds of formula (I), wherein the groups $R^1$ to $R^5$, X, Y and W have the meanings given in the claims and specification, their use as inhibitors of BCL6, pharmaceutical compositions which contain compounds of this kind and their use as medicaments, especially as agents for treatment and/or prevention of oncological diseases.

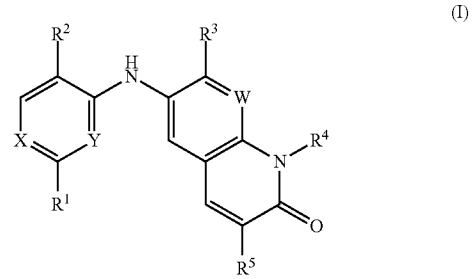

14 Claims, No Drawings

6-AMINO-QUINOLINONE COMPOUNDS AND DERIVATIVES AS BCL6 INHIBITORS

FIELD OF THE INVENTION

The present invention relates to new 6-amino quinolinone compounds and derivatives of formula (I)

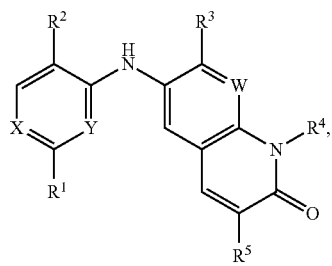

wherein the groups $R^1$ to $R^5$, X, Y and W have the meanings given in the claims and specification, their use as inhibitors of BCL6, pharmaceutical compositions which contain compounds of this kind and their use as medicaments, especially as agents for treatment and/or prevention of oncological diseases.

BACKGROUND OF THE INVENTION

Germinal centers (GCs) are substructures of lymph nodes that are dedicated to the selection of B-cells expressing high-affinity antibodies (Basso and Dalla-Favera Nat Rev Immunol 15, 172-184 (2015)). In the GC reaction B-cells undergo cycles of fast cell division, somatic hypermutation of their immunoglobulin genes and selection for high affinity antibody expression via the interaction with follicular T-helper cells. B-cells producing high-affinity antibodies can leave the GCs and mature to antibody-producing plasma cells or memory B cells. Accidental mutations in the GC reaction can give rise to mutated B-cells that maintain an elevated proliferation and fail to differentiate, contributing to the genesis of diffused large B-cell lymphoma (DLBCL).

The transcription factor BCL6 is required for the GC-reaction (Dent et al. Science 276, 589-592 (1997), Ye et al. Nat. Genet 16, 161-170 (1997)). BCL6 represses the expression of a broad set of genes that are required to sustain mutagenic activity without activating the DNA damage response or apoptosis (Basso and Dalla-Favera Nat Rev Immunol 15, 172-184 (2015)). BCL6 also prevents maturation to plasma or memory cells and helps to maintain a de-differentiated state. Its expression must be switched off to allow the B-cell to exit the GC cycle and differentiate.

BCL6 is an oncogenic driver for DLBCL (Basso and Dalla-Favera Immunol. Rev 247, 172-183 (2012), Hatzi and Melnick Trends Mol. Med 20, 343-352 (2014), Pasqualucci Curr. Opin. Hematol 20, 336-344 (2013)). Its expression is frequently elevated by mutations in DLBCL. Recurrent mutations leading to elevated expression of BCL6 include translocations (Ye et al., Science 262, 747-750 (1993)), promoter mutations (Migliazza et al. Proc. Natl. Acad. Sci. U. S. A 92, 12520-12524 (1995), L. Pasqualucci et al. Blood 101, 2914-2923 (2003)) as well as mutations in regulators of BCL6 expression or stability (Ying et al. Nat Immunol 14, 1084-1092 (2013), Duan et al. Nature 481, 90-93 (2012), Pasqualucci et al. Nature 471, 189-195 (2011).). Dysregulated expression of BCL6 in mice leads to lymphomagenesis (Cattoretti et al. Cancer Cell 7, 445-455 (2005)).

BCL6 functions as a transcriptional repressor that binds specific DNA sequences via its Zn-fingers and recruits transcriptional co-repressor complexes by its BTB/POZ (Broad-Complex, Tramtrack and Bric a brac (Zollman et al. Proc Natl Acad Sci USA 91, 10717-10721 (1994)) or poxvirus and zinc finger (Bardwell and Treisman Genes Dev 8, 1664-1677 (1994)) domain. Mutation of the co-repressor binding interface on BCL6 has been shown to prevent the formation of germinal centers (Huang et al. Nat. Immunol 14, 380-388 (2013)). While germ-line deletion of BCL6 results in inflammatory defects (Dent et al. Science 276, 589-592 (1997), Ye et al. Nat. Genet 16, 161-170 (1997)), mutation of the co-repressor binding surface does not show overt pathological phenotypes. Thus, pharmacological inhibition of the interaction of BCL6 with corepressor proteins promises to block the oncogenic function of the protein with few or no side effects other than the lack of affinity maturation of B-cells.

The BTB domain is a protein interaction motif found at the N-terminus of several zinc finger (ZF) transcription factors, potassium channels and E3 ligase subunits. It forms a tightly intertwined head to tail homodimer (Ahmad et al. Proc Natl Acad Sci USA 95, 12123-12128 (1998)). Each dimer has two identical interfaces at the junction of the two subunits which, in the case of BCL6, can bind to sequences found on transcriptional co-repressors, such as NCOR1, SMRT and BCOR. Co-repressor peptides bind in an extended conformation to a groove formed at the dimer interface (Ahmad et al. Proc Natl Acad Sci USA 95, 12123-12128 (1998)). Low-affinity non-peptidic inhibitors of the BTB domain of BCL6 have been reported (Cerchietti et al. Cancer Cell 17, 400-411 (2010)), with compounds displaying half-maximal cellular activities around 35 µM (Cardenas et al. J Clin Invest, (2016)).

Protein levels of BCL6 are subject to control by regulated degradation. Activation of B-cell receptor signaling causes MAP kinase-dependent phosphorylation and degradation of BCL6 (Niu et al. Genes Dev 12, 1953-1961 (1998)). Genotoxic stress has been shown to cause phosphorylation of BCL6 by ATM and ATR kinases and ubiquitin-dependent degradation of BCL6 (Phan et al. Nat. Immunol 8, 1132-1139 (2007)). In GC cells, BCL6 degradation requires the E3 ligase FBXO11. Mutational inactivation of FBXO11 stabilizes BCL6 and is recurrently observed in DLBCLs (Duan et al. Nature 481, 90-93 (2012)). Mice lacking FBXO11 in the B-cell lineage display expanded dark zones in GCs, higher levels of BCL6 protein and develop lymphoproliferative disorders (Schneider et al. Blood (2016)).

WO2008/066887 (Melnick et al.); Cerchietti et al., Cancer Cell (2010); Cardenas et al., J. Clin. Invest. (2016) disclose various types of BCL6 inhibitors.

The aim of the present invention is to provide further compounds with BCL6 binding affinities and inhibition effects.

According to the invention, "BCL6 inhibitor(s)" means those compounds which inhibit the BCL6 functions as a transcriptional repressor as described above or those compounds which inhibit the BCL6 functions as transcriptional repressor and induce degradation of the BCL6 protein.

DETAILED DESCRIPTION OF THE INVENTION

It has now been found that, surprisingly, compounds of formula (I) wherein the groups $R^1$ to $R^5$, X, Y and W have the meanings given hereinafter act as inhibitors of BCL6 which are involved in controlling cell proliferation. Thus, the compounds according to the invention may be used for example for the treatment of diseases characterised by excessive or abnormal cell proliferation.

The present invention therefore relates to a compound of formula (I), or a salt thereof,

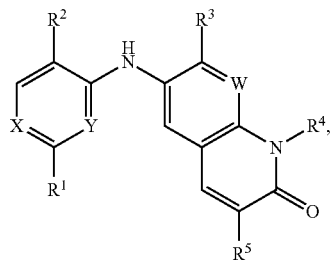

wherein
$R^1$ is selected from the group consisting of 4-12 membered heterocyclyl and 5-12 membered heteroaryl, wherein said heterocyclyl or said heteroaryl contains at least one nitrogen atom and is linked via nitrogen, and wherein the heterocyclyl group is optionally and independently substituted by one or more, identical or different groups independently selected from $R^7$, and the heteroaryl group is optionally and independently substituted by one or more, identical or different group independently selected from $R^8$;

$R^7$ is selected from the group consisting of =O, —CN, —CCH, —OH, —COOH, halogen, —O—$C_{1-6}$alkyl, —$C_{1-6}$haloalkyl, 5 or 6 membered heteroaryl, phenyl, —N($R^9R^{10}$), —C(O)—$R^{11}$, —C(O)N($R^{12}R^{13}$) and 5-8 membered heterocyclyl, which heterocyclyl is optionally substituted with one group selected from —$C_{1-6}$alkyl;

or $R^7$ is —$C_{1-6}$alkyl optionally substituted with —COOH, —OH, —COO($C_{1-6}$alkyl), —CON($C_{1-3}$alkyl)$_2$, —O—$C_{1-6}$alkyl, —N($C_{1-3}$alkyl)$_2$, phenyl and 5 or 6 membered heterocyclyl, which heterocyclyl is optionally substituted with one group selected from —$C_{1-6}$alkyl;

$R^9$ is selected from hydrogen and —$C_{1-4}$alkyl;

$R^{10}$ is selected from the group consisting of hydrogen, —$C_{1-4}$alkyl, —$C_{1-4}$haloalkyl, 6 membered heterocyclyl and 6 membered heteroaryl;

$R^{11}$ is selected from the group consisting of —$C_{1-3}$alkyl-N($C_{1-3}$alkyl)$_2$ and 5 or 6 membered heterocyclyl, which heterocyclyl is optionally substituted with one group selected from —$C_{1-3}$alkyl;

$R^{12}$ is selected from hydrogen and —$C_{1-3}$alkyl;

$R^{13}$ is selected from —$C_{1-6}$alkyl optionally substituted with —NH$_2$, —O—$C_{1-6}$alkyl, —O—$C_{1-6}$alkyl-NH$_2$ and —O—$C_{1-6}$alkyl-O—$C_{1-6}$alkyl-NH$_2$;

or $R^{13}$ is a 6 membered heterocyclyl optionally substituted with —$C_{1-3}$alkyl;

$R^8$ is selected from —COOH, —$C_{1-6}$alkyl, —C(O)—$R^{19}$, —C(O)N($R^{20}R^{21}$);

$R^{19}$ is a 6 membered heterocyclyl optionally substituted with —$C_{1-3}$alkyl;

$R^{20}$ and $R^{21}$ are independently selected from hydrogen and —$C_{1-3}$alkyl;

$R^2$ is selected from the group consisting of chlorine and fluorine;

$R^3$ is selected from the group consisting of hydrogen, —$C_{1-4}$alkyl, —O—$C_{1-4}$alkyl and halogen;

$R^4$ is selected from the group consisting of hydrogen, —$C_{3-6}$cycloalkyl, 4 to 7 membered heterocyclyl, wherein each group is optionally substituted by one group selected from —$C_{1-3}$alkyl, or $R^4$ is —$C_{1-6}$alkyl optionally substituted with one group selected from —OH, —NH$_2$, —O—$C_{1-4}$alkyl, —NH—$C_{1-4}$alkyl, —N($C_{1-4}$alkyl)$_2$, —$C_{3-6}$cycloalkyl and 4 to 7 membered heterocyclyl, wherein each cycloalkyl and heterocyclyl group is optionally and independently substituted by one group selected from —$C_{1-3}$alkyl;

$R^5$ is —$L_1$-C($R^{14}R^{15}$)—$R^{16}$ or —CH=CH—$R^{16}$ wherein
$L_1$ is —O— or —S—;
$R^{14}$ is hydrogen or $C_{1-4}$alkyl;
$R^{15}$ is hydrogen or $C_{1-4}$alkyl;
or $R^{14}$ and $R^{15}$ taken together form a —$C_{3-5}$cycloalkyl;
$R^{16}$ is —COOH, —CONH$_2$, —C(O)$R^{17}$, —C(O)O$R^{17}$, —C(O)N$R^{17}R^{18}$, —S(O)—$C_{1-6}$alkyl, —S(O)$_2$—$C_{1-6}$alkyl, —P(O)—($C_{1-6}$alkyl)$_2$, —C(NH)NH$_2$,
$R^{17}$ is a 3-6 membered heterocyclyl or —$C_{1-4}$alkyl optionally substituted by one or more, identical or different groups selected from —OH, —CF$_3$, —N($C_{1-4}$alkyl)$_2$, —$C_{3-6}$cycloalkyl, 3-6 membered heterocyclyl, —$C_{2-4}$alkenyl, —$C_{2-4}$alkynyl;
$R^{18}$ is hydrogen or $C_{1-4}$alkyl;
W is nitrogen or $CR^6$;
X is nitrogen or CH;
Y is nitrogen or CH;
wherein at least one of X and Y is nitrogen;
$R^6$ is selected from the group consisting of hydrogen, —$C_{1-4}$alkyl, —O—$C_{1-4}$alkyl, —O—$C_{1-4}$haloalkyl, —$C_{1-4}$haloalkyl and halogen.

In another aspect the invention relates to a compound of formula (I)—or a salt thereof—wherein X and Y are both nitrogen.

In another aspect the invention relates to a compound of formula (I)—or a salt thereof—wherein $R^3$ is selected from the group consisting of hydrogen, halogen and —O—$C_{1-4}$alkyl.

In another aspect the invention relates to a compound of formula (I)—or salt thereof—wherein $R^3$ is selected from the group consisting of hydrogen, halogen and —O—CH$_3$.

In another aspect the invention relates to a compound of formula (I)—or salt thereof—wherein $R^4$ is selected from the group consisting of —$C_{1-4}$alkyl, optionally substituted with one group selected from —OH, —$C_{3-6}$cycloalkyl and —N($C_{1-4}$alkyl)$_2$.

In another aspect the invention relates to a compound of formula (I)—or salt thereof—wherein $R^4$ is selected from the group consisting of —CH$_3$, —CH$_2$CH$_3$, —CH$_2$CH$_2$CH$_3$, —CH(CH$_3$)$_2$, —(CH$_2$)$_3$OH, —(CH$_2$)$_2$ (CH$_3$)$_2$, —CH$_2$-cyclopropyl and —(CH$_2$)$_2$N(CH$_3$)$_2$.

In another aspect the invention relates to a compound of formula (I)—or salt thereof—wherein W is $CR^6$ and $R^6$ is selected from the group consisting of hydrogen, $C_{1-4}$alkyl, —O—$C_{1-4}$alkyl, —O—$C_{1-4}$haloalkyl, and halogen.

In another aspect the invention relates to a compound of formula (I)—or salt thereof—wherein $R^6$ is selected from the group consisting of hydrogen, —O—CH$_3$.

In another aspect the invention relates to a compound of formula (I)—or salt thereof—wherein W is N.

In another aspect the invention relates to a compound of formula (I)—or salt thereof—wherein $R^5$ is selected from the group consisting of

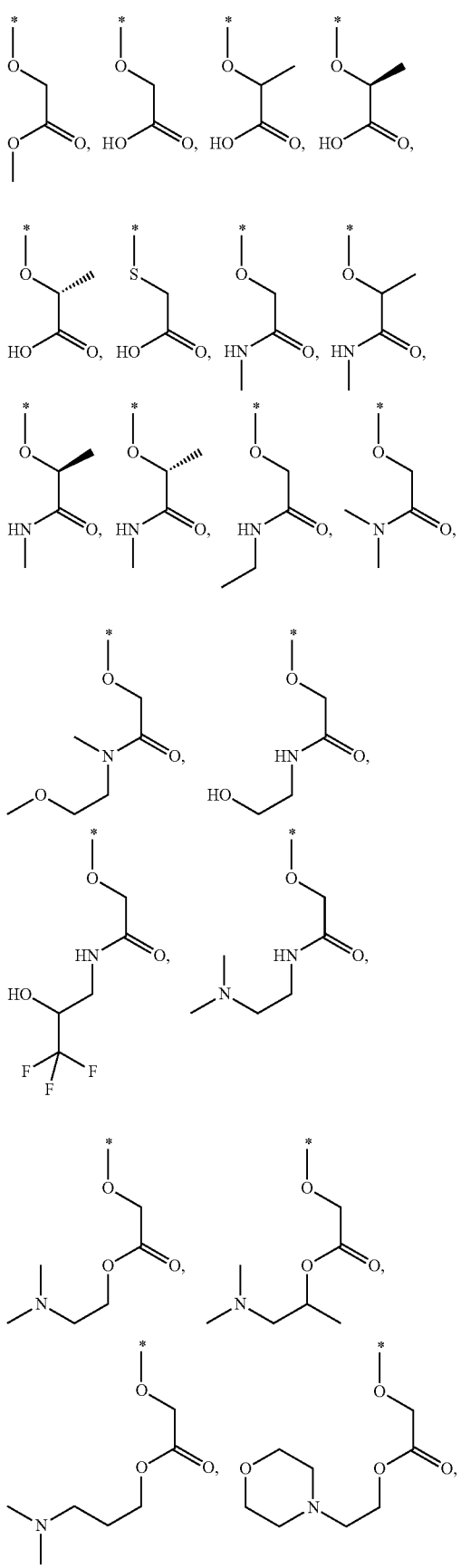
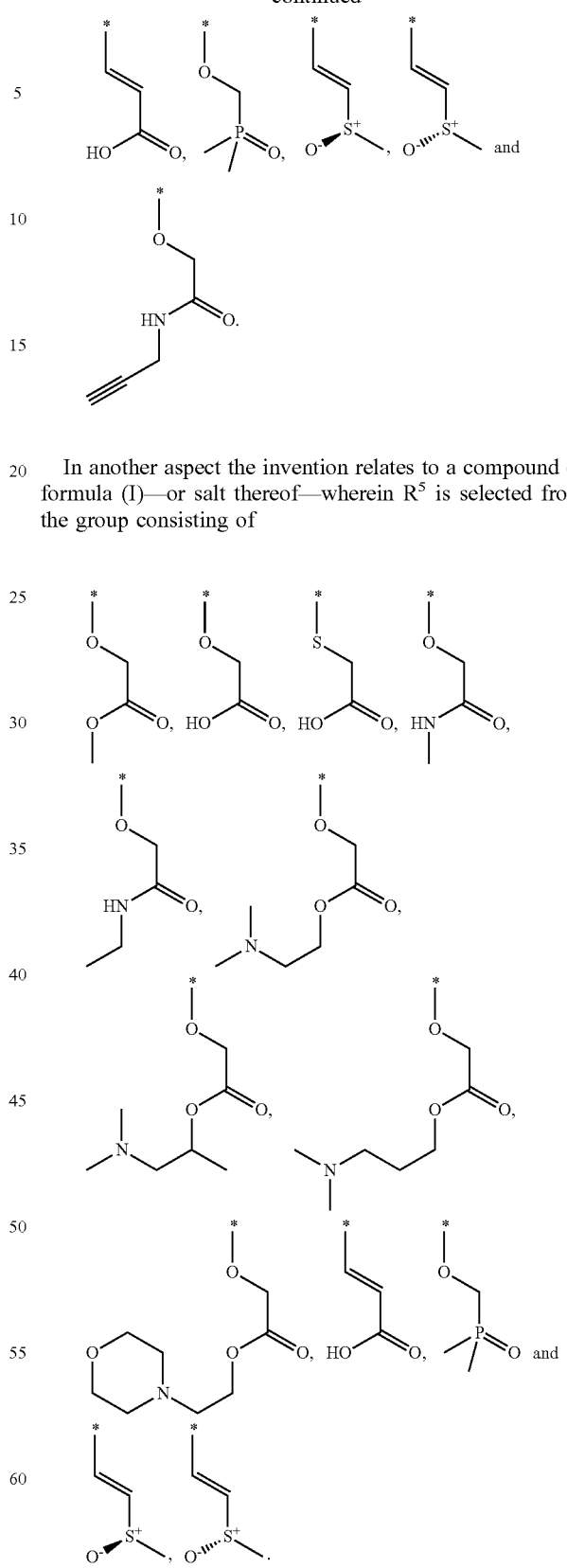
In another aspect the invention relates to a compound of formula (I)—or salt thereof—wherein $R^5$ is selected from the group consisting of
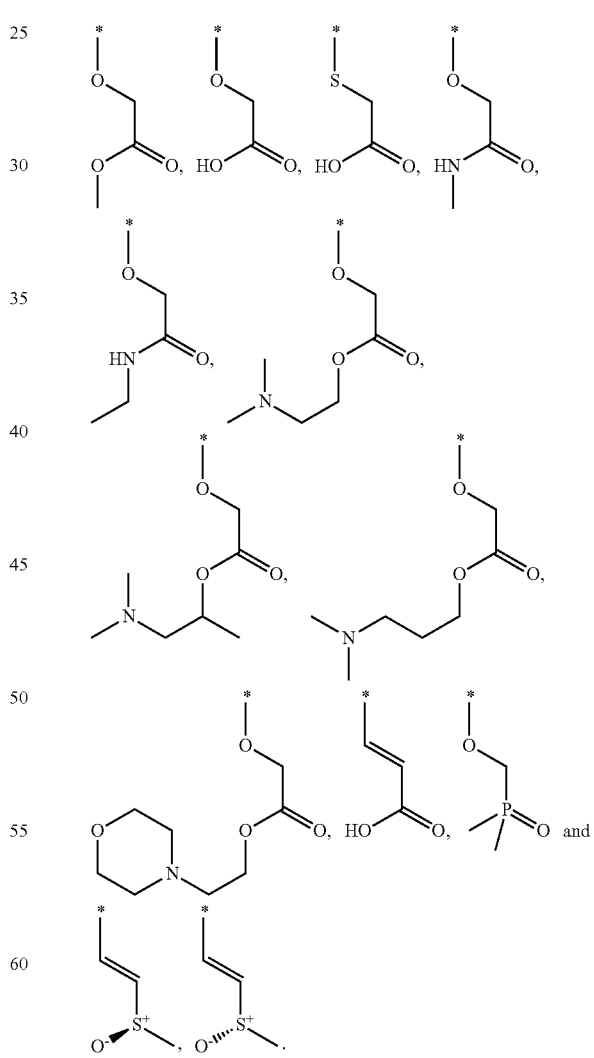
In another aspect the invention relates to a compound of formula (I)—or a salt thereof—wherein $R^5$ is selected from

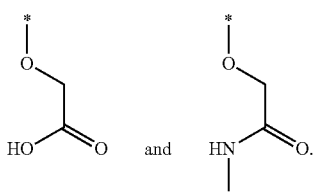

In another aspect the invention relates to a compound of formula (I)—or a salt thereof—wherein R¹ is selected from the group consisting of 5, 6 to 8, 11 and 12 membered heterocyclyl and 5, 9 and 10 membered heteroaryl, wherein said heterocyclyl or said heteroaryl contains at least one nitrogen atom and is linked via nitrogen, and the heterocyclyl group is optionally and independently substituted by one or more, identical or different groups independently selected from R⁷, and the heteroaryl group is optionally and independently substituted by one or more, identical or different group independently selected from R⁸ and wherein R⁷ and R⁸ are defined as described herein above and below.

In another aspect the invention relates to a compound of formula (I)—or a salt thereof—wherein R¹ is a heterocyclyl selected from the group consisting of 5 to 7 membered heterocyclyl,

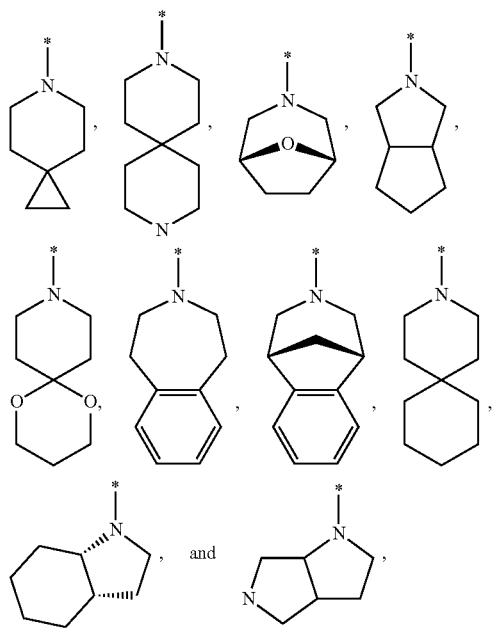

or R₁ is a heteroaryl selected from the group consisting of 5 to 7 membered heteroaryl,

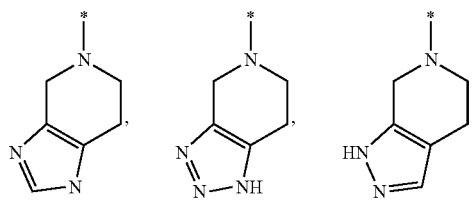

and

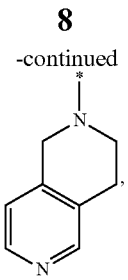

wherein said heterocyclyl or said heteroaryl contains at least one nitrogen atom and is linked via nitrogen, and the heterocyclyl group is optionally and independently substituted by one or more, identical or different groups independently selected from R⁷, and the heteroaryl group is optionally and independently substituted by one or more, identical or different group independently selected from R⁸, wherein R⁷ is selected from the group consisting of =O, —CN, —CCH, —OH, —COOH, halogen, —O—C₁₋₆alkyl, —C₁₋₆haloalkyl, 5 or 6 membered heteroaryl, phenyl, —N(R⁹R¹⁰), —C(O)—R¹¹, —C(O)N(R¹²R¹³) and 5-8 membered heterocyclyl, which heterocyclyl is optionally substituted with one group selected from —C₁₋₆alkyl;

or R⁷ is —C₁₋₆alkyl optionally substituted with —COOH, —OH, —COO(C₁₋₆alkyl), —CON(C₁₋₃alkyl)₂, —O—C₁₋₆alkyl, —N(C₁₋₃alkyl)₂, phenyl and 5 or 6 membered heterocyclyl, which heterocyclyl is optionally substituted with one group selected from —C₁₋₆alkyl;

R⁹ is selected from hydrogen and —C₁₋₄alkyl;

R¹⁰ is selected from the group consisting of hydrogen, —C₁₋₄alkyl, —C₁₋₄haloalkyl, 6 membered heterocyclyl and 6 membered heteroaryl;

R¹¹ is selected from the group consisting of —C₁₋₃alkyl-N(C₁₋₃alkyl)₂ and 5 or 6 membered heterocyclyl, which heterocyclyl is optionally substituted with one group selected from —C₁₋₃alkyl;

R¹² is selected from hydrogen and —C₁₋₃alkyl;

R¹³ is selected from —C₁₋₆alkyl optionally substituted with —NH₂, —O—C₁₋₆alkyl, —O—C₁₋₆alkyl-NH₂ and —O—C₁₋₆alkyl-O—C₁₋₆alkyl-NH₂;

or R¹³ is a 6 membered heterocyclyl optionally substituted with —C₁₋₃alkyl;

R⁸ is selected from —COOH, —C₁₋₆alkyl, —C(O)—R¹⁹, —C(O)N(R²⁰R²¹);

R¹⁹ is a 6 membered heterocyclyl optionally substituted with —C₁₋₃alkyl;

R²⁰ and R²¹ are independently selected from hydrogen and —C₁₋₃alkyl.

In another aspect the invention relates to a compound of formula (I)—or salt thereof—wherein R¹ is a heterocyclyl selected from among -continued

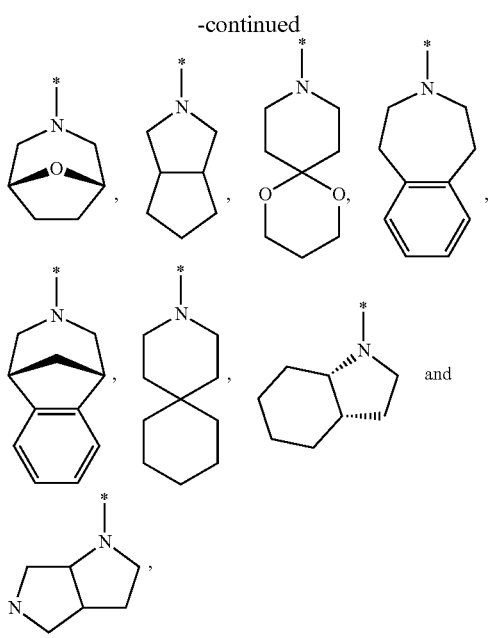

which heterocyclyl is optionally and independently substituted with one, two, three or four substituents independently selected from the group $R^7$ and when $R^1$ is substituted with three or four independently selected $R^7$ at least two of them are independently selected from the group —$C_{1-3}$alkyl; or $R^1$ is a heteroaryl selected from the group consisting of

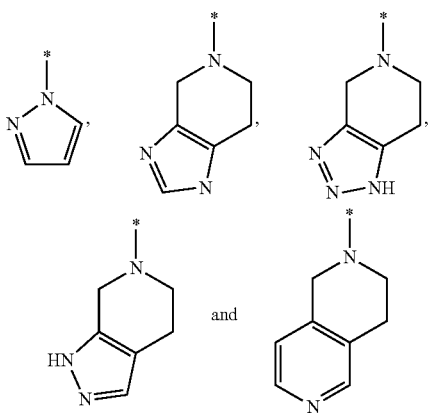

which heteroaryl is optionally and independently substituted with one or two substituents independently selected from the group $R^8$,
wherein $R^7$ is selected from the group consisting of =O, —CCH, —CN, —OH, —COOH, halogen, —O—$C_{1-6}$alkyl, —$C_{1-6}$haloalkyl, 5 or 6 membered heteroaryl, phenyl —N($R^9R^{10}$), —C(O)—$R^{11}$, —C(O)N($R^{12}R^{13}$) and 5-8 membered heterocyclyl, which heterocyclyl is optionally substituted with one group selected from —$C_{1-3}$alkyl;
or $R^7$ is —$C_{1-6}$alkyl optionally substituted with —COOH, —OH, —COO($C_{1-6}$alkyl), —CON($C_{1-3}$alkyl)$_2$, —O—$C_{1-6}$alkyl, —N($C_{1-3}$alkyl)$_2$, phenyl and 5 or 6 membered heterocyclyl, which heterocyclyl is optionally substituted with one group selected from —$C_{1-3}$alkyl;
$R^9$ is selected from hydrogen and —$C_{1-4}$alkyl;
$R^{10}$ is selected from the group consisting of hydrogen, —$C_{1-4}$alkyl, —$C_{1-4}$haloalkyl, 5 or 6 membered heterocyclyl and 6 membered heteroaryl;

$R^{11}$ is selected from the group consisting of —$C_{1-3}$alkyl-N($C_{1-3}$alkyl)$_2$ and 5 or 6 membered heterocyclyl, which heterocyclyl is optionally substituted with one group selected from —$C_{1-3}$alkyl;
$R^{12}$ is selected from hydrogen and —$C_{1-3}$alkyl;
$R^{13}$ is selected from —$C_{1-6}$alkyl, optionally substituted with —NH$_2$, —O—$C_{1-6}$alkyl, —O—$C_{1-6}$alkyl-NH$_2$ and —O—$C_{1-6}$alkyl-O—$C_{1-6}$alkyl-NH$_2$;
or $R^{13}$ is a 6 membered heterocyclyl optionally substituted with —$C_{1-3}$alkyl;
and wherein
$R^8$ is selected from —COOH, —$C_{1-6}$alkyl, —C(O)—$R^{19}$, —C(O)N($R^{20}R^{21}$);
$R^{19}$ is a 6 membered heterocyclyl optionally substituted with —$C_{1-3}$alkyl;
$R^{20}$ and $R^{21}$ are independently selected from hydrogen and —$C_{1-3}$alkyl.

In another aspect the invention relates to a compound of formula (I)—or salt thereof—
wherein $R^1$ is

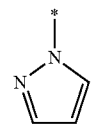

optionally substituted with one or two groups independently selected from $R^8$, or
$R^1$ is selected from the group consisting of

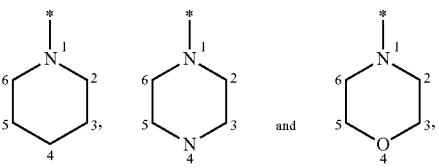 [SMILES: *N1CCCCC1 ; *N1CCNCC1 ; *N1CCOCC1]

wherein the piperidinyl and piperazinyl groups can be optionally and independently substituted in 3, 4, and/or 5 position and the morpholinyl group can be optionally and independently substituted in 3 and/or 5 position with one, two, three or four substituents independently selected from the group $R^7$ and wherein when $R^1$ is substituted with three or four independently selected $R^7$ at least two of those substituents are —$C_{1-3}$alkyl, wherein
$R^7$ is selected from the group consisting of =O, —CCH, —CN, —OH, —COOH, halogen, —O—$C_{1-6}$alkyl, —$C_{1-6}$haloalkyl, 5 or 6 membered heteroaryl, phenyl —N($R^9R^{10}$), —C(O)—$R^{11}$, —C(O)N($R^{12}R^{13}$) and 5-8 membered heterocyclyl, which heterocyclyl is optionally substituted with one group selected from —$C_{1-3}$alkyl;
or $R^7$ is —$C_{1-6}$alkyl optionally substituted with —COOH, —OH, —COO($C_{1-6}$alkyl), —CON($C_{1-3}$alkyl)$_2$, —O—$C_{1-6}$alkyl, —N($C_{1-3}$alkyl)$_2$, phenyl and 5 or 6 membered heterocyclyl, which heterocyclyl is optionally substituted with one group selected from —$C_{1-3}$alkyl;
$R^9$ is selected from hydrogen and —$C_{1-4}$alkyl;
$R^{10}$ is selected from the group consisting of hydrogen, —$C_{1-4}$alkyl, —$C_{1-4}$haloalkyl, 6 membered heterocyclyl and 6 membered heteroaryl;
$R^{11}$ is selected from the group consisting of —$C_{1-3}$alkyl-N($C_{1-3}$alkyl)$_2$ and 5 or 6 membered heterocyclyl, which heterocyclyl is optionally substituted with —$C_{1-3}$alkyl;

R[12] is selected from hydrogen and —C$_{1-3}$alkyl;
R[13] is selected from —C$_{1-6}$alkyl, optionally substituted with —NH$_2$, —O—C$_{1-6}$alkyl, —O—C$_{1-6}$alkyl-NH$_2$ and —O—C$_{1-6}$alkyl-O—C$_{1-6}$alkyl-NH$_2$;
or R[13] is a 6 membered heterocyclyl optionally substituted with —C$_{1-3}$alkyl;
and wherein
R[8] is selected from —COOH, —C$_{1-6}$alkyl, —C(O)—R[19], —C(O)N(R[20]R[21]);
R[19] is a 6 membered heterocyclyl optionally substituted with —C$_{1-3}$alkyl;
R[20] and R[21] are independently selected from hydrogen and —C$_{1-3}$alkyl.

The preferred heterocycyl groups of the compounds of the invention contain one or two nitrogen atoms, one nitrogen atom and one oxygen atom, one nitrogen atom and one sulfur atom, one nitrogen atom and two oxygen atoms. Most preferred heterocyclyl of the compounds of the invention contain one or two nitrogen atoms, one nitrogen atom and one oxygen atom.

The preferred heteroaryl of the compounds of the invention contain two to four nitrogen atoms, most preferably two nitrogen atoms.

In a preferred embodiment, the heterocyclyl group of R[1] is optionally substituted with one, two, three or four substituents independently selected from the group R[7] and wherein when R[1] is substituted with three or four independently selected R[7] at least two of those substituents are —C$_{1-3}$alkyl, wherein R[1] and R[7] are defined as described herein above and below.

In a preferred embodiment, the heteroaryl group of R[1] is optionally substituted with one or two groups independently selected from R[8], wherein R[8] is defined as described herein above and below.

As the person skilled in the art would recognize, when R[1] is piperazinyl or morpholinyl—or any heterocyclyl, and R[7] is selected to be —OH or —NR[9]R[10]— or any substituent attached to the molecule via an heteroatom, this substituent cannot be in positions 3 or 4 of the piperazinyl or of the morpholinyl ring, i.e., this substituent R[7] cannot be attached to the ring in a position next to the heteroatom of the ring.

In another aspect the invention relates to a compound of formula (I)—or a salt thereof—
wherein R[1] is selected from among

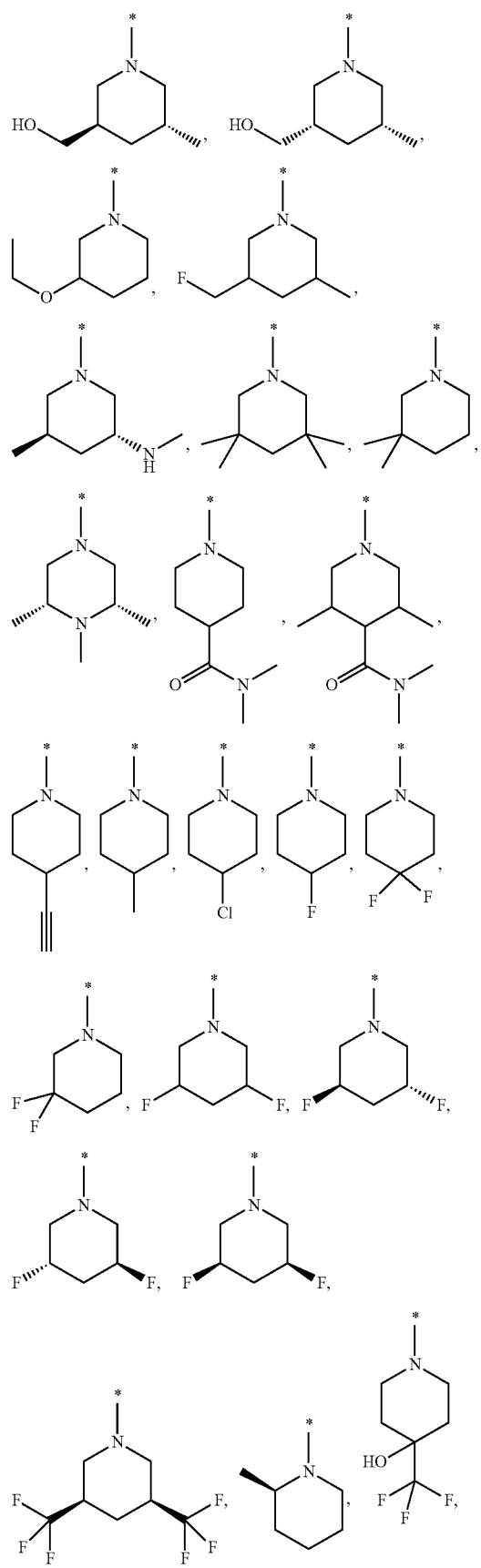

-continued
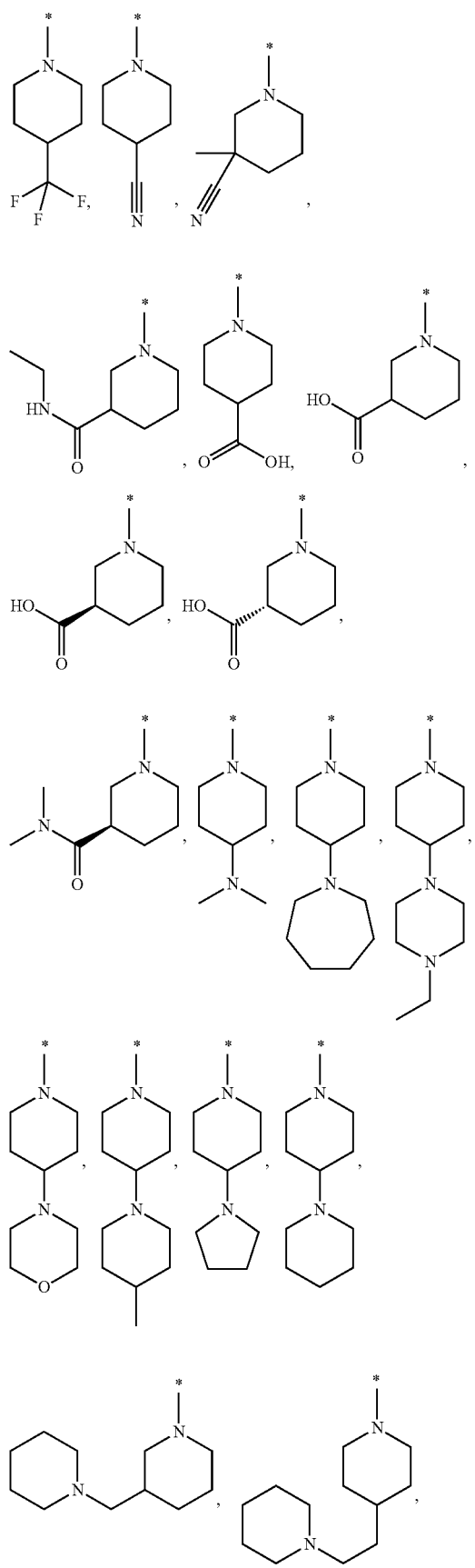
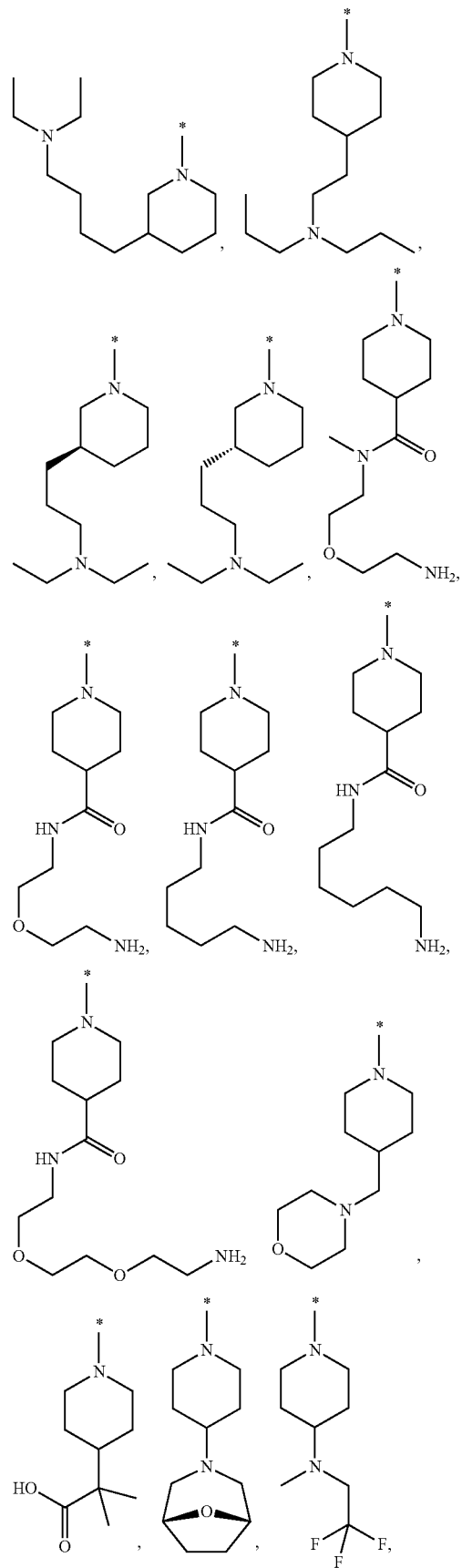

-continued
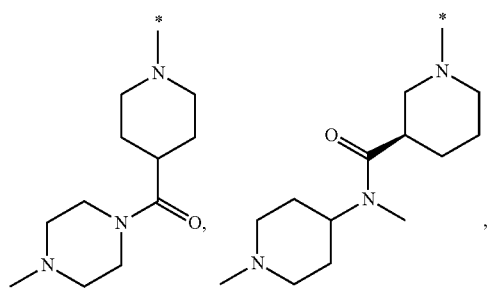
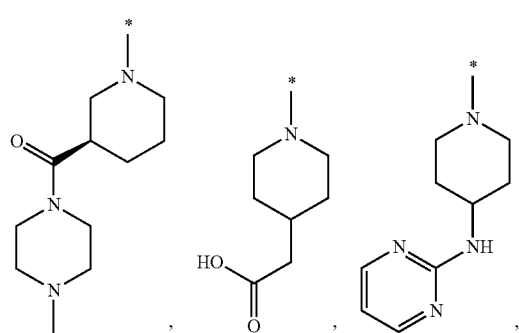
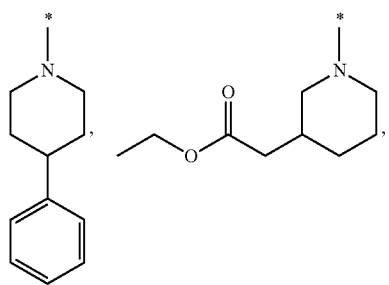
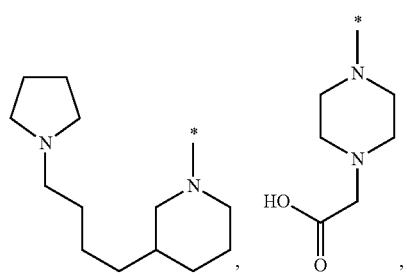
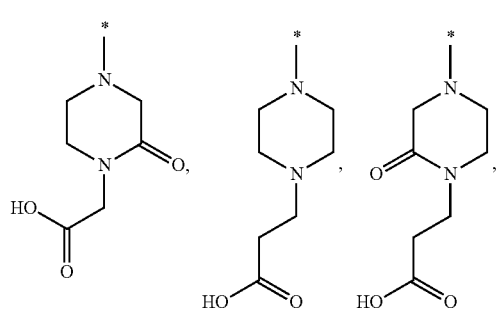
-continued
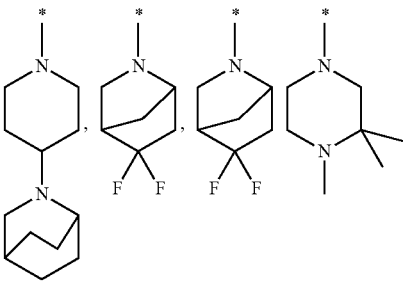
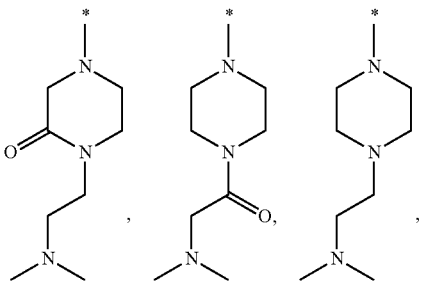
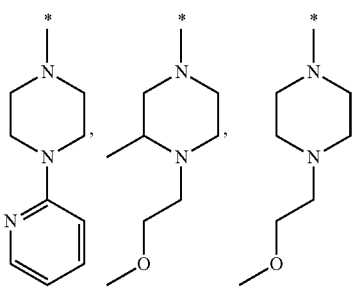
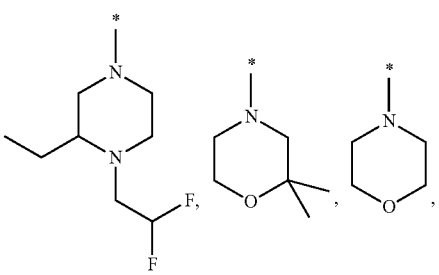
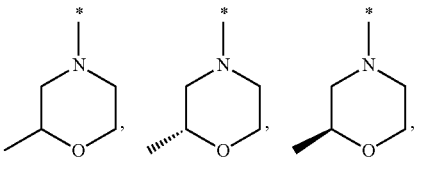
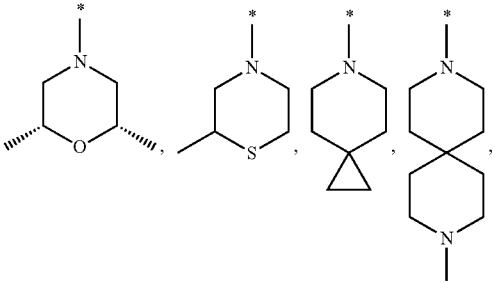

-continued
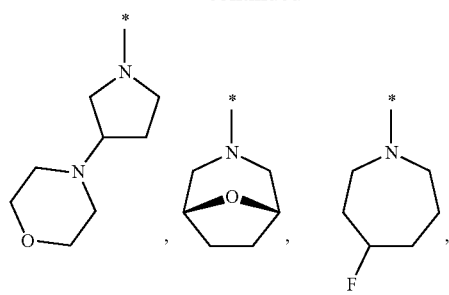
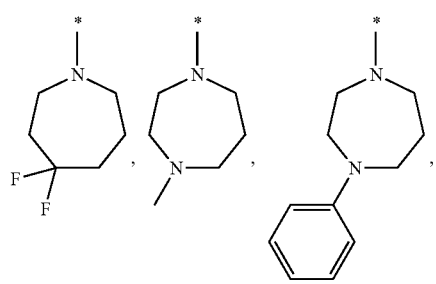
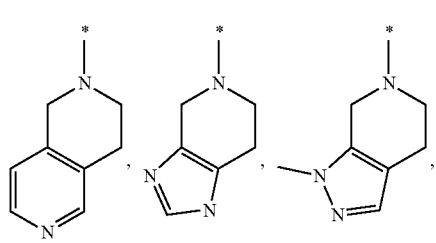
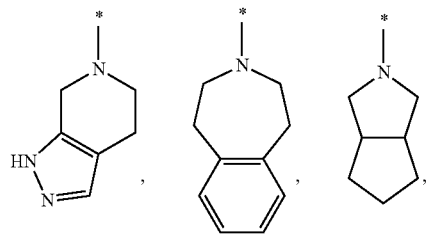
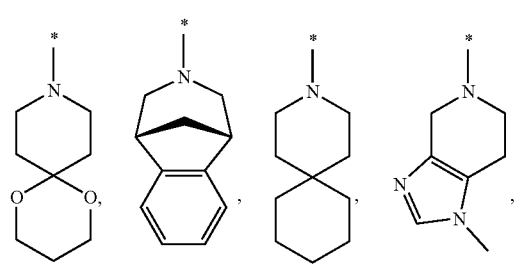
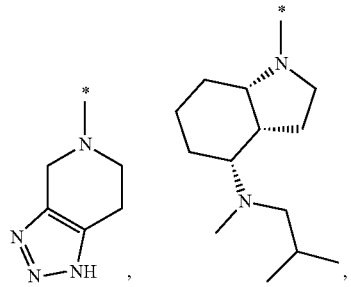
-continued
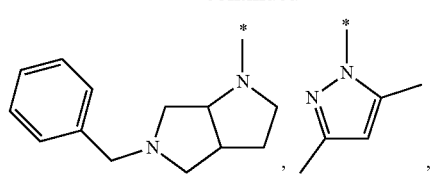
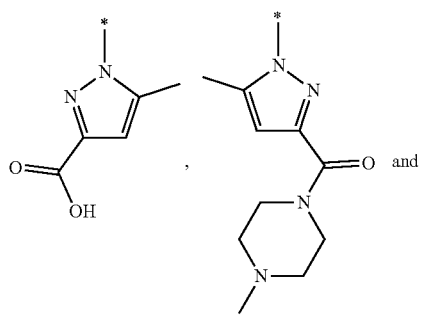 and
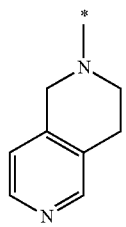
In another aspect the invention relates to a compound of formula (I)—or salt thereof—wherein $R^1$ is selected from among
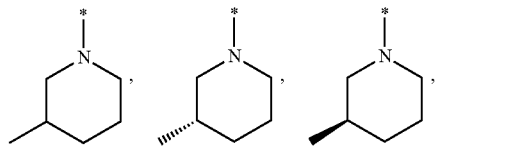
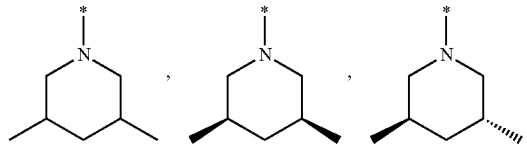
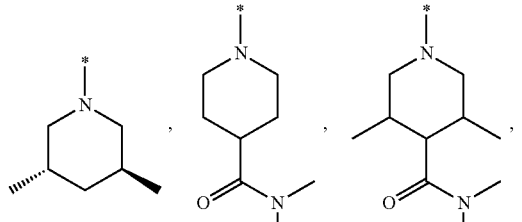
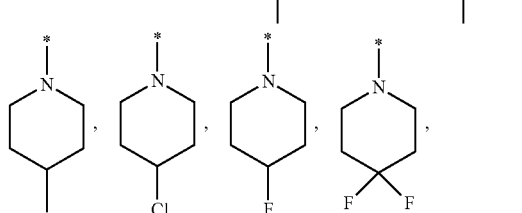

-continued

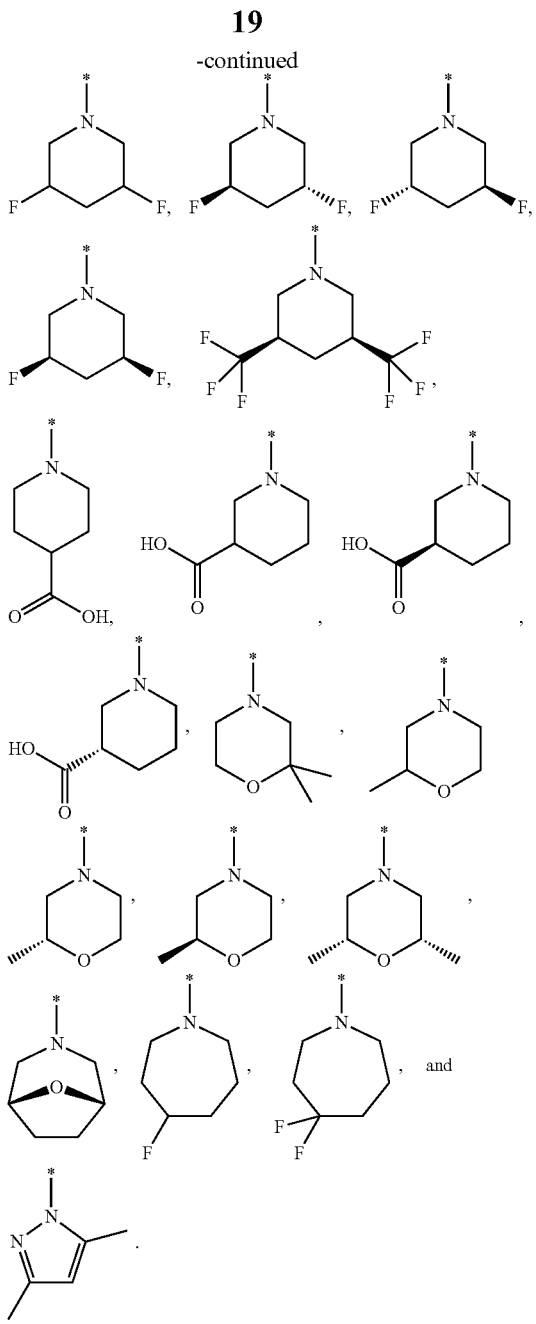

In another aspect the invention relates to a compound of formula (I)—or salt thereof—wherein $R^1$ is selected from among

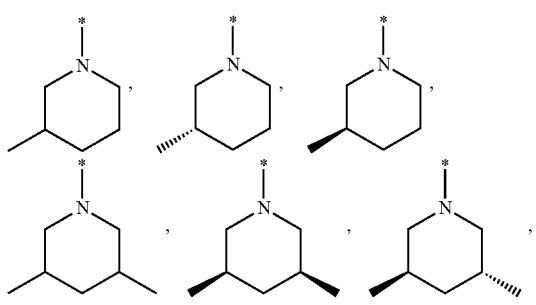

-continued

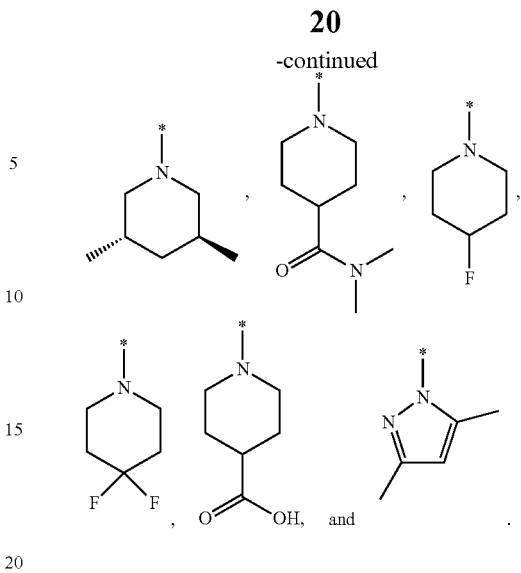

In another aspect the invention relates to a compound of formula (I)—or a salt thereof—wherein $R^7$ is selected from the group consisting of =O, —CCH, —CN, —OH, —COOH, halogen, —O—$C_{1-6}$alkyl, —$C_{1-6}$haloalkyl, 6 membered heteroaryl, phenyl —N($R^9R^{10}$), —C(O)—$R^{11}$, —C(O)N($R^{12}R^{13}$), 5-8 membered heterocyclyl, which heterocyclyl is optionally substituted with one group selected from —$C_{1-3}$alkyl;

or $R^7$ is —$C_{1-6}$alkyl optionally substituted with —COOH, —OH, —COO($C_{1-6}$alkyl), —CON($C_{1-3}$alkyl)$_2$, —O—$C_{1-6}$alkyl, —N($C_{1-3}$alkyl)$_2$, phenyl and 5 or 6 membered heterocyclyl, which heterocyclyl is optionally substituted with one group selected from —$C_{1-3}$alkyl;

$R^9$ is selected from hydrogen and —$C_{1-4}$alkyl;

$R^{10}$ is selected from the group consisting of hydrogen, —$C_{1-4}$alkyl, —$C_{1-4}$haloalkyl, 6 membered heterocyclyl and 6 membered heteroaryl;

$R^{11}$ is selected from the group consisting of —$C_{1-3}$alkyl-N($C_{1-3}$alkyl)$_2$ and 6 membered heterocyclyl, which heterocyclyl is optionally substituted with —$C_{1-3}$alkyl;

$R^{12}$ is selected from hydrogen and —$C_{1-3}$alkyl;

$R^{13}$ is selected from —$C_{1-6}$alkyl, optionally substituted with —NH$_2$, —O—$C_{1-6}$alkyl, —O—$C_{1-6}$alkyl-NH$_2$ and —O—$C_{1-6}$alkyl-O—$C_{1-6}$alkyl-NH$_2$;

or $R^{13}$ is a 6 membered heterocyclyl optionally substituted with —$C_{1-3}$alkyl.

In another aspect the invention relates to a compound of formula (I)—or a salt thereof—wherein $R^7$ is selected from the group consisting of —COOH, —$C_{1-3}$alkyl, —C(O)N($C_{1-3}$alkyl)$_2$, —$C_{1-3}$haloalkyl and halogen.

In another aspect the invention relates to a compound of formula (I)—or a salt thereof—wherein $R^8$ are is selected from the group consisting of —COOH, —$C_{1-3}$alkyl, —C(O)N($C_{1-3}$alkyl)$_2$,

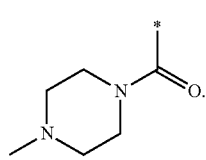

In another aspect the invention relates to a compound of formula (I)—or a salt thereof—wherein $R^7$ is selected from the group consisting of —COOH, —CH$_3$, —C(O)N(—CH$_3$)$_2$, —CF$_3$, —F and —Cl.

In another aspect the invention relates to a compound of formula (I)—or a salt thereof—wherein R⁸ is selected from —$C_{1-6}$alkyl, —COOH, —C(O)—R¹⁹ wherein R¹⁹ is a 6 membered heterocyclyl optionally substituted with one group selected from —$C_{1-3}$alkyl.

In another aspect the invention relates to a compound of formula (I)—or a salt thereof—wherein R⁸ are independently selected from the group consisting of —COOH, —CH₃, and

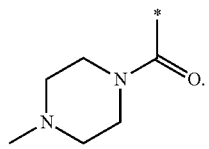 [SMILES: *C(=O)N1CCN(C)CC1]

In another aspect the invention relates to a compound of formula (I)—or salt thereof—wherein R⁷ is selected from the group consisting of =O, —CH₃, —F, —Cl, —OH, —CN, —OCH₂CH₃, —NH—CH₃, —N(CH₃)₂, —CH₂OH, —C(O)OH, —CH₂C(O)OH, —CCH, —CH₂F, —CH₂CHF₂, —CF₃, —CONHCH₃, —CONHCH₂CH₃, —COCH₂N(CH₃)₂, —CON(CH₃)₂, -pyridyl, -morpholine, methyl-piperidine-, -piperidine, -pyrrolidine, -phenyl, —CH₂-phenyl, —CH₂-piperidinyl,

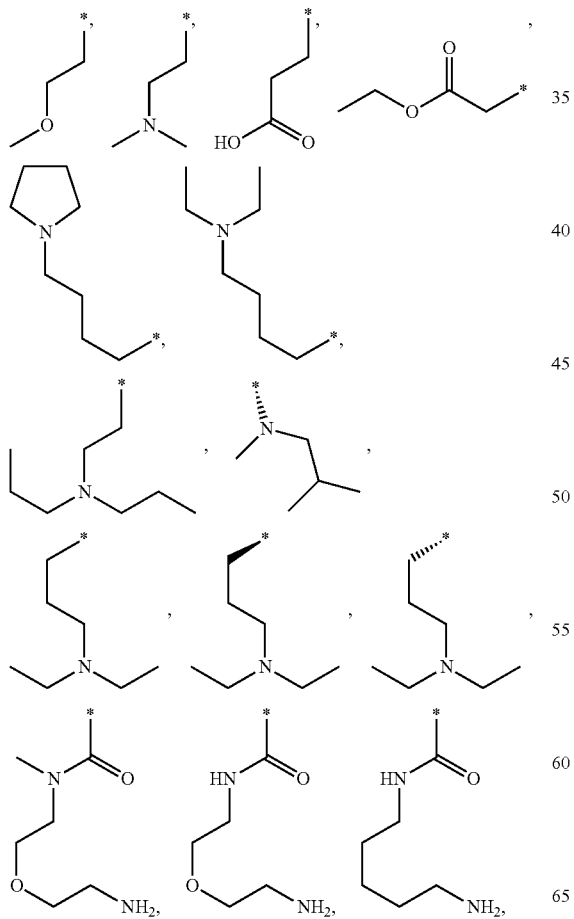

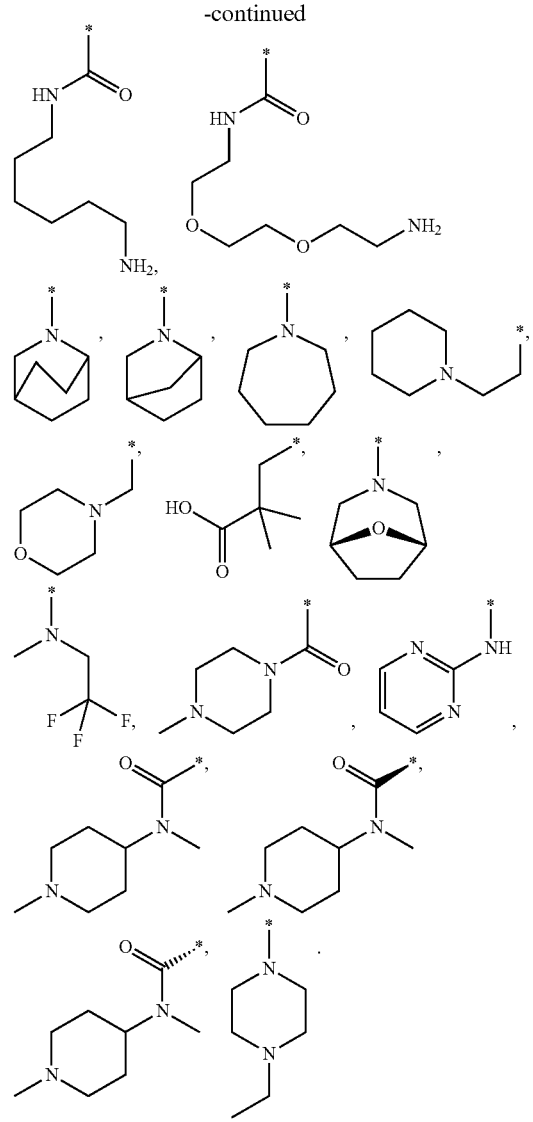

Some example compounds as disclosed herein have chiral centers. Although not separately depicted in the tables stereoisomers of such example compounds are meant to be embodiments of the invention and shall be deemed to be specifically disclosed, i.e. the compound as depicted in the tables, the corresponding diastereoisomer and/or enantiomer not specifically depicted in the tables and the racemate of both enantiomers are separate embodiments of the invention.

All synthetic intermediates generically defined as well as specifically disclosed herein and their salts are also part of the invention.

The present invention further relates to hydrates, solvates, polymorphs, metabolites, derivatives, isomers and prodrugs of a compound of formula (I).

The present invention further relates to a hydrate of a compound of formula (I).

The present invention further relates to a solvate of a compound of formula (I).

The present invention further relates to a polymorph of a compound of formula (I).

Compounds of formula (I) which e.g. bear ester groups are potential prodrugs and the ester being cleaved under physiological conditions.

The present invention further relates to a pharmaceutically acceptable salt of a compound of formula (I).

The present invention further relates to a co-crystal, preferably a pharmaceutically acceptable co-crystal, of a compound of formula (I).

The present invention further relates to a pharmaceutically acceptable salt of a compound of formula (I) with anorganic or organic acids or bases.

The present invention is directed to compounds of formula (I) which are useful in the prevention and/or treatment of a disease and/or condition wherein the inhibition of the BCL6 is of therapeutic benefit, including but not limited to the treatment and/or prevention of cancer.

In another aspect the invention relates to a compound of formula (I)—or a pharmaceutically acceptable salt thereof—for use as a medicament.

In another aspect the invention relates to a compound of formula (I)—or a pharmaceutically acceptable salt thereof—for use in a method of treatment of the human or animal body.

In another aspect the invention relates to a compound of formula (I)—or a pharmaceutically acceptable salt thereof—for use in the treatment and/or prevention of a disease and/or condition wherein the inhibition of BCL6 is of therapeutic benefit.

In another aspect the invention relates to a compound of formula (I)—or a pharmaceutically acceptable salt thereof—for use in the treatment and/or prevention of cancer, infections, inflammations or autoimmune diseases.

In another aspect the invention relates to a compound of formula (I)—or a pharmaceutically acceptable salt thereof—for use in a method of treatment and/or prevention of cancer, infections, inflammations or autoimmune diseases in the human or animal body.

In another aspect the invention relates to the use of a compound of formula (I)—or a pharmaceutically acceptable salt thereof—for preparing a pharmaceutical composition for the treatment and/or prevention of cancer, infections, inflammations or autoimmune diseases.

In another aspect the invention relates to a compound of formula (I)—or a pharmaceutically acceptable salt thereof—for use in the treatment and/or prevention of cancer.

In another aspect the invention relates to the use of a compound of formula (I)—or a pharmaceutically acceptable salt thereof—for preparing a pharmaceutical composition for the treatment and/or prevention of cancer.

In another aspect the invention relates to a compound of formula (I)—or a pharmaceutically acceptable salt thereof—for use in a method of treatment and/or prevention of cancer in the human or animal body.

In another aspect the invention relates to a compound of formula (I)—or a pharmaceutically acceptable salt thereof—for use in the treatment and/or prevention of a hematological cancer.

In another aspect the invention relates to a compound of formula (I)—or a pharmaceutically acceptable salt thereof—for use in the treatment and/or prevention of non-Hodgkin lymphomas (NHL).

In another aspect the invention relates to the use of a compound of formula (I)—or a pharmaceutically acceptable salt thereof—for preparing a pharmaceutical composition for the treatment and/or prevention of a non-Hodgkin lymphomas (NHL) cancer.

In another aspect the invention relates to the use of a compound of formula (I)—or a pharmaceutically acceptable salt thereof—for preparing a pharmaceutical composition for the treatment and/or prevention of follicular lymphoma (FL) or diffuse large B-cell lymphoma (DLBCL).

In another aspect the invention relates to a method for the treatment and/or prevention of a disease and/or condition wherein the inhibition of BCL6 is of therapeutic benefit comprising administering a therapeutically effective amount of a compound of formula (I)—or a pharmaceutically acceptable salt thereof—to a human being.

In another aspect the invention relates to a method for the treatment and/or prevention of cancer comprising administering a therapeutically effective amount of a compound of formula (I)—or a pharmaceutically acceptable salt thereof—to a human being.

In another aspect the invention relates to a pharmaceutical composition comprising at least one compound of formula (I)—or a pharmaceutically acceptable salt thereof—and a pharmaceutically acceptable carrier.

In another aspect the invention relates to a pharmaceutical preparation comprising a compound of formula (I)—or a pharmaceutically acceptable salt thereof—and at least one other cytostatic and/or cytotoxic active substance.

In another aspect the invention relates to a compound of formula (I)—or a pharmaceutically acceptable salt thereof—for use in the treatment and/or prevention of cancer, infections, inflammations or autoimmune diseases wherein said compound is administered before, after or together with at least one other cytostatic or cytotoxic active substance.

In another aspect the invention relates to the use of a compound of formula (I)—or a pharmaceutically acceptable salt thereof—for preparing a medicament for the treatment and/or prevention of cancer, infections, inflammations or autoimmune diseases wherein said compound is administered before, after or together with at least one other cytostatic or cytotoxic active substance.

In another aspect the invention relates to a cytostatic or cytotoxic active substance prepared for being administered before, after or together with a compound of formula (I)—or a pharmaceutically acceptable salt thereof—for use in the treatment and/or prevention of cancer, infections, inflammations or autoimmune diseases.

In another aspect the invention relates to a method for the treatment and/or prevention of cancer, infections, inflammations or autoimmune diseases comprising administering to a patient in need thereof a therapeutically effective amount of a compound of formula (I)—or a pharmaceutically acceptable salt thereof—before, after or together with at least one other cytostatic or cytotoxic active substance.

Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to:

The use of the prefix $C_{x-y}$, wherein x and y each represent a natural number (x<y), indicates that the chain or ring structure or combination of chain and ring structure as a whole, specified and mentioned in direct association, may consist of a maximum of y and a minimum of x carbon atoms.

The indication of the number of members in groups that contain one or more heteroatom(s) (e.g. heteroalkyl, heteroaryl, heteroarylalkyl, heterocyclyl, heterocycylalkyl)

relates to the total number of atoms of all the ring members or chain members or the total of all the ring and chain members.

The indication of the number of carbon atoms in groups that consist of a combination of carbon chain and carbon ring structure (e.g. cycloalkylalkyl, arylalkyl) relates to the total number of carbon atoms of all the carbon ring and carbon chain members. Obviously, a ring structure has at least three members.

In general, for groups comprising two or more subgroups (e.g. heteroarylalkyl, heterocycylalkyl, cycloalkylalkyl, arylalkyl) the last named subgroup is the radical attachment point, for example, the substituent aryl-$C_{1-6}$alkyl means an aryl group which is bound to a $C_{1-6}$alkyl group, the latter of which is bound to the core or to the group to which the substituent is attached.

In groups like OH, $NH_2$, S(O), $S(O)_2$, CN (cyano), COOH, $CF_3$ or the like, the skilled artisan can see the radical attachment point(s) to the molecule from the free valences of the group itself.

As it will be clear to the person skilled in the art, the radical attachment point(s) to the molecule from the free valences of the group itself is indicated with the following symbols "–" or "*".

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

The term "$C_{1-5}$alkyl" includes for example $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

Further examples of alkyl are methyl (Me; —$CH_3$), ethyl (Et; —$CH_2CH_3$), 1-propyl (n-propyl; n-Pr; —$CH_2CH_2CH_3$), 2-propyl (i-Pr; iso-propyl; —$CH(CH_3)_2$), 1-butyl (n-butyl; n-Bu; —$CH_2CH_2CH_2CH_3$), 2-methyl-1-propyl (iso-butyl; i-Bu; —$CH_2CH(CH_3)_2$), 2-butyl (sec-butyl; sec-Bu; —$CH(CH_3)CH_2CH_3$), 2-methyl-2-propyl (tert-butyl; t-Bu; —$C(CH_3)_3$), 1-pentyl (n-pentyl; —$CH_2CH_2CH_2CH_2CH_3$), 2-pentyl (—$CH(CH_3)CH_2CH_2CH_3$), 3-pentyl (—$CH(CH_2CH_3)_2$), 3-methyl-1-butyl (iso-pentyl; —$CH_2CH_2CH(CH_3)_2$), 2-methyl-2-butyl (—$C(CH_3)_2CH_2CH_3$), 3-methyl-2-butyl (—$CH(CH_3)CH(CH_3)_2$), 2,2-dimethyl-1-propyl (neo-pentyl; —$CH_2C(CH_3)_3$), 2-methyl-1-butyl (—$CH_2CH(CH_3)CH_2CH_3$), 1-hexyl (n-hexyl; —$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 2,3-dimethyl-1-butyl (—$CH_2CH(CH_3)CH(CH_3)CH_3$), 2,2-dimethyl-1-butyl (—$CH_2C(CH_3)_2CH_2CH_3$), 3,3-dimethyl-1-butyl (—$CH_2CH_2C(CH_3)_3$), 2-methyl-1-pentyl (—$CH_2CH(CH_3)CH_2CH_2CH_3$), 3-methyl-1-pentyl (—$CH_2CH_2CH(CH_3)CH_2CH_3$), 1-heptyl (n-heptyl), 2-methyl-1-hexyl, 3-methyl-1-hexyl, 2,2-dimethyl-1-pentyl, 2,3-dimethyl-1-pentyl, 2,4-dimethyl-1-pentyl, 3,3-dimethyl-1-pentyl, 2,2,3-trimethyl-1-butyl, 3-ethyl-1-pentyl, 1-octyl (n-octyl), 1-nonyl (n-nonyl); 1-decyl (n-decyl) etc.

By the terms propyl, butyl, pentyl, hexyl, heptyl, octyl, nonyl, decyl etc. without any further definition are meant saturated hydrocarbon groups with the corresponding number of carbon atoms, wherein all isomeric forms are included.

The above definition for alkyl also applies if alkyl is a part of another (combined) group such as for example $C_{x-y}$alkylamino or $C_{x-y}$alkyloxy.

The term alkylene can also be derived from alkyl. Alkylene is bivalent, unlike alkyl, and requires two binding partners. Formally, the second valency is produced by removing a hydrogen atom in an alkyl. Corresponding groups are for example —$CH_3$ and —$CH_2$—, —$CH_2CH_3$ and —$CH_2CH_2$— or >$CHCH_3$ etc.

The term "$C_{1-4}$alkylene" includes for example —($CH_2$)—, —($CH_2$—$CH_2$)—, —($CH(CH_3)$)—, —($CH_2$—$CH_2$—$CH_2$)—, —($C(CH_3)_2$)—, —($CH(CH_2CH_3)$)—, —($CH(CH_3)$—$CH_2$)—, —($CH_2$—$CH(CH_3)$)—, —($CH_2$—$CH_2$—$CH_2$—$CH_2$)—, —($CH_2$—$CH_2$—$CH(CH_3)$)—, —($CH(CH_3)$—$CH_2$—$CH_2$)—, —($CH_2$—$CH(CH_3)$—$CH_2$)—, —($CH_2$—$C(CH_3)_2$)—, —($C(CH_3)_2$—$CH_2$)—, —($CH(CH_3)$—$CH(CH_3)$)—, —($CH_2$—$CH(CH_2CH_3)$)—, —($CH(CH_2CH_3)$—$CH_2$)—, —($CH(CH_2CH_2CH_3)$)—, —($CH(CH(CH_3))_2$)— and —$C(CH_3)(CH_2CH_3)$—.

Other examples of alkylene are methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, hexylene etc.

By the generic terms propylene, butylene, pentylene, hexylene etc. without any further definition are meant all the conceivable isomeric forms with the corresponding number of carbon atoms, i.e. propylene includes 1-methylethylene and butylene includes 1-methylpropylene, 2-methylpropylene, 1,1-dimethylethylene and 1,2-dimethylethylene.

The above definition for alkylene also applies if alkylene is part of another (combined) group such as for example in HO—$C_{x-y}$alkyleneamino or $H_2N$—$C_{x-y}$alkyleneoxy.

Unlike alkyl, alkenyl consists of at least two carbon atoms, wherein at least two adjacent carbon atoms are joined together by a C—C double bond and a carbon atom can only be part of one C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Examples of alkenyl are vinyl (ethenyl), prop-1-enyl, allyl (prop-2-enyl), isopropenyl, but-1-enyl, but-2-enyl, but-3-enyl, 2-methyl-prop-2-enyl, 2-methyl-prop-1-enyl, 1-methyl-prop-2-enyl, 1-methyl-prop-1-enyl, 1-methylidenepropyl, pent-1-enyl, pent-2-enyl, pent-3-enyl, pent-4-enyl, 3-methyl-but-3-enyl, 3-methyl-but-2-enyl, 3-methyl-but-1-enyl, hex-1-enyl, hex-2-enyl, hex-3-enyl, hex-4-enyl, hex-5-enyl, 2,3-dimethyl-but-3-enyl, 2,3-dimethyl-but-2-enyl, 2-methylidene-3-methylbutyl, 2,3-dimethyl-but-1-enyl, hexa-1,3-dienyl, hexa-1,4-dienyl, penta-1,4-dienyl, penta-1,3-dienyl, buta-1,3-dienyl, 2,3-dimethylbuta-1,3-diene etc.

By the generic terms propenyl, butenyl, pentenyl, hexenyl, butadienyl, pentadienyl, hexadienyl, heptadienyl, octadienyl, nonadienyl, decadienyl etc. without any further definition are meant all the conceivable isomeric forms with the corresponding number of carbon atoms, i.e. propenyl includes prop-1-enyl and prop-2-enyl, butenyl includes but-1-enyl, but-2-enyl, but-3-enyl, 1-methyl-prop-1-enyl, 1-methyl-prop-2-enyl etc.

Alkenyl may optionally be present in the cis or trans or E or Z orientation with regard to the double bond(s).

The above definition for alkenyl also applies when alkenyl is part of another (combined) group such as for example in $C_{x-y}$alkenylamino or $C_{x-y}$alkenyloxy.

Unlike alkylene, alkenylene consists of at least two carbon atoms, wherein at least two adjacent carbon atoms are joined together by a C—C double bond and a carbon atom can only be part of one C—C double bond. If in an alkylene as hereinbefore defined having at least two carbon atoms, two hydrogen atoms at adjacent carbon atoms are formally removed and the free valencies are saturated to form a second bond, the corresponding alkenylene is formed.

Examples of alkenylene are ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene etc.

By the generic terms propenylene, butenylene, pentenylene, hexenylene etc. without any further definition are meant all the conceivable isomeric forms with the corresponding number of carbon atoms, i.e. propenylene includes 1-methylethenylene and butenylene includes 1-methylpropenylene, 2-methylpropenylene, 1,1-dimethylethenylene and 1,2-dimethylethenylene.

Alkenylene may optionally be present in the cis or trans or E or Z orientation with regard to the double bond(s).

The above definition for alkenylene also applies when alkenylene is a part of another (combined) group as for example in HO—$C_{x-y}$alkenyleneamino or $H_2N$—$C_{x-y}$alkenyleneoxy.

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Examples of alkynyl are ethynyl, prop-1-ynyl, prop-2-ynyl, but-1-ynyl, but-2-ynyl, but-3-ynyl, 1-methyl-prop-2-ynyl, pent-1-ynyl, pent-2-ynyl, pent-3-ynyl, pent-4-ynyl, 3-methyl-but-1-ynyl, hex-1-ynyl, hex-2-ynyl, hex-3-ynyl, hex-4-ynyl, hex-5-ynyl etc.

By the generic terms propynyl, butynyl, pentynyl, hexynyl, heptynyl, octynyl, nonynyl, decynyl etc. without any further definition are meant all the conceivable isomeric forms with the corresponding number of carbon atoms, i.e. propynyl includes prop-1-ynyl and prop-2-ynyl, butynyl includes but-1-ynyl, but-2-ynyl, but-3-ynyl, 1-methyl-prop-1-ynyl, 1-methyl-prop-2-ynyl, etc.

If a hydrocarbon chain carries both at least one double bond and also at least one triple bond, by definition it belongs to the alkynyl subgroup.

The above definition for alkynyl also applies if alkynyl is part of another (combined) group, as for example in $C_{x-y}$alkynylamino or $C_{x-y}$alkynyloxy.

Unlike alkylene, alkynylene consists of at least two carbon atoms, wherein at least two adjacent carbon atoms are joined together by a C—C triple bond. If in an alkylene as hereinbefore defined having at least two carbon atoms, two hydrogen atoms in each case at adjacent carbon atoms are formally removed and the free valencies are saturated to form two further bonds, the corresponding alkynylene is formed.

Examples of alkynylene are ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene, hexynylene etc.

By the generic terms propynylene, butynylene, pentynylene, hexynylene etc. without any further definition are meant all the conceivable isomeric forms with the corresponding number of carbon atoms, i.e. propynylene includes 1-methylethynylene and butynylene includes 1-methylpropynylene, 2-methylpropynylene, 1,1-dimethylethynylene and 1,2-dimethylethynylene.

The above definition for alkynylene also applies if alkynylene is part of another (combined) group, as for example in HO—$C_{x-y}$alkynyleneamino or $H_2N$—$C_{x-y}$alkynyleneoxy.

By heteroatoms are meant oxygen, nitrogen and sulphur atoms.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —C≡C—$CF_3$, —$CHFCH_2CH_3$, —$CHFCH_2CF_3$ etc.

From the previously defined haloalkyl (haloalkenyl, haloalkynyl) are also derived the terms haloalkylene (haloalkenylene, haloalkynylene). Haloalkylene (haloalkenylene, haloalkynylene), unlike haloalkyl (haloalkenyl, haloalkynyl), is bivalent and requires two binding partners. Formally, the second valency is formed by removing a hydrogen atom from a haloalkyl (haloalkenyl, haloalkynyl).

Corresponding groups are for example —$CH_2F$ and —CHF—, —$CHFCH_2F$ and —$CHFCHF$— or >$CFCH_2F$ etc.

The above definitions also apply if the corresponding halogen-containing groups are part of another (combined) group.

Halogen relates to fluorine, chlorine, bromine and/or iodine atoms.

Cycloalkyl is made up of the subgroups monocyclic hydrocarbon rings, bicyclic hydrocarbon rings and spirohydrocarbon rings. The systems are saturated. In bicyclic hydrocarbon rings two rings are joined together so that they have at least two carbon atoms in common. In spirohydrocarbon rings one carbon atom (spiroatom) belongs to two rings together.

If a cycloalkyl is to be substituted, the substitutions may take place independently of one another, in the form of mono- or polysubstitutions in each case, on all the hydrogen-carrying carbon atoms. Cycloalkyl itself may be linked as a substituent to the molecule via every suitable position of the ring system.

Examples of cycloalkyl are cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl (octahydroindenyl), bicyclo[4.4.0]

decyl (decahydronaphthyl), bicyclo[2.2.1]heptyl (norbornyl), bicyclo[4.1.0]heptyl (norcaranyl), bicyclo[3.1.1]heptyl (pinanyl), spiro[2.5]octyl, spiro[3.3]heptyl etc.

The above definition for cycloalkyl also applies if cycloalkyl is part of another (combined) group as for example in $C_{x-y}$-cycloalkylamino, $C_{x-y}$-cycloalkyloxy or $C_{x-y}$-cycloalkylalkyl.

If the free valency of a cycloalkyl is saturated, then an alicyclic group is obtained.

The term cycloalkylene can thus be derived from the previously defined cycloalkyl. Cycloalkylene, unlike cycloalkyl, is bivalent and requires two binding partners. Formally, the second valency is obtained by removing a hydrogen atom from a cycloalkyl. Corresponding groups are for example:
cyclohexyl and

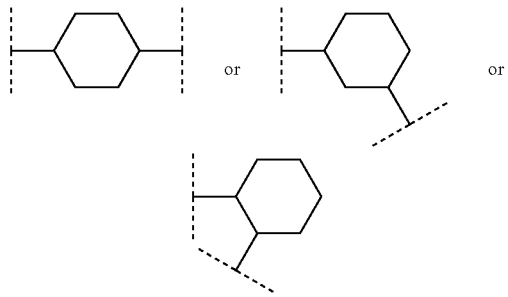

(cyclohexylene).

The above definition for cycloalkylene also applies if cycloalkylene is part of another (combined) group as for example in HO—$C_{x-y}$cycloalkyleneamino or $H_2N$—$C_{x-y}$cycloalkyleneoxy.

Cycloalkenyl is also made up of the subgroups monocyclic hydrocarbon rings, bicyclic hydrocarbon rings and spiro-hydrocarbon rings. However, the systems are unsaturated, i.e. there is at least one C—C double bond but no aromatic system. If in a cycloalkyl as hereinbefore defined two hydrogen atoms at adjacent cyclic carbon atoms are formally removed and the free valencies are saturated to form a second bond, the corresponding cycloalkenyl is obtained.

If a cycloalkenyl is to be substituted, the substitutions may take place independently of one another, in the form of mono- or polysubstitutions in each case, on all the hydrogen-carrying carbon atoms. Cycloalkenyl itself may be linked as a substituent to the molecule via every suitable position of the ring system.

Examples of cycloalkenyl are cycloprop-1-enyl, cycloprop-2-enyl, cyclobut-1-enyl, cyclobut-2-enyl, cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclobuta-1,3-dienyl, cyclopenta-1,4-dienyl, cyclopenta-1,3-dienyl, cyclopenta-2,4-dienyl, cyclohexa-1,3-dienyl, cyclohexa-1,5-dienyl, cyclohexa-2,4-dienyl, cyclohexa-1,4-dienyl, cyclohexa-2,5-dienyl, bicyclo[2.2.1]hepta-2,5-dienyl (norborna-2,5-dienyl), bicyclo[2.2.1]hept-2-enyl (norbornenyl), spiro[4,5]dec-2-enyl etc.

The above definition for cycloalkenyl also applies when cycloalkenyl is part of another (combined) group as for example in $C_{x-y}$cycloalkenylamino, $C_{x-y}$cycloalkenyloxy or $C_{x-y}$cycloalkenylalkyl.

If the free valency of a cycloalkenyl is saturated, then an unsaturated alicyclic group is obtained.

The term cycloalkenylene can thus be derived from the previously defined cycloalkenyl. Cycloalkenylene, unlike cycloalkenyl, is bivalent and requires two binding partners. Formally, the second valency is obtained by removing a hydrogen atom from a cycloalkenyl. Corresponding groups are for example:
cyclopentenyl and

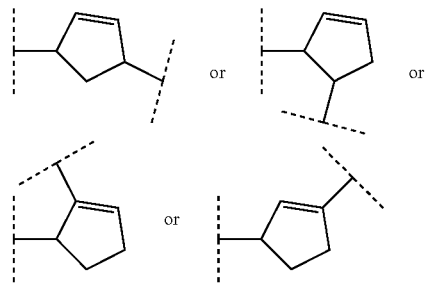

(cyclopentenylene) etc.

The above definition for cycloalkenylene also applies if cycloalkenylene is part of another (combined) group as for example in HO—$C_{x-y}$cycloalkenyleneamino or $H_2N$—$C_{x-y}$cycloalkenyleneoxy.

Aryl denotes mono-, bi- or tricyclic carbocycles with at least one aromatic carbocycle. Preferably, it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be partially saturated.

If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl, naphthyl, indanyl (2,3-dihydroindenyl), indenyl, anthracenyl, phenanthrenyl, tetrahydronaphthyl (1,2,3,4-tetrahydronaphthyl, tetralinyl), dihydronaphthyl (1,2-dihydronaphthyl), fluorenyl etc. Most preferred is phenyl.

The above definition of aryl also applies if aryl is part of another (combined) group as for example in arylamino, aryloxy or arylalkyl.

If the free valency of an aryl is saturated, then an aromatic group is obtained.

The term arylene can also be derived from the previously defined aryl. Arylene, unlike aryl, is bivalent and requires two binding partners. Formally, the second valency is formed by removing a hydrogen atom from an aryl. Corresponding groups are for example:
phenyl and

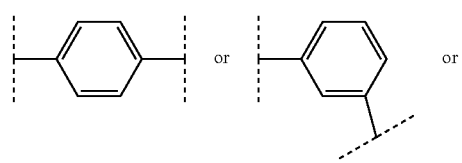

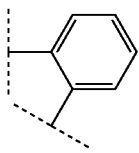

(o, m, p-phenylene),
naphthyl and

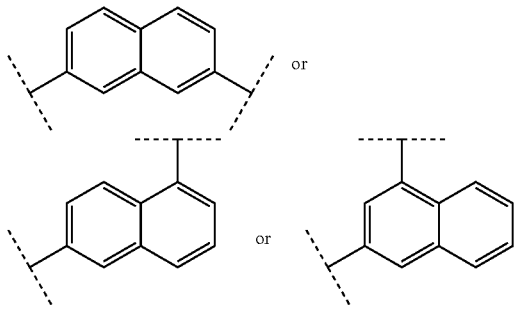

etc.

The above definition for arylene also applies if arylene is part of another (combined) group as for example in HO-aryleneamino or H₂N-aryleneoxy.

Heterocyclyl denotes ring systems, which are derived from the previously defined cycloalkyl, cycloalkenyl and aryl by replacing one or more of the groups —CH₂— independently of one another in the hydrocarbon rings by the groups —O—, —S— or —NH— or by replacing one or more of the groups =CH— by the group =N—, wherein a total of not more than five heteroatoms may be present, at least one carbon atom must be present between two oxygen atoms and between two sulphur atoms or between an oxygen and a sulphur atom and the ring as a whole must have chemical stability. Heteroatoms may optionally be present in all the possible oxidation stages (sulphur→sulphoxide —SO—, sulphone —SO₂—; nitrogen→N-oxide).

As it will be clear to the person skilled in the art, Heterocycloalkyl is derived from cycloalkyl and heterocycloalkenyl is derived from cycloalkenyl, as described above.

A direct result of the derivation from cycloalkyl, cycloalkenyl and aryl is that heterocyclyl is made up of the subgroups monocyclic heterorings, bicyclic heterorings, tricyclic heterorings and spiro-heterorings, which may be present in saturated or unsaturated form.

By unsaturated is meant that there is at least one double bond in the ring system in question, but no heteroaromatic system is formed. In bicyclic heterorings two rings are linked together so that they have at least two (hetero)atoms in common. In spiro-heterorings one carbon atom (spiroatom) belongs to two rings together.

If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system.

Examples of heterocyclyl are tetrahydrofuryl, pyrrolidinyl, pyrrolinyl, imidazolidinyl, thiazolidinyl, imidazolinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, 1,3-dioxolanyl, tetrahydropyranyl, tetrahydrothiopyranyl, [1,4]-oxazepanyl, tetrahydrothienyl, homothiomorpholinyl-S,S-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-S-oxide, tetrahydrothienyl-S,S-dioxide, homothiomorpholinyl-S-oxide, 2,3-dihydroazet, 2H-pyrrolyl, 4H-pyranyl, 1,4-dihydro-pyridinyl, 8-aza-bicyclo[3.2.1]octyl, 8-aza-bicyclo[5.1.0]octyl, 2-oxa-5-azabicyclo[2.2.1]heptyl, 8-oxa-3-aza-bicyclo[3.2.1]octyl, 3,8-diaza-bicyclo[3.2.1]octyl, 2,5-diaza-bicyclo[2.2.1]heptyl, 1-aza-bicyclo[2.2.2]octyl, 3,8-diaza-bicyclo[3.2.1]octyl, 3,9-diaza-bicyclo[4.2.1]nonyl, 2,6-diaza-bicyclo[3.2.2]nonyl, 1,4-dioxa-spiro[4.5]decyl, 1-oxa-3,8-diaza-spiro[4.5]decyl, 2,6-diaza-spiro[3.3]heptyl, 2,7-diaza-spiro[4.4]nonyl, 2,6-diaza-spiro[3.4]octyl, 3,9-diaza-spiro[5.5]undecyl, 2,8-diaza-spiro[4,5]decyl etc.

Further examples are the structures illustrated below, which may be attached via each hydrogen-carrying atom (exchanged for hydrogen):

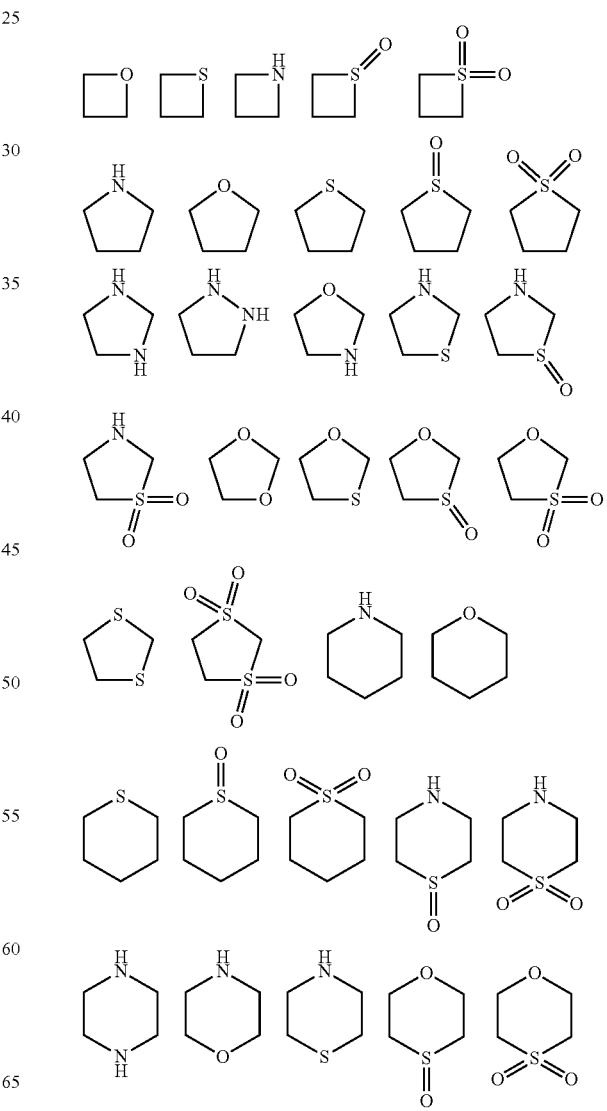

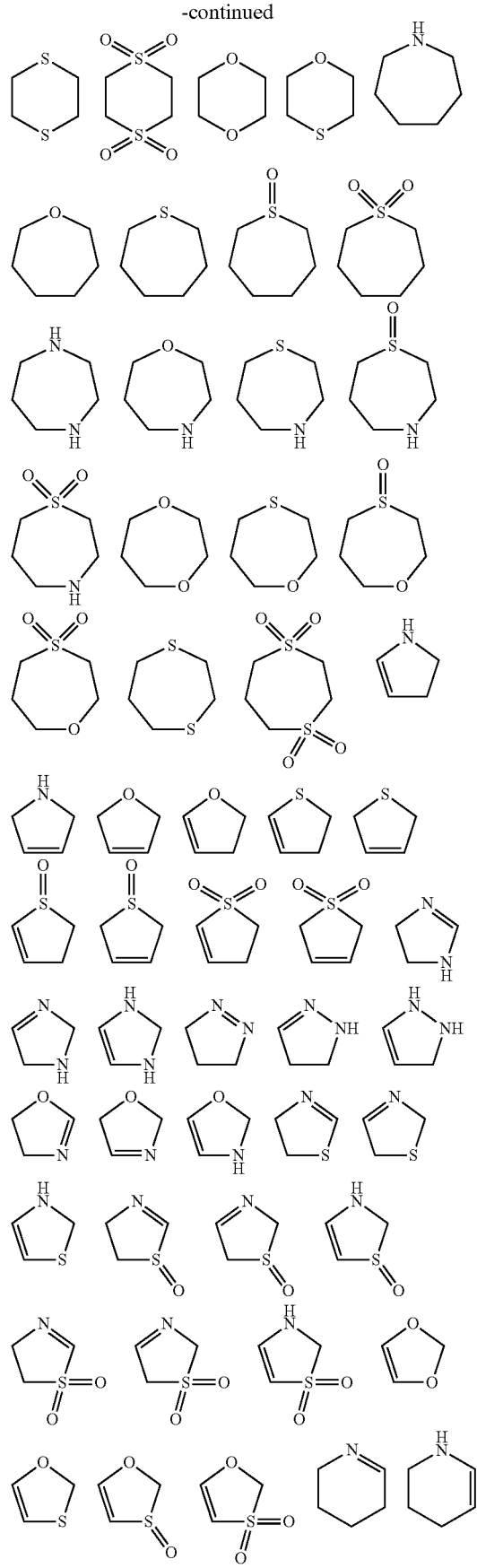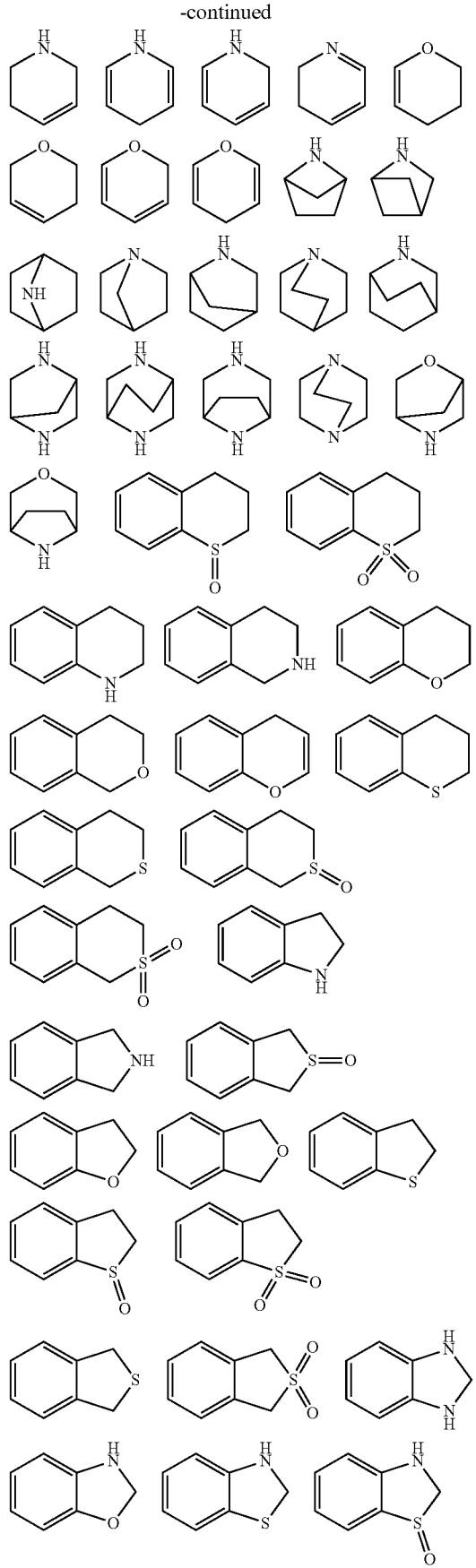

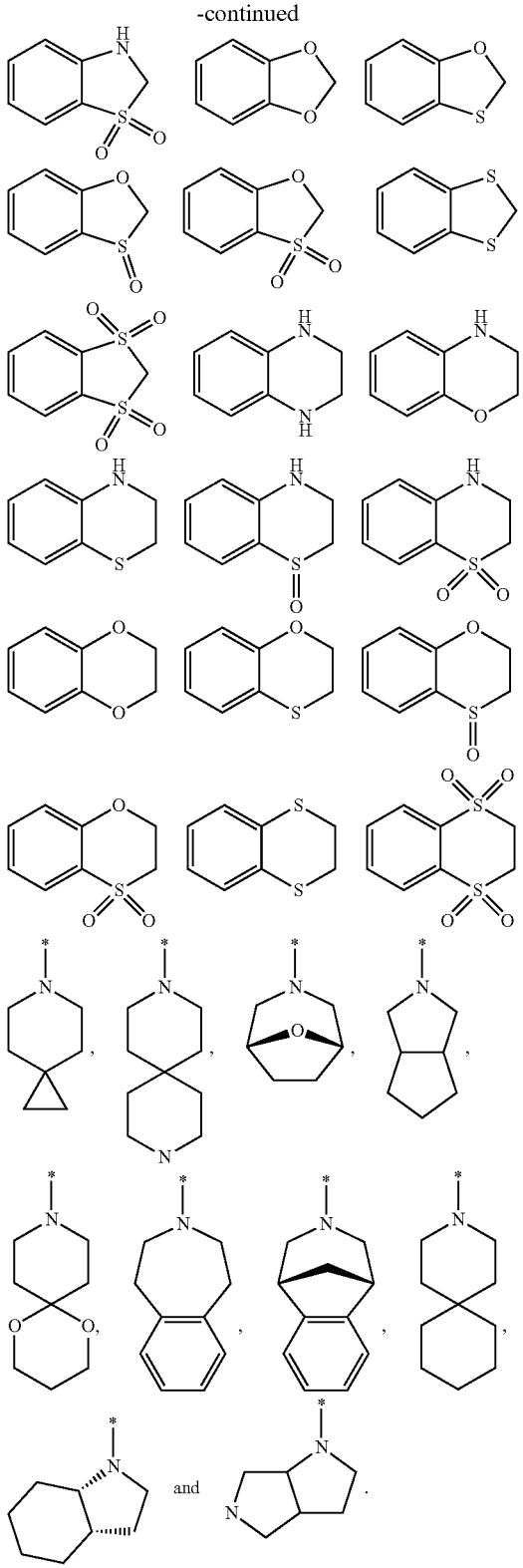

Preferably, heterocyclyls are 4 to 8 membered, monocyclic and have one or two heteroatoms independently selected from oxygen, nitrogen and sulfur.

Preferred heterocyclyls are: piperazinyl, piperidinyl, morpholinyl, pyrrolidinyl, azetidinyl, tetrahydropyranyl, tetrahydrofuranyl.

The above definition of heterocyclyl also applies if heterocyclyl is part of another (combined) group as for example in heterocyclylamino, heterocyclyloxy or heterocyclylalkyl.

If the free valency of a heterocyclyl is saturated, then a heterocyclic group is obtained.

The term heterocyclylene is also derived from the previously defined heterocyclyl. Heterocyclylene, unlike heterocyclyl, is bivalent and requires two binding partners. Formally, the second valency is obtained by removing a hydrogen atom from a heterocyclyl. Corresponding groups are for example:

piperidinyl and

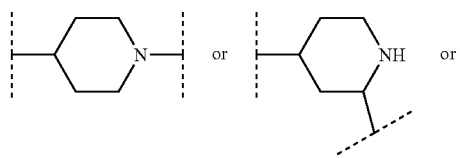

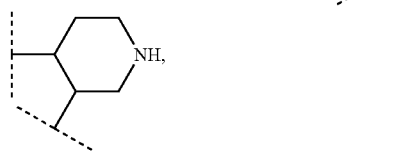

2,3-dihydro-1H-pyrrolyl and

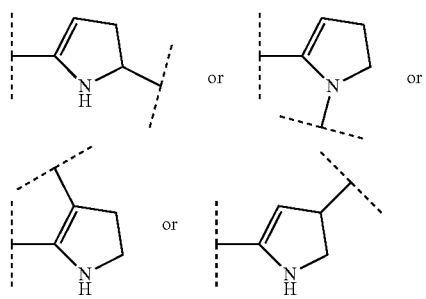

etc.

The above definition of heterocyclylene also applies if heterocyclylene is part of another (combined) group as for example in HO-heterocyclyleneamino or H$_2$N-heterocyclyleneoxy.

Heteroaryl denotes monocyclic heteroaromatic rings or polycyclic rings with at least one heteroaromatic ring, which compared with the corresponding aryl or cycloalkyl (cycloalkenyl) contain, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system.

If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen.

Examples of heteroaryl are furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl, triazinyl, pyridyl-N-oxide, pyrrolyl-N-oxide, pyrimidinyl-N-oxide, pyridazinyl-N- oxide, pyrazinyl-N-oxide, imidazolyl-N-oxide, isoxazolyl-N-oxide, oxazolyl-N-oxide, thiazolyl-N-oxide, oxadiazolyl-N-oxide, thiadiazolyl-N-oxide, triazolyl-N-oxide, tetrazolyl-N-oxide, indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl, benzotriazinyl, indolizinyl, oxazolopyridyl, imidazopyridyl, naphthyridinyl, benzoxazolyl, pyridopyridyl, pyrimidopyridyl, purinyl, pteridinyl, benzothiazolyl, imidazopyridyl, imidazothiazolyl, quinolinyl-N-oxide, indolyl-N-oxide, isoquinolyl-N-oxide, quinazolinyl-N-oxide, quinoxalinyl-N-oxide, phthalazinyl-N-oxide, indolizinyl-N-oxide, indazolyl-N-oxide, benzothiazolyl-N-oxide, benzimidazolyl-N-oxide etc.

Further examples are the structures illustrated below, which may be attached via each hydrogen-carrying atom (exchanged for hydrogen):

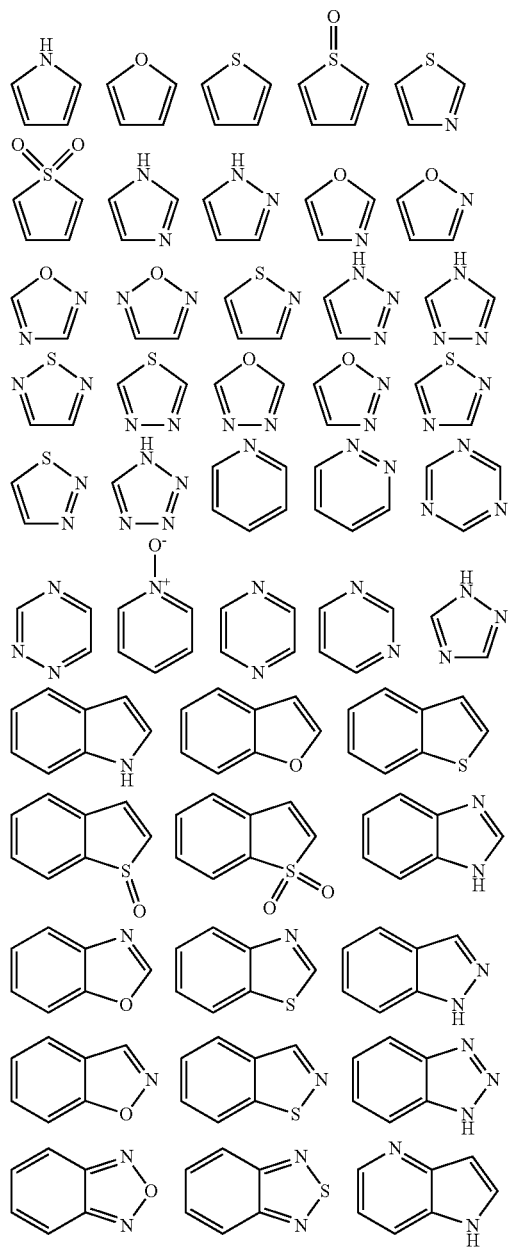

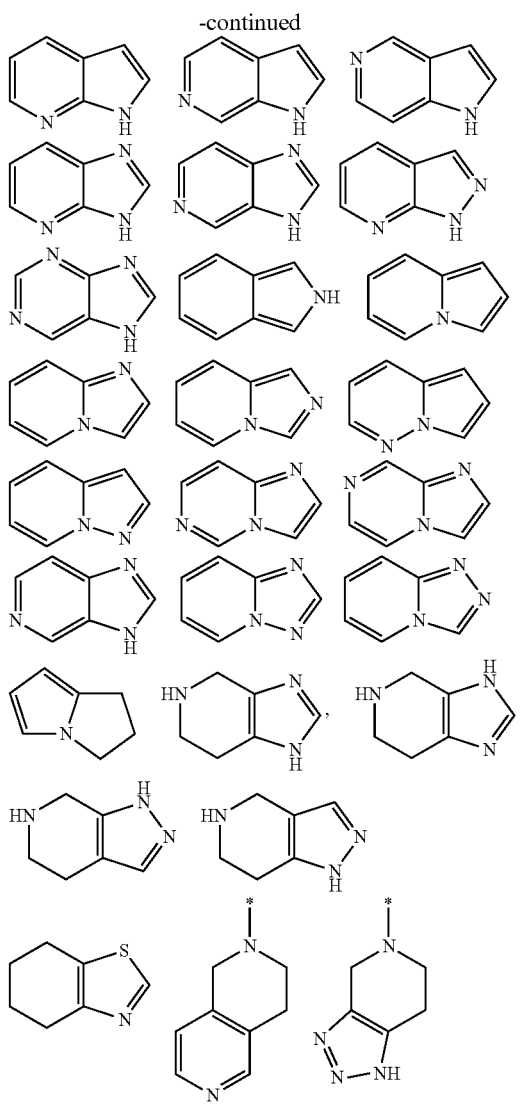

Preferably, heteroaryls are 5-6 membered monocyclic or 9-10 membered bicyclic, each with 1 to 4 heteroatoms independently selected from oxygen, nitrogen and sulfur.

The above definition of heteroaryl also applies if heteroaryl is part of another (combined) group as for example in heteroarylamino, heteroaryloxy or heteroarylalkyl.

If the free valency of a heteroaryl is saturated, a heteroaromatic group is obtained.

The term heteroarylene is also derived from the previously defined heteroaryl. Heteroarylene, unlike heteroaryl, is bivalent and requires two binding partners. Formally, the second valency is obtained by removing a hydrogen atom from a heteroaryl. Corresponding groups are for example:

pyrrolyl and

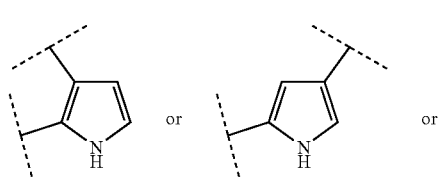

-continued

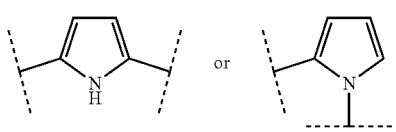

etc.

The above definition of heteroarylene also applies if heteroarylene is part of another (combined) group as for example in HO-heteroaryleneamino or H$_2$N-heteroaryleneoxy.

By substituted is meant that a hydrogen atom which is bound directly to the atom under consideration, is replaced by another atom or another group of atoms (substituent). Depending on the starting conditions (number of hydrogen atoms) mono- or polysubstitution may take place on one atom. Substitution with a particular substituent is only possible if the permitted valencies of the substituent and of the atom that is to be substituted correspond to one another and the substitution leads to a stable compound (i.e. to a compound which is not converted spontaneously, e.g. by rearrangement, cyclisation or elimination).

Bivalent substituents such as =S, =NR, =NOR, =NNRR, =NN(R)C(O)NRR, =N$_2$ or the like, may only be substituents on carbon atoms, whereas the bivalent substituent =O may also be a substituent on sulphur. Generally, substitution may be carried out by a bivalent substituent only at ring systems and requires replacement of two geminal hydrogen atoms, i.e. hydrogen atoms that are bound to the same carbon atom that is saturated prior to the substitution. Substitution by a bivalent substituent is therefore only possible at the group —CH$_2$— or sulphur atoms (=O only) of a ring system.

Stereochemistry/solvates/hydrates: Unless specifically indicated, throughout the specification and appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates and hydrates of the free compound or solvates and hydrates of a salt of the compound.

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents.

Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases, or by resolution of a racemic mixture using an appropriate resolving agent, e.g. by means of diastereomeric salt formation of the racemic compound with optically active acids or bases, subsequent resolution of the salts and release of the desired compound from the salt, or by derivatization of the corresponding racemic compounds with optically active chiral auxiliary reagents, subsequent diastereomer separation and removal of the chiral auxiliary group, or by kinetic resolution of a racemate (e.g. by enzymatic resolution); by enantioselective crystallization from a conglomerate of enantiomorphous crystals under suitable conditions, or by (fractional) crystallization from a suitable solvent in the presence of an optically active chiral auxiliary.

Salts: The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, and commensurate with a reasonable benefit/risk ratio.

As used herein "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxymethyl)-aminomethane.

The pharmaceutically acceptable salts of the present invention can be synthesized from the parent compound which contains a basic or acidic moiety by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts), also comprise a part of the invention.

In a representation such as for example

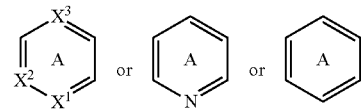

the letter A has the function of a ring designation in order to make it easier, for example, to indicate the attachment of the ring in question to other rings.

For bivalent groups in which it is crucial to determine which adjacent groups they bind and with which valency, the corresponding binding partners are indicated in brackets where necessary for clarification purposes, as in the following representations:

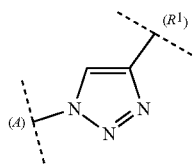

or $(R^2)$—C(O)NH— or $(R^2)$—NHC(O)—;

Groups or substituents are frequently selected from among a number of alternative groups/substituents with a corresponding group designation (e.g. $R^a$, $R^b$ etc). If such a group is used repeatedly to define a compound according to the invention in different parts of the molecule, it is pointed out that the various uses are to be regarded as totally independent of one another.

By a therapeutically effective amount for the purposes of this invention is meant a quantity of substance that is capable of obviating symptoms of illness or of preventing or alleviating these symptoms, or which prolong the survival of a treated patient.

LIST OF ABBREVIATIONS

| | |
|---|---|
| Ac | acetyl |
| aq. | aquatic, aqueous |
| Boc | tert-butyloxycarbonyl |
| BrettPhos | 2-(dicyclohexylphosphino)3,6-dimethoxy-2',4',6'-triisopropyl-1,1'-biphenyl |
| Bu | butyl |
| c | concentration |
| d | day(s) |
| dba | dibenzylideneacetone |
| TLC | thin layer chromatography |
| DCM, MeCN | dichloromethane |
| DEA | diethylamine |
| DIPEA | N-ethyl-N,N-diisopropylamine (Hünig's base) |
| DMAP | 4-N,N-dimethylaminopyridine |
| DME | 1,2-dimethoxyethane |
| DMF | N,N-dimethylformamide |
| DMSO | dimethylsulphoxide |
| DPPA | diphenylphosphorylazide |
| dppf | 1.1'-bis(diphenylphosphino)ferrocene |
| eq | equivalent(s) |
| ESI | electron spray ionization |
| Et | ethyl |
| Et$_2$O | diethyl ether |
| EtOAc | ethyl acetate |
| EtOH | ethanol |
| h | hour |
| HATU | O-(7-azabenzotriazol-1-yl)-N,N,N',N'-tetramethyl-uronium hexafluorophosphate |
| HPLC | high performance liquid chromatography |
| i | iso |
| Kat., kat. | catalyst, catalytic |
| conc. | concentrated |
| LC | liquid chromatography |
| mCPBA | 3-chlorobenzene-1-carboperoxoic acid |
| Me | methyl |
| MeOH | methanol |
| min | minutes |
| MPLC | medium pressure liquid chromatography |
| MS | mass spectrometry |
| MTP | micro titer plate |
| NBS | N-Bromo-succinimide |
| NMM | N-methylmorpholine |
| NMP | N-methylpyrrolidone |
| NP | normal phase |
| n.a. | not available |
| PBS | phosphate-buffered saline |
| PE | petrol ether |
| Ph | phenyl |
| Pr | propyl |
| Py | pyridine |
| rac | racemic |
| R$_f$ (Rf) | retention factor |
| RP | reversed phase |
| rt | ambient temperature |
| S$_N$Ar | nucleophilic aromatic substitution |
| S$_N$ | nucleophilic substitution |
| TBAF | tetrabutylammonium fluoride |
| TBDMS | tert-butyldimethylsilyl |
| TBME | tert-butylmethylether |
| TBTU | O-(benzotriazol-1-yl)-N,N,N',N'-tetramethyl-uronium tetrafluoroborate |
| tBu | tert-butyl |
| TEA | triethylamine |
| temp. | temperature |
| tert | tertiary |
| Tf | triflate |
| TFA | trifluoroacetic acid |
| THF | tetrahydrofuran |
| TMS | trimethylsilyl |
| t$_{Ret.}$ | retention time (HPLC) |
| TRIS | tris(hydroxymethyl)-aminomethane |
| TsOH | p-toluenesulphonic acid |
| UV | ultraviolet |
| xantphos | 4,5-bis(diphenylphosphino)-9,9-dimethylxanthene |

Features and advantages of the present invention will become apparent from the following detailed examples which illustrate the fundamentals of the invention by way of example without restricting its scope.

Preparation of the Compounds According to the Invention

General

Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under protective gas (nitrogen or argon).

The compounds according to the invention are named in accordance with CAS rules using the software MarvinSketch (Chemaxon).

Microwave reactions are carried out in an initiator/reactor made by Biotage or in an Explorer made by CEM or in Synthos 3000 or Monowave 3000 made by Anton Paar in sealed containers (preferably 2, 5 or 20 mL), preferably with stirring.

Chromatography

The thin layer chromatography is carried out on ready-made silica gel 60 TLC plates on glass (with fluorescence indicator F-254) made by Merck.

The preparative high pressure chromatography (RP-HPLC) of the example compounds according to the invention is carried out on Agilent or Gilson systems with columns made by Waters (names: Sunfire™ Prep C18, OBD™ 10 μm, 50×150 mm or Sunfire™ Prep C18 OBD™ 5 μm, 30×50 mm or Sunfire™ Prep C18, OBD 10 μm, 30×100 mm or XBridge™ Prep C18, OBD™ 10 μm, 50×150 mm or XBridge™ Prep C18, OBD™ 5 μm, 30×150 mm or XBridge™ Prep C18, OBD™ 5 µm, 30×50 mm) and YMC (names: Actus-Triart Prep C18, 5 µm, 30×50 mm).

Different gradients of MeCN/H₂O are used to elute the compounds, while for Agilent systems 5% acidic modifier (20 mL HCOOH to 1 L H₂O/acetonitrile (1/1)) is added to the water (acidic conditions). For Gilson systems 0.1% HCOOH is added to the water.

For the chromatography under basic conditions for Agilent systems MeCN/H₂O gradients are used as well, while the water is made alkaline by addition of 5% basic modifier (50 g NH₄HCO₃+50 mL NH₃ (25% in H₂O) to 1 L with H₂O). For Gilson systems the water is made alkaline as follows: 5 mL NH₄HCO₃ solution (158 g in 1 L H₂O) and 2 mL NH₃ (28% in H₂O) are replenished to 1 L with H₂O.

Unless otherwise stated the supercritical fluid chromatography (SFC) of the intermediates and example compounds according to the invention is carried out on a JASCO system equipped with a CO₂-pump (PU 2088), a co-solvent-pump (PU 2086), an autosampler (AS 2059), a column oven (Spark Holland Mistral), an UV-detector (UV 2075), a back pressure regulator (BP 2080) and a fraction collector (FC 2088). Chromatographic separation is obtained by isocratic elution with MeOH (containing 0.1% diethyl amine)/CO₂ at 40° C. The following columns are used: Chiralcel OJ (250×20 mm, 5 µm), Chiralpak AD (250×20 mm, 5 µm), Chiralpak AS (250×20 mm, 5 µm), Chiralpak IC (250×20 mm, 5 µm), Chiralpak IA (250×20 mm, 5 µm), Chiralcel OJ (250×20 mm, 5 µm), Chiralcel OD (250×20 mm, 5 µm), Phenomenex Lux C₂ (250×20 mm, 5 µm).

The analytical HPLC (reaction control) of intermediate and final compounds is carried out using columns made by Waters (names: XBridge™ C18, 2.5 µm, 2.1×20 mm or XBridge™ C18, 2.5 µm, 2.1×30 mm or Aquity UPLC BEH C18, 1.7 µm, 2.1×50 mm) and YMC (names: Triart C18, 3.0 µm, 2.0×30 mm) and Phenomenex (names: Luna C18, 5.0 µm, 2.0×30 mm). The analytical equipment is also equipped with a mass detector in each case.

HPLC-Mass Spectroscopy/UV-Spectrometry of Intermediates

The retention times/MS-ESI⁺ for characterizing the intermediates are produced using different HPLC-MS machines (high performance liquid chromatography with mass detector). Compounds that elute with the injection peak are given the retention time $t_{Ret.}$=0.00 min. The exact methods are as follows:

Method A

| | |
|---|---|
| HPLC | Agilent 1200 Series |
| MS | Agilent SQD - 6140 |
| MSD signal settings | Scan pos 150-750, Scan neg 150-750 |
| Column | YMC Triart C18, 2.0 × 30 mm, 3.0 µm |
| Eluent | A: 0.1% Formic Acid in water |
| | B: 0.1% Formic Acid in Acetonitrile - HPLC grade |
| Detection signal | UV 214/230/254 nm (bandwidth 4, reference off) |
| Spectrum | range: 190-400 nm; step: 4 nm |
| Peak width | 0.005 min (0.1 s) |
| Injection | 0.5 µL injection with needle wash at flush port. |
| Flow rate | 1.4 mL/min |
| Column temperature | 45° C. |
| Gradient | 0.0-1.00 min 15% to 100% B |
| | 1.00-1.13 min 100% B |

Method B

| | |
|---|---|
| HPLC | WATERS UPLC |
| MS | WATERS MICROMASS TRIPLE QUAD (API-ES +/− 3500 V, Cone voltage 25 to 50 V) |
| MSD signal settings | Scan pos 120-900, Scan neg 120-900 |
| Column | Kinetex C18 2.1 × 100 mm, 1.7 µm |
| Eluent | A: 0.1% Formic Acid in water. |
| | B: 0.1% Formic Acid in Acetonitrile. |
| Detection signal | UV 215 nm (bandwidth 1, reference off) |
| Spectrum | range: 200-400 nm; step: 1 nm |
| Peak width | <0.01 min (0.1 s) |
| Injection | 0.5 µL standard injection |
| Flow rate | 0.4 mL/min |
| Column temperature | 35° C. |
| Gradient | 0.0-0.3 min 5% B |
| | 0.3-1.5 min 5% to 50% B |
| | 1.5-3.0 min 50% to 100% B |
| | 3.0-4.5 min 100% B |
| | 4.5-5.0 min 100% to 5% B |

Method C

| | |
|---|---|
| HPLC | Agilent Infinity-1290 Series |
| MS | Agilent SQD -6130 (API-ES +/− 3000 V) |
| MSD signal settings | Scan pos 100-1000, Scan neg 100-1000 |
| Column | Aquity BEH C18, 2.1 × 50 mm, 1.7 µm |
| Eluent | A: 0.1% Formic Acid in water |
| | B: 0.1% Formic Acid in Acetonitrile |
| Detection signal | UV 215 nm (bandwidth 4, reference off) |
| Spectrum | range: 200-400 nm; step: 2 nm |
| Peak width | >0.025 min (0.5 S) |
| Injection | 0.5 µL injection with needle wash at flush port. |
| Flow rate | 0.6 mL/min |
| Column temperature | 25° C. |
| Gradient | 0.0-0.4 min 3% B |
| | 0.4-3.2 min 3% to 98% B |
| | 3.2-3.8 min 98% B |
| | 3.8-4.2 min 98% to 3% B |
| | 4.2-4.5 min 3% B |

Method D

| | |
|---|---|
| HPLC | Agilent Infinity-1290 Series |
| MS | Agilent SQD -6150 (API-ES +/− 3000 V) |
| MSD signal settings | Scan pos 100-1000, Scan neg 100-1000 |
| Column | Aquity BEH C18, 2.1 × 50 mm, 1.7 µm |
| Eluent | A: 0.1% Formic Acid in water |
| | B: 0.1% Formic Acid in Acetonitrile |
| Detection signal | UV 215 nm (bandwidth 4, reference off) |
| Spectrum | range: 200-400 nm; step: 2 nm |
| Peak width | >0.025 min (0.5 S) |
| Injection | 0.5 µL injection with needle wash at flush port. |
| Flow rate | 0.8 mL/min |
| Column temperature | 45° C. |
| Gradient | 0.0-0.2 min 2% B |
| | 0.2-1.5 min 2% to 98% B |
| | 1.5-2.6 min 98% B |
| | 2.6-2.61 min 98% to 2% B |
| | 2.61-3.2 min 2% B |

Method E

| | |
|---|---|
| LC | Agilent Infinity 1290 series |
| MS | Agilent 6130 Quadruple Icms(SQ) |
| MSD signal settings | Scan pos/neg 80-1200 |
| column | Aquity BEH C18 2.1 × 50 mm, 1.7 µm |
| eluant | A: water + 0.1% formic acid |
| | B: acetonitrile (HPLC grade) + 0.1% formic acid |
| detection signal | UV 215/254 nm (bandwidth 4, reference off) |
| spectrum | range: 200-400 nm; step: 2.0 nm |
| peak width | >0.01 min (0.2 s) |
| injection | 0.5 µL standard injection |
| flow | 0.8 mL/min |
| column temperature | 60° C. |

-continued

| gradient | 0.0-0.2 min | 3% B |
| --- | --- | --- |
| | 0.2-1.5 min | 3% to 95% B |
| | 1.5-2.5 min | 95% B |
| | 2.5-2.6 min | 95% to 3% B |
| | 2.6-3.2 min | 3% B |

Method F

| HPLC | WATERS UPLC | |
| --- | --- | --- |
| MS | WATERS MICROMASS TRIPLE QUAD (API-ES +/− 3500 V, Cone voltage 25 to 50 V) | |
| MSD signal settings | Scan pos 100-900, Scan neg 100-900 | |
| Column | Aquity BEH C18 2.1 × 50 mm, 1.7 μm. | |
| Eluent | A: 0.1% Formic Acid in water | |
| | B: 0.1% Formic Acid in Acetonitrile | |
| Detection signal | UV 215 nm (bandwidth 1, reference off) | |
| Spectrum | range: 200-400 nm; step: 1 nm | |
| Peak width | <0.01 min (0.1 s) | |
| Injection | 0.5 μL standard injection | |
| Flow rate | 0.4 mL/min | |
| Column temperature | 35° C. | |
| Gradient | 0.0-0.5 min | 5% B |
| | 0.5-2.0 min | 5% to 50% B |
| | 2.0-3.5 min | 50% to 100% B |
| | 3.5-5.0 min | 100% B |
| | 5.0-5.1 min | 100% to 5% B |

Method G

| HPLC | Agilent RRLC (1200 Series) | |
| --- | --- | --- |
| MS | Agilent SQD-6130 (API-ES/APCI (Multi Mode) +/− 3000 V, Corona Current 4 μA) | |
| MSD signal settings | Scan pos 90-1000, Scan neg 90-1000 | |
| Column | X-bridge C18, 4.6 × 50 mm, 2.5μ | |
| Eluent | A: 5 mM Ammonium Acetate | |
| | B: Acetonitrile | |
| Detection signal | UV 215 nm (bandwidth 4, reference off) | |
| Spectrum | range: 200-400 nm; step: 2 nm | |
| Peak width | >0.1 min (2.0 S) | |
| Injection | 5 μL injection with needle wash. | |
| Flow rate | 0.6 mL/min | |
| Column temperature | 35° C. | |
| Gradient | 0.0-1.0 min | 5% B |
| | 1.0-1.8 min | 5% to 55% B |
| | 1.8-3.5 min | 55% to 98% B |
| | 3.5-5.5 min | 98% B |
| | 5.5-6.0 min | 98% to 5% B |

Method H

| HPLC | Agilent RRLC (1200 Series) | |
| --- | --- | --- |
| MS | Agilent SQD-6130 (API-ES/APCI (Multi Mode) +/− 3000 V, Corona Current 4 μA) | |
| MSD signal settings | Scan pos 90-1000, Scan neg 90-1000 | |
| Column | X-bridge C18, 4.6 × 75 mm, 3.5μ | |
| Eluent | A: 5 mM Ammonium Acetate in Water | |
| | B: Acetonitrile | |
| Detection signal | UV 215/254 nm (bandwidth 4, reference off) | |
| Spectrum | range: 200-400 nm; step: 2 nm | |
| Peak width | >0.1 min (2.0 S) | |
| Injection | 5 μL injection with needle wash. | |
| Flow rate | 1.300 mL/min | |
| Column temperature | 35° C. | |
| Gradient | 0.0-1.0 min | 10% B |
| | 1.0-5.0 min | 10% to 90% B |
| | 5.0-5.5 min | 90% to 98% B |
| | 5.5-7.0 min | 98% B |
| | 7.0-7.01 min | 98% to 10% B |

Method J

| HPLC | Agilent Infinity-1290 Series | |
| --- | --- | --- |
| MS | Agilent SQD-6150 (API-ES +/− 3000 V) | |
| MSD signal settings | Scan pos 100-1000, Scan neg 100-1000 | |
| Column | Aquity BEH C18, 2.1 × 50 mm, 1.7 μm | |
| Eluent | A: 0.1% Formic Acid in Water | |
| | B: 0.1% Formic Acid in Acetonitrile | |
| Detection signal | UV 215/254 nm (bandwidth 4, reference off) | |
| Spectrum | range: 200-400 nm; step: 2 nm | |
| Peak width | >0.025 min (0.5 S) | |
| Injection | 0.5 μL injection with needle wash at flush port. | |
| Flow rate | 0.6 mL/min | |
| Column temperature | 35° C. | |
| Gradient | 0.0-0.2 min | 3% B |
| | 0.2-2.5 min | 3% to 98% B |
| | 2.5-3.8 min | 98% B |
| | 3.8-4.2 min | 98% to 3% B |
| | 4.2-4.5 min | 3% B |

Method K

| HPLC | Agilent Infinity-1290 Series | |
| --- | --- | --- |
| MS | Agilent SQD -6130 (API-ES + 3500 V/−3000 V) | |
| MSD signal settings | Scan pos 100-1200, Scan neg 100-1200 | |
| Column | Aquity BEH C18, 2.1 × 50 mm, 1.7 μm | |
| Eluent | A: 0.1% Formic Acid in Acetonitrile | |
| | B: 0.1% Formic Acid in water | |
| Detection signal | UV 215/254 nm (bandwidth 4, reference off) | |
| Spectrum | range: 200-400 nm; step: 2 nm | |
| Peak width | >0.025 min (0.5 S) | |
| Injection | 0.5 μL injection with needle wash at flush port. | |
| Flow rate | 0.8 mL/min | |
| Column temperature | 60° C. | |
| Gradient | 0.0-0.4 min | 97% B |
| | 0.4-2.2 min | 97% to 2% B |
| | 2.2-2.6 min | 2% B |
| | 2.6-2.61 min | 2% to 97% B |
| | 2.61-3.0 min | 97% B |

Method L

| HPLC | Agilent 1200 Series | |
| --- | --- | --- |
| MS | Agilent SQD - 6130 | |
| MSD signal settings | Scan pos 150-800, Scan neg 150-800 | |
| Column | Waters XBridge C18, 2.1 × 30 mm, 2.5 μm | |
| Eluent | A: 20 mM $NH_4HCO_3/NH_3$ in Water; pH 9.3 | |
| | B: Acetonitrile - HPLC grade | |
| Detection signal | UV 214/230/254 nm (bandwidth 4, reference off) | |
| Spectrum | range: 190-400 nm; step: 4 nm | |
| Peak width | 0.0025 min (0.05 s) | |
| Injection | 0.5 μL injection with needle wash at flush port. | |
| Flow rate | 1.4 mL/min | |
| Column temperature | 45° C. | |
| Gradient | 0.0-1.00 min | 15% –> 95% B |
| | 1.00-1.30 min | 95% B |

Method M

| HPLC | Agilent 1200 RRLC Series | |
| --- | --- | --- |
| MS | Agilent SQD - 6130 | |
| MSD signal settings | Scan pos 150-800, Scan neg 150-800 | |
| Column | Waters XBridge C18, 4.6 × 75 mm, 3.5 μm | |
| Eluent | A: 10 mM $NH_4OAc$ in Water | |
| | B: Acetonitrile - HPLC grade | |
| Detection signal | UV 214/230/254 nm (bandwidth 4, reference off) | |
| Spectrum | range: 190-400 nm; step: 4 nm | |
| Peak width | 0.0025 min (0.05 s) | |
| Injection | 0.5 μL injection with needle wash at flush port. | |
| Flow rate | 2.0 mL/min | |
| Column temperature | 35° C. | |

| | | |
|---|---|---|
| Gradient | 0.00-0.20 min | 10% B |
| | 0.20-2.50 min | 10% to 75% B |
| | 2.50-3.00 min | 75% to 100% B |
| | 3.00-4.80 min | 100% B |
| | 4.80-5.00 min | 100% B to 10% B |

HPLC-mass spectroscopy/UV-spectrometry of example compounds I-1 to I-178

All compounds according to the invention are analyzed on an Agilent 1100 series LC system coupled with an Agilent 6140 mass spectrometer or on a Waters Acquity QDa System. Purity is determined via UV detection. Method 1 is also used for the characterization of some of the intermediates.

Method 1

| | |
|---|---|
| HPLC | Agilent 1100 system |
| MS | 1200 Series LC/MSD (API-ES +/− 3000 V, Quadrupol, G6140) |
| MSD signal settings | Scan pos/neg 120-900 m/z |
| Column | Waters, XBridge C18, 2.5 µm, 2.1 × 20 mm |
| Eluent | A: 20 mM $NH_4HCO_3/NH_3$ pH 9 |
| | B: acetonitrile HPLC grade |
| Detection signal | 315 nm (bandwidth 170 nm, reference off) |
| Spectrum | range: 230-400 nm |
| Peak width | <0.01 min |
| Injection | 5 µL standard injection |
| Column temperature | 60° C. |
| Flow | 1.00 mL/min |
| Gradient | 0.00-1.50 min    10% to 95% B |
| | 1.50-2.00 min    95% B |
| | 2.00-2.10 min    95% to 10% B |

Method 2

| | |
|---|---|
| HPLC-MS | Waters Acquity, QDa Detector system |
| Column | Waters, Sunfire C18, 2.5 µm, 3 × 30 mm |
| Eluent | A: Water with 0.1% TFA (v/v) |
| | B: Acetonitrile HPLC grade with 0.08% TFA (v/v) |
| Column temperature | 60° C. |
| Flow | 1.50 mL/min |
| Gradient | 0.00-1.30 min    5% to 100% B |
| | 1.30-1.50 min    100% B |
| | 1.50-1.60 min    100% to 5% B |

The compounds according to the invention are prepared by the methods of synthesis described hereinafter in which the substituents of the general formulae have the meanings given hereinbefore. These methods are intended as an illustration of the invention without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis.

A. General Preparation Methods for Compounds (I)

FIG. 1: General Formula of Compounds (I)

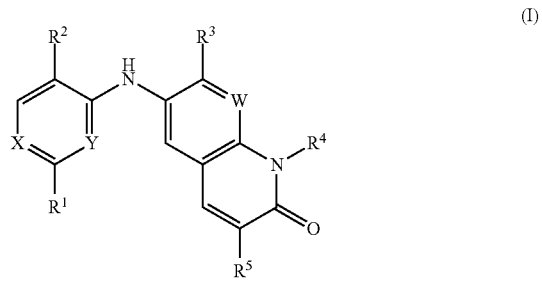

A.1. Preparation Methods for Compounds (I) with X=Y=N

Scheme 1: General synthesis routes to compounds (I) with X = Y = N

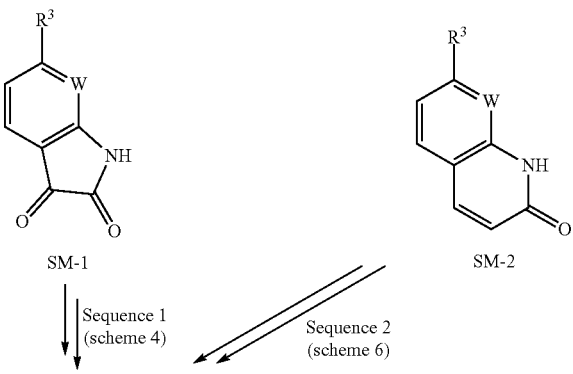

-continued

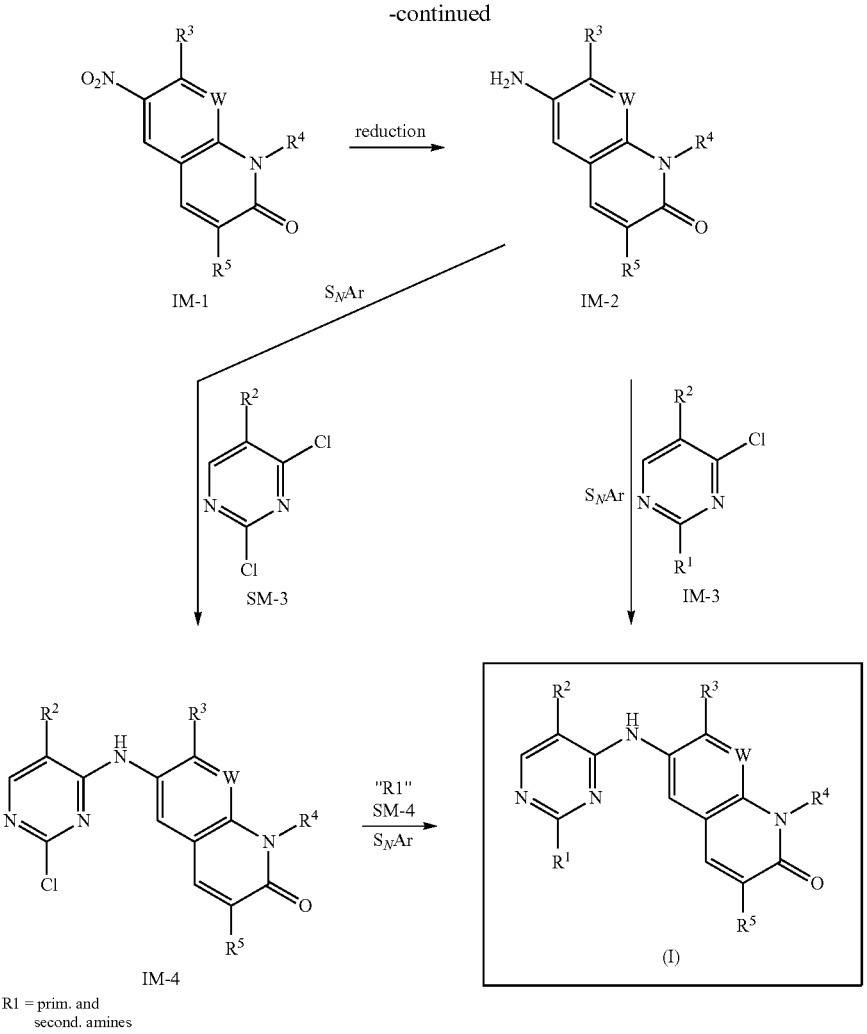

R1 = prim. and second. amines
SM-4

Compounds (I) according to the invention can be prepared as described in scheme 1 starting from starting materials SM-1 to SM-4 which are either commercially available or can be synthesized as described below.

Among other methods compounds (I) can be synthesized from 2-chloro-pyrimidines IM-4 and primary or secondary amines SM-4 by nucleophilic aromatic substitution (S$_N$Ar) under basic, neutral or acidic conditions. The S$_N$Ar reaction can also be used to synthesize 2-chloro-pyrimidines IM-4 form 2,4-dichloro pyrimidines SM-3 and 6-amino-quinolinones IM-2, which can be prepared from 6-nitro-quinolinones IM-1 by reduction of the nitro group. For this reduction classical conditions such as catalytic hydrogenation, iron in the presence of ammonium chloride or SnCl$_2$ in hydrochloric acid or others can be used. 6-Nitro quinolinones IM-1 can be prepared in 3 to 4 steps from isatin derivatives SM-1 by selective nitration in the 5-position and alkylation of the —NH followed by a ring extension reaction (Sequence 1; scheme 4). This method is mainly used for examples where R5 of the general formula (I) is —OH or —OR. Alternatively, 6-nitro quinolinones IM-1 are prepared from quinolinone derivatives SM-2. In this sequence, selective nitration of the 6-position, halogenation of the 3-position and alkylation of the —NH followed by transition metal catalyzed cross-coupling reactions are used to generate intermediates IM-1 (Sequence 2; scheme 6). This method is mainly used for examples where R$^5$ of the general formula (I) is "—CR" or —SR. Starting from 6-amino quinolinones IM-2 compounds (I) can also be synthesized directly in one step using 4-chloro pyrimidines IM-3 under S$_N$Ar conditions.

All residues, R1 to R5 in the compounds of the general formula (I) can be chemically modified at most stages of the general reaction scheme. Especially residues R1 and R5, respectively, are often modified after the last reaction step of the general scheme. Commonly used late stage modifications are e.g. alkylation reactions of —NH or —OH groups, saponification reactions of esters to carboxylic acids and subsequent amide coupling reactions using well established methods. Such late stage modifications are described with the respective examples.

A.2. General Preparation Methods for Compounds (I) with X=CH and Y=N

A.3. General Preparation Methods for Compounds (I) with X=N and Y=CH

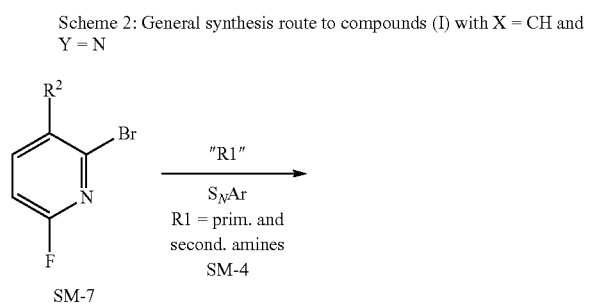

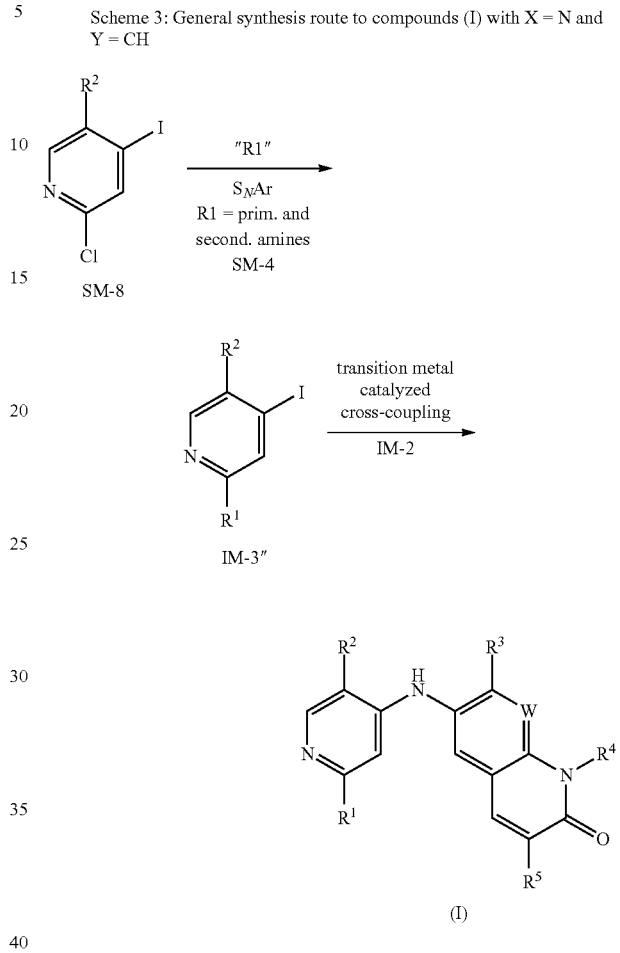

Compounds (I) with X=CH and Y=N can be prepared from 2-bromo-pyridines IM-3' by transition metal catalyzed cross-coupling reactions such as Buchwald-Hartwig type reactions with 6-amino quinolinone intermediates IM-2. 2-Bromo-pyridines IM-3' can be synthesized from 2-bromo-6-fluoro-pyridines SM-7 by S$_N$Ar reactions using primary or secondary amines SM-4 as nucleophiles.

Compounds (I) with X=N and Y=CH can be prepared from 4-iodo-pyridines IM-3" by transition metal catalyzed cross-coupling reactions such as Buchwald-Hartwig type reactions with 6-amino quinolinone intermediates IM-2. 4-Iodo-pyridines IM-3" can be synthesized from 2-chloro-6-iodo-pyridines SM-8 by S$_N$Ar reactions using primary or secondary amines SM-4 as nucleophiles.

A.4. General Preparation Methods for Intermediates IM-1

Scheme 4: General preparation of 6-nitro quinolinones IM-1 from SM-1 (Sequence 1)

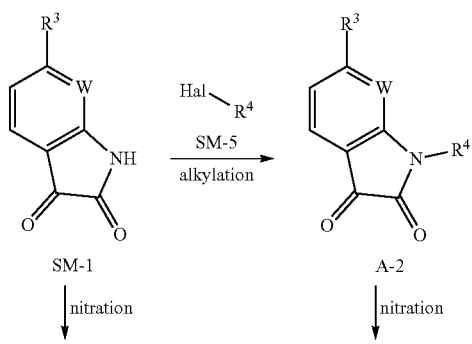

-continued

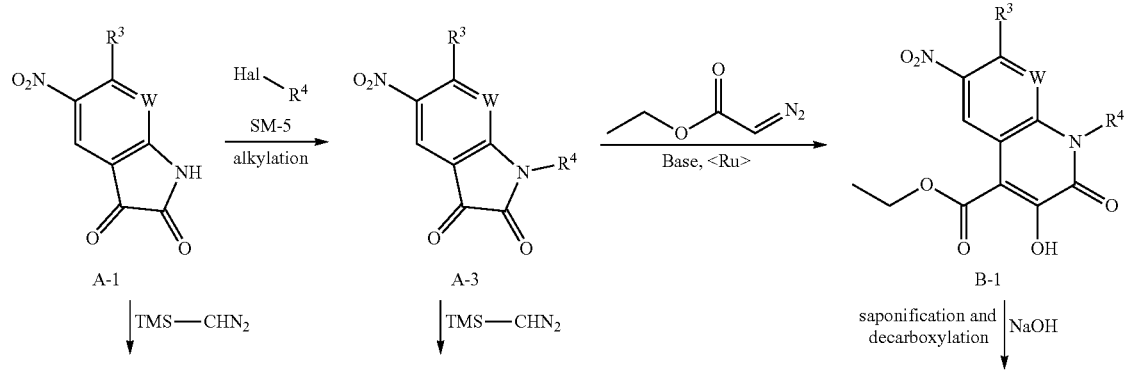

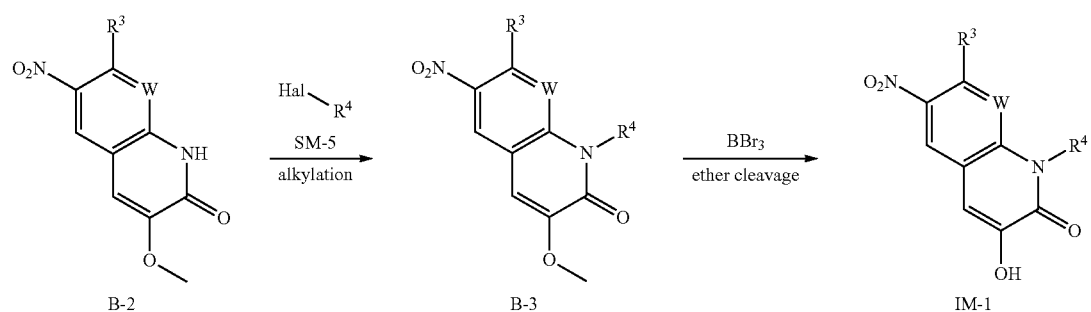

IM-1 can be synthesized as outlined in scheme 4 starting from the corresponding isatin derivatives SM-1. Isatins A-1 can be generated by nitration of isatins SM-1 using known nitration protocols such as $HNO_3/H_2SO_4$, $NaNO_3$, $KNO_3$ and others. Isatins A-3 can be prepared by alkylation of A-1 with alkyl halogenides, activated alcohols or other alkylating reagents under standard conditions. Isatins A-3 are also accessible starting from SM-1 via A-2 by inverting the two reaction steps. Some isatins A-1, A-2 and A-3, respectively are commercially available. Ru-catalyzed ring extension reaction of A-3 with ethyl diazoacetate and strong bases such as DBU leads to quinolinones B-1. The ester moiety is then cleaved and the resulting carboxylic acid is decarboxylated to give 3-hydroxy-6-nitro-quinolinones IM-1. Ring extension of isatins A-1 and A-3 to 3-methoxy-quinolinones B-2 and B-3, respectively can also be achieved using TMS-diazomethane under basic conditions. Alkylation under standard conditions transforms quinolinones B-2 to quinolinones B-3. Ether cleavage of B-3 using e.g. $BBr_3$ results in 3-hydroxy-6-nitro-quinolinones IM-1.

Scheme 5: Additional IM-1 derivatives by modification of the 3-hydroxy function

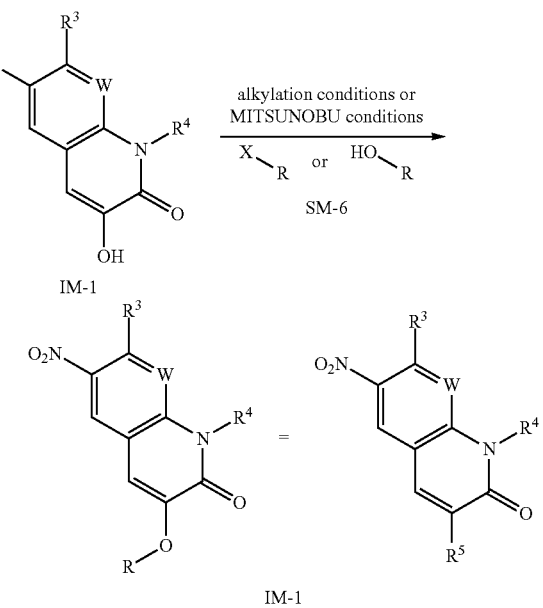

Additional IM-1 derivatives are obtained by chemical modification of the 3-hydroxy group (Scheme 5). Alkyl moieties are introduced by alkylation conditions using alkyl halogenides SM-6 or via MITSUNOBU conditions using the corresponding alkyl alcohols SM-6.

Scheme 6: General preparation of 6-nitro quinolinones IM-1 from SM-2 (Sequence 2)

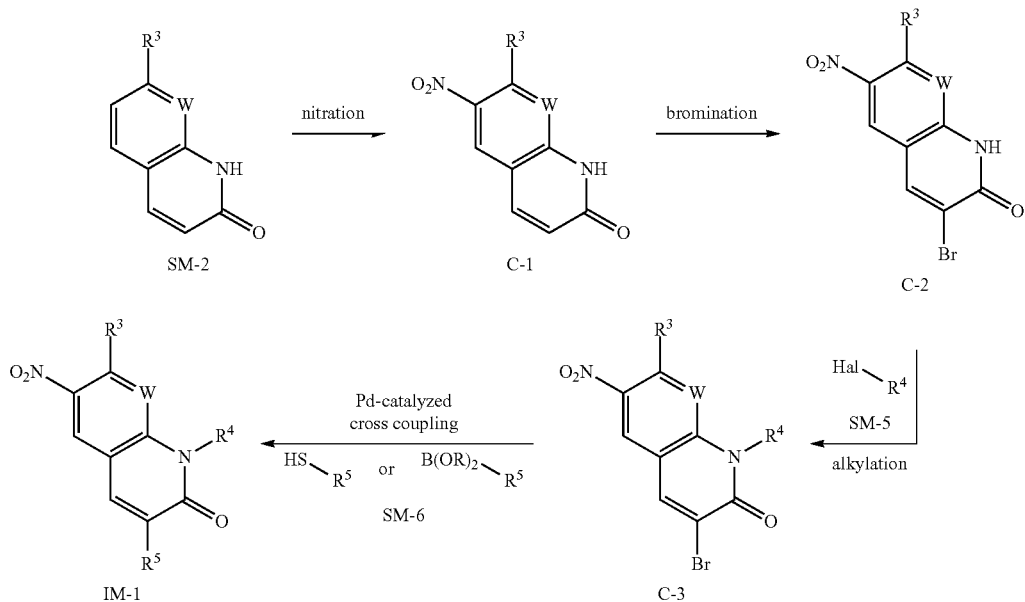

IM-1 derivatives with R5="—CR" or —SR are prepared starting from quinolinones SM-2. Nitration at the 6-position using e.g. mixtures of sulphuric and nitric acid generates 6-nitro quinolinones C-1. Subsequent selective bromination in 3-position with e.g. sodium bromate and hydrobromic acid yields bromo quinolinones C-2, which can be alkylated at the —NH to C-3 using alkyl halogenides SM-5 under standard alkylation conditions. Further modification at the 3-position by transition metal catalyzed cross-coupling reactions using thiols or boronic acid or esters thereof SM-6 delivers the corresponding IM-1 derivatives.

A.5. General Preparation Methods for Intermediates IM-3

Scheme 7: General preparation of IM-3 from SM-3

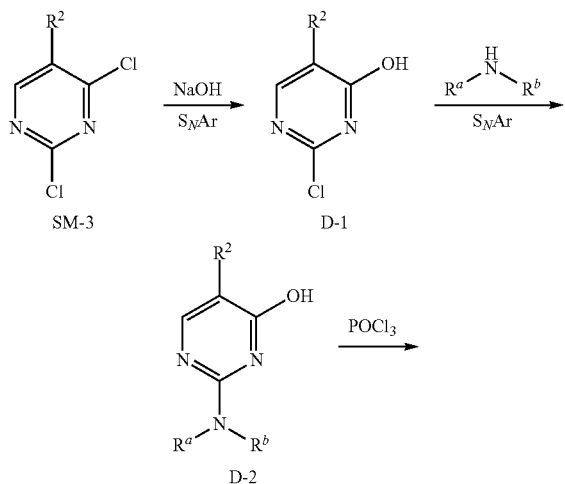

-continued

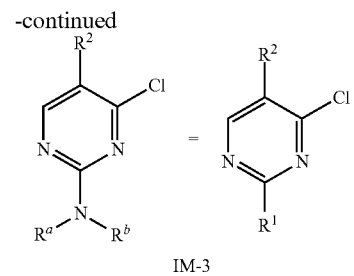

2-substituted chloro pyrimidines IM-3 can be synthesized as outlined in scheme 7 starting from 2,4-dichloro-pyrimidines SM-3. Selective hydrolysis of the chlorine in 4-position using NaOH gives 2-chloro-4-hydroxy-pyrimidines D-1. Subsequent $S_NAr$ reaction with primary or secondary amines under standard conditions gives the corresponding 2-substituted 4-hydroxy-pyrimidines D-2, which are re-chlorinated in 4-position using $POCl_3$ or $POCl_3/PCl_5$ to yield the intermediates IM-3. Derivatization of D-1 in the 2-position is not limited to primary or secondary amines. Other nucleophiles such as alcohols, thiols or carbon nucleophiles can also be used to introduce various R1 residues. Possible reactions to modify R1 are not limited to $S_NAr$ reactions. Transition metal catalyzed reactions can also be used to introduce e.g. aromatic or heteroaromatic substituents in the 2-position of D-1.

SM-1 to SM-8 are commercially available or individually synthesized as described for the concrete example.

B. Synthesis of Intermediates
B.1. Synthesis of IM-1 from Isatins SM-1
B.1.1. Experimental Procedure for the Synthesis of IM-1a

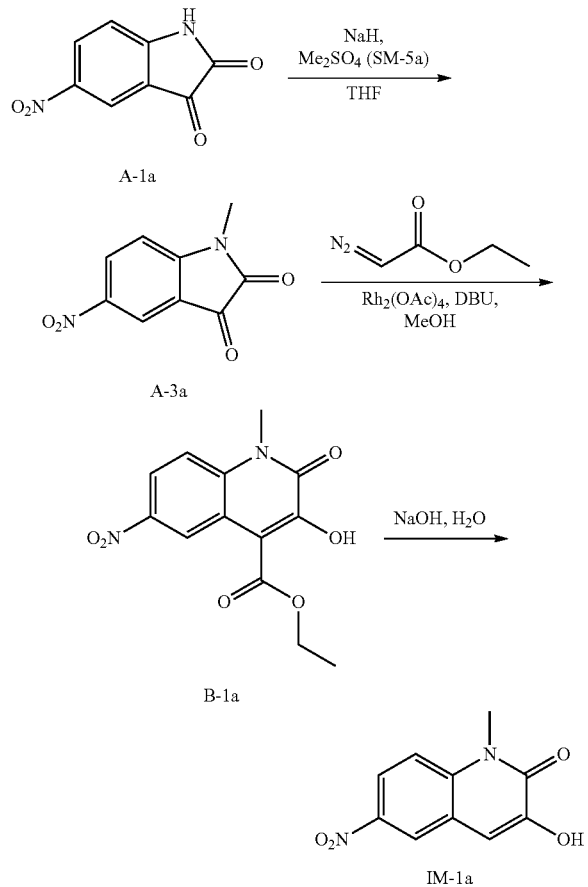

Sodium hydride (13.7 g; 573 mmol) is added to a solution of 5-nitro-2,3-dihydro-1H-indole-2,3-dione A-1a (100 g; 520 mmol) in THF (1.0 L) at rt. The mixture is heated to 50° C. for 1 h. Dimethylsulfate (SM-5a) (98.5 g; 781 mmol) is added and stirring is continued for 2 h at 50° C. After cooling to rt water is added, whereupon a precipitation occurs. After 30 min the solid is collected by filtration and dried in vacuo to give 1-methyl-5-nitro-2,3-dihydro-1H-indole-2,3-dione (A-3a) (HPLC-MS: $t_{Ret.}$=1.83 min; MS (M+H)$^+$=207; method C).

A-3a (56.0 g; 272 mmol) is dissolved in MeOH (600 mL). DBU (8.27 g; 54.3 mmol) and ethyldiazoacetate (37.2 g; 326 mmol) is added and the mixture is stirred at rt for 1 h. Rhodium(II)acetate (1.20 g; 2.72 mmol) is added and stirring is continued for 12 h. The resulting solid is filtered, washed with MeOH and dried in vacuo to give ethyl 3-hydroxy-1-methyl-6-nitro-2-oxo-1,2-dihydroquinoline-4-carboxylate (B-1a) (HPLC-MS: $t_{Ret.}$=2.11 min; MS (M+H)$^+$=293; method C).

B-1a (27 g; 92.4 mmol), NaOH (7.39 g; 185 mmol) and water (500 mL) are mixed and heated under reflux for 16 h. After cooling to rt the reaction mixture is acidified with 2 N HCl$_{aq.}$ to pH=1-2, whereupon a precipitate occurs. The solid is collected by filtration, washed with water and dried. The crude material is purified by flash chromatography on SiO$_2$ using EtOAc/hexane (70:30) as eluent to give pure 3-hydroxy-1-methyl-6-nitro-1,2-dihydroquinolin-2-one (IM-1a) (HPLC-MS: $t_{Ret.}$=0.37 min; MS (M+H)$^+$=221; method 1).

B.1.2. Experimental Procedure for the Synthesis of IM-1b

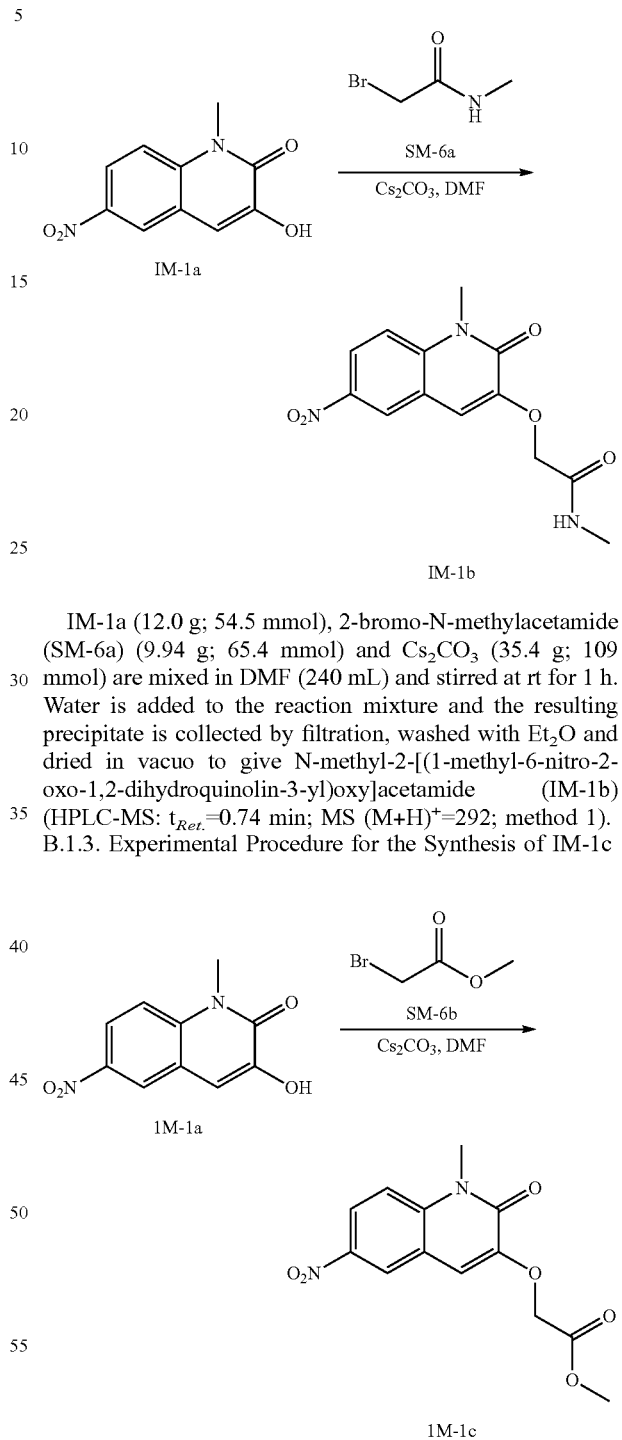

IM-1a (12.0 g; 54.5 mmol), 2-bromo-N-methylacetamide (SM-6a) (9.94 g; 65.4 mmol) and Cs$_2$CO$_3$ (35.4 g; 109 mmol) are mixed in DMF (240 mL) and stirred at rt for 1 h. Water is added to the reaction mixture and the resulting precipitate is collected by filtration, washed with Et$_2$O and dried in vacuo to give N-methyl-2-[(1-methyl-6-nitro-2-oxo-1,2-dihydroquinolin-3-yl)oxy]acetamide (IM-1b) (HPLC-MS: $t_{Ret.}$=0.74 min; MS (M+H)$^+$=292; method 1).

B.1.3. Experimental Procedure for the Synthesis of IM-1c

IM-1a (18.0 g; 81.8 mmol), bromo-acetic acid methyl ester (SM-6b) (18.8 g; 123 mmol) and Cs$_2$CO$_3$ (53.1 g; 164 mmol) are mixed in DMF (90 mL) and stirred at rt for 1 h. Water is added to the reaction mixture and the resulting precipitate is collected by filtration, washed with pentane and dried in vacuo to give methyl 2-[(1-methyl-6-nitro-2-oxo-1,2-dihydro-quinolin-3-yl)oxy]acetate (IM-1c) (HPLC-MS: $t_{Ret.}$=1.04 min; MS (M+H)$^+$=293; method E).

B.1.4. Experimental Procedure for the Synthesis of IM-1d and IM-1e

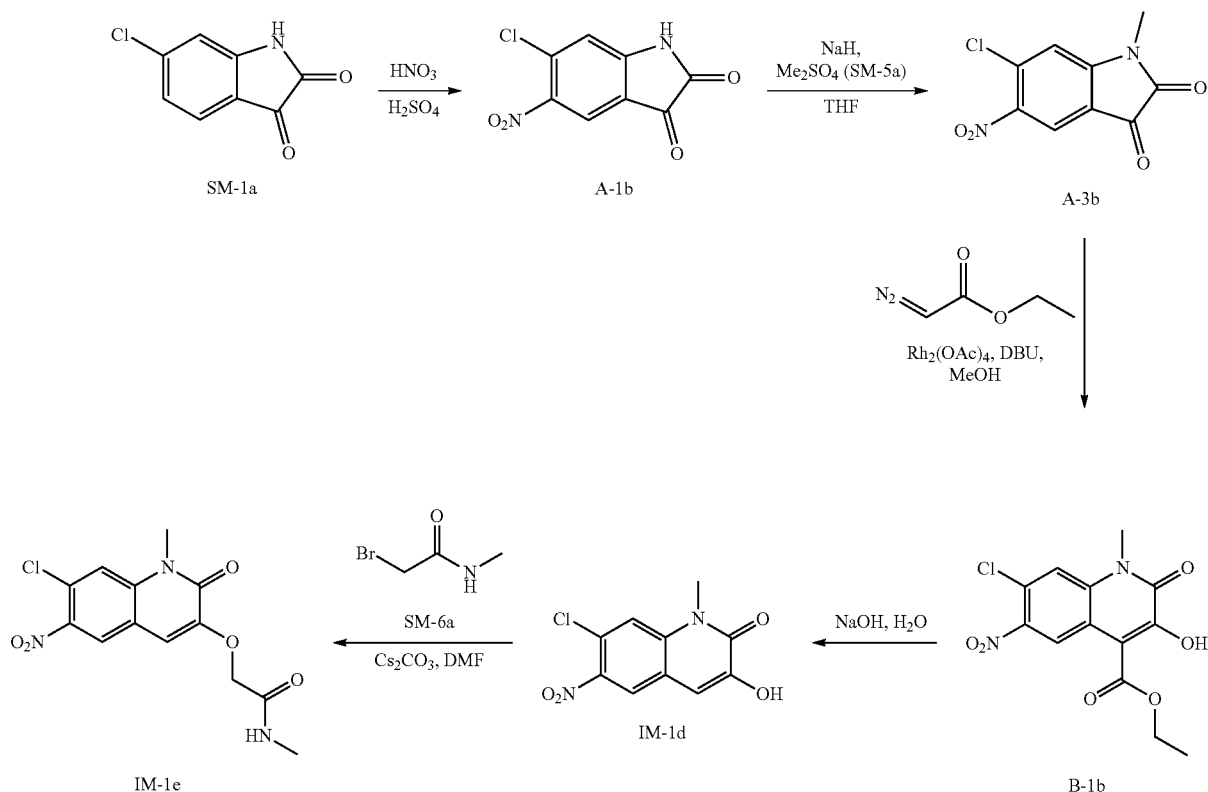

To a solution of sodium nitrate (4.68 g; 55.1 mmol) in sulfuric acid (50.0 mL) is added dropwise a solution of 6-chloro-1H-indole-2,3-dione (SM-1a) (10.0 g; 55.1 mmol) in sulfuric acid (50.0 mL) over a period of 1 h at 0° C. The reaction mixture is then poured into ice water and the resulting precipitate is collected by filtration, washed with water and dried to give 6-chloro-5-nitro-2,3-dihydro-1H-indole-2,3-dione (A-1b) (HPLC-MS: $t_{Ret.}$ 1.85 min; MS $(M-H)^-$=225; method C).

From A-1b onwards the same reaction sequence and conditions as described under B.1.1. and B.1.2. for the synthesis of IM-1a and IM-1b are used to obtain 7-chloro-3-hydroxy-1-methyl-6-nitro-1,2-dihydroquinolin-2-one (IM-1d) (HPLC-MS: $t_{Ret.}$=2.20 min; MS $(M+H)^+$=255; method C) and 2-[(7-chloro-1-methyl-6-nitro-2-oxo-1,2-dihydroquinolin-3-yl)oxy]-N-methylacetamide (IM-1e) (HPLC-MS: $t_{Ret.}$=1.35 min; MS $(M+H)^+$=326; method K).

B.1.5. Experimental Procedure for the Synthesis of IM-1f and IM-1g

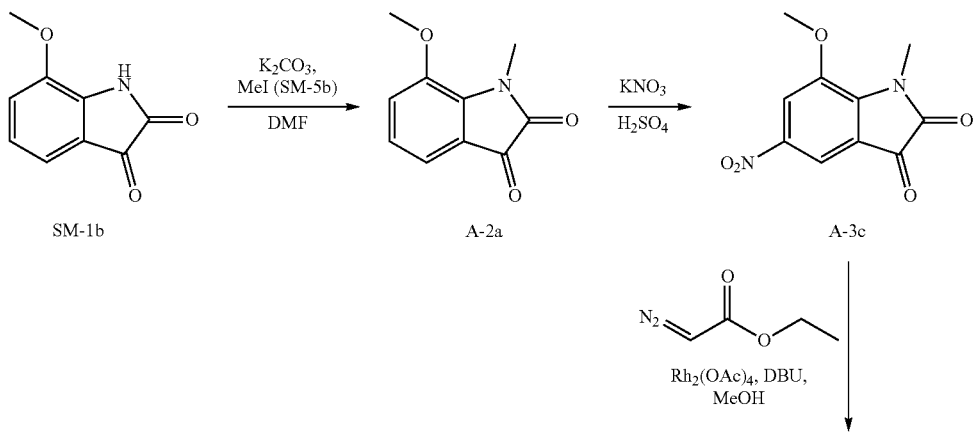

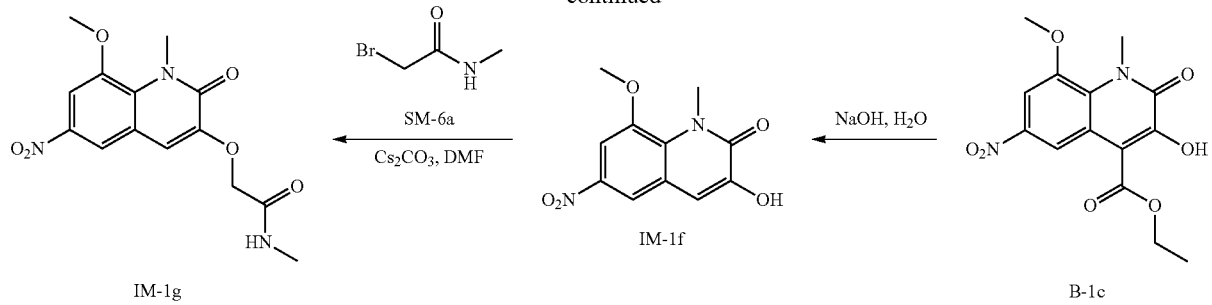

To 7-methoxy-1H-indole-2,3-dione (SM-1b) (500 mg; 2.82 mmol) in DMF (5.0 mL) is added $K_2CO_3$ (585 mg; 4.23 mmol) in one portion. The reaction mixture is stirred at rt for min before iodomethane (SM-5b) (0.230 mL; 3.67 mmol) is added and stirring is continued at rt for 2 h. The reaction mixture is poured into water, acidified with 4 N $HCl_{aq.}$ and stirred for 30 min. The resulting precipitate is collected by filtration, washed with water and dried in vacuo to give 7-methoxy-1-methyl-2,3-dihydro-1H-indole-2,3-dione (A-2a) (HPLC-MS: $t_{Ret.}$=0.87 min; MS $(M+H)^+$=192; method 1).

A-2a (440 mg; 2.30 mmol) is dissolved in conc. sulfuric acid (5.00 mL) and cooled to 0° C. Potassium nitrate (233 mg; 2.30 mmol) is added slowly and the mixture is stirred for 30 min at 0° C. The ice bath is removed and stirring is continued for 18 h. Additional potassium nitrate (100 mg; 0.989 mmol) is added and stirring continued for 1 h to get complete conversion. The reaction mixture is poured into ice water and stirred for 30 min. The aqueous phase is extracted with EtOAc. The combined organic layers are washed with brine, dried over $MgSO_4$, filtered and evaporated to give 7-methoxy-1-methyl-5-nitro-2,3-dihydro-1H-indole-2,3-dione (A-3c) (HPLC-MS: $t_{Ret.}$=0.53 min; MS $(M+H)^+$=237; method 1).

From A-3c onwards the same reaction sequence and conditions as described under B.1.1. and B.1.2. for the synthesis of IM-1a and IM-1b are used to obtain 3-hydroxy-8-methoxy-1-methyl-6-nitro-1,2-dihydroquinolin-2-one (IM-1f) (HPLC-MS: $t_{Ret.}$=0.72 min; MS $(M+H)^+$=251; method 1) and 2-[(8-methoxy-1-methyl-6-nitro-2-oxo-1,2-dihydro-quinolin-3-yl)oxy]-N-methylacetamide (IM-1g) (HPLC-MS: $t_{Ret.}$=0.45 min; MS $(M+H)^+$=322; method 1).

B.1.6. Experimental Procedure for the Synthesis of IM-1h and IM-1i

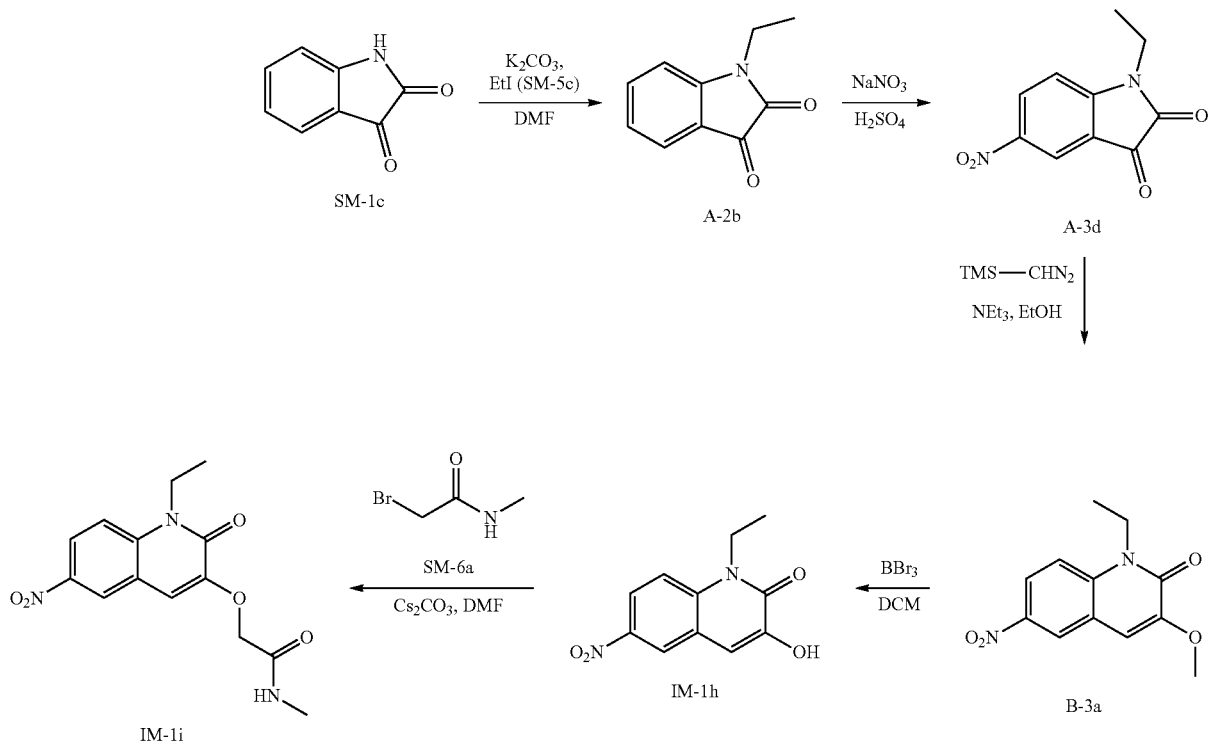

2,3-dihydro-1H-indole-2,3-dione (SM-1c) (20.0 g; 0.134 mol) is dissolved in DMF (120 mL) and cooled to 0° C. K$_2$CO$_3$ (27.8 g; 0.201 mol) is added in one portion followed by iodoethane (SM-5c) (11.8 mL; 0.148 mol) and the mixture is stirred at rt for 16 h. The reaction mixture is poured into ice water and the resulting precipitate is collected by filtration, washed with water and dried in vacuo to give 1-ethyl-2,3-dihydro-1H-indole-2,3-dione (A-2b) (HPLC-MS: t$_{Ret.}$=1.09 min; MS (M−H)$^-$=176; method E).

A-2b is dissolved in sulphuric acid (150 mL) and cooled to 0° C. Sodium nitrate (6.96 g; 0.08 mol) is added in small portions and the reaction mixture is stirred at 0° C. for 1 h. The mixture is poured into ice water and the resulting precipitation is collected by filtration, washed twice with water and dried in vacuo to give 1-ethyl-5-nitro-2,3-dihydro-1H-indole-2,3-dione (A-3d) (HPLC-MS: t$_{Ret.}$=1.09 min; MS (M+H)$^+$=223; method E).

To a stirred solution of A-3d (7.00 g; 0.03 mol) in EtOH (150 mL) is added triethylamine (9.17 mL; 63.6 mmol) followed by (trimethylsilyl)diazomethane solution (106 mL; 63.6 mmol; 0.6 M in hexane) at rt. The reaction mixture is stirred at rt for 3 h. The reaction is quenched with water and extracted with EtOAc. The combined organic layer is washed with brine, dried over Na$_2$SO$_4$ and concentrated in vacuo to give 1-ethyl-3-methoxy-6-nitro-1,2-dihydroquinolin-2-one (B-3a) (HPLC-MS: t$_{Ret.}$=1.19 min; MS (M+H)$^+$=249; method E).

B-3a (4.00 g; 16.1 mmol) is dissolved in DCM (20.0 mL) and cooled to 0° C. Borontribromide (4.65 mL; 48.3 mmol; 1 M in DCM) is slowly added, the ice bath is removed and the reaction mixture is allowed to warm to rt and stirring is continued for additional 2 h. The reaction is quenched with sat. NaHCO$_3$ solution and extracted with EtOAc. The combined organic layer is dried over Na$_2$SO$_4$ and concentrated in vacuo. The crude product is triturated with Et$_2$O to give pure 1-ethyl-3-hydroxy-6-nitro-1,2-dihydroquinolin-2-one (IM-1h) (HPLC-MS: t$_{Ret.}$=1.19 min; MS (M−H)$^-$=233; method D).

From IM-1h onwards the same reaction sequence and conditions as described under B.1.2. for the synthesis IM-1b are used to obtain 2-[(1-ethyl-6-nitro-2-oxo-1,2-dihydroquinolin-3-yl)oxy]-N-methylacetamide (IM-1i) (HPLC-MS: t$_{Ret.}$=1.12 min; MS (M+H)$^+$=306; method E).

B.1.7. Experimental Procedure for the Synthesis of IM-1j and IM-1k

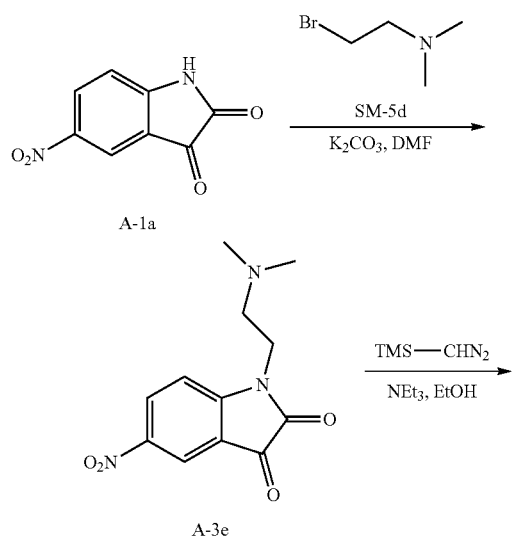

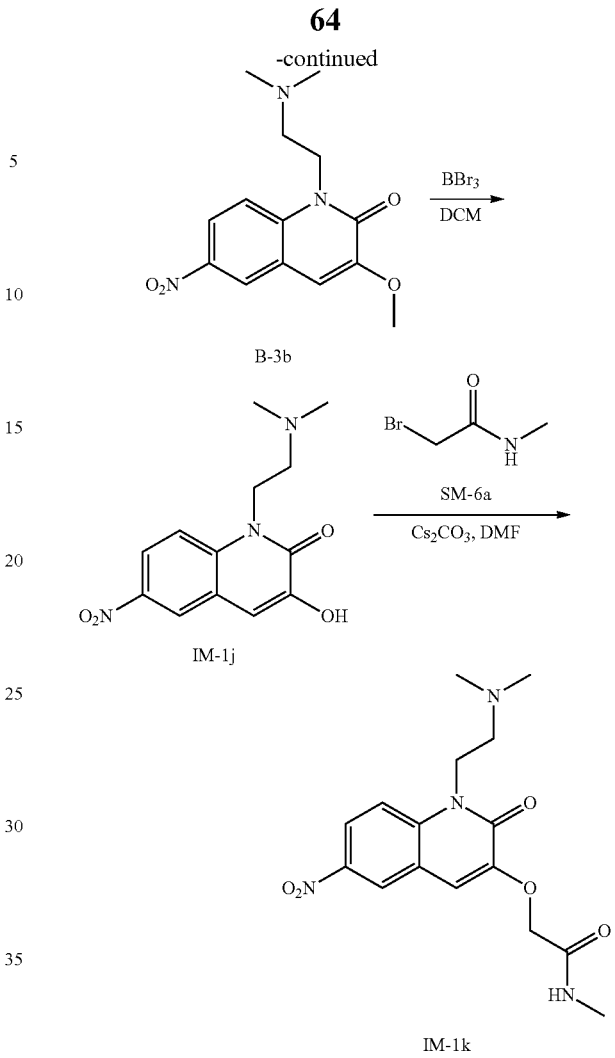

A-1a (500 mg; 2.60 mmol) is dissolved in DMF (5.00 mL) and potassium carbonate (1.26 g; 9.11 mmol) is added in one portion. The reaction mixture is stirred at rt for 30 min. (2-bromoethyl)dimethylamine hydrobromide (SM-5d) (788 mg; 3.38 mmol) is added and stirring is continued for 4 h. Water is added and stirring is continued for 18 h. The volatiles are evaporated and the residue is dried in vacuo. The crude mass is triturated with a mixture of EtOH and MeOH (1:1), filtered and washed with EtOH. The filtrate is evaporated and purified by preparative HPLC under basic conditions to give 1-[2-(dimethylamino)ethyl]-5-nitro-2,3-dihydro-1H-indole-2,3-dione (A-3e).

To a stirred solution of A-3e (325 mg; 1.24 mmol) in EtOH (6.50 mL) is added trimethylamine (684 μL; 4.94 mmol) followed by (trimethylsilyl)diazomethane solution (2.45 mL; 4.94 mmol; 2.0 M in hexane) at rt and stirring is continued for 3 h. The reaction mixture is quenched with water and the material is adsorbed to silica gel and purified by NP MPLC (Companion; 40 g SiO$_2$, DCM/MeOH=100:0 to 90:10, 25 min) to give 1-[2-(dimethylamino)ethyl]-3-methoxy-6-nitro-1,2-dihydroquinolin-2-one (B-3b).

B-3b (228 mg; 783 μmol) is dissolved in DCM (20.0 mL) with stirring at rt. Borontribromide (1.57 mL; 1.57 mmol; 1 M in DCM) is slowly added and stirring is continued for 1.5 h. The reaction is quenched with water and the volatiles are evaporated. Water is added and the mixture is stirred until a precipitation occurs. The solid is collected by filtration and dried in vacuo to give 1-[2-(dimethylamino)ethyl]-3-hydroxy-6-nitro-1,2-dihydroquinolin-2-one (IM-1j) (HPLC-MS: $t_{Ret.}$=0.68 min; MS (M–H)$^-$=278; method 1). More material can be obtained from the filtrate by RP-HPLC using a MeCN/H$_2$O gradient from 5:95 to 98:2 in 10 min.

From IM-1j onwards the same reaction sequence and conditions as described under B.1.2. for the synthesis IM-1b are used to obtain 2-({1-[2-(dimethylamino)ethyl]-6-nitro-2-oxo-1,2-dihydroquinolin-3-yl}oxy)-N-methylacetamide (IM-1k) (HPLC-MS: $t_{Ret.}$=1.24 min; MS (M+H)$^+$=349; method 1).

B.1.8. Experimental Procedure for the Synthesis of IM-1l, IM-1m and IM-1n

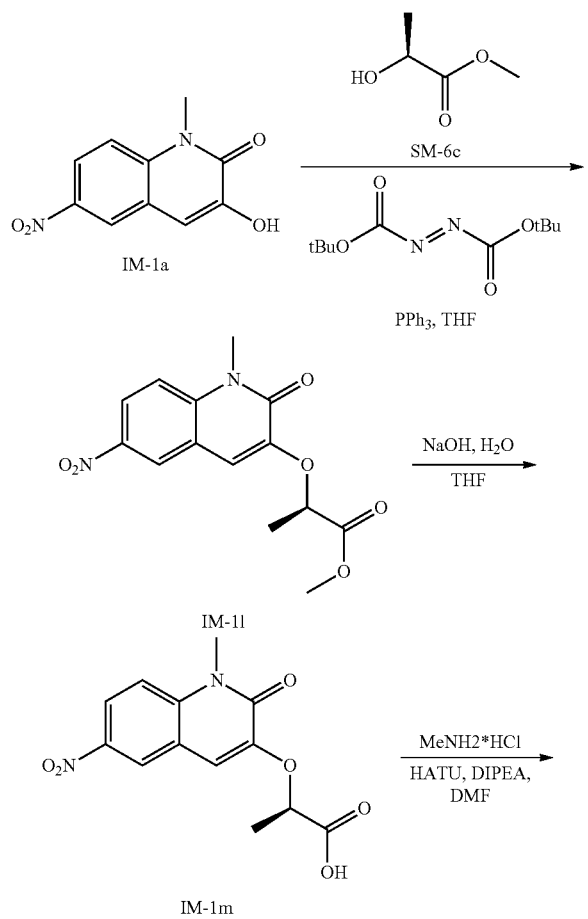

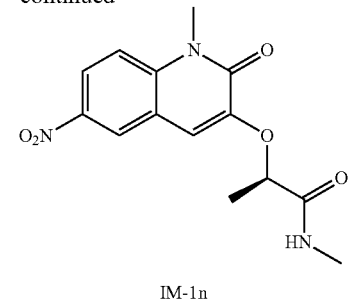

IM-1n

To a solution of methyl (2S)-2-hydroxypropanoate (SM-6c) (141 mg; 1.36 mmol), SM-1a (200 mg; 0.91 mmol) and triphenylphosphine (376 mg; 1.36 mmol) in THF (3.0 mL) at 0° C. is added dropwise di-tert-butyl azodicarboxylate (DTAD) (293 mg; 1.27 mmol, dissolved in 3.0 mL THF) with stirring. The ice bath is removed and stirring is continued for 2 h. For completion another equivalent of SM-2c, PPh$_3$ and DTAD is added and stirring is continued for 18 h. The reaction mixture is evaporated and the residue is taken up in MeCN/H$_2$O/DMF and purified by preparative RP-HPLC under acidic conditions using a MeCN/H$_2$O gradient from 25:75 to 70:30 in 8 min as eluent (column: Sunfire Prep C18; 30×50 mm; 5 μm; flow: 50 mL/min) to yield methyl (2R)-2-[(1-methyl-6-nitro-2-oxo-1,2-dihydroquinolin-3-yl)oxy]propanoate (IM-1l) (HPLC-MS: $t_{Ret.}$=0.52 min; MS (M+H)$^+$=307, method A).

To IM-1l (275 mg; 0.90 mmol) in THF (10.0 mL) is added NaOH (4.50 mL; 4.50 mmol; 1 M solution in H$_2$O). The reaction mixture is stirred at rt for 1h. Water is added and the mixture is extracted with DCM. The aqueous phase is acidified with 1 N HCl$_{aq.}$ and extracted with DCM. The combined organic layer is dried over MgSO$_4$, filtered and evaporated to give (2R)-2-[(1-methyl-6-nitro-2-oxo-1,2-dihydroquinolin-3-yl)oxy]propanoic acid (IM-1m) (HPLC-MS: $t_{Ret.}$=0.27 min; MS (M+H)$^+$=293, method 1).

To IM-1m (160 mg; 0.55 mmol) in DMF (5.0 mL) is added DIPEA (372 μL; 2.19 mmol) and HATU (312 mg; 821 mmol) and the mixture is stirred for 5 min at rt. Methylamine hydrochloride (55.4 mg; 0.82 mmol) is added and stirring is continued for 18 h. The reaction mixture is diluted with H$_2$O/MeCN and purified by preparative RP-HPLC under acidic conditions using a MeCN/H$_2$O gradient from 10:90 to 98:2 in 8 min as eluent (column: YMC Triart C18; 30×50 mm; 5 μm; flow: 50 mL/min) to yield (2R)—N-methyl-2-[(1-methyl-6-nitro-2-oxo-1,2-dihydroquinolin-3-yl)oxy]propanamide (IM-1n) (HPLC-MS: $t_{Ret.}$=0.41 min; MS (M+H)$^+$=306, method A).

B.1.9. Experimental Procedure for the Synthesis of IM-1o and IM-1p

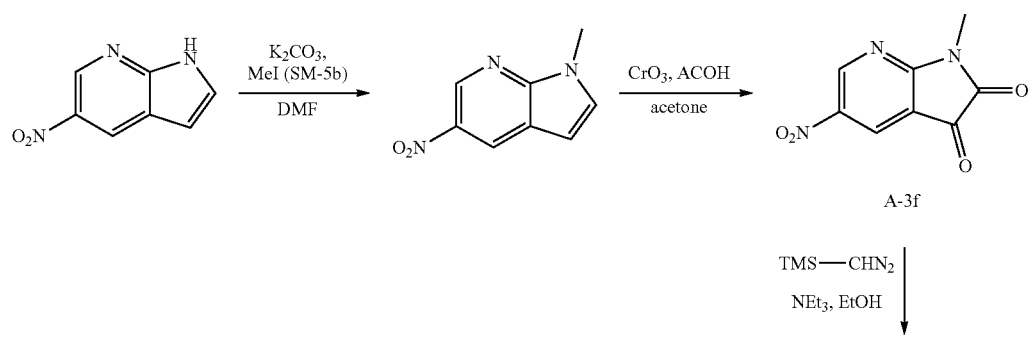

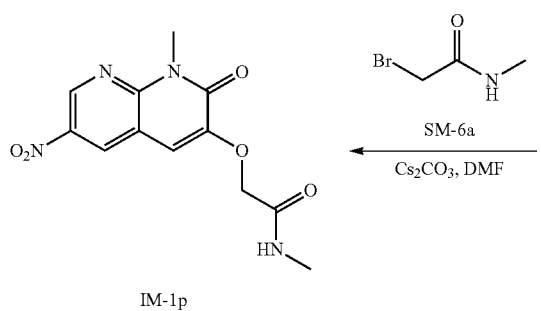
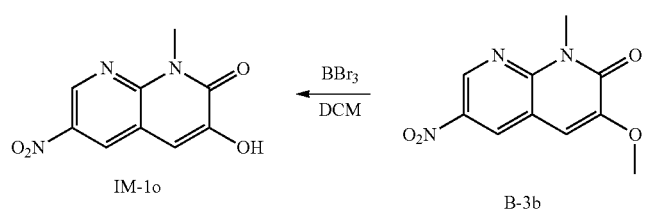

5-nitro-1H-pyrrolo[2,3-b]pyridine (960 mg; 5.89 mmol) and K₂CO₃ (1.22 g; 8.83 mmol) are dissolved in DMF (20 mL) and stirred for 30 min at rt. Iodomethane (SM-5b) (554 µL; 8.83 mmol) is added dropwise and stirring is continued at rt for 18 h. The reaction mixture is poured onto ice water, the resulting precipitate is collected by filtration and dried in vacuo to give 1-methyl-5-nitro-1H-pyrrolo[2,3-b]pyridine (HPLC-MS: $t_{Ret.}$=0.98 min; MS (M+H)⁺=178; method 1).

To 1-methyl-5-nitro-1H-pyrrolo[2,3-b]pyridine (470 mg; 2.65 mmol) in acetone (3.0 mL), AcOH (15.0 mL) and water (4.6 mL) is slowly added CrO₃ (3.45 g; 34.5 mmol) at rt. The reaction mixture is stirred for 30 min. Water and DCM are added and the layers are separated. The aqueous layer is extracted with DCM. The combined organic layer is washed with brine, dried over MgSO₄, filtered and evaporated to give crude 1-methyl-5-nitro-1H,2H,3H-pyrrolo[2,3-b]pyridine-2,3-dione (A-3f) (HPLC-MS: $t_{Ret.}$=0.20 min; MS (M+H+H₂O)+=226; method A) as a hydrate.

From A-3f onwards the same reaction sequence and conditions as described under B.1.6. for the synthesis of IM-1i and B.1.2. for the synthesis of IM-1b are used to obtain 3-hydroxy-1-methyl-6-nitro-1,2-dihydro-1,8-naphthyridin-2-one (IM-1o) (HPLC-MS: $t_{Ret.}$=0.34 min; MS (M+H)⁺=222; method 1) and N-methyl-2-[(1-methyl-6-nitro-2-oxo-1,2-dihydro-1,8-naphthyridin-3-yl)oxy]acetamide (IM-1p) (HPLC-MS: $t_{Ret.}$=0.79 min; MS (M+H)⁺=293; method 1).

B.2. Synthesis of IM-1 from Quinolinones SM-2

B.2.1. Experimental Procedure for the Synthesis of IM-1q

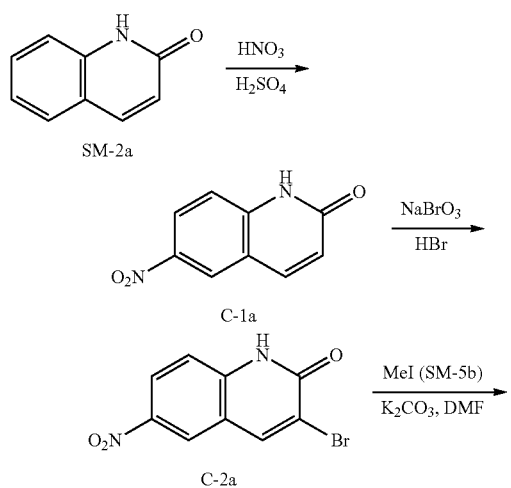

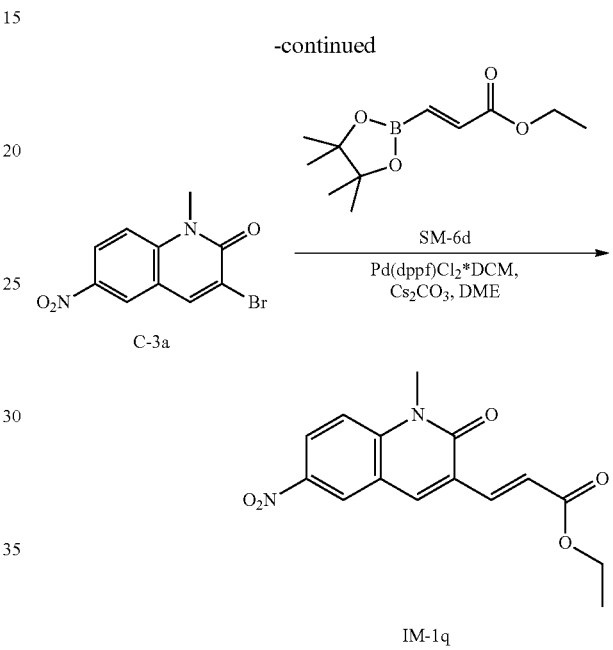

To a cooled (EtOH/ice) solution of 1,2-dihydroquinolin-2-one (SM-2a) (500 mg; 3.45 mmol) in H₂SO₄ (2.50 mL; 45.0 mmol; 96%) is added HNO₃ (0.25 mL; 3.59 mmol) dropwise and stirring is continued for 30 min. The reaction mixture is poured into ice water, the resulting precipitate is filtered, washed with water and dried in vacuo to give 6-nitro-1,2-dihydroquinolin-2-one (C-1a) (HPLC-MS: $t_{Ret.}$=0.50 min; MS (M+H)⁺=191; method 1).

To C-1a (400 mg; 2.10 mmol) and sodium bromate (380 mg; 2.52 mmol) is added water (200 µL) and hydrobromic acid (10 mL) and the mixture is stirred for 18 h at 100° C. Another equivalent of NaBrO₃ is added and stirring is continued for 3 h at 100° C. After cooling the reaction mixture is poured into ice water, the resulting precipitate is filtered, washed with water and dried in vacuo to give 3-bromo-6-nitro-1,2-dihydroquinolin-2-one (C-2a) (HPLC-MS: $t_{Ret.}$=0.76 min; MS (M+H)⁺=269/271 (Br); method 1).

To C-1a (550 mg; 2.04 mmol) in DMF (5.0 mL) is added K₂CO₃ (424 mg; 3.07 mmol) and iodomethane (SM-5b) (0.20 mL; 3.15 mmol) and the resulting mixture is stirred at rt for 2 h. The reaction mixture is poured into water, the resulting precipitate is collected by filtration, washed with water and dried in vacuo to give 3-bromo-1-methyl-6-nitro-1,2-dihydroquinolin-2-one (C-3a) (HPLC-MS: $t_{Ret.}$=0.94 min; MS (M+H)⁺=283/285 (Br); method 1).

C-3a (400 mg; 1.41 mmol) and Cs$_2$CO$_3$ (1.41 g; 4.24 mmol) are suspended in DME (7.5 mL) and water (2.5 mL). Argon is purged through the mixture and ethyl (2E)-3-(4,4,5,5-tetramethyl-1,3,2-dioxaborolan-2-yl)prop-2-enoate (SM-6d) (383 mg; 1.70 mmol) and Pd(dppf)C$_2$.DCM (118 mg; 0.14 mmol) are added, the vial is sealed and heated to 100° C. under microwave irradiation for 30 min. After cooling to rt EtOAc and water are added and the layers are separated. The aqueous layer is extracted with EtOAc. The combined organic layer is washed with water and brine, dried over MgSO$_4$, filtered and evaporated. The residue is triturated with MeOH, the solid is collected by filtration and dried in vacuo to give ethyl (2E)-3-(1-methyl-6-nitro-2-oxo-1,2-dihydroquinolin-3-yl)prop-2-enoate (IM-1q) (HPLC-MS: t$_{Ret.}$=1.14 min; MS (M+H)$^+$=303; method 1).

B.2.2. Experimental Procedure for the Synthesis of IM-1r

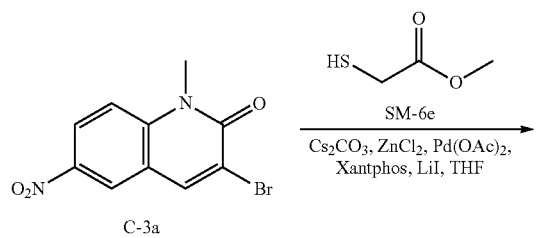

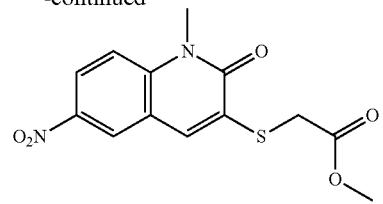

IM-1r

Cs$_2$CO$_3$ (2.07 g; 6.36 mmol) and methyl thioglycolate (SM-6e) (598 μL; 6.36 mmol) are suspended in THF (5.0 mL) and stirred for 10 min at rt. ZnCl$_2$ (1.11 g; 1.11 mmol) is added and stirring is continued for 10 min (solution 1). In a separate flask, Pd(OAc)$_2$ (35.7 mg; 0.16 mmol) and xantphos (187 mg; 0.32 mmol) are dissolved in THF (5.0 mL) and the solution is flushed with argon for 20 min with stirring (solution 2). LiI (106 mg; 0.80 mmol) and C-3a (450 mg; 1.59 mmol) are added to solution 1 followed by the addition of solution 2. The reaction mixture is stirred under an inert atmosphere (argon) for 12 h at 60° C. After cooling to rt the reaction mixture is poured into water, the resulting precipitate is collected by filtration, washed with water and dried in vacuo to give methyl 2-[(1-methyl-6-nitro-2-oxo-1,2-dihydroquinolin-3-yl)sulfanyl]acetate (IM-1r) (HPLC-MS: t$_{Ret.}$=1.04 min; MS (M+H)$^+$=309; method 1) along with ca. 70% unreacted C-3a which can't be separated at this stage.

Analogously to the procedures described under B.1.1. to B.1.9. and B2.1. to B.2.2. additional 6-nitro-quinolinones IM-1 can be prepared using different isatin or quinolinone starting materials SM-1, SM-2, A-1, A-2 and A-3 as well as different reagents SM-5 and SM-6.

TABLE 1

| # | structure | starting material | alkylating reagent (R4 or R5) | procedures | t$_{Ret.}$ HPLC [min] | MS (M + H)$^+$ |
|---|---|---|---|---|---|---|
| IM-1a | 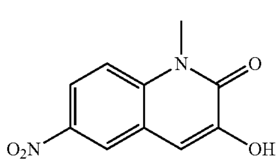 | A-1a | Me$_2$SO$_4$ (SM-5a) | B.1.1. | 0.37 (method 1) | 221 |
| IM-1b | 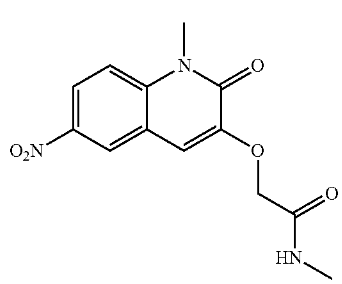 [SMILES: CNC(=O)COc1cc2cc([N+](=O)[O-])ccc2n(C)c1=O] | A-1a/IM-1a | SM-6a | B.1.2. | 0.74 (method 1) | 292 |

TABLE 1-continued

Synthesized 6-nitro-quinolinones IM-1

| # | structure | starting material | alkylating reagent (R4 or R5) | procedures | $t_{Ret.}$ HPLC [min] | MS $(M + H)^+$ |
|---|---|---|---|---|---|---|
| IM-1c | 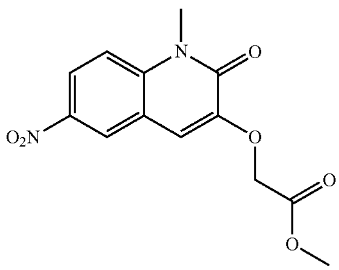 [SMILES: COC(=O)COc1cc2cc([N+](=O)[O-])ccc2n(C)c1=O] | A-1a/IM-1a | SM-6b | B.1.3. | 1.04 (method E) | 293 |
| IM-1d | 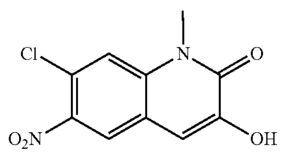 [SMILES: Cn1c(=O)c(O)cc2cc([N+](=O)[O-])c(Cl)cc21] | SM-5a | SM-1a | B.1.4. | 2.20 (method C) | 255 |
| IM-1e | 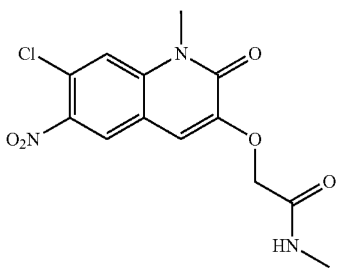 [SMILES: CNC(=O)COc1cc2cc([N+](=O)[O-])c(Cl)cc2n(C)c1=O] | SM-1a/IM-1d | SM-6a | B.1.4. | 1.35 (method K) | 326 |
| IM-1f | 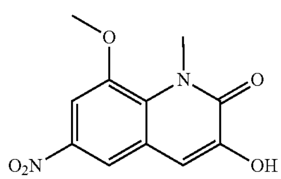 | MeI (SM-5b) | SM-1b | B.1.5. | 0.72 (method 1) | 251 |
| IM-1g | 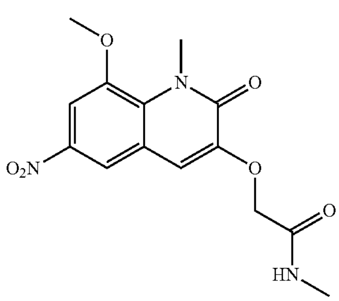 [SMILES: CNC(=O)COc1cc2cc([N+](=O)[O-])cc(OC)c2n(C)c1=O] | SM-1b/IM-1f | SM-6a | B.1.5. | 0.45 (method 1) | 322 |
| IM-1h | 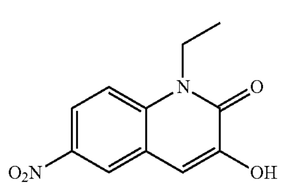 [SMILES: CCn1c(=O)c(O)cc2cc([N+](=O)[O-])ccc21] | EtI (SM-5c) | SM-1c | B.1.6. | 1.19 (method D) | 233 |

TABLE 1-continued

Synthesized 6-nitro-quinolinones IM-1

| # | structure | starting material | alkylating reagent (R4 or R5) | procedures | $t_{Ret.}$ HPLC [min] | MS $(M + H)^+$ |
|---|---|---|---|---|---|---|
| IM-1i | 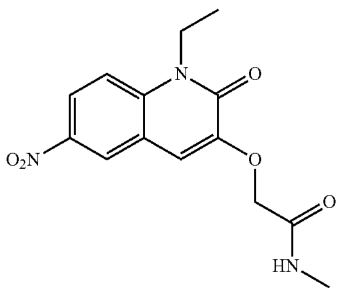 [SMILES: CCn1c(=O)c(OCC(=O)NC)cc2cc([N+](=O)[O-])ccc21] | SM-1c/IM-1h | SM-6a | B.1.6. | 1.12 (method E) | 306 |
| IM-1j | 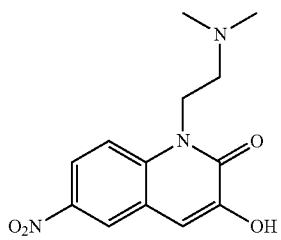 [SMILES: CN(C)CCn1c(=O)c(O)cc2cc([N+](=O)[O-])ccc21] | A-1a | SM-5d | B.1.7. | 0.68 (method 1) | 278 $(M - H)^-$ |
| IM-1k | 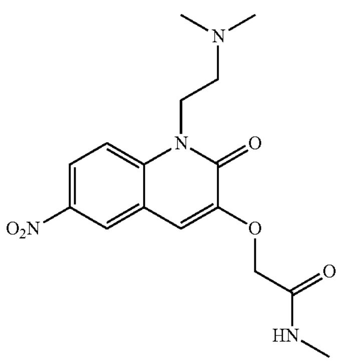 [SMILES: CNC(=O)COc1cc2cc([N+](=O)[O-])ccc2n(CCN(C)C)c1=O] | A-1a/IM-1j | SM-6a | B.1.7. | 1.24 (method 1) | 349 |
| IM-1l | 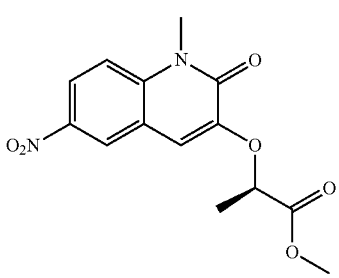 [SMILES: COC(=O)[C@@H](C)Oc1cc2cc([N+](=O)[O-])ccc2n(C)c1=O] | IM-1a | SM-6c | B.1.8. | 0.52 (method A) | 307 |
| IM-1m | 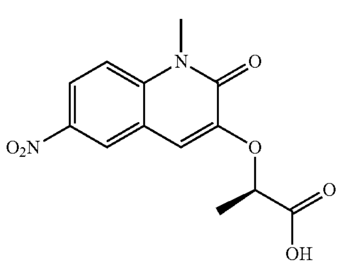 [SMILES: C[C@@H](Oc1cc2cc([N+](=O)[O-])ccc2n(C)c1=O)C(=O)O] | IM-1l | — | B.1.8. | 0.27 (method 1) | 293 |

TABLE 1-continued

Synthesized 6-nitro-quinolinones IM-1

| # | structure | starting material | alkylating reagent (R4 or R5) | procedures | $t_{Ret.}$ HPLC [min] | MS $(M + H)^+$ |
|---|---|---|---|---|---|---|
| IM-1n | 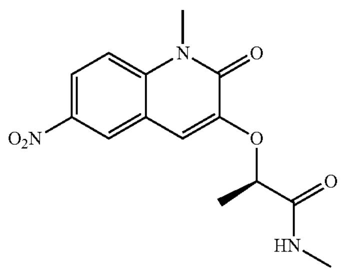 [SMILES: CNC(=O)[C@@H](C)Oc1cc2cc([N+](=O)[O-])ccc2n(C)c1=O] | IM-1m | — | B.1.8. | 0.41 (method A) | 306 |
| IM-1o | 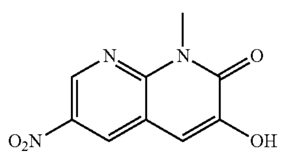 [SMILES: Cn1c(=O)c(O)cc2cc([N+](=O)[O-])cnc21] | | SM-5b | B.1.9. | 0.34 (method 1) | 222 |
| IM-1p | 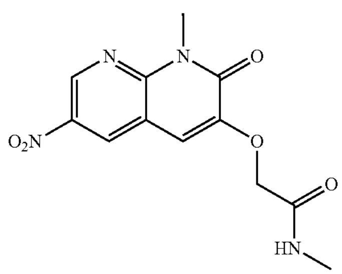 [SMILES: CNC(=O)COc1cc2cc([N+](=O)[O-])cnc2n(C)c1=O] | IM-1o | SM-6a | B.1.9. | 0.79 (method 1) | 293 |
| IM-1q | 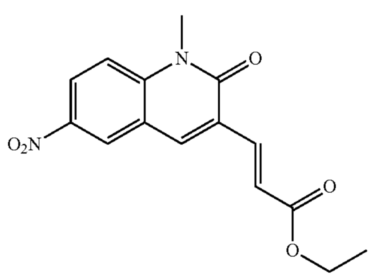 [SMILES: CCOC(=O)/C=C/c1cc2cc([N+](=O)[O-])ccc2n(C)c1=O] | SM-2a | SM-5b | B.2.1. | 1.14 (method 1) | 303 |
| IM-1r | 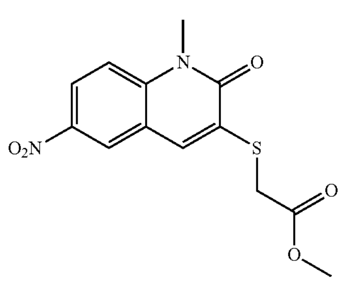 [SMILES: COC(=O)CSc1cc2cc([N+](=O)[O-])ccc2n(C)c1=O] | SM-2a | SM-5b | B.2.2. | 1.04 (method 1) | 309 |
| IM-1s | 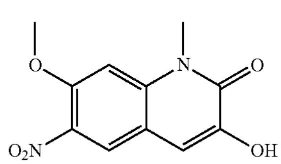 | | SM-5a | B.1.4. | 1.29 (method K) | 251 |

TABLE 1-continued

Synthesized 6-nitro-quinolinones IM-1

| # | structure | starting material | alkylating reagent (R4 or R5) | procedures | t$_{Ret.}$ HPLC [min] | MS (M + H)$^+$ |
|---|---|---|---|---|---|---|
| IM-1t | 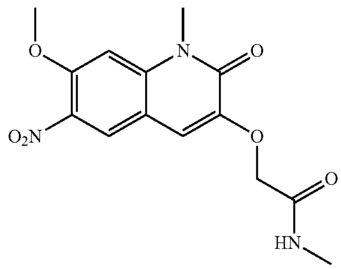 [SMILES: CNC(=O)COc1cc2cc([N+](=O)[O-])c(OC)cc2n(C)c1=O] | IM-1s | SM-6a | B.1.4. | 1.22 (method K) | 322 |
| IM-1u | 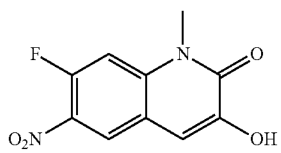 | | SM-5b | B.1.4. | 1.45 (method K) | 239 |
| IM-1v | 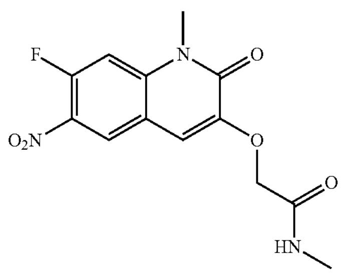 [SMILES: CNC(=O)COc1cc2cc([N+](=O)[O-])c(F)cc2n(C)c1=O] | IM-1u | SM-6a | B.1.4. | 1.24 (method K) | 310 |
| IM-1w | 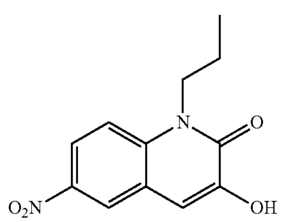 [SMILES: CCCn1c(=O)c(O)cc2cc([N+](=O)[O-])ccc21] | SM-1c | | B.1.6. | 1.30 (method E) | 249 |
| IM-1x | 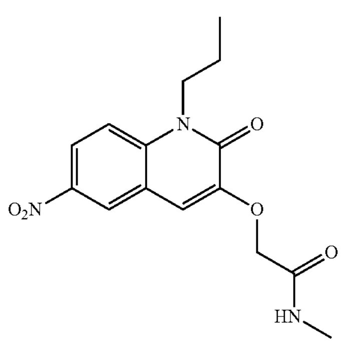 [SMILES: CCCn1c(=O)c(OCC(=O)NC)cc2cc([N+](=O)[O-])ccc21] | IM-1w | SM-6a | B.1.6. | 1.21 (method E) | 320 |
| IM-1y | 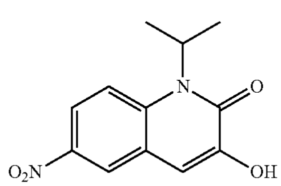 [SMILES: CC(C)n1c(=O)c(O)cc2cc([N+](=O)[O-])ccc21] | SM-1c | | B.1.6. | 1.29 (method E) | 247 (M − H)$^-$ |

TABLE 1-continued

Synthesized 6-nitro-quinolinones IM-1

| # | structure | starting material | alkylating reagent (R4 or R5) | procedures | $t_{Ret.}$ HPLC [min] | MS $(M + H)^+$ |
|---|---|---|---|---|---|---|
| IM-1z | 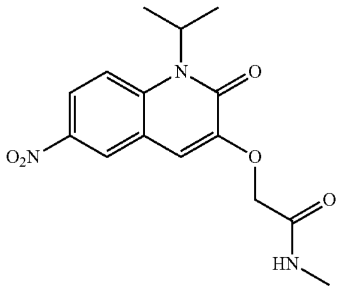 [SMILES: CNC(=O)COc1cc2cc([N+](=O)[O-])ccc2n(C(C)C)c1=O] | IM-1y | SM-6a | B.1.6. | 1.19 (method E) | 320 |
| IM-1aa | 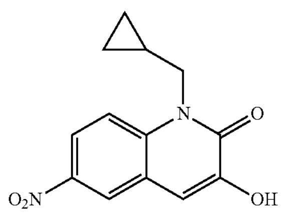 [SMILES: O=c1c(O)cc2cc([N+](=O)[O-])ccc2n1CC1CC1] | SM-1c | cyclopropylmethyl-Br | B.1.6. | 1.31 (method E) | 261 |
| IM-1ab | 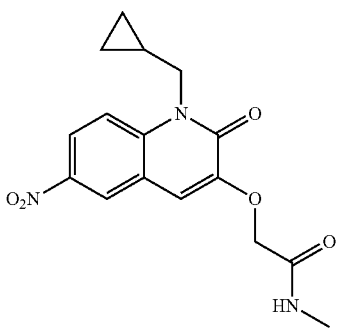 [SMILES: CNC(=O)COc1cc2cc([N+](=O)[O-])ccc2n(CC2CC2)c1=O] | IM-1aa | SM-6a | B.1.6. | 1.22 (method E) | 332 |
| IM-1ac | 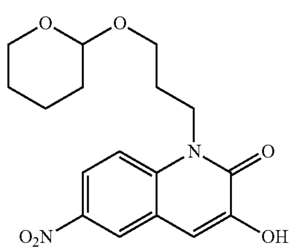 [SMILES: O=c1c(O)cc2cc([N+](=O)[O-])ccc2n1CCCOC1CCCCO1] | A-1a | THP-O-propyl-Br | B.1.7. (alkylation) B.1.1. (ring extension) | n.d. | n.d. |
| IM-1ad | 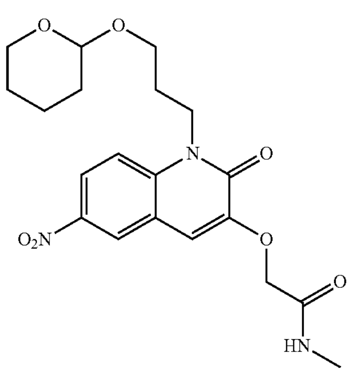 [SMILES: CNC(=O)COc1cc2cc([N+](=O)[O-])ccc2n(CCCOC2CCCCO2)c1=O] | IM-1ac | SM-6a | B.1.2. | n.d. | n.d. |

B.3. Synthesis of IM-2 from IM-1

B.3.1. Experimental Procedure for the Synthesis of IM-2a

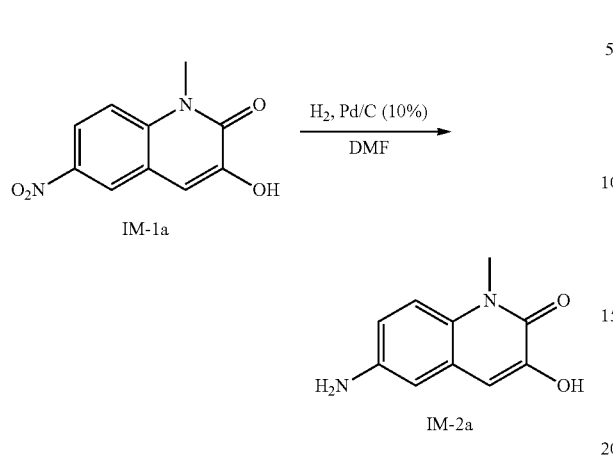

IM-1a (300 mg; 1.36 mmol) is dissolved in DMF (5.0 mL) and Pd/C (145 mg, 0.14 mmol; 10%) is added and the mixture is hydrogenated (6 bar $H_2$ pressure) at rt for 18 h. The catalyst is filtered off (celite) and the filtrate is evaporated to give 6-amino-3-hydroxy-1-methyl-1,2-dihydroquinolin-2-one (IM-2a) (HPLC-MS: $t_{Ret.}$=0.11 min; MS $(M+H)^+$=191; method L).

B.3.2. Experimental Procedure for the Synthesis of IM-2b

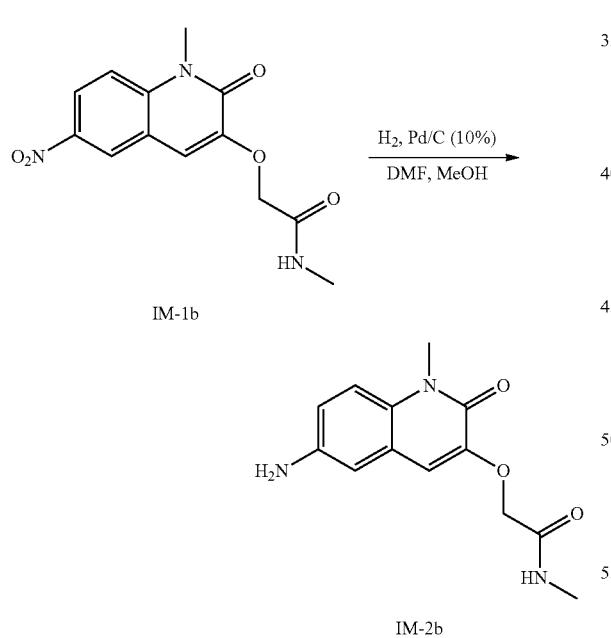

IM-1a (6.50 g; 22.3 mmol) is dissolved in DMF (60.0 mL) and MeOH (60.0 mL), Pd/C (1.50 g, 10%) is added and the mixture is hydrogenated (6.9 bar $H_2$ pressure) at 40° C. for 3 h. The catalyst is filtered off (celite) and the filtrate is evaporated to give 2-[(6-amino-1-methyl-2-oxo-1,2-dihydroquinolin-3-yl)oxy]-N-methylacetamide (IM-2b) (HPLC-MS: $t_{Ret.}$=0.26 min; MS $(M+H)^+$=262; method 1).

B.3.3. Experimental Procedure for the Synthesis of IM-2c

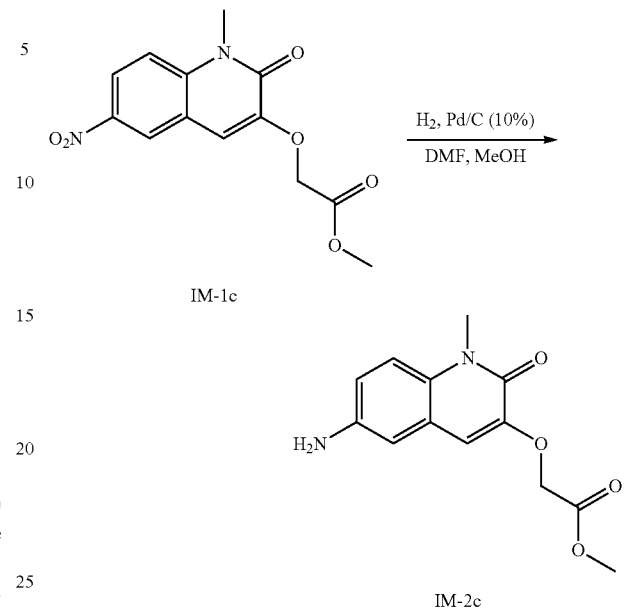

Methyl 2-[(6-amino-1-methyl-2-oxo-1,2-dihydroquinolin-3-yl)oxy]acetate (IM-2c) is synthesized from IM-1c (5.00 g; 17.1 mmol) using the same procedure as described for IM-2b under B.3.2.

B.3.4. Experimental Procedure for the Synthesis of IM-2d

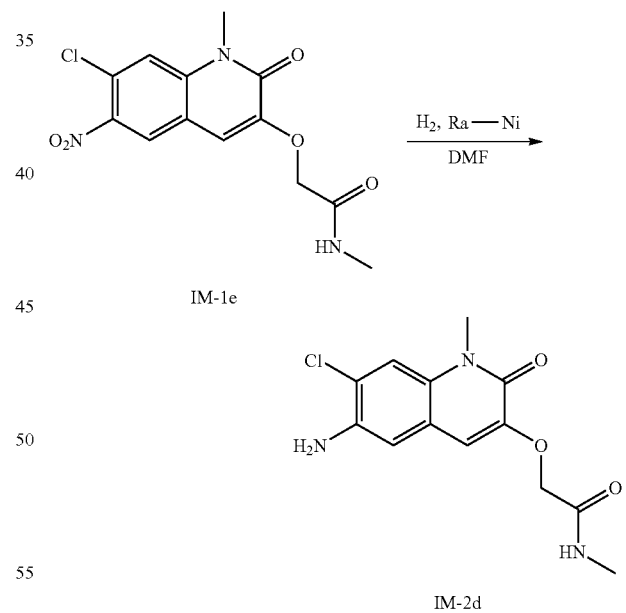

IM-1e (50.0 mg; 0.15 mmol) is dissolved in DMF (10.0 mL) and hydrogenated in a flow reactor (mode: full $H_2$; flow: 1 mL/min; H-Cube, Thales Nano) using a Ra—Ni cartridge (CatCart Holder by Thales Nano) at 40° C. The procedure is repeated until completion of the reaction. The solvents are removed under reduced pressure and the crude material of 2-[(6-amino-7-chloro-1-methyl-2-oxo-1,2-dihydroquinolin-3-yl)oxy]-N-methylacetamide (IM-2d) (HPLC-MS: $t_{Ret.}$=0.34 min; MS $(M+H)^+$=296; method A) is used without further purification.

B.3.5. Experimental Procedure for the Synthesis of IM-2e

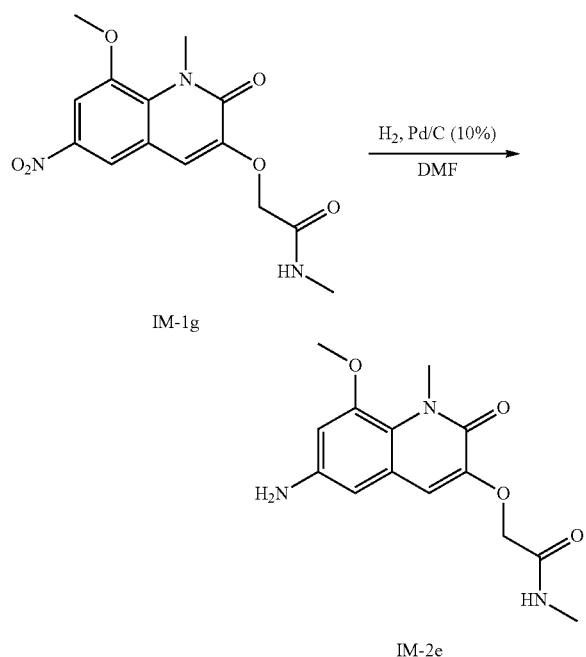

IM-1g (400 mg; 1.25 mmol) is dissolved in DMF (20.0 mL) and Pd/C (132 mg, 10%) is added and the mixture is hydrogenated (6 bar H₂ pressure) at rt for 18 h. The catalyst is filtered off (celite) and the filtrate is evaporated to give 2-[(6-amino-8-methoxy-1-methyl-2-oxo-1,2-dihydroquinolin-3-yl)oxy]-N-methylacetamide (IM-2e) (HPLC-MS: $t_{Ret.}$=0.17 min; MS (M+H)⁺=292; method A).

B.3.6. Experimental Procedure for the Synthesis of IM-2f and IM-2g

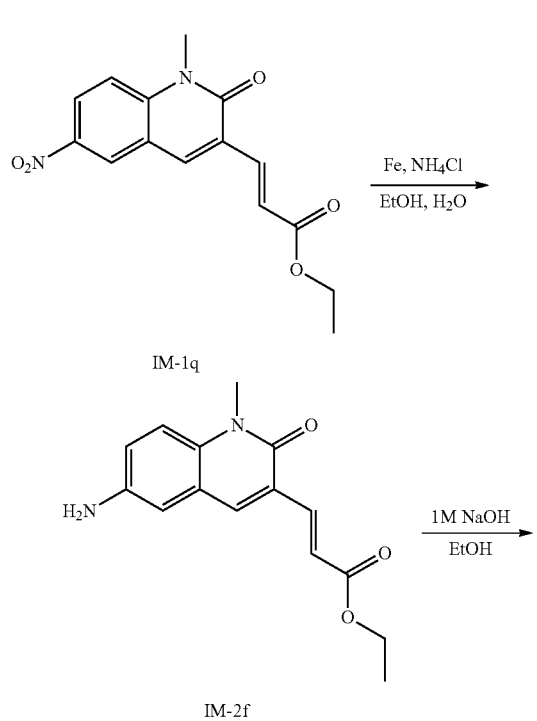

To IM-1q (250 mg; 0.83 mmol) in EtOH (20.0 mL) is added NH₄Cl (21.9 mg; 0.41 mmol) in water (5.0 mL) and the mixture is heated to 60° C. with stirring. Iron turnings (219 mg; 3.93 mmol) are added and stirring is continued at 60° C. for 1 h. After cooling to rt the mixture is filtered through celite, washed with MeOH and concentrated in vacuo. The residue is taken up in DCM and water and the layers are separated. The aqueous layer is extracted with DCM. The combined organic layer is dried over MgSO₄, filtered and evaporated to give ethyl (2E)-3-(6-amino-1-methyl-2-oxo-1,2-dihydroquinolin-3-yl)prop-2-enoate (IM-2f).

IM-2f (105 mg; 0.39 mmol) is dissolved in EtOH (3.0 mL), aqueous NaOH solution (771 μL, 1 M) is added and the resulting mixture is stirred at 50° C. for 2 h. The reaction mixture is adjusted to pH 6 with 1 N HCl$_{aq.}$ and evaporated. The residue contains ~10% by weight (quantified by QNMR) of (2E)-3-(6-amino-1-methyl-2-oxo-1,2-dihydroquinolin-3-yl)prop-2-enoic acid (IM-2g) (HPLC-MS: $t_{Ret.}$=0.0 min; MS (M+H)⁺=245; method 1) and is directly used for the next step.

B.3.7. Experimental Procedure for the Synthesis of IM-2h

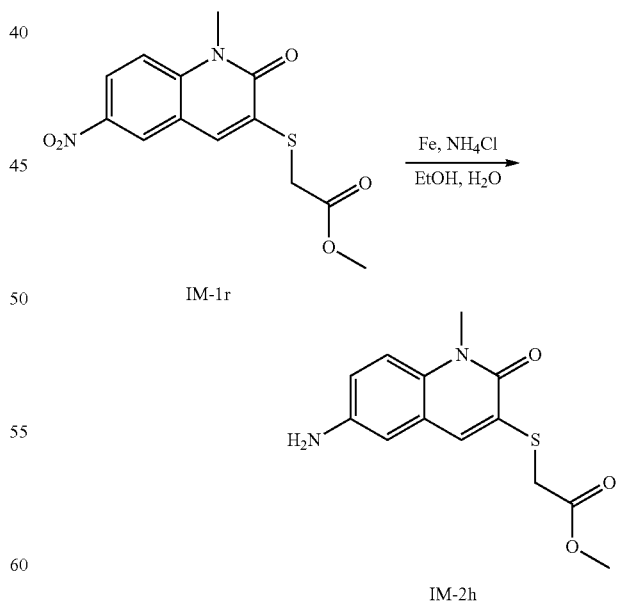

To IM-1r (340 mg; 1.10 mmol, crude material from B.2.2.) in EtOH (20.0 mL) is added NH₄Cl (29.3 mg; 0.55 mmol) in water (5.0 mL) and the mixture is heated to 60° C. with stirring. Iron turnings (292 mg; 5.24 mmol) are added and stirring is continued at 60° C. for 2 h. After cooling to rt the mixture is filtered through celite, washed with MeOH and concentrated in vacuo. The residue is taken up in DCM and water and the layers are separated. The aqueous layer is extracted with DCM. The combined organic layer is dried over MgSO$_4$, filtered and evaporated. The crude material is dissolved in DMF and purified by RP-HPLC under acidic conditions using a MeCN/H$_2$O gradient from 5:95 to 45:55 in 6 min as eluent (column: Sunfire C18; 30×50 mm; 5 μm) to give methyl 2-[(6-amino-1-methyl-2-oxo-1,2-dihydroquinolin-3-yl)sulfanyl]acetate (IM-2h).

In analogy to the procedures described under B.3.1. and B.3.7. additional 6-amino quinolinones IM-2 are prepared using 6-nitro quinolinones IM-1.

TABLE 2

Synthesized 6-amino-quinolinone derivatives IM-2

| # | structure | Procedure | $t_{Ret.}$ HPLC [min] | MS (M + H)$^+$ |
|---|---|---|---|---|
| IM-2a | 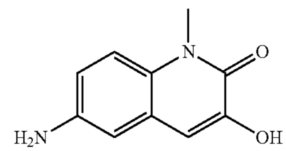 | B.3.1. | 0.11 (method L) | 191 |
| IM-2b | 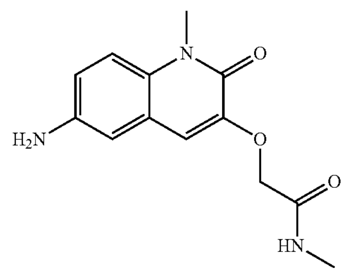 | B.3.2. | 0.26 (method 1) | 262 |
| IM-2c | 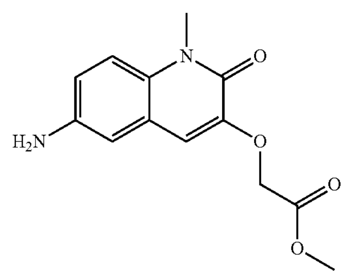 | B.3.3. | n.d. | n.d. |
| IM-2d | 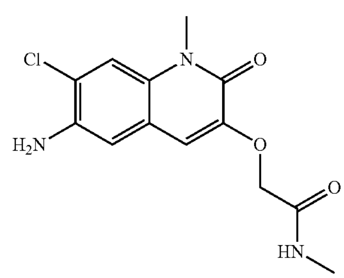 | B.3.4. | 0.34 (method A) | 296 |
| IM-2e | 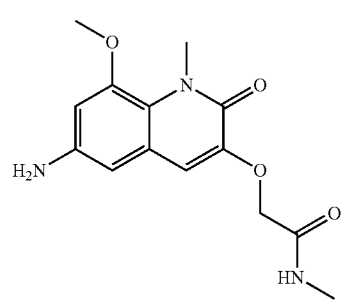 | B.3.5. | 0.17 (method A) | 292 |

TABLE 2-continued

Synthesized 6-amino-quinolinone derivatives IM-2

| # | structure | Procedure | $t_{Ret.}$ HPLC [min] | MS $(M + H)^+$ |
|---|---|---|---|---|
| IM-2f | 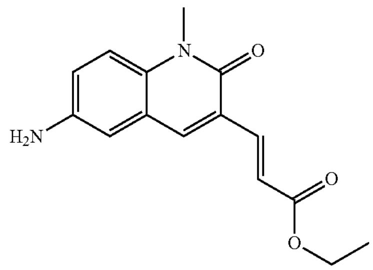 | B.3.6. | n.d. | n.d. |
| IM-2g | 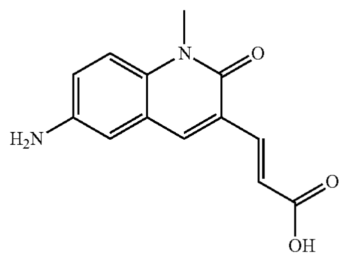 [SMILES: Cn1c(=O)c(/C=C/C(=O)O)cc2cc(N)ccc21] | B.3.6. | 0.00 (method 1) | 245 |
| IM-2h | 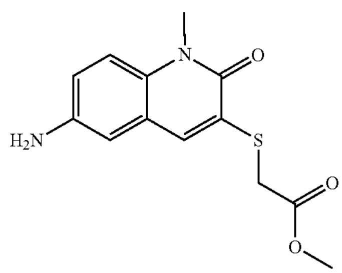 | B.3.7. | n.d. | n.d. |
| IM-2i | 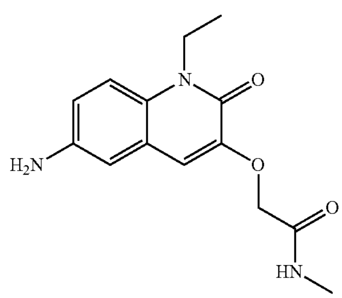 | B.3.1. | n.d. | n.d. |
| IM-2j | 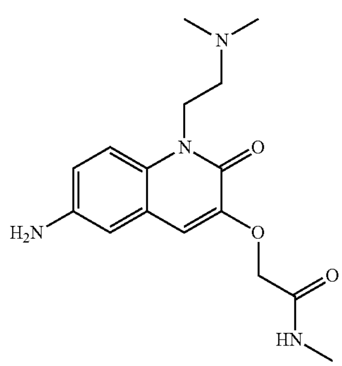 | B.3.1. | n.d. | n.d. |

TABLE 2-continued

Synthesized 6-amino-quinolinone derivatives IM-2

| # | structure | Procedure | $t_{Ret.}$ HPLC [min] | MS $(M + H)^+$ |
|---|---|---|---|---|
| IM-2k | 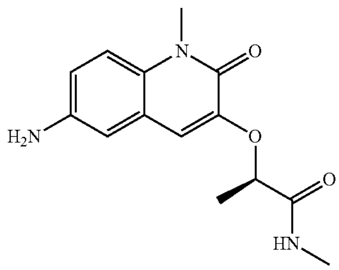 | B.3.1. | 0.10 (method A) | 276 |
| IM-2l | 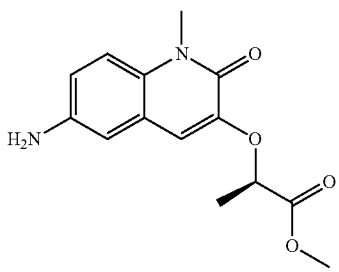 | B.3.1. | 0.64 (method 1) | 277 |
| IM-2m | 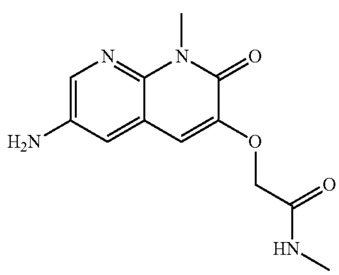 | B.3.1. | 0.14 (method A) | 263 |
| IM-2n | 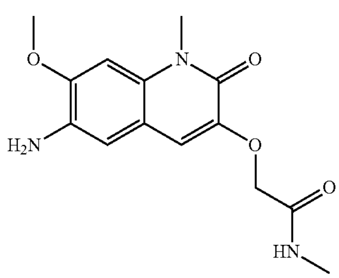 | B.3.1. | 0.14 (method A) | 292 |
| IM-2o | 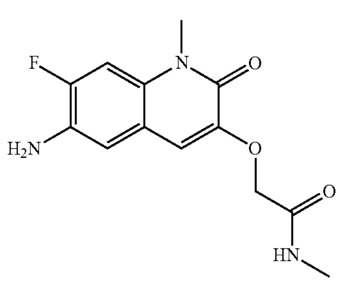 | B.3.1. | 0.18 (method A) | 280 |

TABLE 2-continued

Synthesized 6-amino-quinolinone derivatives IM-2

| # | structure | Procedure | $t_{Ret.}$ HPLC [min] | MS $(M + H)^+$ |
|---|---|---|---|---|
| IM-2p | 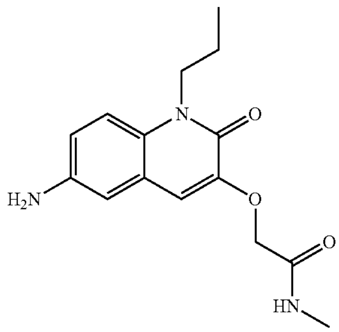 | B.3.1. | n.d. | n.d. |
| IM-2q | 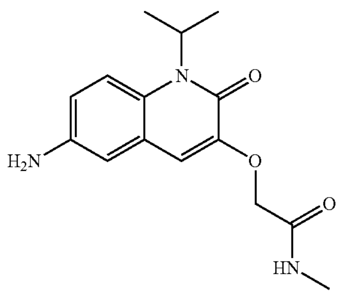 | B.3.1. | n.d. | n.d. |
| IM-2r | 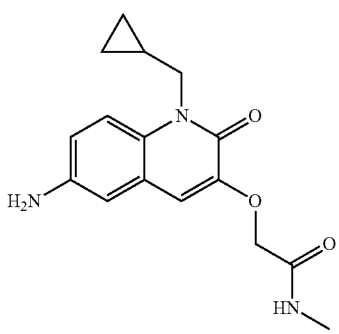 | B.3.1. | 0.24 (method A) | 302 |
| IM-2s | 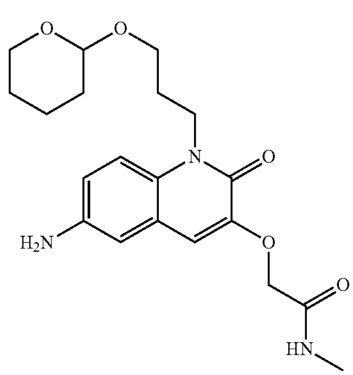 | B.3.1. | n.d. | n.d. |

B.4. Synthesis of IM-3 from SM-3

B.4.1. Experimental Procedure for the Synthesis of IM-3a

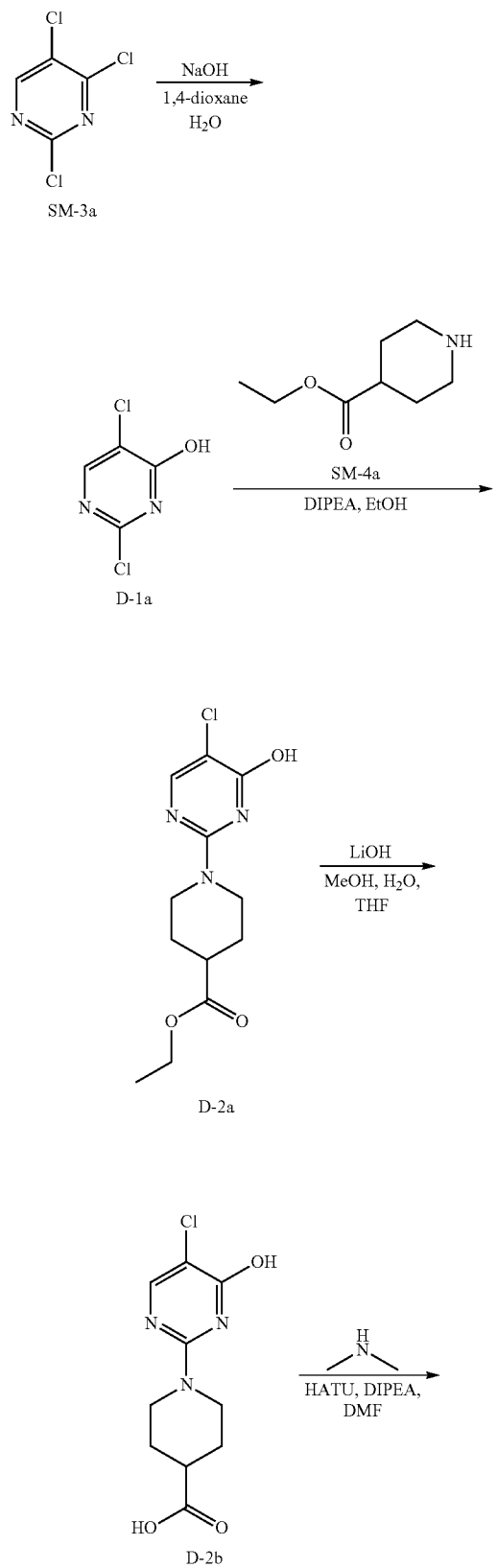

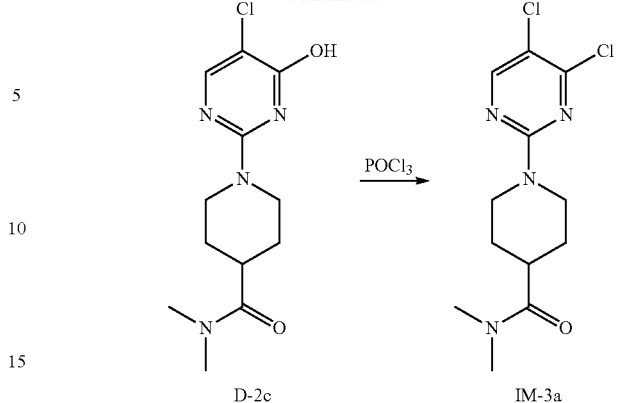

To a stirred solution of 2,4,5-trichloro-pyrimidine (SM-3a) (50.0 g; 273 mmol) in THF (160 mL) is added sodium hydroxide solution (20.0 g in 500 mL $H_2O$) and the reaction mixture is stirred at rt for 36 h. The mixture is concentrated under reduced pressure and the residue is washed twice with $Et_2O$. The aqueous layer is neutralized with 1 N $HCl_{aq.}$ and extracted with EtOAc. The combined organic layers are washed with brine, dried over $Na_2SO_4$, filtered and concentrated in vacuo to give crude 2,5-dichloropyrimidin-4-ol (D-1a) (HPLC-MS: $t_{Ret.}$=1.10 min; MS $(M+H)^+$=165; method C).

To a stirred solution of D-1a (28.0 g; 170 mmol) in EtOH (150 mL) is added ethyl 4-piperidinecarboxylate (SM-4a) (32.0 g; 204 mmol) followed by DIPEA (32.8 g; 255 mmol) and the mixture is heated and stirred at reflux for 5 h. After cooling the reaction mixture is diluted with water and extracted with $CHCl_3$. The combined organic layers are dried over $Na_2SO_4$, filtered and evaporated. The crude product is purified by flash chromatography on $SiO_2$ using EtOAc/hexane=70:30 as eluent to yield pure ethyl 1-(5-chloro-4-hydroxypyrimidin-2-yl)piperidine-4-carboxylate (D-2a) (HPLC-MS: $t_{Ret.}$=1.70 min; MS $(M+H)^+$=286; method B).

To a stirred solution of D-2a (18.0 g; 63.0 mmol) in MeOH (20.0 mL), $H_2O$ (40.0 mL) and THF (80.0 mL) is added lithium hydroxide (10.6 g; 252 mmol) and the reaction mixture is stirred at rt for 16h. The reaction mixture is diluted with water and acidified with conc. $HCl_{aq.}$. The resulting precipitate is filtered and dried in vacuo to give 1-(5-chloro-4-hydroxypyrimidin-2-yl)piperidine-4-carboxylic acid (D-2b) (HPLC-MS: $t_{Ret.}$=1.34 min; MS $(M+H)^+$=258; method B).

To a stirred solution of D-2b (8.00 g; 31.0 mmol) in DMF (20.0 mL) is added dimethylamine hydrochloride (12.6 g; 155 mmol) and HATU (17.7 g; 46.6 mmol). The reaction mixture is cooled to 0-5° C., DIPEA (13.8 mL; 77.6 mmol) is added and stirring is continued for 16 h at rt. The reaction mixture is poured into ice water and extracted with EtOAc. The crude material is purified by flash chromatography on $SiO_2$ using DCM/MeOH=95:5 as eluent to give pure 1-(5-chloro-4-hydroxypyrimidin-2-yl)-N,N-dimethylpiperidine-4-carboxamide (D-2c) (HPLC-MS: $t_{Ret.}$=1.35 min; MS $(M+H)^+$=285; method B).

A stirred solution of D-2c (5.00 g; 17.6 mmol) in POCl$_3$ (50.0 mL) is refluxed for 4 h. After cooling saturated NaHCO$_3$ solution is added slowly to the reaction mixture. At a neutral pH the aqueous phase is extracted with CHCl$_3$. The combined organic layer is dried over Na$_2$SO$_4$, filtered and evaporated. The crude material is purified by flash chromatography on SiO$_2$ using EtOAc/hexane=10:90 as eluent to give pure 1-(4,5-dichloropyrimidin-2-yl)-N,N-dimethylpiperidine-4-carboxamide (IM-3a) (HPLC-MS: t$_{Ret.}$=2.19 min; MS (M+H)+=303; method B).

B.4.2. Experimental Procedure for the Synthesis of IM-3b

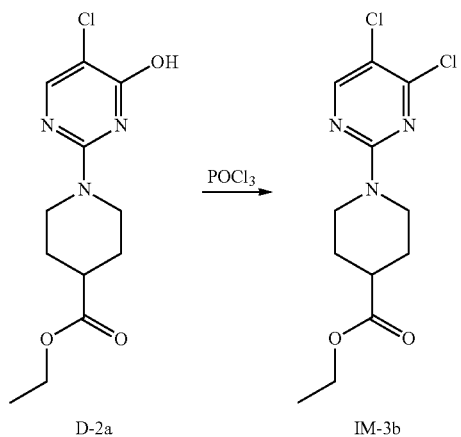

A stirred solution of D-2a (8.00 g; 28.0 mmol) in POCl$_3$ (80.000 mL) is refluxed for 4 h. After cooling saturated NaHCO$_3$ solution is added slowly to the reaction mixture. At a neutral pH the aqueous phase is extracted with CHCl$_3$. The combined organic layer is dried over Na$_2$SO$_4$, filtered and evaporated. The crude material is purified by flash chromatography on SiO$_2$ using EtOAc/hexane=10:90 as eluent to give pure ethyl 1-(4,5-dichloropyrimidin-2-yl)piperidine-4-carboxylate (IM-3b) (HPLC-MS: t$_{Ret.}$=1.46 min; MS (M+H)$^+$=304; method G).

B.4.3. Experimental Procedure for the Synthesis of IM-3c

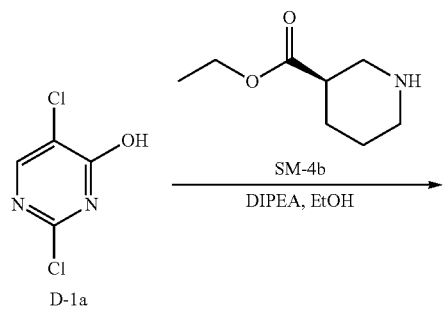

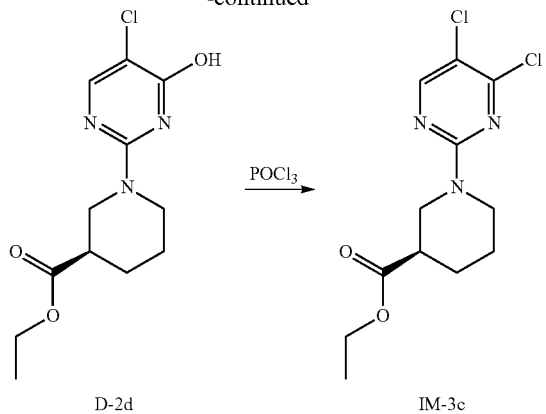

Starting from D-1a (10.0 g; 60.6 mmol) the same experimental conditions as described for the synthesis of IM-3a under B.4.1. are used to synthesize ethyl (3R)-1-(5-chloro-4-hydroxypyrimidin-2-yl)piperidine-3-carboxylate (IM-3c) (HPLC-MS: t$_{Ret.}$=1.46 min; MS (M+H)$^+$=304; method 1) via ethyl (3R)-1-(5-chloro-4-hydroxypyrimidin-2-yl)piperidine-3-carboxylate (D-2d).

B.4.4. Experimental Procedure for the Synthesis of IM-3d

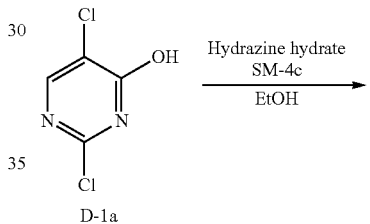

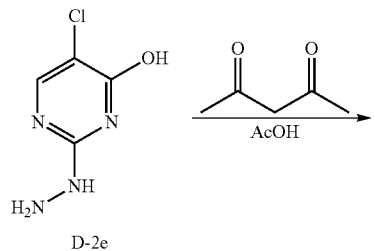

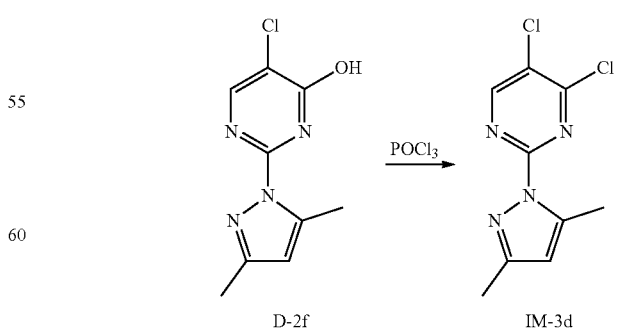

To a stirred solution of D-1a (55.0 g; 333 mmol) in EtOH (1.00 L) is added hydrazine hydrate (SM-4c) (33.3 g; 667 mmol) at rt. The reaction mixture is heated under reflux for 15 h. After cooling to rt the volatiles are evaporated and the crude product is triturated with hexane to give pure 5-chloro-2-hydrazinylpyrimidin-4-ol (D-2e) (HPLC-MS: $t_{Ret.}$=0.81 min; MS (M+H)$^+$=161; method H).

To a stirred solution of D-2e (50.0 g; 311 mmol) in AcOH (500 mL) is added acetyl acetone (37.4 g; 374 mmol) at rt and the reaction mixture is heated to 90° C. for 4 h. After cooling to rt the volatiles evaporated and the residue is taken up in EtOAc, washed with water and brine, dried over Na$_2$SO$_4$ and evaporated to give 5-chloro-2-(3,5-dimethyl-1H-pyrazol-1-yl)pyrimidin-4-ol (D-2f) (HPLC-MS: $t_{Ret.}$=1.77 min; MS (M+H)$^+$=225; method F).

A stirred solution of D-2f (40.0 g; 134 mmol) in POCl$_3$ (400 mL) is refluxed for 4 h. After cooling to rt saturated NaHCO$_3$ solution is added slowly to the reaction mixture. At a neutral pH the aqueous phase is extracted with EtOAc. The combined organic layer is washed with water and brine, dried over Na$_2$SO$_4$, filtered, evaporated and the crude material is purified by flash chromatography on SiO$_2$ using EtOAc/hexane=30:70 as eluent to yield pure 4,5-dichloro-2-(3,5-dimethyl-1H-pyrazol-1-yl)pyrimidine (IM-3d) (HPLC-MS: $t_{Ret.}$=1.11 min; MS (M+H)$^+$=243; method 1).

B.4.5. Experimental Procedure for the Synthesis of IM-3e

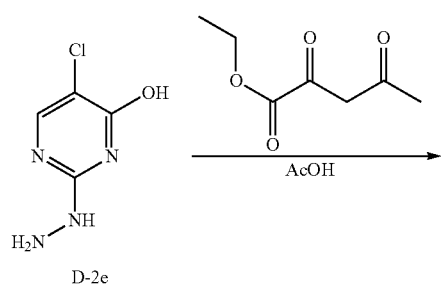

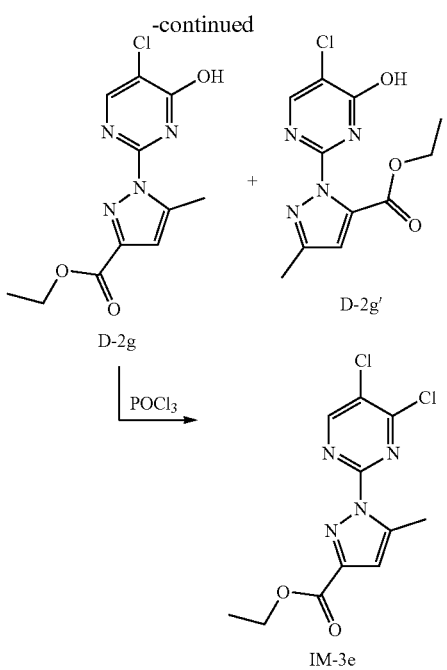

To a stirred solution of D-2e (0.90 g; 5.61 mmol) in AcOH (10.0 mL) is added ethyl 2,4-dioxopentanoate (1.06 g; 6.70 mmol) at rt and the reaction mixture is heated to 90° C. for 3 h. After cooling to rt the volatiles are evaporated and the residue is taken up in EtOAc. The regioisomeric mixture of D-2g and D-2g' is separated by flash chromatography on silica gel to give isomerically pure ethyl 1-(5-chloro-4-hydroxypyrimidin-2-yl)-5-methyl-1H-pyrazole-3-carboxylate (D-2g).

A stirred solution of D-2g (0.15 g; 0.53 mmol) in POCl$_3$ (2.0 mL) is refluxed for 1 h. After cooling to rt saturated NaHCO$_3$ solution is added slowly to the reaction mixture. At a neutral pH the aqueous phase is extracted with EtOAc. The combined organic layer is washed with water and brine, dried over Na$_2$SO$_4$, filtered and the volatiles are evaporated. The crude material is purified by flash chromatography on SiO$_2$ using EtOAc/hexane=10:90 as eluent to give ethyl 1-(4,5-dichloropyrimidin-2-yl)-5-methyl-1H-pyrazole-3-carboxylate (IM-3e) (HPLC-MS: $t_{Ret.}$=1.21 min; MS (M+H)$^+$=301; method 1).

B.4.6. Experimental Procedure for the Synthesis of IM-3f Synthesis of Amine SM-4d and rac-SM-4e

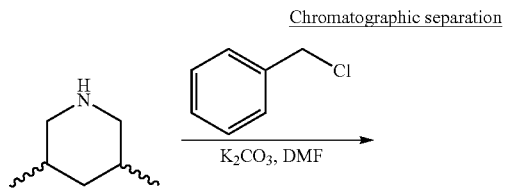

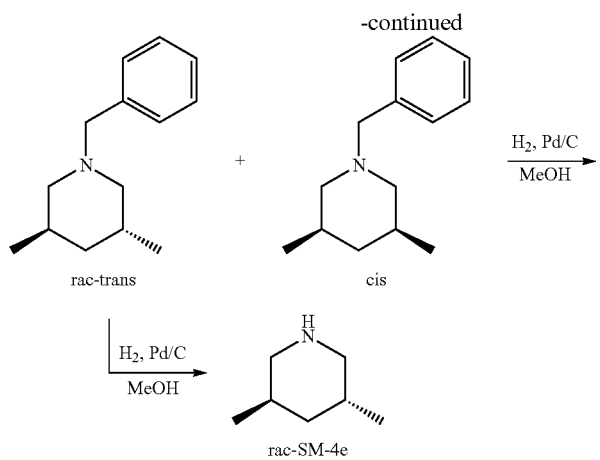
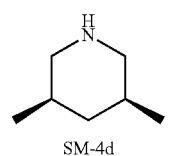

To a stirred solution of 3,5-dimethylpiperidine (20.0 g; 177 mmol) in DMF (200 mL) is added potassium carbonate (48.8 g; 353 mmol) followed by (chloromethyl)benzene (24.6 g; 194 mmol) and the reaction mixture is heated to 60° C. for 16 h. After cooling to rt the reaction mixture is diluted with EtOAc, washed with water and brine, dried over $Na_2SO_4$, filtered and concentrated in vacuo. The residue is purified including a separation of the stereoisomeric mixture of rac-trans-1-benzyl-3,5-dimethylpiperidine and cis-1-benzyl-3,5-dimethylpiperidine by column chromatography on $SiO_2$ using a gradient of EtOAc/PE 0:100 to 10:90 as eluent.

A suspension of cis-1-benzyl-3,5-dimethylpiperidine (18.0 g; 88.5 mmol) in MeOH (180 mL) and Pd/C (5.00 g, 10%) is stirred under $H_2$ (100 PSI) for 24 h at 40° C. After cooling to rt the reaction mixture is filtered over celite and washed with cold MeOH. The filtrate is evaporated under reduced pressure to give cis-3,5-dimethylpiperidine (SM-4d).

A suspension of rac-trans-1-benzyl-3,5-dimethylpiperidine (3.00 g; 14.8 mmol) in MeOH (10.0 mL) and Pd/C (1.00 g, 20%) is stirred under $H_2$ (100 PSI) for 24 h at 40° C. After cooling to rt the reaction mixture is filtered over celite and washed with cold MeOH. Hydrochloric acid (4.0 M in 1,4-dioxane; 10 mL) is added, the filtrate is stirred at rt for 2 h and then evaporated under reduced pressure to give rac-trans-3,5-dimethylpiperidine (rac-SM-4e) as HCl salt.

Synthesis of IM-3f

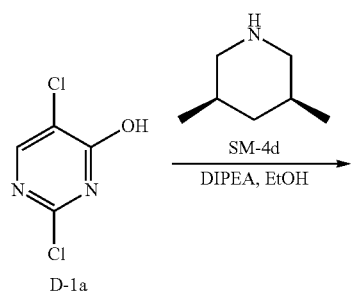

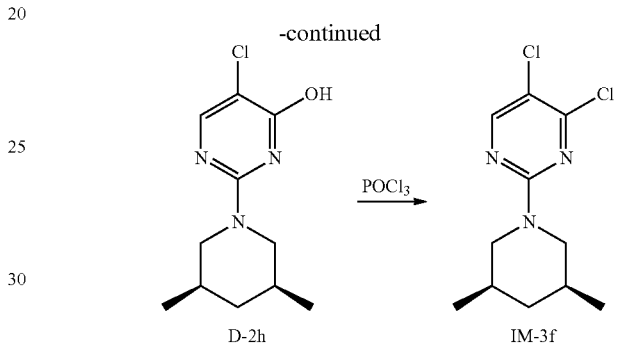

To a stirred solution of SM-4d (4.80 g; 42.4 mmol) and DIPEA (15.2 mL; 84.8 mmol) in EtOH (70.0 mL) is added D-1a (7.00 g; 42.4 mmol). The reaction mixture is heated at 80° C. for 6 h. After cooling to rt the reaction mixture is concentrated in vacuo and the residue is taken up in water and neutralized with 1 N $HCl_{aq}$. The resulting precipitate is filtered, washed with water and dried in vacuo to give 5-chloro-2-[cis-3,5-dimethylpiperidin-1-yl]pyrimidin-4-ol (D-2g) (HPLC-MS: $t_{Ret.}$=1.27 min; MS $(M+H)^+$=242; method E).

A stirred solution of D-2h (6.50 g; 26.8 mmol) in $POCl_3$ (65.0 mL) is heated at 120° C. for 3 h. After cooling to rt saturated $NaHCO_3$ solution is added slowly to the reaction mixture. At a neutral pH the aqueous phase is extracted three times with EtOAc. The combined organic layer is washed with saturated $NaHCO_3$ solution and brine, dried over $Na_2SO_4$, filtered and evaporated. The crude material is purified by flash chromatography on $SiO_2$ using EtOAc/PE=0:100 to 5:95 as eluent to yield ethyl 4,5-dichloro-2-[cis-3,5-dimethylpiperidin-1-yl]pyrimidine (IM-3e) (HPLC-MS: $t_{Ret.}$=1.88 min; MS $(M+H)^+$=260; method E).

B.5. Synthesis of IM-3' from SM-7

B.5.1. Experimental procedure for the synthesis of IM-3'a

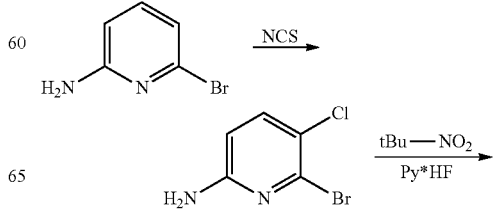

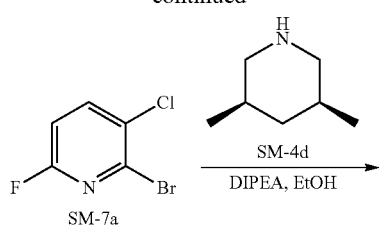

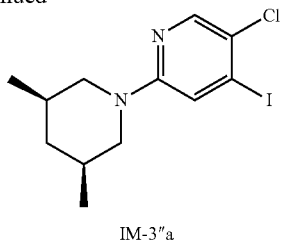

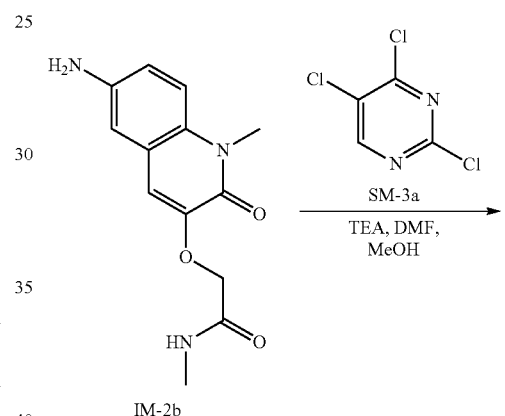

To 6-bromopyridin-2-amine (1.00 g; 5.78 mmol) in CH$_3$CN (10 mL) is added NCS (849 mg; 6.36 mmol) and the resulting mixture is stirred at 80° C. for 16 h. After cooling to rt the mixture is filtered, the filtrate is evaporated and the residue is purified by NP flash chromatography (40 g SiO$_2$; cyclohexene/EtOAc=100:0 to 50:50; 25 min, Companion) to give 6-bromo-5-chloropyridin-2-amine.

To a cooled solution (ice bath) of 6-bromo-5-chloropyridin-2-amine (650 mg; 3.13 mmol) in DCM (6.5 mL) is added tert-butyl nitrite (745 µL; 6.27 mmol) and pyridinium hydrofluoride (162 µL; 6.27 mmol; 70% in pyridine). The reaction mixture is stirred at 0° C. for 30 min. H$_2$O is added and stirring continued for 10 min. DCM is added and the layers are separated. The aqueous layer is extracted with DCM. The combined organic layer is dried over MgSO$_4$, filtered and evaporated to give crude 2-bromo-3-chloro-6-fluoropyridine (SM-7a).

To SM-7a (530 mg; 2.52 mmol) and SM-4d (428 mg; 3.78 mmol) in EtOH (10.0 mL) is added DIPEA (1.29 mL; 7.56 mmol) and the resulting mixture is stirred at 80° C. for 3 h. After cooling to rt the volatiles are evaporated, the residue is taken up in MeCN/H$_2$O and purified by preparative RP-HPLC under acidic conditions using a MeCN/H$_2$O gradient from 20:80 to 2:98 as eluent over 10 min. The product containing fractions are freeze dried to give 2-bromo-3-chloro-6-[cis-3,5-dimethylpiperidin-1-yl]pyridine (IM-3'a).

B.6. Synthesis of IM-3' from SM-8

B.6.1. Experimental Procedure for the Synthesis of IM-3"a

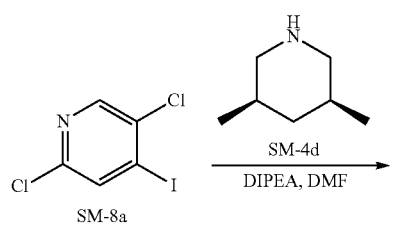

To 2,5-dichloro-4-iodopyridine (SM-8a) (1.00 g; 3.65 mmol) and SM-4d (413 mg; 3.65 mmol) in DMF (4.0 mL) is added DIPEA (943 mg; 7.30 mmol) and the reaction mixture is stirred at 100° C. for 18 h. After cooling to rt the mixture is filtered, evaporated and the residue is purified by preparative RP-HPLC under basic conditions using a MeCN/H$_2$O gradient from 40:60 to 80:20 as eluent over 6 min. The product containing fractions are freeze dried to give 5-chloro-2-[cis-3,5-dimethylpiperidin-1-yl]-4-iodopyridine (IM-3"a).

B.7. Synthesis of Intermediates IM-4

B.7.1. Experimental Procedure for the Synthesis of IM-4a

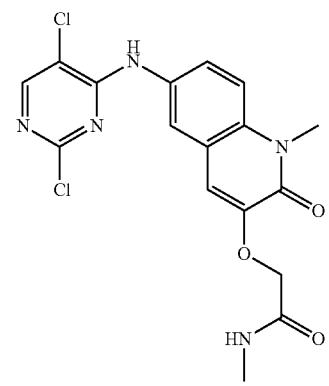

To IM-2b (4.50 g; 17.2 mmol) and 2,4,5-trichloropyrimidine (SM-3a) (3.78 g; 20.6 mmol) dissolved in DMF (40.0 mL) and MeOH (40.0 mL) is added triethylamine (3.50 g; 34.4 mmol) and the mixture is stirred at 70° C. for 12 h. After cooling to rt the reaction mixture is concentrated in vacuo and the residue is taken up in water. The resulting precipitate is collected by filtration, washed with Et$_2$O and dried in vacuo to give 2-({6-[(2,5-dichloropyrimidin-4-yl)amino]-1-methyl-2-oxo-1,2-dihydroquinolin-3-yl}oxy)-N-methyl-acetamide (IM-4a) (HPLC-MS: t$_{Ret.}$=0.92 min; MS (M+H)$^+$=408; method 1).

B.7.2. Experimental Procedure for the Synthesis of IM-4b and IM-4c

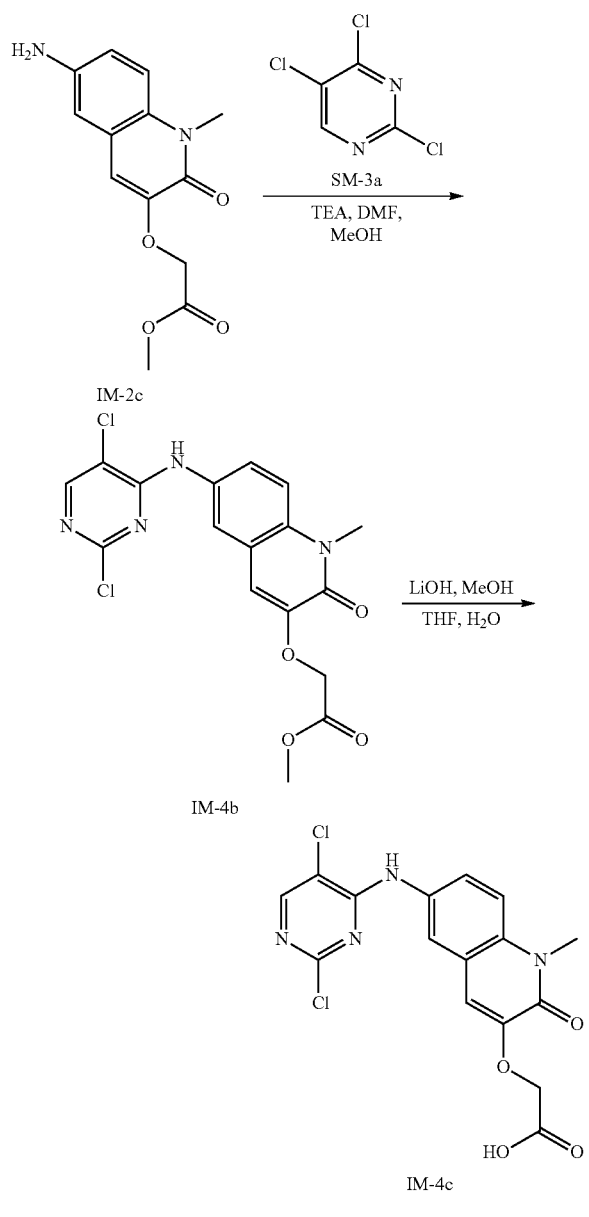

IM-2c

IM-4b

IM-4c

To IM-2c (8.10 g; 31.0 mmol) and 2,4,5-trichloropyrimidine (SM-3a) (6.78 g; 37.0 mmol) dissolved in DMF (30.0 mL) and MeOH (80.0 mL) is added triethylamine (6.24 g; 61.8 mmol) and the mixture is stirred at 70° C. for 12 h. After cooling to rt the reaction mixture is concentrated in vacuo and the residue is taken up in water. The resulting precipitate is collected by filtration, washed with Et₂O and dried in vacuo to give methyl 2-({6-[(2,5-dichloropyrimidin-4-yl)amino]-1-methyl-2-oxo-1,2-dihydroquinolin-3-yl}oxy)acetate (IM-4b) (HPLC-MS: $t_{Ret.}$=0.99 min; MS (M+H)⁺=409; method 1).

To IM-4b (7.00 g; 17.0 mmol) in THF (2.5 mL), MeOH (2.5 mL) and water (1.5 mL) is added LiOH (1.37 g; 34.2 mmol) and the mixture is stirred at rt for 2 h. The reaction mixture is acidified with 1 N HCl$_{aq.}$ and the resulting precipitate is collected by filtration, washed with Et₂O and dried in vacuo to give 2-({6-[(2,5-dichloropyrimidin-4-yl)amino]-1-methyl-2-oxo-1,2-dihydroquinolin-3-yl}oxy)acetic acid (IM-4c) (HPLC-MS: $t_{Ret.}$=0.67 min; MS (M+H)⁺=396; method 1).

B.7.3. Experimental Procedure for the Synthesis of IM-4d

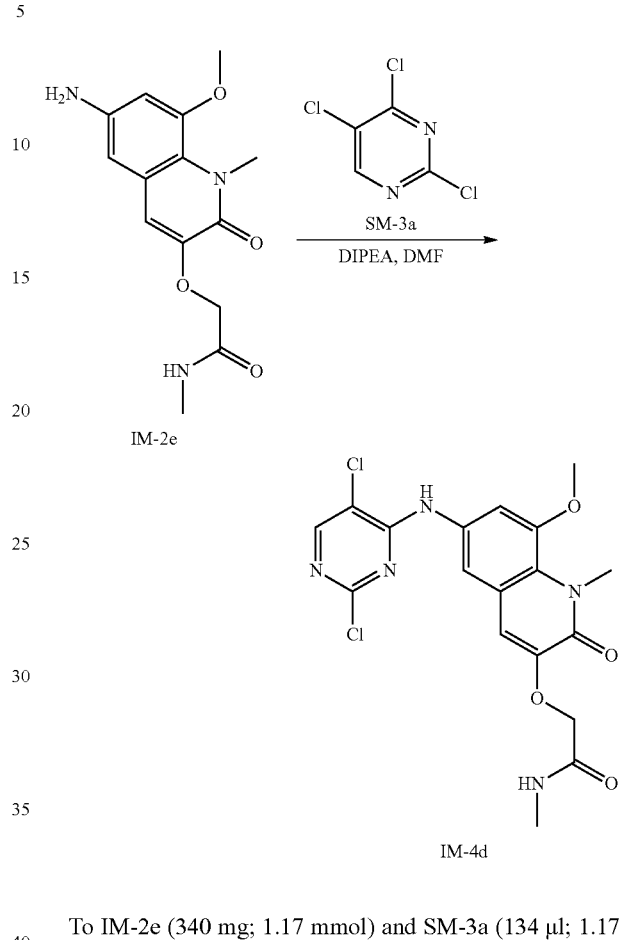

IM-2e

IM-4d

To IM-2e (340 mg; 1.17 mmol) and SM-3a (134 µL; 1.17 mmol) in DMF (10.0 mL) is added DIPEA (602 µL; 3.50 mmol) and the mixture is stirred at 70° C. for 16 h. After cooling to rt water is added and stirring is continued for 10 min. The resulting precipitate is collected by filtration, washed with water and dried in vacuo at 50° C. to give 2-({6-[(2,5-dichloropyrimidin-4-yl)amino]-8-methoxy-1-methyl-2-oxo-1,2-dihydroquinolin-3-yl}oxy)-N-methylacetamide (IM-4d) (HPLC-MS: $t_{Ret.}$=0.55 min; MS (M+H)⁺=438; method A).

B.7.3. Experimental Procedure for the Synthesis of IM-4e

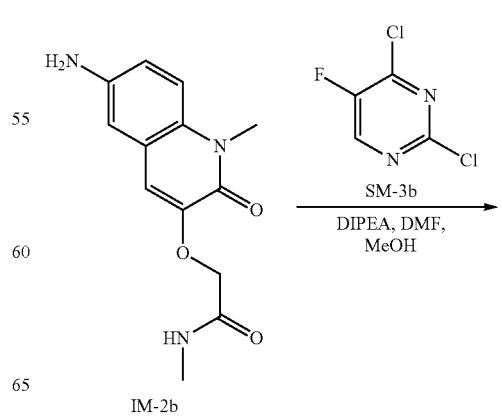

IM-2b

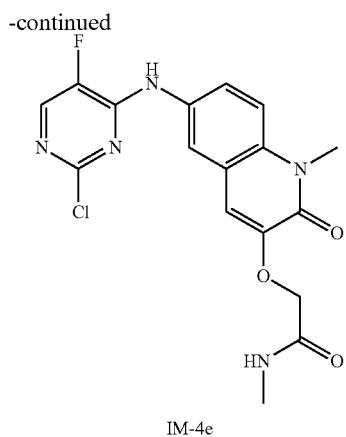

IM-4e

To IM-2b (3.30 g; 12.6 mmol) and 2,4-dichloro-5-fluoropyrimidine (SM-3b) (2.77 g; 16.6 mmol) dissolved in DMF (35.0 mL) and MeOH (35.0 mL) is added DIPEA (3.26 g; 25.3 mmol) and the mixture is stirred at 70° C. for 12 h. After cooling to rt the reaction mixture is concentrated in vacuo and the residue is taken-up in water. The resulting precipitate is collected by filtration, washed with Et$_2$O and dried in vacuo to give 2-({6-[(2-chloro-5-fluoropyrimidin-4-yl)amino]-1-methyl-2-oxo-1,2-dihydroquinolin-3-yl}oxy)-N-methyl-acetamide (IM-4e) (HPLC-MS: t$_{Ret.}$=0.86 min; MS (M+H)$^+$=392; method 1).

B.7.4. Experimental Procedure for the Synthesis of IM-4f

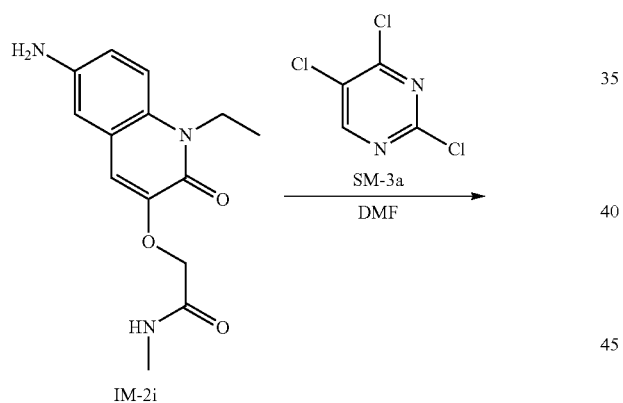

IM-2i (345 mg; 1.25 mmol) and SM-3a (147 µL; 1.25 mmol) in DMF (3.5 mL) are stirred at 70° C. for 2 h. After cooling to rt H$_2$O (35 mL) is added to the reaction mixture and stirring is continued for 30 min. The resulting precipitate is collected by filtration, washed with H$_2$O and dried in vacuo to give 2-({6-[(2,5-dichloropyrimidin-4-yl)amino]-1-ethyl-2-oxo-1,2-dihydro-quinolin-3-yl}oxy)-N-methylacetamide (IM-4f).

B.7.5. Experimental Procedure for the Synthesis of IM-4g

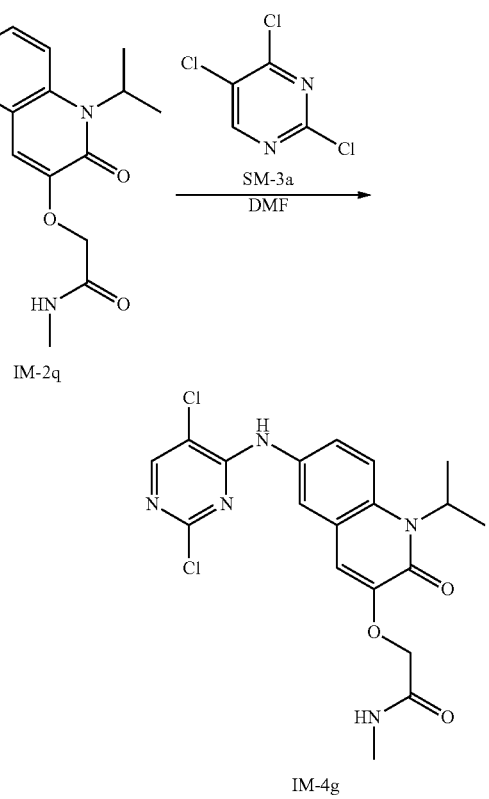

IM-2q (300 mg; 1.04 mmol) and SM-3a (121 µL; 1.04 mmol) in DMF (3.0 mL) are stirred at 70° C. for 2 h. After cooling to rt H$_2$O (30 mL) is added to the reaction mixture and stirring is continued for 30 min. The resulting precipitate is collected by filtration, washed with H$_2$O and dried in vacuo to give 2-({6-[(2,5-dichloropyrimidin-4-yl)amino]-2-oxo-1-(propan-2-yl)-1,2-dihydroquinolin-3-yl}oxy)-N-methylacetamide (IM-4g).

B.7.6. Experimental procedure for the synthesis of IM-4h

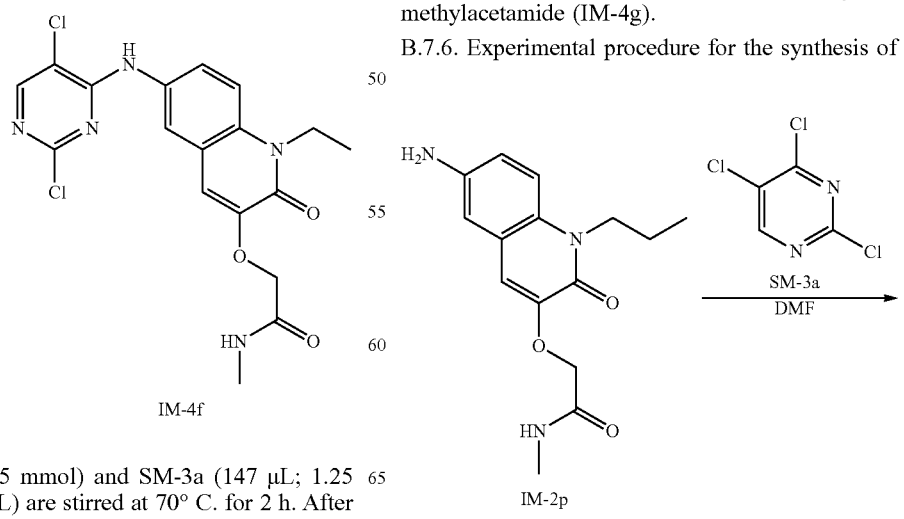

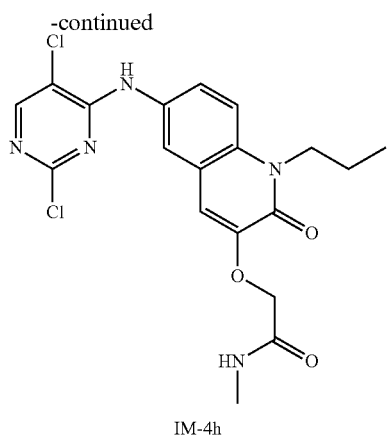

IM-4h

IM-2p (190 mg; 0.66 mmol) and SM-3a (76.8 µL; 0.66 mmol) in DMF (2.0 mL) are stirred at 70° C. for 2 h. After cooling to rt H₂O (20 mL) is added to the reaction mixture and stirring is continued for 30 min. The resulting precipitate is collected by filtration, washed with H₂O and dried in vacuo to give 2-({6-[(2,5-dichloropyrimidin-4-yl)amino]-2-oxo-1-propyl-1,2-dihydroquinolin-3-yl}oxy)-N-methylacetamide (IM-4h).

B.7.7. Experimental Procedure for the Synthesis of IM-4i

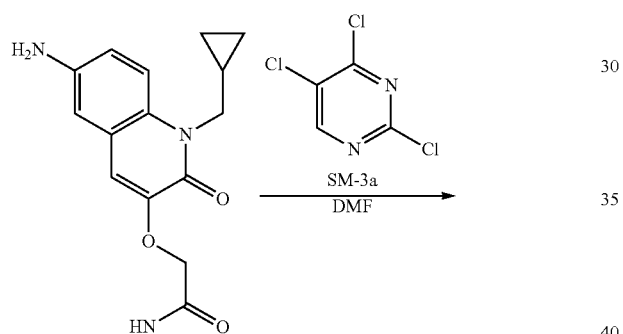

IM-2r

IM-2r (215 mg; 0.71 mmol) and SM-3a (118 mg; 0.64 mmol) in DMF (2.5 mL) are stirred at 70° C. for 4 h. After cooling to rt H₂O (25 mL) is added to the reaction mixture and stirring is continued for 30 min. The resulting precipitate is collected by filtration, washed with H₂O and dried in vacuo 2-{[1-(cyclopropylmethyl)-6-[(2,5-dichloropyrimidin-4-yl)amino]-2-oxo-1,2-dihydroquinolin-3-yl]oxy}-N-methylacetamide (IM-4i) (HPLC-MS: $t_{Ret.}$=0.59 min; MS $(M+H)^+$=448; method A).

C. Synthesis of Compounds (I)

C. 1. Experimental Procedures for the Synthesis of Compounds (I) from IM-4

C.1.1. Experimental Procedure for the Synthesis of I-1

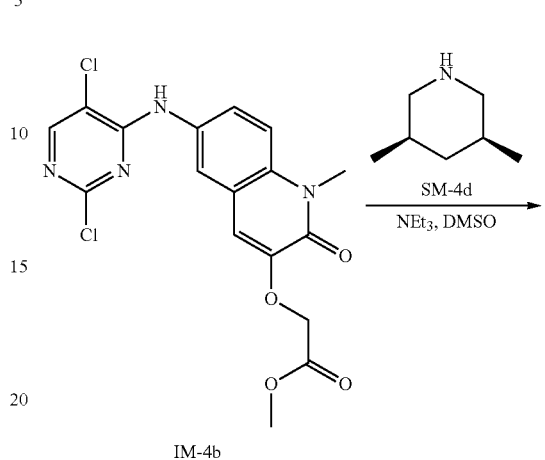

IM-4b

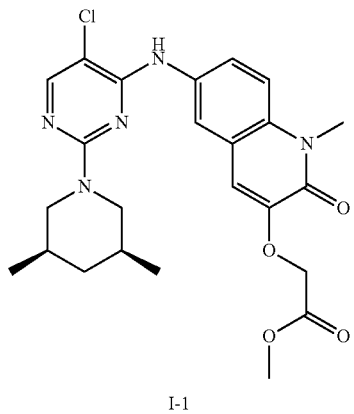

I-1

A mixture of IM-4b (100 mg; 0.24 mmol), SM-4d (33.2 mg; 0.29 mmol) and NEt₃ (136 µL; 0.98 mmol) in DMSO (2.0 mL) is stirred at 100° C. for 1 h. After cooling to rt the resulting precipitate is collected by filtration, washed with H₂O and triturated with MeOH/H₂O (1:1) for 10 min. The solid is collected by filtration, washed with MeOH/H₂O (1:1), taken up in MeCN/H₂O and freeze dried to give methyl 2-{[6-({5-chloro-2-[cis-3,5-dimethylpiperidin-1-yl]pyrimidin-4-yl}amino)-1-methyl-2-oxo-1,2-dihydroquinolin-3-yl]oxy}acetate (I-1) (HPLC-MS: $t_{Ret.}$=1.48 min; MS $(M+H)^+$=486; method 1).

C.1.2. Experimental Procedure for the Synthesis of I-2

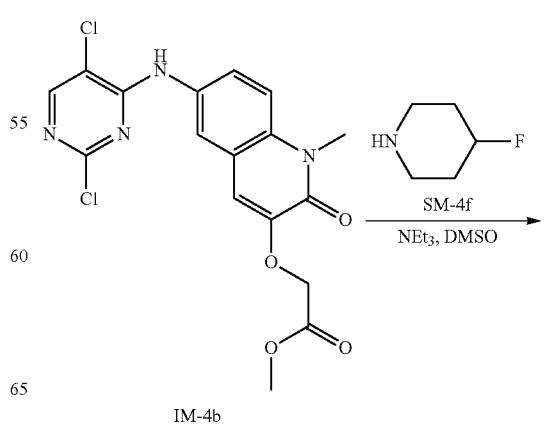

IM-4b

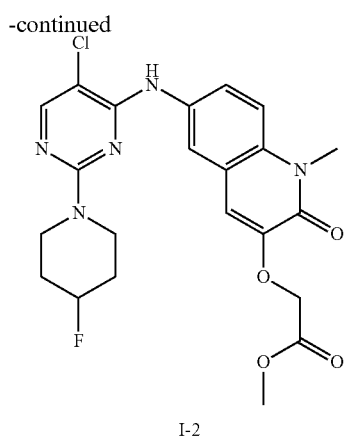

I-2

A mixture of IM-4b (100 mg; 0.24 mmol), SM-4f (40.9 mg; 0.29 mmol) and NEt₃ (136 μL; 0.98 mmol) in DMSO (2.0 mL) is stirred at 100° C. for 1 h. After cooling to rt the mixture is purified by preparative RP-HPLC under basic conditions using a MeCN/H₂O gradient from 5:95 to 98:2 over 8 min as eluent (column: XBridge C18; 30×50 mm; 5 μm; flow: 50 mL/min). The product containing fractions are freeze dried to give methyl 2-[(6-{[5-chloro-2-(4-fluoropiperidin-1-yl)pyrimidin-4-yl]amino}-1-methyl-2-oxo-1,2-dihydro-quinolin-3-yl)oxy]-acetate (I-2) (HPLC-MS: $t_{Ret.}$=1.23 min; MS (M+H)⁺=476; method 1).

C.1.3. Experimental Procedure for the Synthesis of I-3

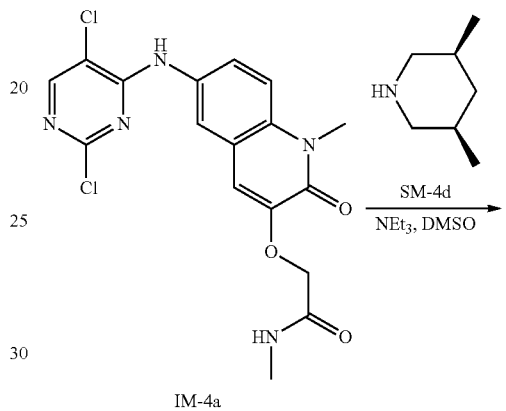

A mixture of IM-4a (40.0 mg; 98.0 μmol) and SM-4g (17.8 μL; 118 μmol) in NMP (1.0 mL) is stirred at 120° C. for 2 h. After cooling to rt MeCN (0.5 mL) and H₂O (0.5 mL) are added and the mixture is purified by preparative RP-HPLC under acidic conditions using a MeCN/H₂O gradient as eluent (column: Triart C18; 30×50 mm; 5 μm; flow: 50 mL/min).

The product containing fractions are freeze dried to give 2-{[6-({5-chloro-2-[4-(2-methoxyethyl)piperazin-1-yl]pyrimidin-4-yl}amino)-1-methyl-2-oxo-1,2-dihydroquinolin-3-yl]oxy}-N-methylacetamide (I-3) (HPLC-MS: $t_{Ret.}$=1.01 min; MS (M+H)⁺=516; method 1).

C.1.4. Experimental Procedure for the Synthesis of I-4

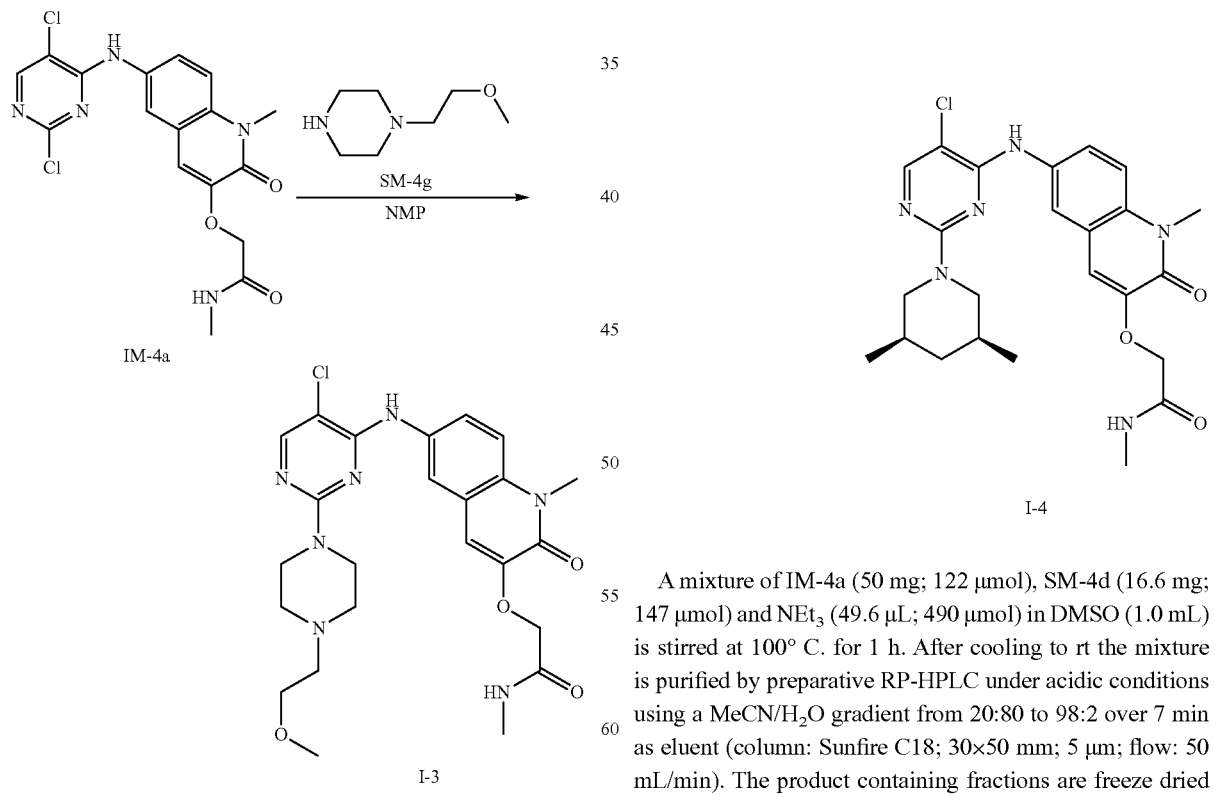

A mixture of IM-4a (50 mg; 122 μmol), SM-4d (16.6 mg; 147 μmol) and NEt₃ (49.6 μL; 490 μmol) in DMSO (1.0 mL) is stirred at 100° C. for 1 h. After cooling to rt the mixture is purified by preparative RP-HPLC under acidic conditions using a MeCN/H₂O gradient from 20:80 to 98:2 over 7 min as eluent (column: Sunfire C18; 30×50 mm; 5 μm; flow: 50 mL/min). The product containing fractions are freeze dried to give 2-[(6-{[5-chloro-2-(cis-3,5-dimethylpiperidin-1-yl)pyrimidin-4-yl]amino}-1-methyl-2-oxo-1,2-dihydro-quinolin-3-yl)oxy]-N-methylacetamide (I-4) (HPLC-MS: $t_{Ret.}$=1.38 min; MS (M+H)⁺=485; method 1).

C.1.5. Experimental Procedure for the Synthesis of I-5 and I-6

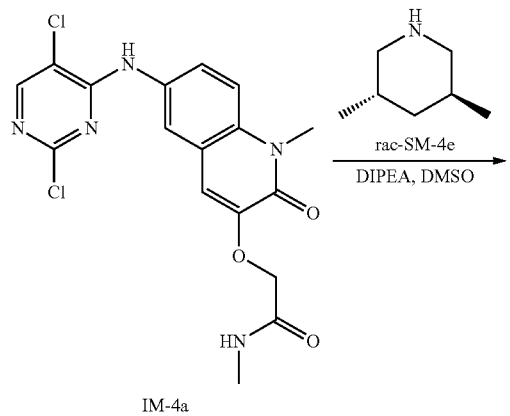

IM-4a

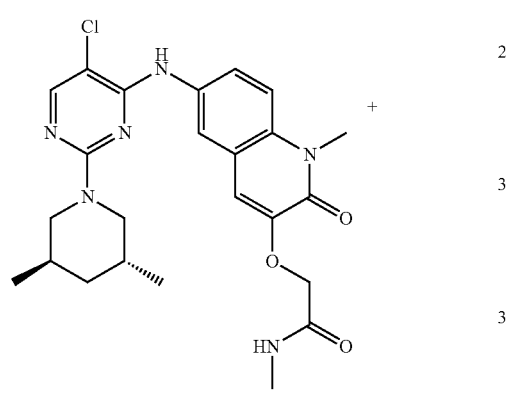

I-5

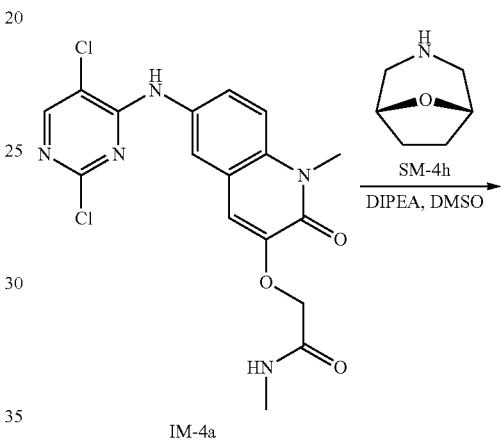

I-6

To a mixture of IM-4a (50 mg; 122 μmol) and rac-SM-4e (36.7 mg; 245 μmol) in DMSO (1.0 mL) is added DIPEA (63.2 μL; 367 μmol) and the mixture is stirred at 100° C. for 16 h. After cooling to rt the mixture is purified by preparative RP-HPLC under basic conditions using a MeCN/H$_2$O gradient from 40:60 to 80:20 over 6 min as eluent to give a racemic mixture of (I-5) and (I-6) (HPLC-MS: t$_{Ret.}$=1.35 min; MS (M+H)$^+$=485; method 1) which is separated by preparative SFC (Method SFC1; column: Chiralpak IC; MeOH/CO$_2$=50/50; total flow=40 mL/min; injection volume: 500 μL; backpressure: 200 bar). The product containing fractions are freeze dried to give 2-{[6-({5-chloro-2-[(3R,5SR)-3,5-dimethylpiperidin-1-yl]pyrimidin-4-yl}amino)-1-methyl-2-oxo-1,2-dihydro-quinolin-3-yl]oxy}-N-methylacetamide (I-5) (SFC: t$_{Ret.}$=4.1 min) and 2-{[6-({5-chloro-2-[(3S,5SS)-3,5-dimethylpiperidin-1-yl]pyrimidin-4-yl}amino)-1-methyl-2-oxo-1,2-dihydro-quinolin-3-yl]oxy}-N-methylacetamide (I-6) (SFC: t$_{Ret.}$=4.7 min). The absolute configuration of the two enantiomeric products is randomly assigned.

C.1.6. Experimental Procedure for the Synthesis of I-7

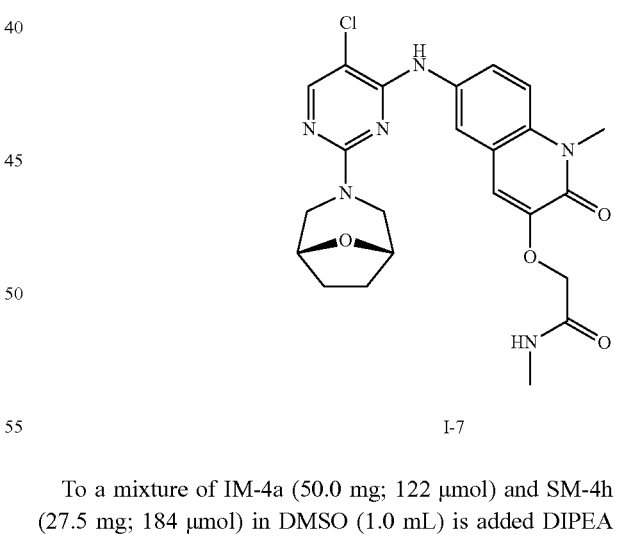

IM-4a

I-7

To a mixture of IM-4a (50.0 mg; 122 μmol) and SM-4h (27.5 mg; 184 μmol) in DMSO (1.0 mL) is added DIPEA (84.3 μL; 490 μmol) and the mixture is stirred at 100° C. for 16 h. After cooling to rt MeCN (0.5 mL) and H$_2$O (0.5 mL) are added and the mixture is purified by preparative RP-HPLC using a MeCN/H$_2$O gradient from 10:90 to 70:30 over 8 min as eluent (column: Sunfire C18; 30×50 mm; 5 μm; flow: 50 mL/min). The product containing fractions are freeze dried to give 2-({6-[(5-chloro-2-{8-oxa-3-azabicyclo

[3.2.1]octan-3-yl}pyrimidin-4-yl)amino]-1-methyl-2-oxo-1,2-dihydroquinolin-3-yl}oxy)-N-methylacetamide (I-7) (HPLC-MS: $t_{Ret.}$=1.05 min; MS (M+H)$^+$=485; method 1).

C.1.7. Experimental Procedure for the Synthesis of I-8

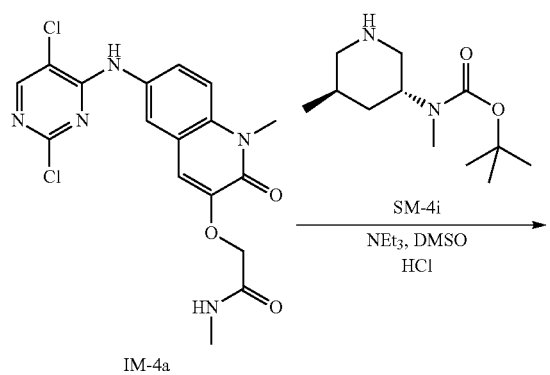

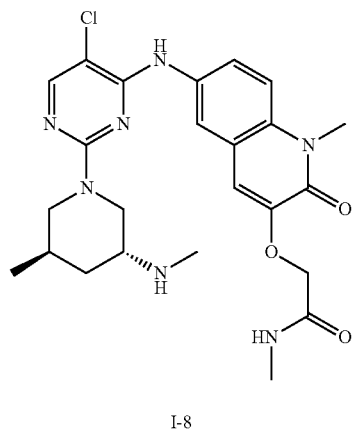

To a mixture of IM-4a (100.0 mg; 245 µmol) and SM-4i (61.5 mg; 269 µmol) in DMSO (1.0 mL) is added NEt$_3$ (85.4 µL; 612 µmol) and the mixture is stirred at 100° C. for 2 h. The mixture is cooled to 50° C. and HCl (306 µL; 1.23 mmol; 4N in dioxane) is added and stirring is continued at 50° C. for 14 h. After cooling to rt the mixture is neutralized with NEt$_3$, diluted with DMF/H2O, filtered and purified by preparative RP-HPLC under basic conditions using a MeCN/H$_2$O gradient from 15:85 to 98:2 over 8 min as eluent (column: XBridge C18; 50×150 mm; 10 µm; flow: 150 mL/min). The product containing fractions are freeze dried to give 2-{[6-({5-chloro-2-[(3R,5R)-3-methyl-5-(methylamino)piperidin-1-yl]pyrimidin-4-yl}amino)-1-methyl-2-oxo-1,2-dihydroquinolin-3-yl]oxy}-N-methylacetamide (I-8) (HPLC-MS: $t_{Ret.}$=1.01 min; MS (M+H)$^+$=500; method 1).

C.1.8. Experimental Procedures for the Synthesis of I-9, I-10 and I-11

C.1.8.1. Synthesis of Piperazine Precursors E-3, E-4, E-5 and E-6

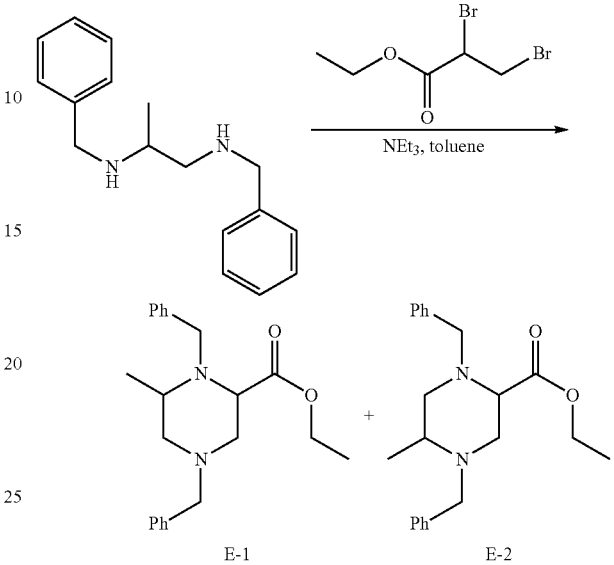

To a stirred solution of N,N'-bibenzyl-propane-1,2-diamine (5.00 g; 19.7 mmol) in toluene (25 mL) is added NEt$_3$ (5.36 g; 53.1 mmol) and the mixture is heated to 40° C. 2,3-dibromo-propionic acid ethyl ester (5.62 g; 21.6 mmol) in toluene (3.0 mL) is added dropwise and the mixture is stirred at 80° C. for 3 h. After cooling to rt the reaction mixture is filtered through celite and evaporated to give a crude mixture of the two cyclized products E-1 and E-2. E-1 and E-2 are separated by flash chromatography on silica gel using EtOAc/PE as eluent. The product containing fractions are evaporated to give E-1 (polar spot; mixture of four stereoisomers; HPLC-MS: $t_{Ret.}$=1.74 min; MS (M+H)$^+$=353; method D) and E-2 (less polar spot; mixture of four stereoisomers; HPLC-MS: $t_{Ret.}$=1.76 min; MS (M+H)$^+$=353; method D).

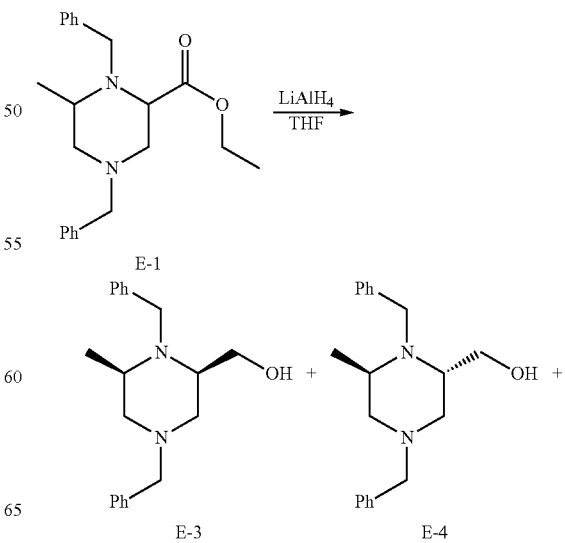

-continued

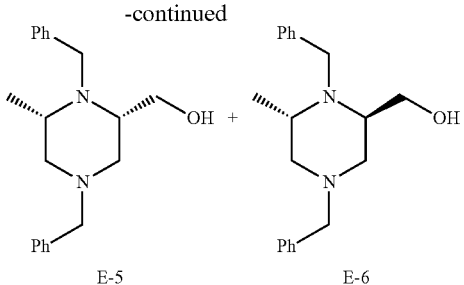

E-5      E-6

To a stirred solution of E-1 (2.50 g; 7.09 mmol) in THF (25.0 mL) is added LiAlH$_4$ (11.3 mL; 11.3 mmol; 1 M in THF) at 0° C. The reaction is warmed to rt, stirred for 30 min, quenched with saturated Na$_2$SO$_4$ solution and extracted with EtOAc. The combined organic layer is washed with water and brine, dried over Na$_2$SO$_4$, filtered and evaporated to give a crude mixture of the stereoisomers E-3, E-4, E-5 and E-6 (HPLC-MS: $t_{Ret.}$=1.56 min; MS (M+H)$^+$=311; method D). The stereoisomers are separated by preparative SFC (Thar SFC-200-002; column: Chiralcel OD-H; 250×30 mm; 5 μm; total flow: 90 g/min; backpressure: 100 bar; stack time: 7.26 min; load/injection: 15 mg) using 15% EtOH (with 0.5% DEA) as co-solvent. The product containing fractions are evaporated to give E-3 (chiral HPLC: $t_{Ret.}$=9.79 min), E-4 (chiral HPLC: $t_{Ret.}$=10.67 min), E-5 (chiral HPLC: $t_{Ret.}$=10.92 min) and E-6 (chiral HPLC: $t_{Ret.}$=13.62 min). The absolute configuration of the enatiomeric pairs is randomly assigned.

C. 1.8.2. Synthesis of I-9

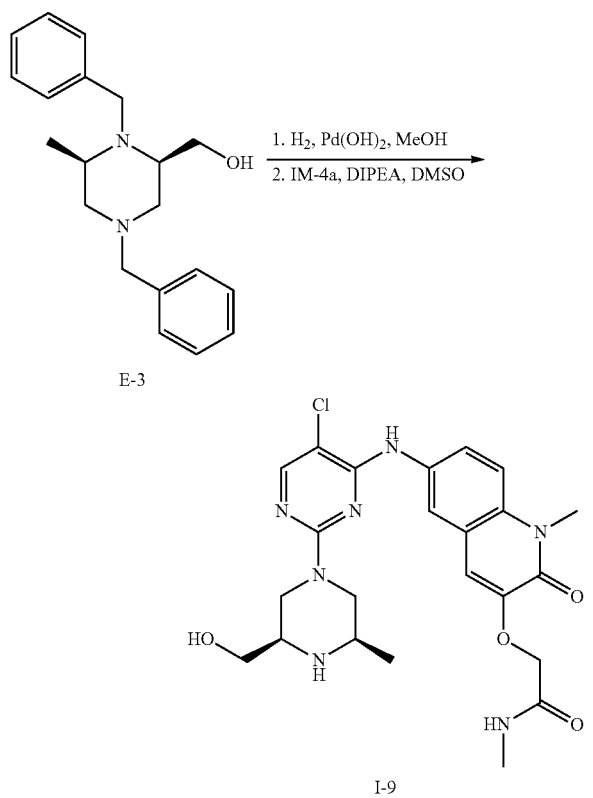

To E-3 (500 mg; 1.61 mmol) in MeOH (10.0 mL) is added Pd(OH)$_2$ (50.0 mg; 20% on C) and the mixture is hydrogenated in a steel reactor at 100° C. under H$_2$ (500 Psi) for 16 h. After cooling to rt the mixture is filtered through celite and evaporated to give the de-benzylated piperazine, which is directly used for the next step.

To a mixture of IM-4a (70.0 mg; 171 μmol) and an aliquot of the de-benzylated piperazine from the previous step (44.5 mg; 342 μmol) in DMSO (1.0 mL) is added DIPEA (60.0 μL; 325 μmol) and the mixture is stirred at 100° C. for 3 h. After cooling to rt the mixture is filtered and purified by preparative RP-HPLC under acidic conditions using a MeCN/H$_2$O gradient from 10:90 to 50:50 over 6 min as eluent (column: Sunfire C18; 30×100 mm; 5 μm). The product containing fractions are freeze dried to give 2-{[6-({5-chloro-2-[(3R,5R)-3-(hydroxymethyl)-5-methylpiperazin-1-yl]pyrimidin-4-yl}amino)-1-methyl-2-oxo-1,2-dihydroquinolin-3-yl]oxy}-N-methylacetamide (I-9) (HPLC-MS: $t_{Ret.}$=0.91 min; MS (M+H)$^+$=502; method 1). The absolute configuration of the product is randomly assigned.

C. 1.8.3. Synthesis of I-10 and I-11

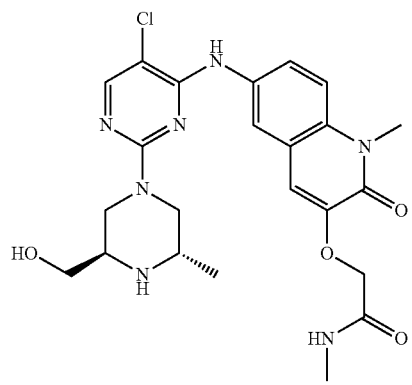

from E-6

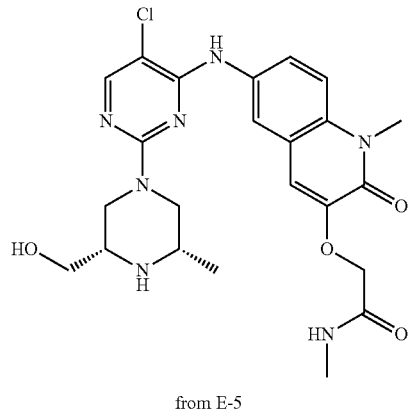

from E-5

2-{[6-({5-chloro-2-[(3R,5S)-3-(hydroxymethyl)-5-methylpiperazin-1-yl]pyrimidin-4-yl}amino)-1-methyl-2-oxo-1,2-dihydroquinolin-3-yl]oxy}-N-methylacetamide (I-10) (HPLC-MS: $t_{Ret.}$=0.91 min; MS (M+H)$^+$=502; method 1) and 2-{[6-({5-chloro-2-[(3S,5S)-3-(hydroxymethyl)-5-methylpiperazin-1-yl]pyrimidin-4-yl}amino)-1-methyl-2-oxo-1,2-dihydroquinolin-3-yl]oxy}-N-methylacetamide (I-11) (HPLC-MS: $t_{Ret.}$=0.91 min; method 1) are prepared analogously to the procedure described for I-9 from E-6 and E-5, respectively. The absolute configuration of the products is randomly assigned.

C.1.9. Experimental Procedures for the Synthesis of I-12
C.1.9.1. Synthesis of Piperazine Precursors E-7

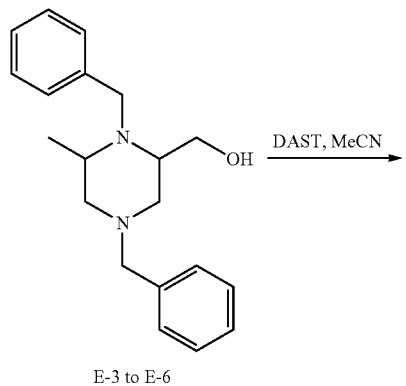

E-3 to E-6

A stirred solution of (1,4-dibenzyl-6-methyl-piperazin-2-yl)methanol (2.00 g; 6.44 mmol, mixture of stereoisomers E-3 to E-6) in MeCN (20.0 mL) is cooled to −78° C. and DAST (2.08 g; 12.9 mmol) is added dropwise. After completion of the addition the mixture is allowed to warm to rt and stirring is continued for 16 h. The reaction mixture is diluted with MeCN (20.0 mL), washed with saturated NaHCO$_3$ solution (3×10.0 mL) and brine (20.0 mL), dried over Na$_2$SO$_4$ and evaporated. The crude material is purified by flash chromatography on SiO$_2$ using PE/EtOAc as eluent. The product containing fractions are evaporated to give 1,4-dibenzyl-2-(fluoromethyl)-6-methylpiperazine (E-7) (HPLC-MS: $t_{Ret.}$=1.72 min; MS (M+H)$^+$=313; mixture of stereoisomers; method D).

C.1.9.2. Synthesis of I-12

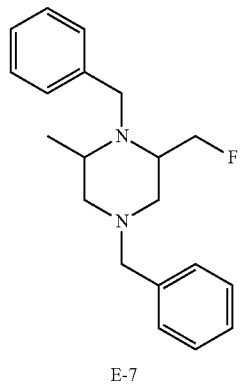

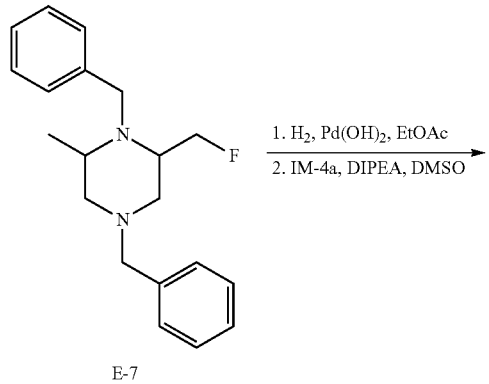

E-7

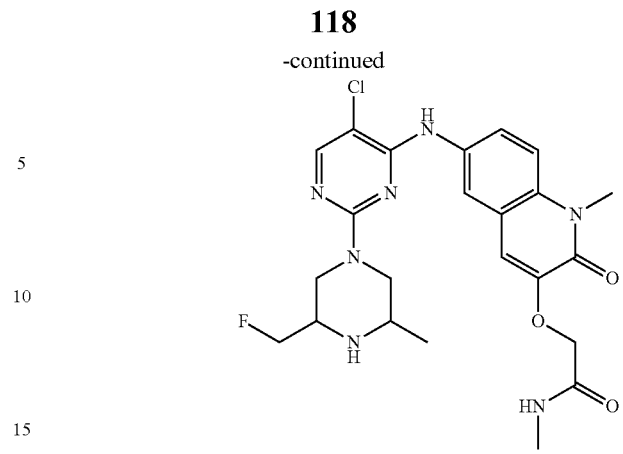

I-12

To E-7 (350 mg; 1.12 mmol) in EtOAc (10.0 mL) is added Pd(OH)$_2$ (20.0 mg; 20% on C) and the mixture is hydrogenated in a steel reactor at 100° C. under H$_2$ (500 Psi) for 16 h. After cooling to rt the mixture is filtered through celite, evaporated and purified by flash chromatography on SiO$_2$ to give the de-benzylated piperazine, which is directly used for the next step.

To a mixture of IM-4a (70.0 mg; 171 μmol) and an aliquot of the de-benzylated piperazine from the previous step (45.2 mg; 342 μmol) in DMSO (1.0 mL) is added DIPEA (60.0 μL; 325 μmol) and the mixture is stirred at 100° C. for 3 h. After cooling to rt the mixture is filtered and purified by preparative RP-HPLC under acidic conditions using a MeCN/H$_2$O gradient from 10:90 to 50:50 over 6 min as eluent (column: Sunfire C18; 30×100 mm; 10 μm). The product containing fractions are freeze dried to give 2-{[6-({5-chloro-2-[3-(fluoromethyl)-5-methylpiperazin-1-yl]pyrimidin-4-yl}amino)-1-methyl-2-oxo-1,2-dihydroquinolin-3-yl]oxy}-N-methylacetamide (I-12) (HPLC-MS: $t_{Ret.}$=1.00 min; MS (M+H)$^+$=504; method 1).

C.1.10. Experimental Procedures for the Synthesis of I-13
C.1.10.1. Synthesis of Piperidine Precursors E-8, E-9 and E-10

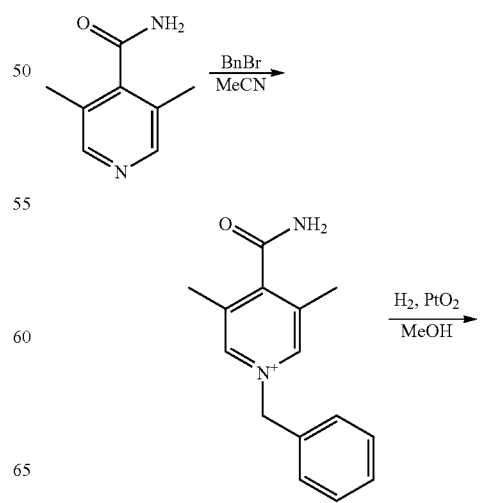

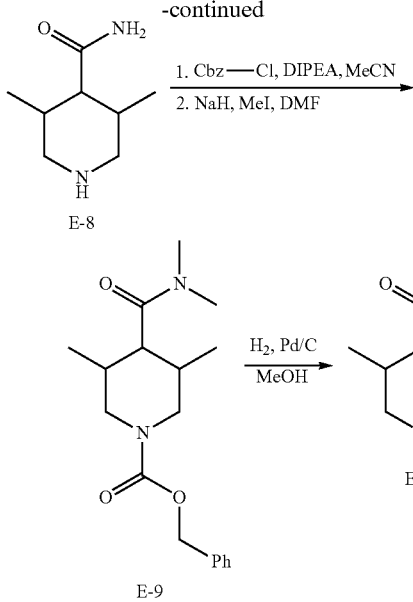

A solution of 3,5-dimethylpyridine-4-carboxamide (1.00 g; 6.66 mmol) and benzyl bromide (1.25 g; 7.33 mmol) in MeCN (10.0 mL) is stirred at 70° C. for 3 h. After cooling to rt the reaction mixture is evaporated and the crude solid is washed with n-pentane to give 1-benzyl-4-carbamoyl-3,5-dimethylpyridin-1-ium (HPLC-MS: $t_{Ret.}$=1.24 min; MS $(M+H)^+$=241; method D), which is used without further purification.

To 1-benzyl-4-carbamoyl-3,5-dimethylpyridin-1-ium (1.00 g; 4.14 mmol) in MeOH (10 mL) is added PtO$_2$ (1.00 g; 4.41 mmol) and the mixture is stirred under an H$_2$ atmosphere (1 bar) at rt for 2 h. The reaction mixture is filtered over celite and evaporated. The crude solid is washed with n-pentane to give 3,5-dimethylpiperidine-4-carboxamide (E-8) (HPLC-MS: $t_{Ret.}$=0.46 min; MS $(M+H)^+$=157; method M), which is directly used.

To a stirred solution of E-8 (600 mg; 3.84 mmol) in MeCN (10.0 mL) and DIPEA (2.48 g; 19.2 mmol) is added benzyl chloroformate (1.97 g; 11.5 mmol) dropwise over a period of 30 min at 0° C. The mixture is heated to 45° C. and stirred for 16 h. After cooling to rt the reaction mixture is diluted with MeCN and saturated NaHCO$_3$ solution and the layers are separated. The organic layer is dried over Na$_2$SO$_4$, filtered and evaporated. The crude material is purified by flash chromatography using a hexane/EtOAc gradient from 50:50 to 0:100 as eluent to give benzyl 4-carbamoyl-3,5-dimethylpiperidine-1-carboxylate.

To a stirred solution of benzyl 4-carbamoyl-3,5-dimethylpiperidine-1-carboxylate (500 mg; 1.72 mmol) in DMF (5.0 mL) is added NaH (248 mg; 10.3 mmol) at 0° C. After 30 min MeI (1.47 g; 10.3 mmol) is added dropwise and stirring is continued at 0° C. for 2 h. The reaction mixture is quenched with ice water and extracted with EtOAc. The combined organic layer is dried over Na$_2$SO$_4$, filtered and evaporated. The crude material is purified by flash chromatography on SiO$_2$ to give benzyl 4-(dimethylcarbamoyl)-3,5-dimethylpiperidine-1-carboxylate (E-9) (HPLC-MS: $t_{Ret.}$=2.56 min; MS $(M+H)^+$=319; method M). Chiral HPLC analytics and NMR indicates that E-9 generated as described above is one diastereoisomerically pure compound.

To E-9 (200 mg; 628 µmol) in MeOH (10 mL) is added Pd (200 mg; 10% on carbon) and the mixture is stirred under an H$_2$ atmosphere (1 bar) at rt for 2 h. The reaction mixture is filtered over celite and evaporated to give N,N,3,5-tetramethylpiperidine-4-carboxamide as a single stereoisomer (E-10) (HPLC-MS: $t_{Ret.}$=0.73 min; MS $(M+H)^+$=185; method M).

C. 1.10.2. Synthesis of I-13

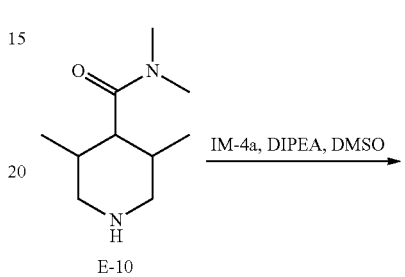

To a mixture of IM-4a (70.0 mg; 171 µmol) and E-10 (63.0 mg; 342 µmol) in DMSO (1.0 mL) is added DIPEA (60.0 µL; 325 µmol) and the mixture is stirred at 100° C. for 3 h. After cooling to rt the mixture is filtered and purified by preparative RP-HPLC under acidic conditions using a MeCN/H$_2$O gradient from 10:90 to 50:50 over 6 min as eluent (column: Sunfire C18; 30×100 mm; 10 µm). The product containing fractions are freeze dried to give 1-[5-chloro-4-({1-methyl-3-[(methylcarbamoyl)-methoxy]-2-oxo-1,2-dihydroquinolin-6-yl}amino)pyrimidin-2-yl]-N,N,3,5-tetramethylpiperidine-4-carboxamide as a single diastereoisomer (I-13) (HPLC-MS: $t_{Ret.}$=1.12 min; MS $(M+H)^+$=556; method 1).

C.1.11. Experimental Procedures for the Synthesis of I-14

C. 1.11.1. Synthesis of Piperidine Precursor E-11

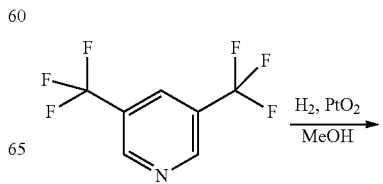

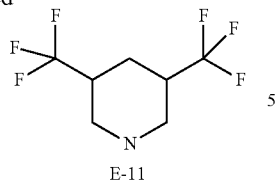

E-11

To a solution of 3,5-bis(trifluoromethyl)pyridine (200 mg; 0.93 mmol) in MeOH (50.0 mL) is added HCl (465 μL; 1.86 mmol; 4 M in 1,4-dioxane) and PtO$_2$ (25.0 mg) and the mixture is stirred under an H$_2$ atmosphere (7 bar) for 18 h at rt. The reaction mixture is filtered through celite and evaporated to give 3,5-bis(trifluoromethyl)piperidine (E-11) as a mixture of stereoisomers.

C.1.11.2. Synthesis of I-14

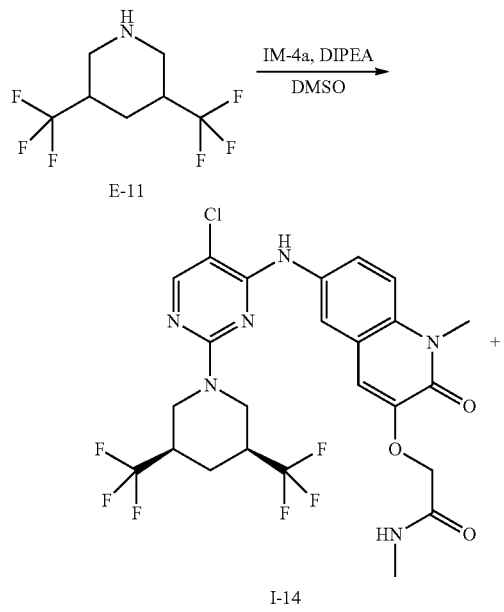

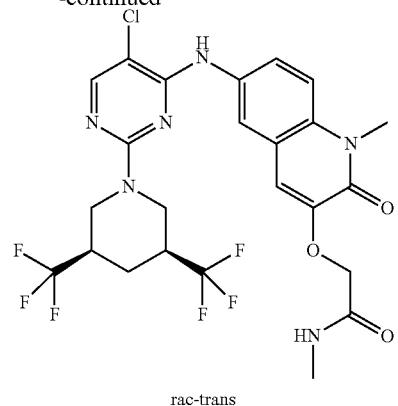

rac-trans

To a mixture of IM-4a (50.0 mg; 122 μmol) and E-11 (54.2 mg; 245 μmol) in DMSO (1.0 mL) is added DIPEA (63.2 μL; 367 μmol) and the mixture is stirred at 100° C. for 18 h. After cooling to rt the mixture is filtered and purified by preparative RP-HPLC under basic conditions using a MeCN/H$_2$O gradient from 40:60 to 80:20 over 6 min as eluent (column: XBridge C18; 30×100 mm; 10 μM). The product containing fractions are freeze dried to give 2-{[6-({2-[cis-3,5-bis(trifluoromethyl)piperidin-1-yl]-5-chloropyrimidin-4-yl}amino)-1-methyl-2-oxo-1,2-dihydroquinolin-3-yl]oxy}-N-methyl-acetamide (I-14) (HPLC-MS: $t_{Ret.}$=1.33 min; MS (M+H)$^+$=593; method 1) and 2-{[6-({2-[trans-3,5-bis(trifluoromethyl)piperidin-1-yl]-5-chloro-pyrimidin-4-yl}amino)-1-methyl-2-oxo-1,2-dihydroquinolin-3-yl]oxy}-N-methyl-acetamide (rac-trans) (HPLC-MS: $t_{Ret.}$=1.39 min; MS (M+H)$^+$=593; method 1).

Analogously to the procedures described under C.1.1. to C.1.11. for the synthesis of I-1 to I-14 additional examples I-15 to I-100 are synthesized starting from the corresponding intermediates IM-4 and commercially available or described amines SM-4.

TABLE 3

Compounds I-1 to I-100

| # | structure | $t_{Ret.}$ HPLC [min] | MS (M + H)$^+$ | method |
|---|---|---|---|---|
| I-1 | 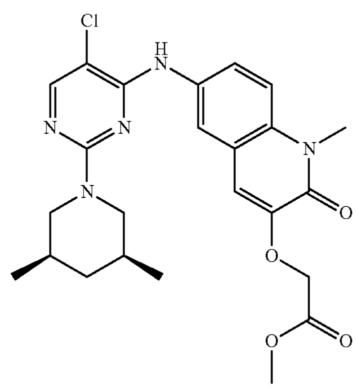 [SMILES: COC(=O)COc1cc2cc(Nc3nc(N4C[C@H](C)C[C@H](C)C4)ncc3Cl)ccc2n(C)c1=O] | 1.48 | 486 | Method 1 |

TABLE 3-continued

Compounds I-1 to I-100

| # | structure | $t_{Ret.}$ HPLC [min] | MS $(M + H)^+$ | method |
|---|---|---|---|---|
| I-2 | 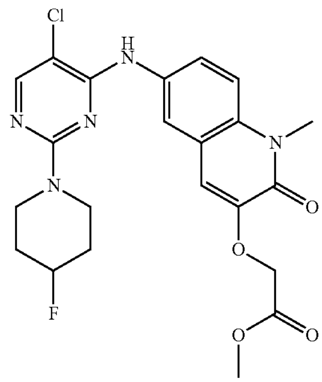 [SMILES: COC(=O)COc1cc2cc(Nc3nc(N4CCC(F)CC4)ncc3Cl)ccc2n(C)c1=O] | 1.23 | 476 | Method 1 |
| I-3 | 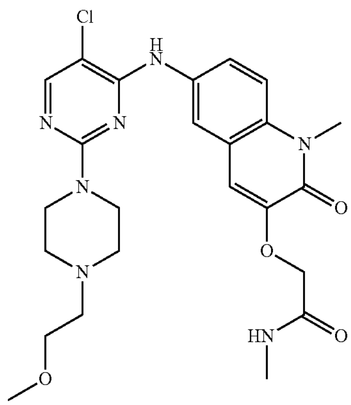 [SMILES: CNC(=O)COc1cc2cc(Nc3nc(N4CCN(CCOC)CC4)ncc3Cl)ccc2n(C)c1=O] | 1.01 | 516 | Method 1 |
| I-4 | 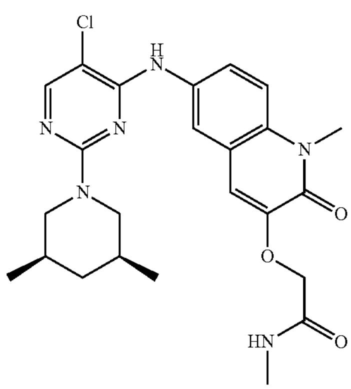 | 1.38 | 485 | Method 1 |
| I-5 | 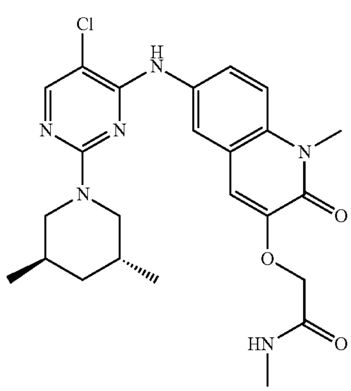 [SMILES: CNC(=O)COc1cc2cc(Nc3nc(N4C[C@H](C)C[C@@H](C)C4)ncc3Cl)ccc2n(C)c1=O] | 1.35 | 485 | Method 1 |

TABLE 3-continued

Compounds I-1 to I-100

| # | structure | $t_{Ret.}$ HPLC [min] | MS $(M + H)^+$ | method |
|---|---|---|---|---|
| I-6 | 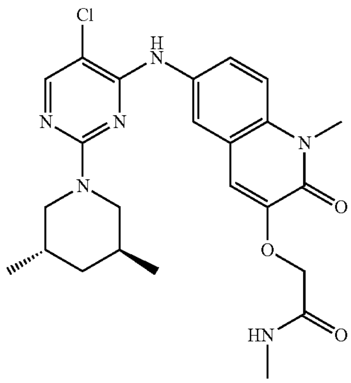 [SMILES: CNC(=O)COc1cc2cc(Nc3nc(N4C[C@@H](C)C[C@H](C)C4)ncc3Cl)ccc2n(C)c1=O] | 1.35 | 485 | Method 1 |
| I-7 | 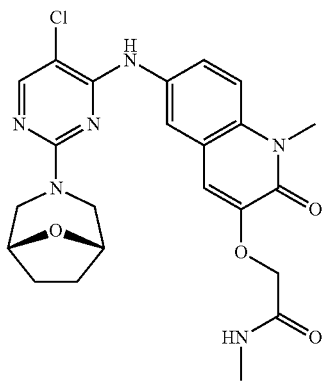 [SMILES: CNC(=O)COc1cc2cc(Nc3nc(N4C[C@H]5CC[C@@H](C4)O5)ncc3Cl)ccc2n(C)c1=O] | 1.05 | 485 | Method 1 |
| I-8 | 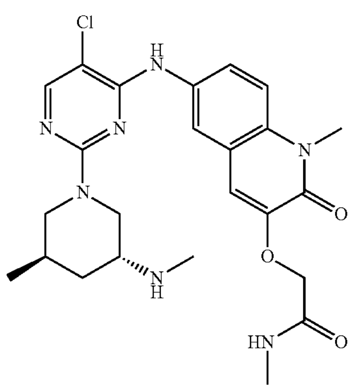 [SMILES: CNC(=O)COc1cc2cc(Nc3nc(N4C[C@H](C)C[C@@H](NC)C4)ncc3Cl)ccc2n(C)c1=O] | 1.01 | 500 | Method 1 |
| I-9 | 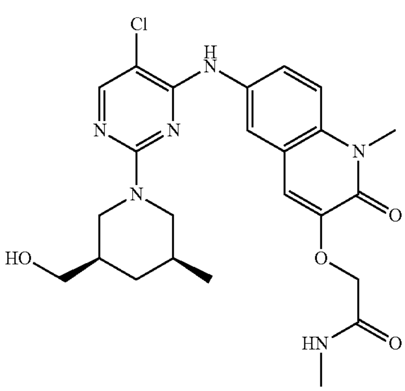 [SMILES: CNC(=O)COc1cc2cc(Nc3nc(N4C[C@@H](C)C[C@@H](CO)C4)ncc3Cl)ccc2n(C)c1=O] | 0.91 | 502 | Method 1 |

TABLE 3-continued

Compounds I-1 to I-100

| # | structure | $t_{Ret.}$ HPLC [min] | MS $(M + H)^+$ | method |
|---|---|---|---|---|
| I-10 | 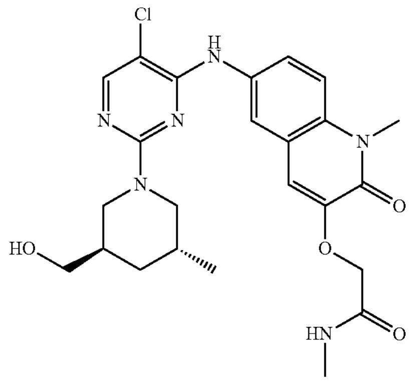 [SMILES: CNC(=O)COc1cc2cc(Nc3nc(N4C[C@H](C)C[C@@H](CO)C4)ncc3Cl)ccc2n(C)c1=O] | 0.91 | 502 | Method 1 |
| I-11 | 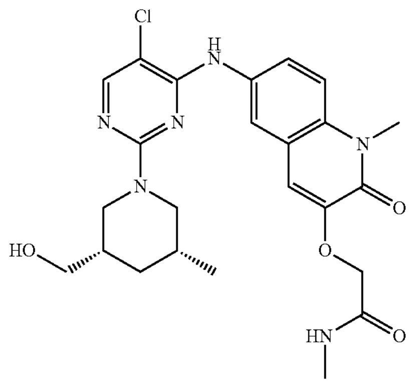 [SMILES: CNC(=O)COc1cc2cc(Nc3nc(N4C[C@H](C)C[C@H](CO)C4)ncc3Cl)ccc2n(C)c1=O] | 0.91 | 502 | Method 1 |
| I-12 | 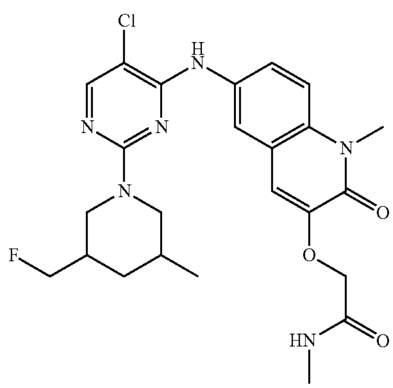 [SMILES: CNC(=O)COc1cc2cc(Nc3nc(N4CC(C)CC(CF)C4)ncc3Cl)ccc2n(C)c1=O] | 1.00 | 504 | Method 1 |
| I-13 | 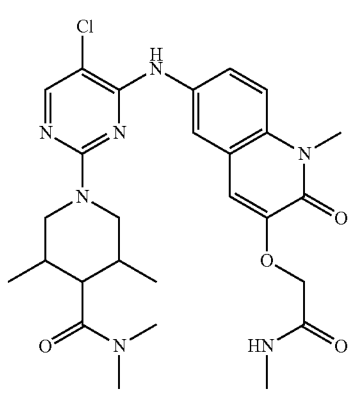 [SMILES: CNC(=O)COc1cc2cc(Nc3nc(N4CC(C)C(C(=O)N(C)C)C(C)C4)ncc3Cl)ccc2n(C)c1=O] | 1.12 | 556 | Method 1 |

TABLE 3-continued

Compounds I-1 to I-100

| # | structure | t_Ret. HPLC [min] | MS (M + H)+ | method |
|---|---|---|---|---|
| I-14 | 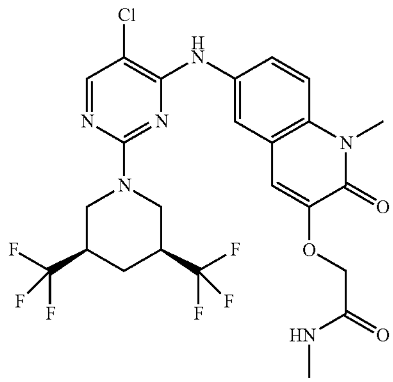 [SMILES: CNC(=O)COc1cc2cc(Nc3nc(N4C[C@H](C(F)(F)F)C[C@H](C(F)(F)F)C4)ncc3Cl)ccc2n(C)c1=O] | 1.33 | 593 | Method 1 |
| I-15 | 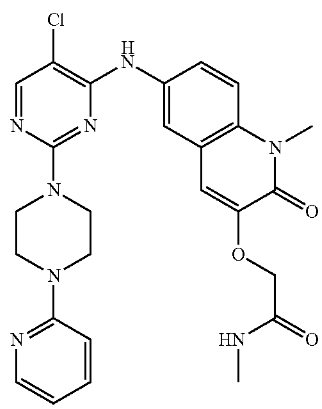 [SMILES: CNC(=O)COc1cc2cc(Nc3nc(N4CCN(c5ccccn5)CC4)ncc3Cl)ccc2n(C)c1=O] | 1.16 | 535 | Method 1 |
| I-16 | 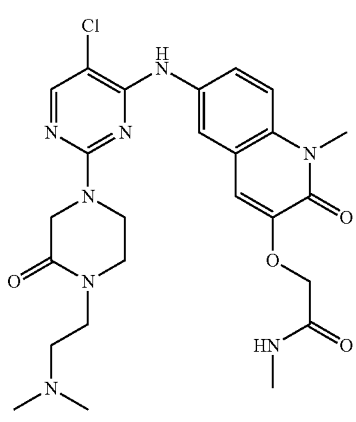 [SMILES: CNC(=O)COc1cc2cc(Nc3nc(N4CCN(CCN(C)C)C(=O)C4)ncc3Cl)ccc2n(C)c1=O] | 0.95 | 543 | Method 1 |

TABLE 3-continued

Compounds I-1 to I-100

| # | structure | $t_{Ret.}$ HPLC [min] | MS $(M + H)^+$ | method |
|---|---|---|---|---|
| I-17 | 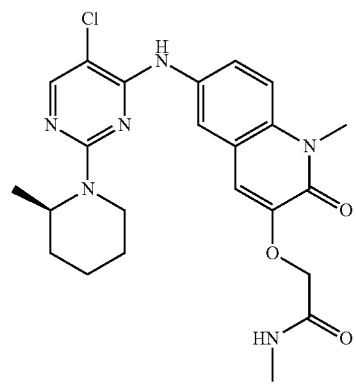 [SMILES: CNC(=O)COc1cc2cc(Nc3nc(N4CCCC[C@H]4C)ncc3Cl)ccc2n(C)c1=O] | 1.25 | 471 | Method 1 |
| I-18 | 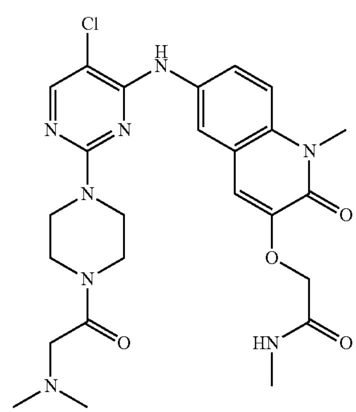 [SMILES: CNC(=O)COc1cc2cc(Nc3nc(N4CCN(C(=O)CN(C)C)CC4)ncc3Cl)ccc2n(C)c1=O] | 0.98 | 543 | Method 1 |
| I-19 | 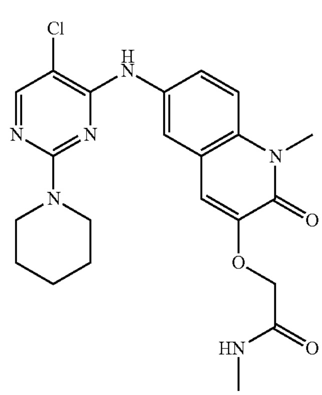 | 1.19 | 457 | Method 1 |

TABLE 3-continued

Compounds I-1 to I-100

| # | structure | $t_{Ret.}$ HPLC [min] | MS $(M + H)^+$ | method |
|---|---|---|---|---|
| I-20 | 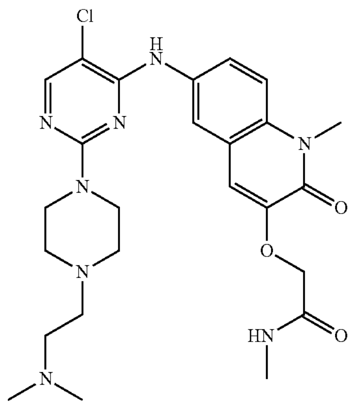 [SMILES: CNC(=O)COc1cc2cc(Nc3nc(N4CCN(CCN(C)C)CC4)ncc3Cl)ccc2n(C)c1=O] | 1.06 | 530 | Method 1 |
| I-21 | 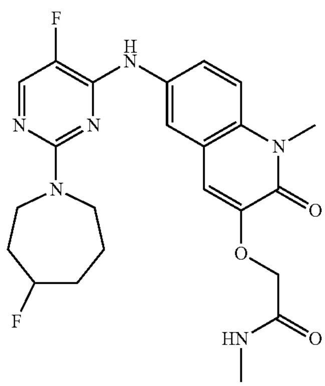 [SMILES: CNC(=O)COc1cc2cc(Nc3nc(N4CCCC(F)CC4)ncc3F)ccc2n(C)c1=O] | 1.08 | 473 | Method 1 |
| I-22 | 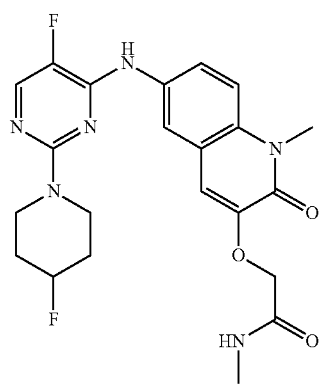 [SMILES: CNC(=O)COc1cc2cc(Nc3nc(N4CCC(F)CC4)ncc3F)ccc2n(C)c1=O] | 1.06 | 459 | Method 1 |
| I-23 | 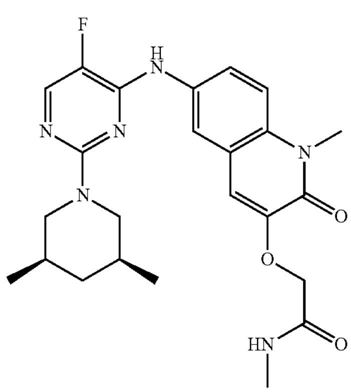 [SMILES: CNC(=O)COc1cc2cc(Nc3nc(N4C[C@H](C)C[C@H](C)C4)ncc3F)ccc2n(C)c1=O] | 1.27 | 469 | Method 1 |

TABLE 3-continued

Compounds I-1 to I-100

| # | structure | $t_{Ret.}$ HPLC [min] | MS $(M + H)^+$ | method |
|---|---|---|---|---|
| I-24 | 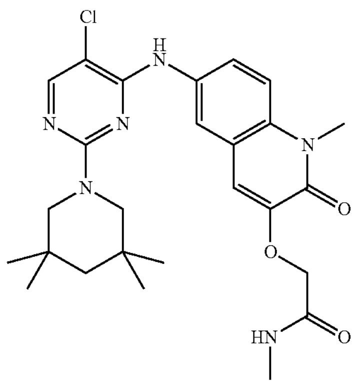 [SMILES: CNC(=O)COc1cc2cc(Nc3nc(N4CC(C)(C)CC(C)(C)C4)ncc3Cl)ccc2n(C)c1=O] | 1.48 | 513 | Method 1 |
| I-25 | 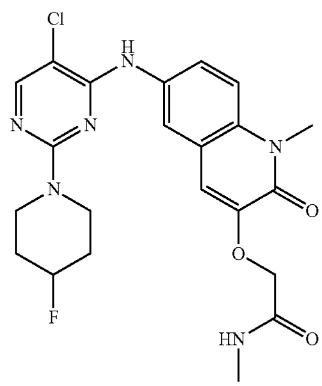 | 1.15 | 475 | Method 1 |
| I-26 | 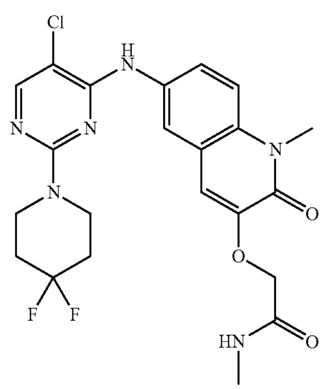 | 1.18 | 493 | Method 1 |
| I-27 | 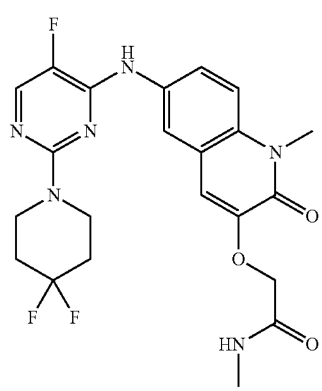 [SMILES: CNC(=O)COc1cc2cc(Nc3nc(N4CCC(F)(F)CC4)ncc3F)ccc2n(C)c1=O] | 1.13 | 477 | Method 1 |

TABLE 3-continued

Compounds I-1 to I-100

| # | structure | $t_{Ret.}$ HPLC [min] | MS $(M + H)^+$ | method |
|---|---|---|---|---|
| I-28 | 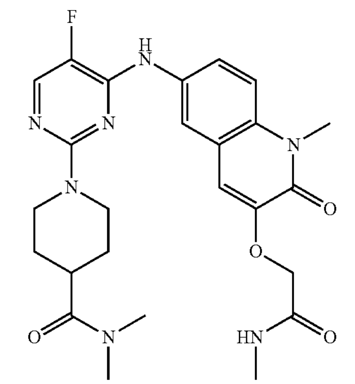 [SMILES: CNC(=O)COc1cc2cc(Nc3nc(N4CCC(C(=O)N(C)C)CC4)ncc3F)ccc2n(C)c1=O] | 0.93 | 512 | Method 1 |
| I-29 | 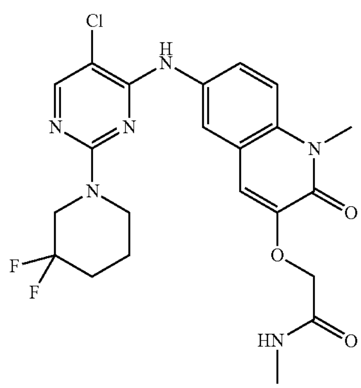 [SMILES: CNC(=O)COc1cc2cc(Nc3nc(N4CCCC(F)(F)C4)ncc3Cl)ccc2n(C)c1=O] | 1.17 | 493 | Method 1 |
| I-30 | 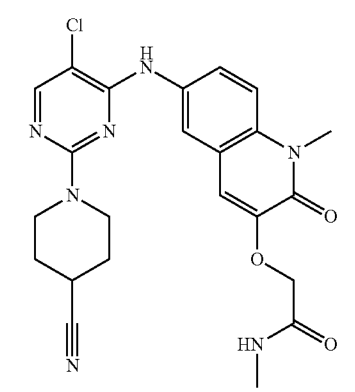 [SMILES: CNC(=O)COc1cc2cc(Nc3nc(N4CCC(C#N)CC4)ncc3Cl)ccc2n(C)c1=O] | 1.08 | 482 | Method 1 |
| I-31 | 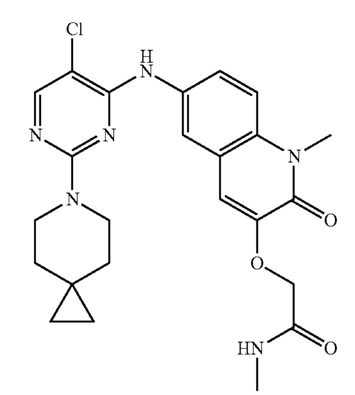 [SMILES: CNC(=O)COc1cc2cc(Nc3nc(N4CCC5(CC4)CC5)ncc3Cl)ccc2n(C)c1=O] | 1.31 | 483 | Method 1 |

TABLE 3-continued

Compounds I-1 to I-100

| # | structure | $t_{Ret.}$ HPLC [min] | MS $(M + H)^+$ | method |
|---|---|---|---|---|
| I-32 | 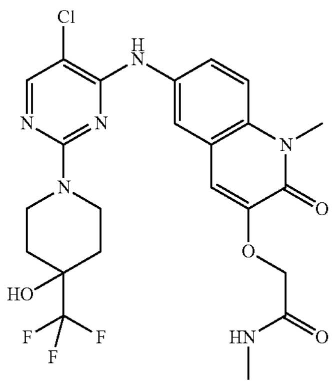 [SMILES: CNC(=O)COc1cc2cc(Nc3nc(N4CCC(O)(C(F)(F)F)CC4)ncc3Cl)ccc2n(C)c1=O] | 1.14 | 541 | Method 1 |
| I-33 | 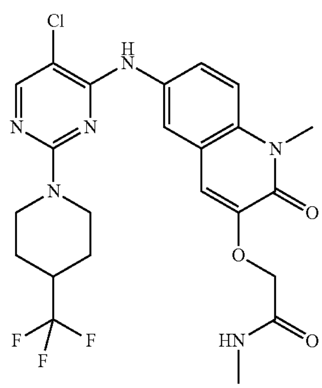 [SMILES: CNC(=O)COc1cc2cc(Nc3nc(N4CCC(C(F)(F)F)CC4)ncc3Cl)ccc2n(C)c1=O] | 1.30 | 525 | Method 1 |
| I-34 | 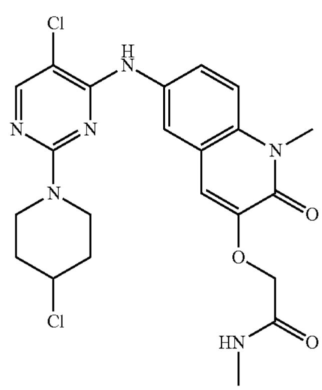 | 1.24 | 491 | Method 1 |
| I-35 | 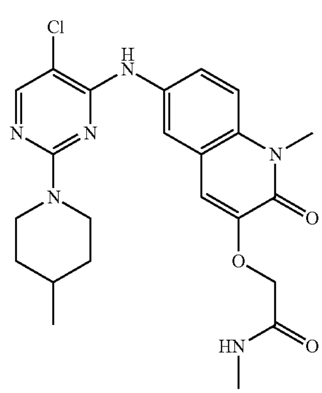 | 1.30 | 471 | Method 1 |

TABLE 3-continued
Compounds I-1 to I-100
| # | structure | $t_{Ret.}$ HPLC [min] | MS $(M + H)^+$ | method |
|---|---|---|---|---|
| I-36 | 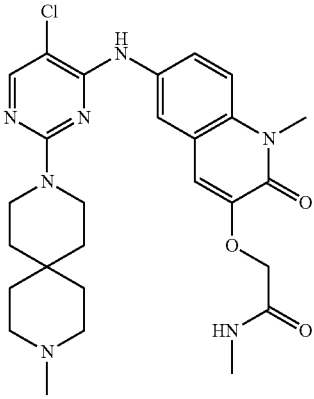 [SMILES: CNC(=O)COc1cc2cc(Nc3nc(N4CCC5(CCN(C)CC5)CC4)ncc3Cl)ccc2n(C)c1=O] | 1.15 | 540 | Method 1 |
| I-37 | 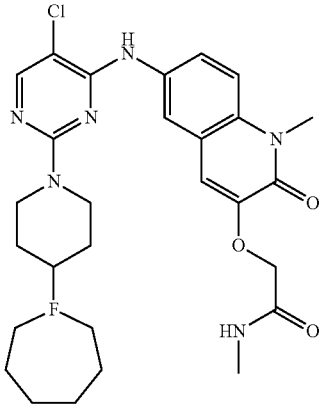 | 1.23 | 554 | Method 1 |
| I-38 | 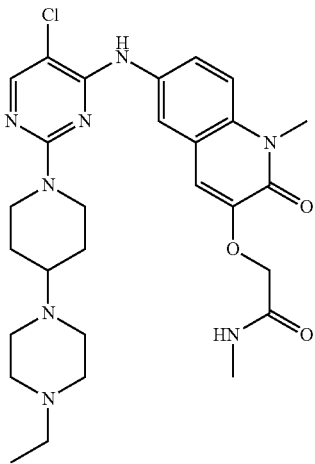 [SMILES: CCN1CCN(C2CCN(c3ncc(Cl)c(Nc4ccc5c(c4)cc(OCC(=O)NC)c(=O)n5C)n3)CC2)CC1] | 1.03 | 570 | Method 1 |

TABLE 3-continued
Compounds I-1 to I-100
| # | structure | t_{Ret.} HPLC [min] | MS (M + H)+ | method |
|---|---|---|---|---|
| I-39 | 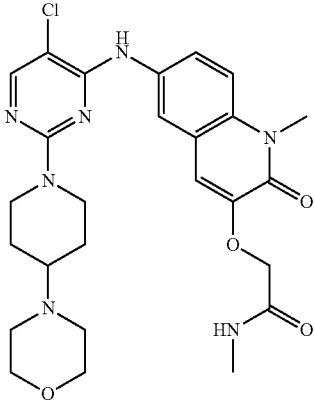 [SMILES: CNC(=O)COc1cc2cc(Nc3nc(N4CCC(N5CCOCC5)CC4)ncc3Cl)ccc2n(C)c1=O] | 1.02 | 542 | Method 1 |
| I-40 | 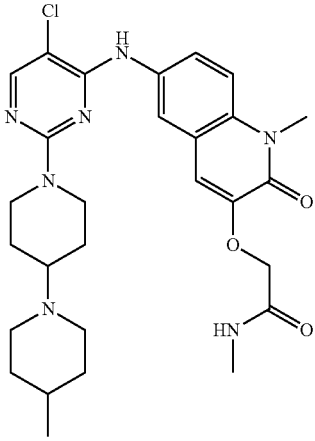 [SMILES: CNC(=O)COc1cc2cc(Nc3nc(N4CCC(N5CCC(C)CC5)CC4)ncc3Cl)ccc2n(C)c1=O] | 1.24 | 554 | Method 1 |
| I-41 | 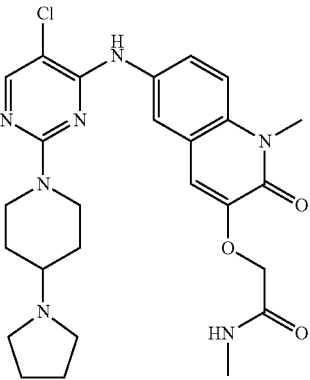 [SMILES: CNC(=O)COc1cc2cc(Nc3nc(N4CCC(N5CCCC5)CC4)ncc3Cl)ccc2n(C)c1=O] | 1.11 | 526 | Method 1 |

TABLE 3-continued

Compounds I-1 to I-100

| # | structure | $t_{Ret.}$ HPLC [min] | MS $(M + H)^+$ | method |
|---|---|---|---|---|
| I-42 | 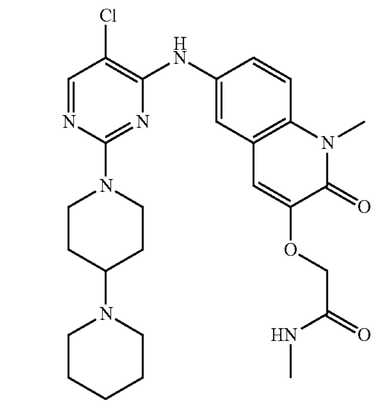 [SMILES: CNC(=O)COc1cc2cc(Nc3nc(N4CCC(N5CCCCC5)CC4)ncc3Cl)ccc2n(C)c1=O] | 1.17 | 540 | Method 1 |
| I-43 | 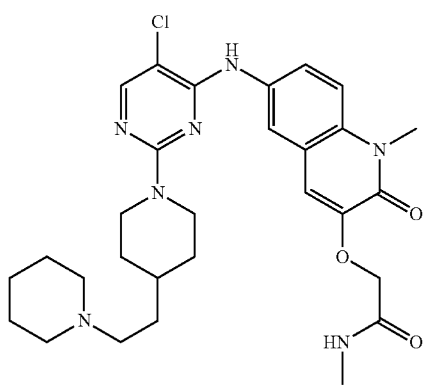 [SMILES: CNC(=O)COc1cc2cc(Nc3nc(N4CCC(CCN5CCCCC5)CC4)ncc3Cl)ccc2n(C)c1=O] | 1.26 | 568 | Method 1 |
| I-44 | 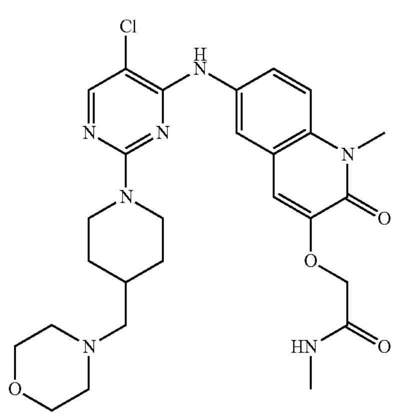 [SMILES: CNC(=O)COc1cc2cc(Nc3nc(N4CCC(CN5CCOCC5)CC4)ncc3Cl)ccc2n(C)c1=O] | 1.12 | 557 | Method 1 |

TABLE 3-continued
Compounds I-1 to I-100
| # | structure | $t_{Ret.}$ HPLC [min] | MS $(M + H)^+$ | method |
|---|---|---|---|---|
| I-45 | 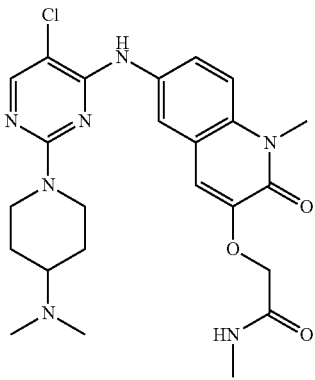 [SMILES: CNC(=O)COc1cc2cc(Nc3nc(N4CCC(N(C)C)CC4)ncc3Cl)ccc2n(C)c1=O] | 1.09 | 500 | Method 1 |
| I-46 | 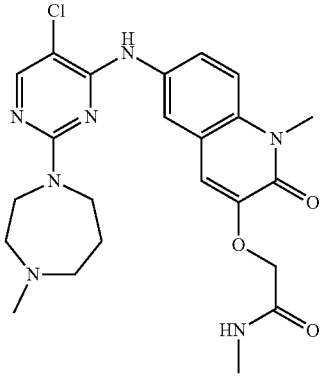 [SMILES: CNC(=O)COc1cc2cc(Nc3nc(N4CCCN(C)CC4)ncc3Cl)ccc2n(C)c1=O] | 1.04 | 486 | Method 1 |
| I-47 | 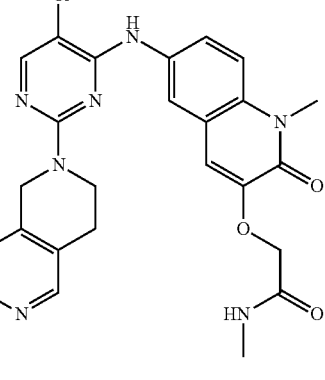 | 1.07 | 506 | Method 1 |
| I-48 | 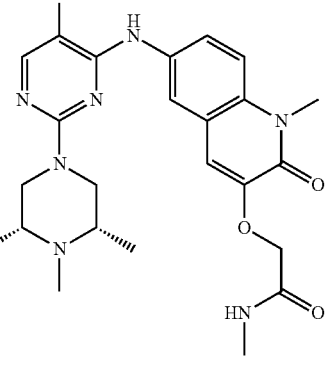 | 1.06 | 500 | Method 1 |

TABLE 3-continued

Compounds I-1 to I-100

| # | structure | $t_{Ret.}$ HPLC [min] | MS $(M + H)^+$ | method |
|---|---|---|---|---|
| I-49 | 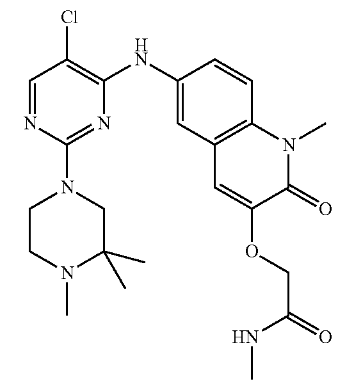 [SMILES: CNC(=O)COc1cc2cc(Nc3nc(N4CCN(C)C(C)(C)C4)ncc3Cl)ccc2n(C)c1=O] | 1.05 | 500 | Method 1 |
| I-50 | 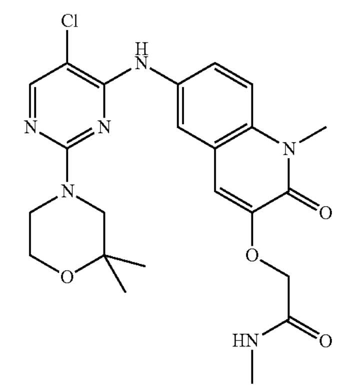 [SMILES: CNC(=O)COc1cc2cc(Nc3nc(N4CCOC(C)(C)C4)ncc3Cl)ccc2n(C)c1=O] | 1.10 | 487 | Method 1 |
| I-51 | 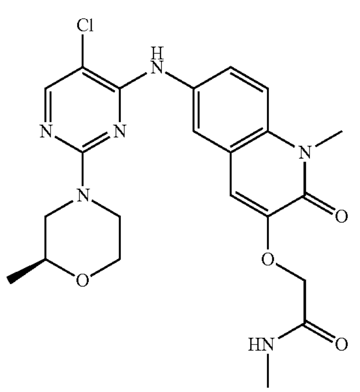 | 1.07 | 473 | Method 1 |
| I-52 | 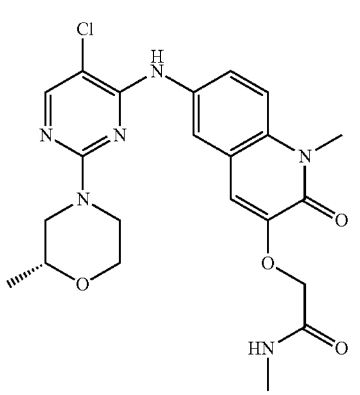 | 1.07 | 473 | Method 1 |

TABLE 3-continued

Compounds I-1 to I-100

| # | structure | t_Ret. HPLC [min] | MS (M + H)+ | method |
|---|---|---|---|---|
| I-53 | 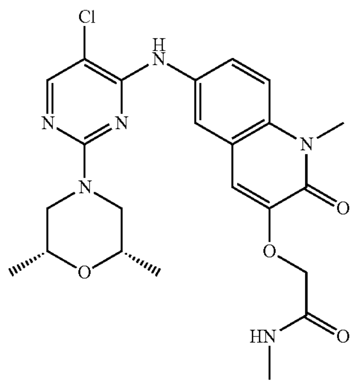 | 1.13 | 487 | Method 1 |
| I-54 | 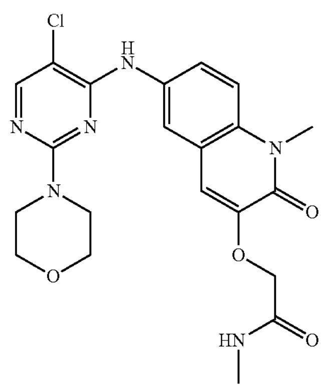 [SMILES: CNC(=O)COc1cc2cc(Nc3nc(N4CCOCC4)ncc3Cl)ccc2n(C)c1=O] | 1.02 | 459 | Method 1 |
| I-55 | 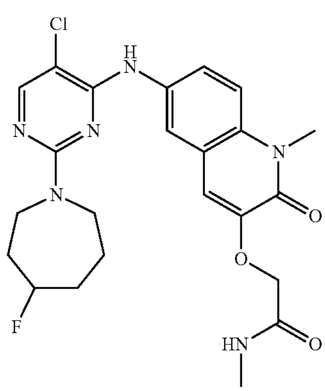 | 1.17 | 489 | Method 1 |
| I-56 | 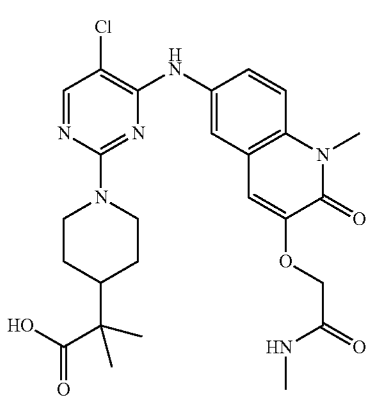 [SMILES: CNC(=O)COc1cc2cc(Nc3nc(N4CCC(C(C)(C)C(=O)O)CC4)ncc3Cl)ccc2n(C)c1=O] | 0.87 | 543 | Method 1 |

TABLE 3-continued

Compounds I-1 to I-100

| # | structure | $t_{Ret.}$ HPLC [min] | MS $(M + H)^+$ | method |
|---|---|---|---|---|
| I-57 | 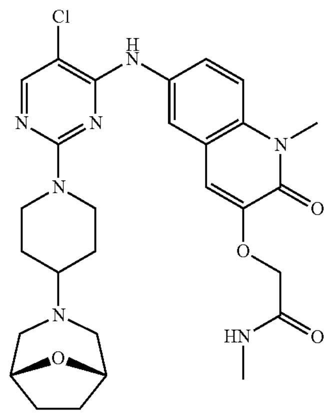 [SMILES: CNC(=O)COc1cc2cc(Nc3nc(N4CCC(N5C[C@H]6CC[C@@H](C5)O6)CC4)ncc3Cl)ccc2n(C)c1=O] | 1.17 | 568 | Method 1 |
| I-58 | 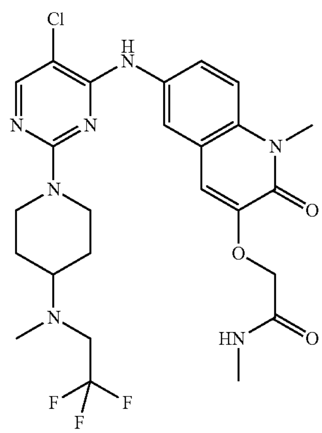 [SMILES: CNC(=O)COc1cc2cc(Nc3nc(N4CCC(N(C)CC(F)(F)F)CC4)ncc3Cl)ccc2n(C)c1=O] | 1.27 | 568 | Method 1 |
| I-59 | 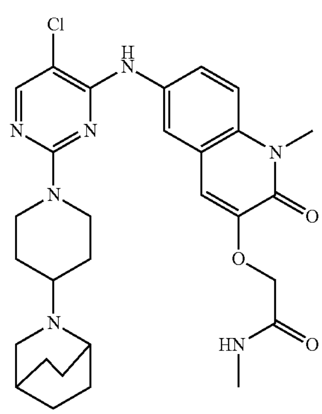 [SMILES: CNC(=O)COc1cc2cc(Nc3nc(N4CCC(N5CC6CCC5CC6)CC4)ncc3Cl)ccc2n(C)c1=O] | 1.07 | 566 | Method 1 |

TABLE 3-continued

Compounds I-1 to I-100

| # | structure | t$_{Ret.}$ HPLC [min] | MS (M + H)$^+$ | method |
|---|---|---|---|---|
| I-60 | 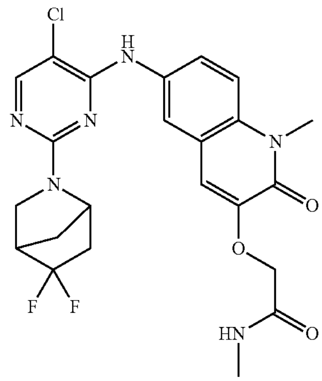 [SMILES: CNC(=O)COc1cc2cc(Nc3nc(N4CC5CC4CC5(F)F)ncc3Cl)ccc2n(C)c1=O] | 1.13 | 505 | Method 1 |
| I-61 | 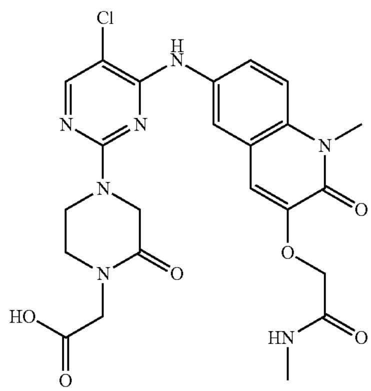 [SMILES: CNC(=O)COc1cc2cc(Nc3nc(N4CCN(CC(=O)O)C(=O)C4)ncc3Cl)ccc2n(C)c1=O] | 0.75 | 530 | Method 1 |
| I-62 | 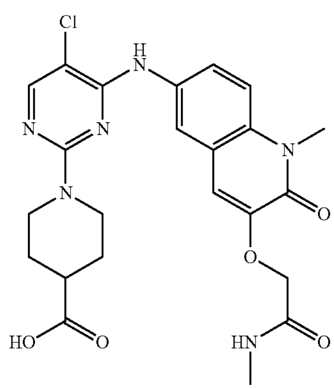 [SMILES: CNC(=O)COc1cc2cc(Nc3nc(N4CCC(C(=O)O)CC4)ncc3Cl)ccc2n(C)c1=O] | 0.78 | 501 | Method 1 |
| I-63 | 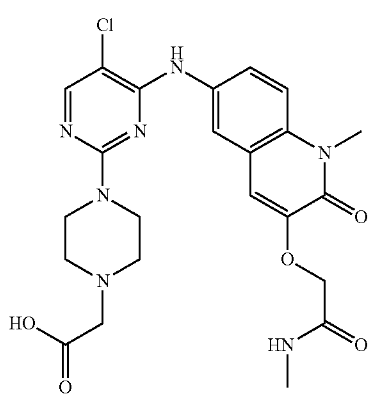 [SMILES: CNC(=O)COc1cc2cc(Nc3nc(N4CCN(CC(=O)O)CC4)ncc3Cl)ccc2n(C)c1=O] | 0.76 | 516 | Method 1 |

TABLE 3-continued

Compounds I-1 to I-100

| # | structure | $t_{Ret.}$ HPLC [min] | MS $(M + H)^+$ | method |
|---|---|---|---|---|
| I-64 | 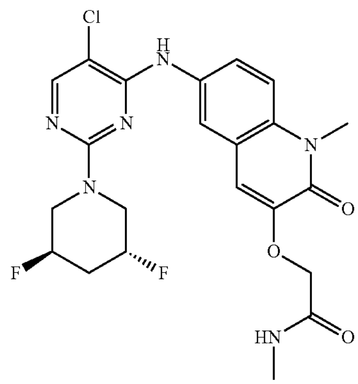 [SMILES: CNC(=O)COc1cc2cc(Nc3nc(N4C[C@H](F)C[C@@H](F)C4)ncc3Cl)ccc2n(C)c1=O] | 1.08 | 493 | Method 1 |
| I-65 | 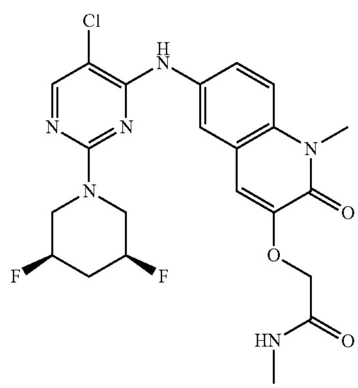 [SMILES: CNC(=O)COc1cc2cc(Nc3nc(N4C[C@H](F)C[C@H](F)C4)ncc3Cl)ccc2n(C)c1=O] | 1.02 | 493 | Method 1 |
| I-66 | 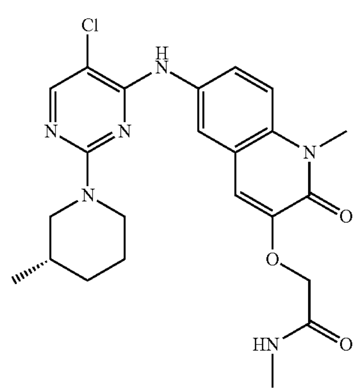 | 1.29 | 471 | Method 1 |
| I-67 | 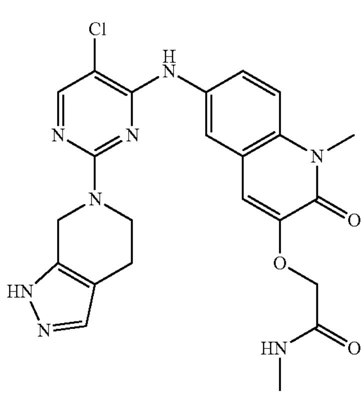 [SMILES: CNC(=O)COc1cc2cc(Nc3nc(N4CCc5cn[nH]c5C4)ncc3Cl)ccc2n(C)c1=O] | 0.99 | 495 | Method 1 |

TABLE 3-continued

Compounds I-1 to I-100

| # | structure | t_Ret. HPLC [min] | MS (M + H)+ | method |
|---|---|---|---|---|
| I-68 | 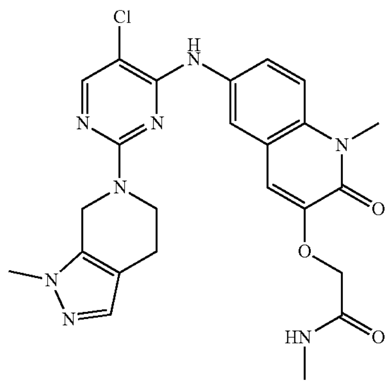 | 1.05 | 509 | Method 1 |
| I-69 | 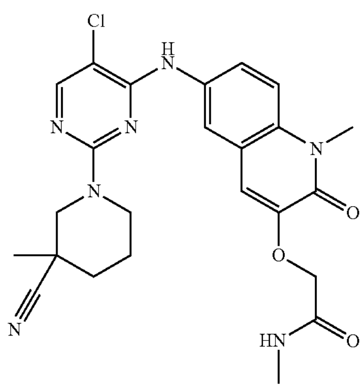 | 1.10 | 496 | Method 1 |
| I-70 | 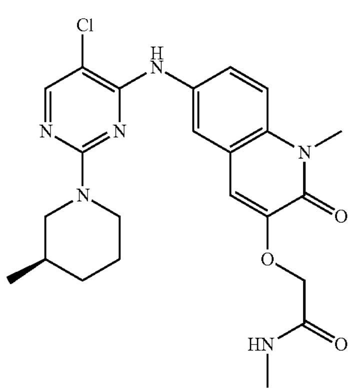 | 1.29 | 471 | Method 1 |
| I-71 | 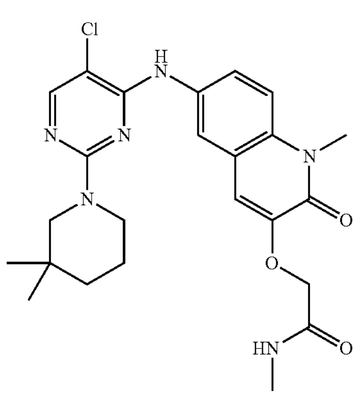 | 1.34 | 485 | Method 1 |

TABLE 3-continued

Compounds I-1 to I-100

| # | structure | t$_{Ret.}$ HPLC [min] | MS (M + H)$^+$ | method |
|---|---|---|---|---|
| I-72 | 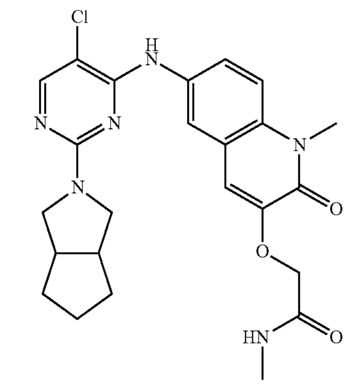 [SMILES: CNC(=O)COc1cc2cc(Nc3nc(N4CC5CCCC5C4)ncc3Cl)ccc2n(C)c1=O] | 1.25 | 483 | Method 1 |
| I-73 | 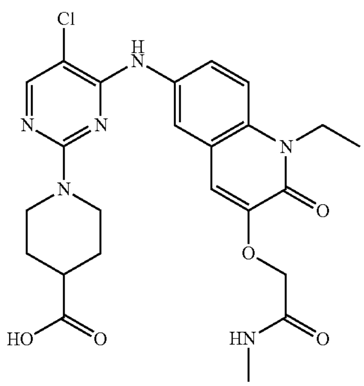 [SMILES: CCn1c(=O)c(OCC(=O)NC)cc2cc(Nc3nc(N4CCC(C(=O)O)CC4)ncc3Cl)ccc21] | 0.81 | 515 | Method 1 |
| I-74 | 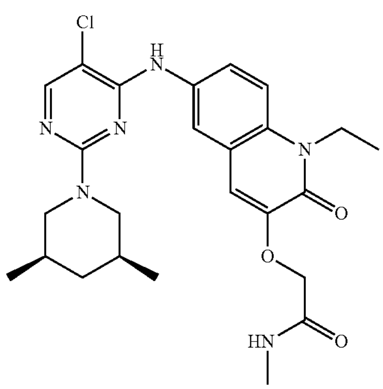 [SMILES: CCn1c(=O)c(OCC(=O)NC)cc2cc(Nc3nc(N4C[C@H](C)C[C@H](C)C4)ncc3Cl)ccc21] | 1.44 | 499 | Method 1 |
| I-75 | 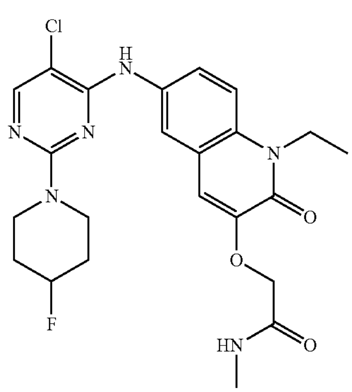 [SMILES: CCn1c(=O)c(OCC(=O)NC)cc2cc(Nc3nc(N4CCC(F)CC4)ncc3Cl)ccc21] | 1.20 | 489 | Method 1 |

TABLE 3-continued

Compounds I-1 to I-100

| # | structure | t_Ret. HPLC [min] | MS (M + H)+ | method |
|---|---|---|---|---|
| I-76 | 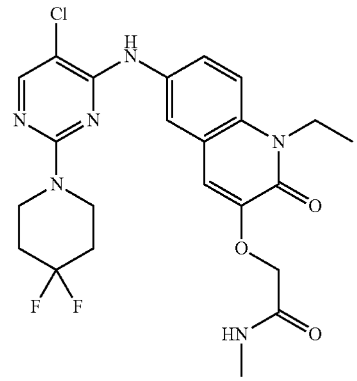 [SMILES: CCn1c(=O)c(OCC(=O)NC)cc2cc(Nc3nc(N4CCC(F)(F)CC4)ncc3Cl)ccc21] | 1.25 | 507 | Method 1 |
| I-77 | 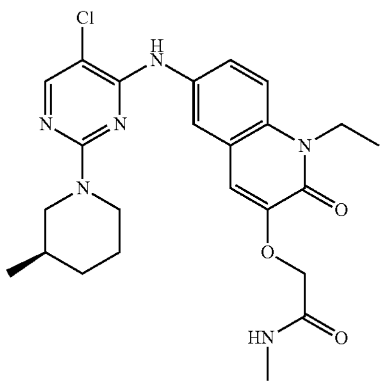 [SMILES: CCn1c(=O)c(OCC(=O)NC)cc2cc(Nc3nc(N4CCC[C@@H](C)C4)ncc3Cl)ccc21] | 1.35 | 485 | Method 1 |
| I-78 | 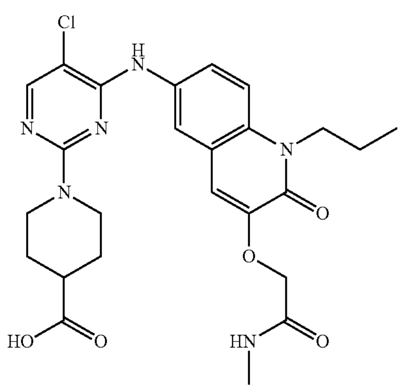 [SMILES: CCCn1c(=O)c(OCC(=O)NC)cc2cc(Nc3nc(N4CCC(C(=O)O)CC4)ncc3Cl)ccc21] | 0.86 | 529 | Method 1 |
| I-79 | 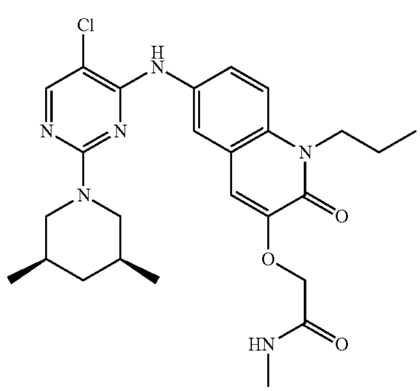 [SMILES: CCCn1c(=O)c(OCC(=O)NC)cc2cc(Nc3nc(N4C[C@H](C)C[C@H](C)C4)ncc3Cl)ccc21] | 1.52 | 513 | Method 1 |

TABLE 3-continued

Compounds I-1 to I-100

| # | structure | $t_{Ret.}$ HPLC [min] | MS $(M + H)^+$ | method |
|---|---|---|---|---|
| I-80 | 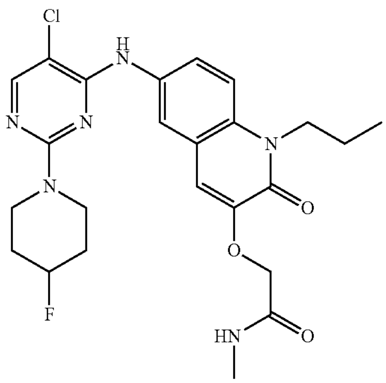 [SMILES: CCCn1c(=O)c(OCC(=O)NC)cc2cc(Nc3nc(N4CCC(F)CC4)ncc3Cl)ccc21] | 1.27 | 503 | Method 1 |
| I-81 | 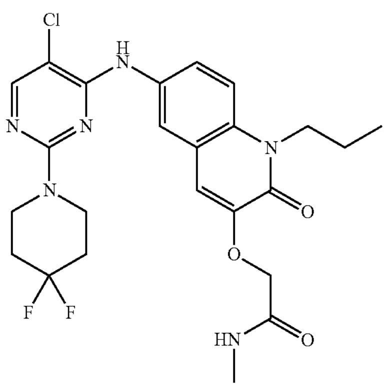 [SMILES: CCCn1c(=O)c(OCC(=O)NC)cc2cc(Nc3nc(N4CCC(F)(F)CC4)ncc3Cl)ccc21] | 1.33 | 521 | Method 1 |
| I-82 | 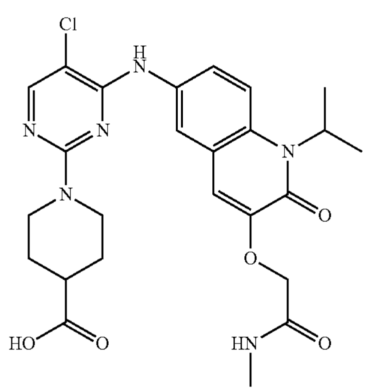 [SMILES: CNC(=O)COc1cc2cc(Nc3nc(N4CCC(C(=O)O)CC4)ncc3Cl)ccc2n(C(C)C)c1=O] | 0.87 | 529 | Method 1 |
| I-83 | 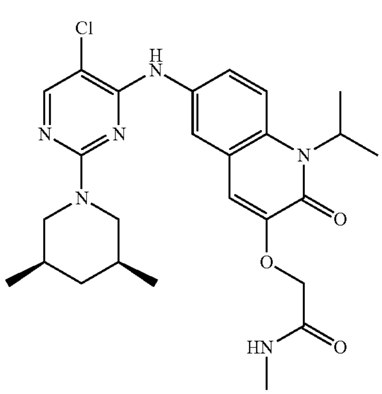 [SMILES: CNC(=O)COc1cc2cc(Nc3nc(N4C[C@H](C)C[C@H](C)C4)ncc3Cl)ccc2n(C(C)C)c1=O] | 1.50 | 513 | Method 1 |

TABLE 3-continued

Compounds I-1 to I-100

| # | structure | t_Ret. HPLC [min] | MS (M + H)+ | method |
|---|---|---|---|---|
| I-84 | 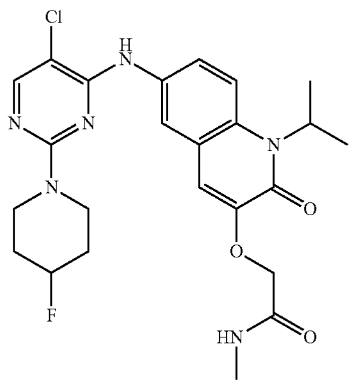 [SMILES: CNC(=O)COc1cc2cc(Nc3nc(N4CCC(F)CC4)ncc3Cl)ccc2n(C(C)C)c1=O] | 1.26 | 503 | Method 1 |
| I-85 | 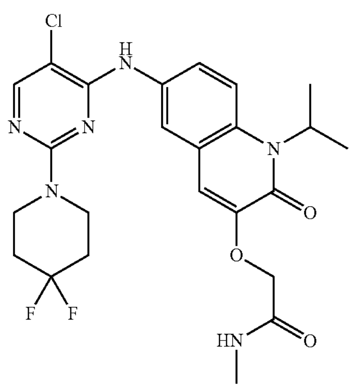 [SMILES: CNC(=O)COc1cc2cc(Nc3nc(N4CCC(F)(F)CC4)ncc3Cl)ccc2n(C(C)C)c1=O] | 1.31 | 521 | Method 1 |
| I-86 | 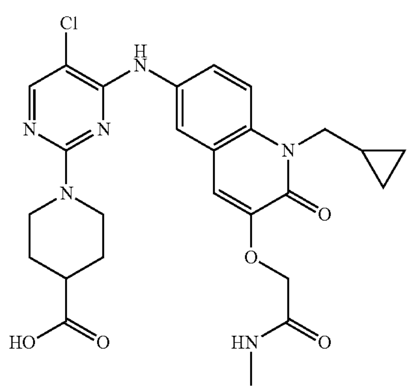 [SMILES: CNC(=O)COc1cc2cc(Nc3nc(N4CCC(C(=O)O)CC4)ncc3Cl)ccc2n(CC2CC2)c1=O] | 0.88 | 541 | Method 1 |
| I-97 | 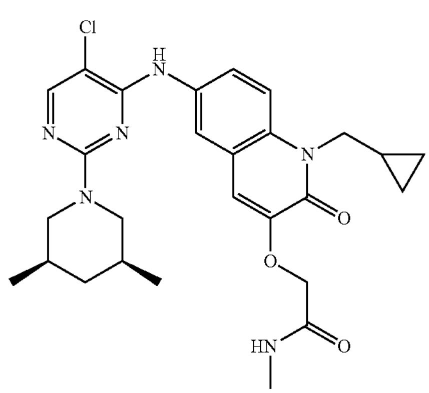 [SMILES: CNC(=O)COc1cc2cc(Nc3nc(N4C[C@H](C)C[C@H](C)C4)ncc3Cl)ccc2n(CC2CC2)c1=O] | 1.53 | 525 | Method 1 |

TABLE 3-continued
Compounds I-1 to I-100
| # | structure | $t_{Ret.}$ HPLC [min] | MS (M + H)$^+$ | method |
|---|---|---|---|---|
| I-88 | 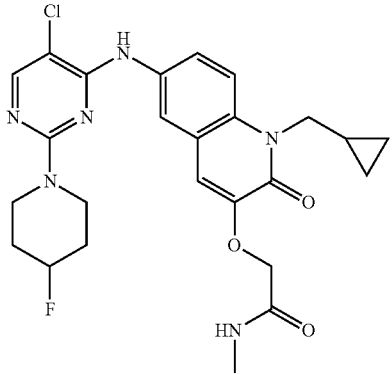 [SMILES: CNC(=O)COc1cc2cc(Nc3nc(N4CCC(F)CC4)ncc3Cl)ccc2n(CC2CC2)c1=O] | 1.29 | 515 | Method 1 |
| I-89 | 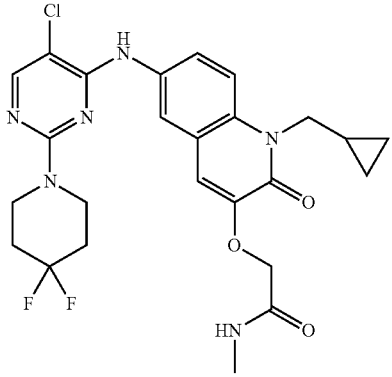 [SMILES: CNC(=O)COc1cc2cc(Nc3nc(N4CCC(F)(F)CC4)ncc3Cl)ccc2n(CC2CC2)c1=O] | 1.34 | 533 | Method 1 |
| I-90 | 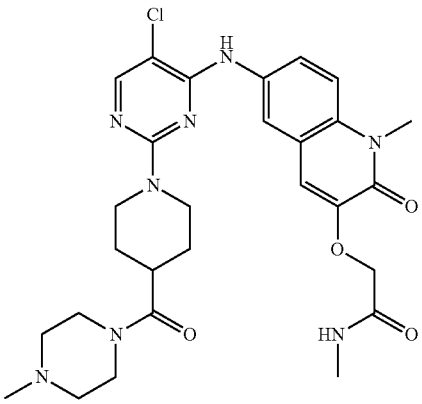 | 0.99 | 583 | Method 1 |

TABLE 3-continued
| | Compounds I-1 to I-100 | | | |
|---|---|---|---|---|
| # | structure | t_Ret. HPLC [min] | MS (M + H)+ | method |
| I-91 | 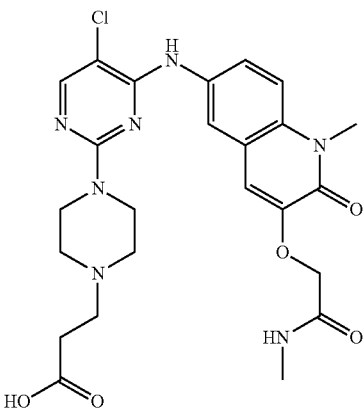 [SMILES: CNC(=O)COc1cc2cc(Nc3nc(N4CCN(CCC(=O)O)CC4)ncc3Cl)ccc2n(C)c1=O] | 0.77 | 530 | Method 1 |
| I-92 | 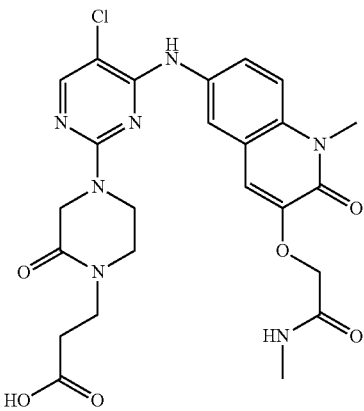 [SMILES: CNC(=O)COc1cc2cc(Nc3nc(N4CCN(CCC(=O)O)C(=O)C4)ncc3Cl)ccc2n(C)c1=O] | 0.73 | 544 | Method 1 |
| I-93 | 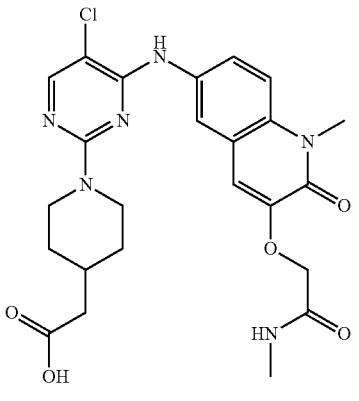 [SMILES: CNC(=O)COc1cc2cc(Nc3nc(N4CCC(CC(=O)O)CC4)ncc3Cl)ccc2n(C)c1=O] | 0.79 | 515 | Method 1 |

TABLE 3-continued

Compounds I-1 to I-100

| # | structure | $t_{Ret.}$ HPLC [min] | MS $(M + H)^+$ | method |
|---|---|---|---|---|
| I-94 | 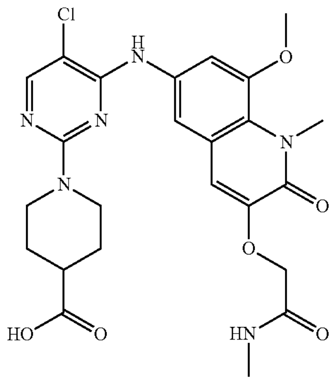 [SMILES: CNC(=O)COc1cc2cc(Nc3nc(N4CCC(C(=O)O)CC4)ncc3Cl)cc(OC)c2n(C)c1=O] | 0.82 | 531 | Method 1 |
| I-95 | 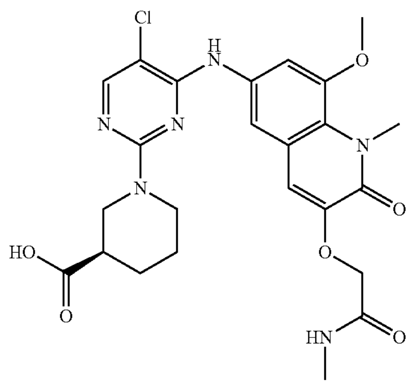 [SMILES: CNC(=O)COc1cc2cc(Nc3nc(N4CCC[C@@H](C(=O)O)C4)ncc3Cl)cc(OC)c2n(C)c1=O] | 0.82 | 531 | Method 1 |
| I-96 | 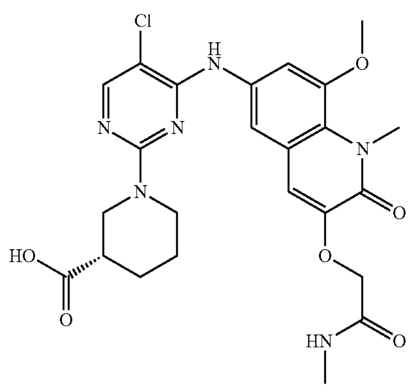 [SMILES: CNC(=O)COc1cc2cc(Nc3nc(N4CCC[C@H](C(=O)O)C4)ncc3Cl)cc(OC)c2n(C)c1=O] | 0.82 | 531 | Method 1 |
| I-97 | 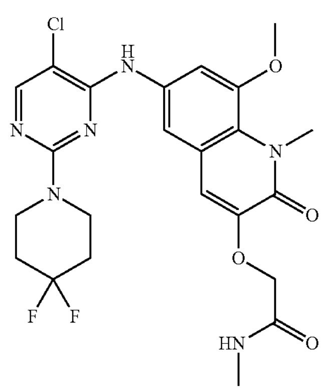 [SMILES: CNC(=O)COc1cc2cc(Nc3nc(N4CCC(F)(F)CC4)ncc3Cl)cc(OC)c2n(C)c1=O] | 1.27 | 523 | Method 1 |

TABLE 3-continued
Compounds I-1 to I-100
| # | structure | $t_{Ret.}$ HPLC [min] | MS $(M + H)^+$ | method |
|---|---|---|---|---|
| I-98 | 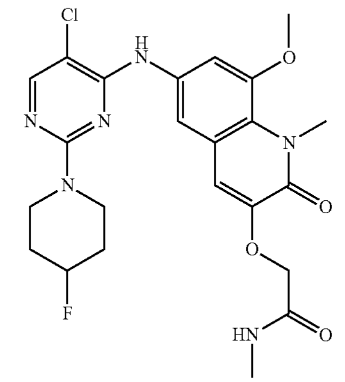 [SMILES: CNC(=O)COc1cc2cc(Nc3nc(N4CCC(F)CC4)ncc3Cl)cc(OC)c2n(C)c1=O] | 1.21 | 505 | Method 1 |
| I-99 | 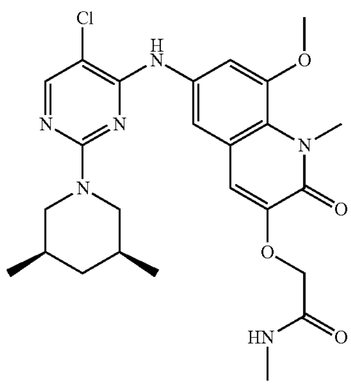 | 1.46 | 515 | Method 1 |
| I-100 | 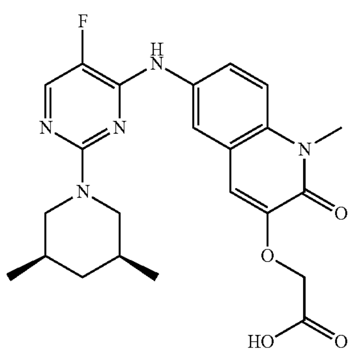 | 1.02 | 456 | Method 1 |
C.1.12. General Experimental Procedure for the Synthesis of I-101 to I-121
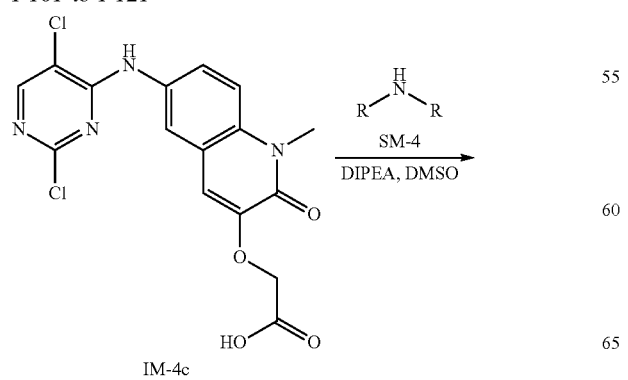
IM-4c
-continued
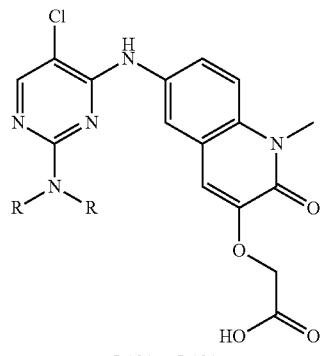
I-101 to I-121

To a solution of the amine SM-4 (300 μL; 50.0 μmol of a DMSO stock solution) which contains DIPEA (19.4 mg; 150 μmol, 3 eq.) in a MTP is added a solution of IM-4c (200 μL; 10 μmol of a DMSO stock solution) which contains DIPEA (1.38 mg; 10 μmol, 1 eq.). The mixture is shaken for 4 h at 100° C. and then for 18 h at rt. The volatiles are evaporated in a vacuum centrifuge. For amines SM-4 bearing additional Boc-protected or tBu ester moieties 400 μL of TFA/MeCN (1:1) is added and the plate is shaken for additional 2 h at rt. The volatiles are evaporated again and all probes are taken up in 400 μL DMF for analysis (20 μL aliquot). The volatiles are evaporated in a vacuum centrifuge at 60° C. to give the compounds I-101 to I-121 with a purity of at least 60% (majority is >80%).

TABLE 4

Compounds I-101 to I-121

| # | structure | $t_{RET.}$ HPLC [min] | MS (M + H)$^+$ | method |
|---|---|---|---|---|
| I-101 | 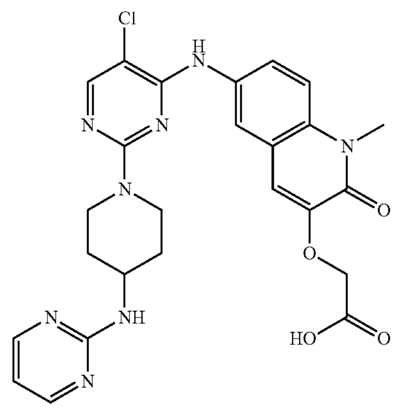 [SMILES: Cn1c(=O)c(OCC(=O)O)cc2cc(Nc3nc(N4CCC(Nc5ncccn5)CC4)ncc3Cl)ccc21] | 0.41 | 537 | Method 2 |
| I-102 | 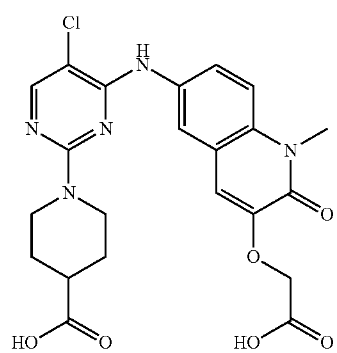 [SMILES: Cn1c(=O)c(OCC(=O)O)cc2cc(Nc3nc(N4CCC(C(=O)O)CC4)ncc3Cl)ccc21] | 0.53 | 488 | Method 2 |
| I-103 | 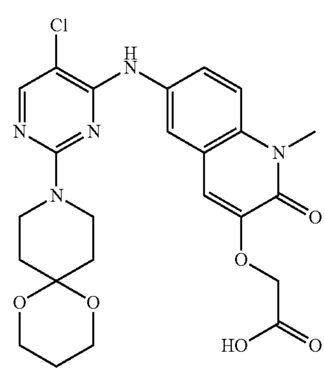 [SMILES: Cn1c(=O)c(OCC(=O)O)cc2cc(Nc3nc(N4CCC5(CC4)OCCCO5)ncc3Cl)ccc21] | 0.48 | 516 | Method 2 |

TABLE 4-continued

Compounds I-101 to I-121

| # | structure | t_RET. HPLC [min] | MS (M + H)+ | method |
|---|---|---|---|---|
| I-104 | 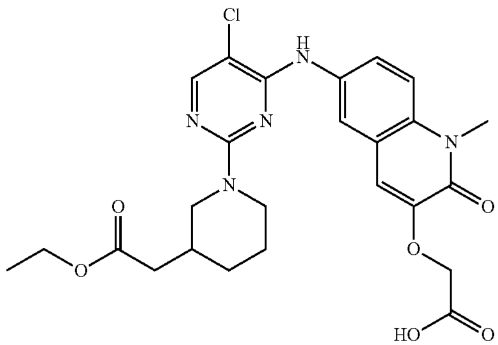 [SMILES: CCOC(=O)CC1CCCN(c2ncc(Cl)c(Nc3ccc4c(c3)cc(OCC(=O)O)c(=O)n4C)n2)C1] | 0.55 | 530 | Method 2 |
| I-105 | 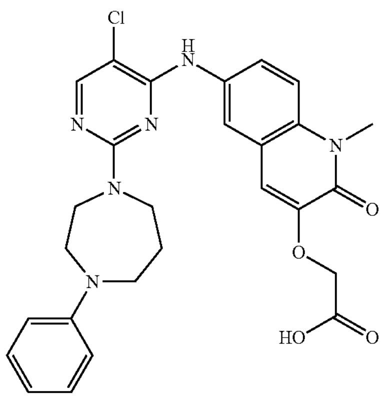 [SMILES: Cn1c(=O)c(OCC(=O)O)cc2cc(Nc3nc(N4CCCN(c5ccccc5)CC4)ncc3Cl)ccc21] | 0.58 | 535 | Method 2 |
| I-106 | 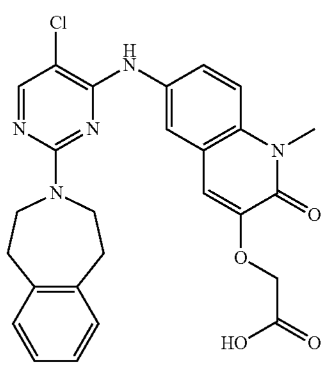 [SMILES: Cn1c(=O)c(OCC(=O)O)cc2cc(Nc3nc(N4CCc5ccccc5CC4)ncc3Cl)ccc21] | 0.59 | 506 | Method 2 |
| I-107 | 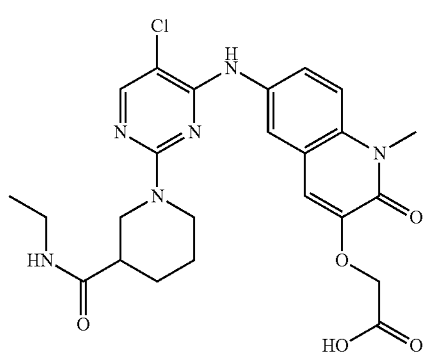 [SMILES: CCNC(=O)C1CCCN(c2ncc(Cl)c(Nc3ccc4c(c3)cc(OCC(=O)O)c(=O)n4C)n2)C1] | 0.44 | 515 | Method 2 |

TABLE 4-continued
Compounds I-101 to I-121
| # | structure | $t_{RET.}$ HPLC [min] | MS $(M + H)^+$ | method |
|---|---|---|---|---|
| I-108 | 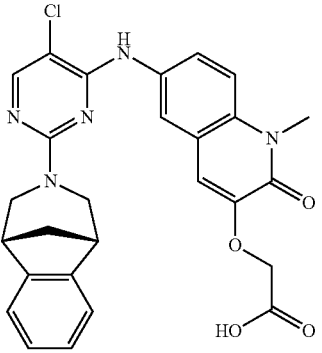 [SMILES: Cn1c(=O)c(OCC(=O)O)cc2cc(Nc3nc(N4C[C@H]5C[C@@H](C4)c4ccccc45)ncc3Cl)ccc21] | 0.57 | 518 | Method 2 |
| I-109 | 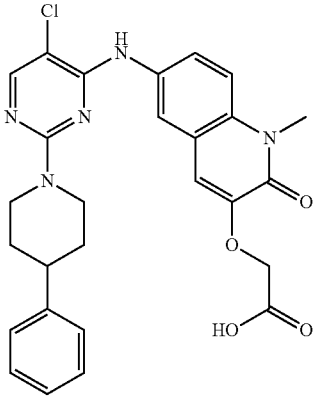 [SMILES: Cn1c(=O)c(OCC(=O)O)cc2cc(Nc3nc(N4CCC(c5ccccc5)CC4)ncc3Cl)ccc21] | 0.62 | 520 | Method 2 |
| I-110 | 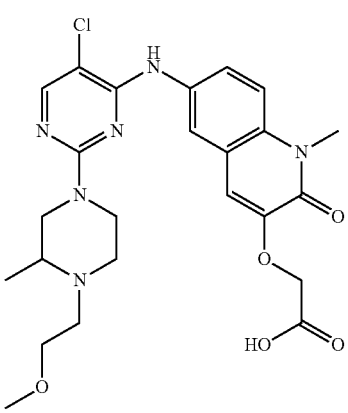 [SMILES: COCCN1CCN(c2ncc(Cl)c(Nc3ccc4c(c3)cc(OCC(=O)O)c(=O)n4C)n2)CC1C] | 0.43 | 517 | Method 2 |
| I-111 | 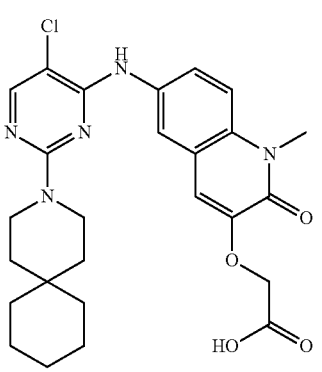 | 0.66 | 512 | Method 2 |

TABLE 4-continued

Compounds I-101 to I-121

| # | structure | t_RET. HPLC [min] | MS (M + H)+ | method |
|---|---|---|---|---|
| I-112 | 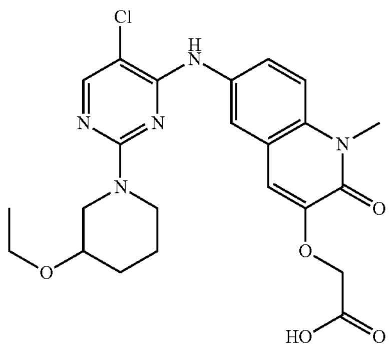 [SMILES: CCOC1CCCN(c2ncc(Cl)c(Nc3ccc4c(c3)cc(OCC(=O)O)c(=O)n4C)n2)C1] | 0.49 | 488 | Method 2 |
| I-113 | 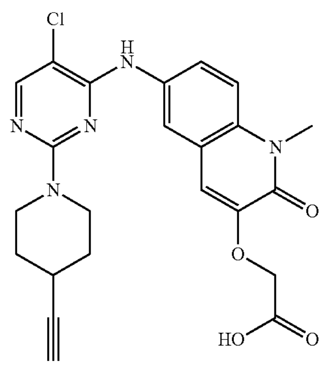 [SMILES: C#CC1CCN(c2ncc(Cl)c(Nc3ccc4c(c3)cc(OCC(=O)O)c(=O)n4C)n2)CC1] | 0.52 | 468 | Method 2 |
| I-114 | 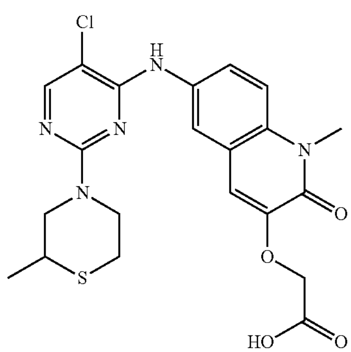 | 0.55 | 476 | Method 2 |
| I-115 | 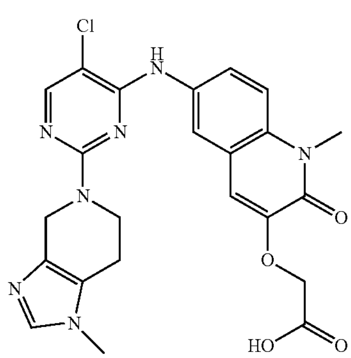 [SMILES: Cn1cnc2c1CCN(c1ncc(Cl)c(Nc3ccc4c(c3)cc(OCC(=O)O)c(=O)n4C)n1)C2] | 0.41 | 496 | Method 2 |

TABLE 4-continued

Compounds I-101 to I-121

| # | structure | $t_{RET.}$ HPLC [min] | MS $(M + H)^+$ | method |
|---|---|---|---|---|
| I-116 | 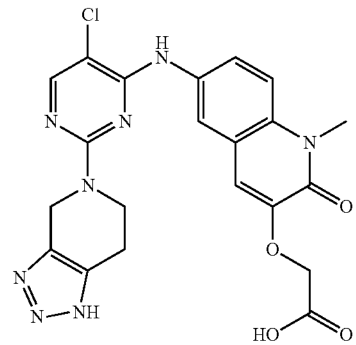 [SMILES: Cn1c(=O)c(OCC(=O)O)cc2cc(Nc3nc(N4CCc5[nH]nnc5C4)ncc3Cl)ccc21] | 0.45 | 483 | Method 2 |
| I-117 | 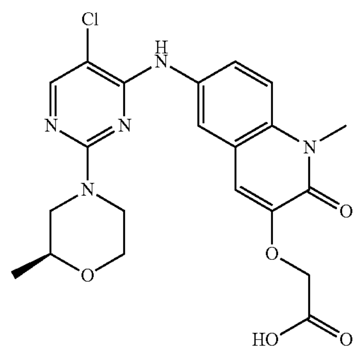 [SMILES: C[C@H]1CN(c2ncc(Cl)c(Nc3ccc4c(c3)cc(OCC(=O)O)c(=O)n4C)n2)CCO1] | 0.48 | 460 | Method 2 |
| I-118 | 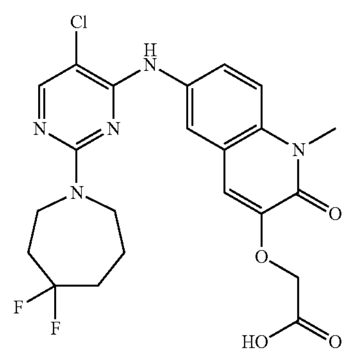 [SMILES: Cn1c(=O)c(OCC(=O)O)cc2cc(Nc3nc(N4CCCC(F)(F)CC4)ncc3Cl)ccc21] | 0.52 | 494 | Method 2 |
| I-119 | 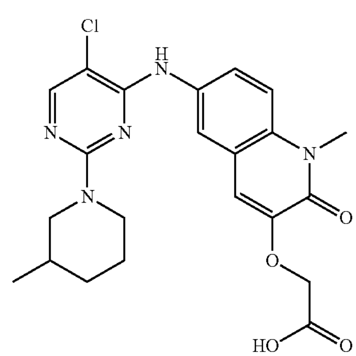 [SMILES: CC1CCCN(c2ncc(Cl)c(Nc3ccc4c(c3)cc(OCC(=O)O)c(=O)n4C)n2)C1] | 0.53 | 458 | Method 2 |

TABLE 4-continued
Compounds I-101 to I-121
| # | structure | $t_{RET.}$ HPLC [min] | MS $(M + H)^+$ | method |
|---|---|---|---|---|
| I-120 | 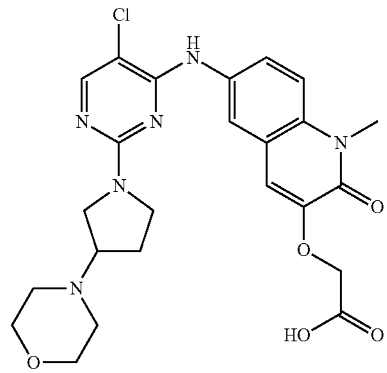 [SMILES: Cn1c(=O)c(OCC(=O)O)cc2cc(Nc3nc(N4CCC(N5CCOCC5)C4)ncc3Cl)ccc21] | 0.34 | 515 | Method 2 |
| I-121 | 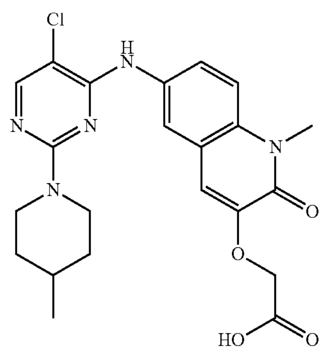 [SMILES: CC1CCN(c2ncc(Cl)c(Nc3ccc4c(c3)cc(OCC(=O)O)c(=O)n4C)n2)CC1] | 0.54 | 458 | Method 2 |
C.1.13. General Experimental Procedure for the Synthesis of I-122 to I-128
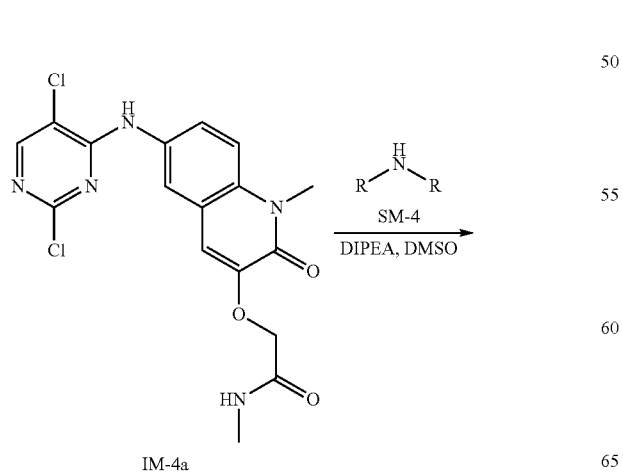
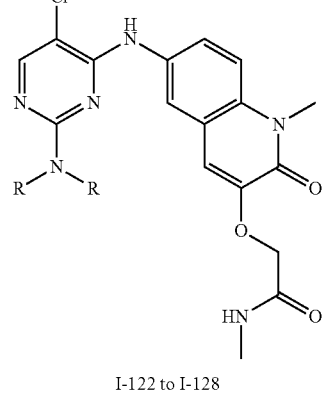
To a solution of the amine SM-4 (150 μL; 60.0 μmol of a DMSO stock solution) which contains DIPEA (41.5 μL; 240 μmol) in a MTP is added a solution of IM-4a (200 μL; 10 μmol of a DMSO stock solution). The mixture is shaken for 12 h at 100° C. After cooling to rt a 15 μL aliquot is taken for analysis and the volatiles are evaporated in a vacuum centrifuge to give the compounds I-122 to I-128 with a purity of at least 60% (majority is >80%).

C.1.14. Experimental Procedures for the Synthesis of I-129 and I-130

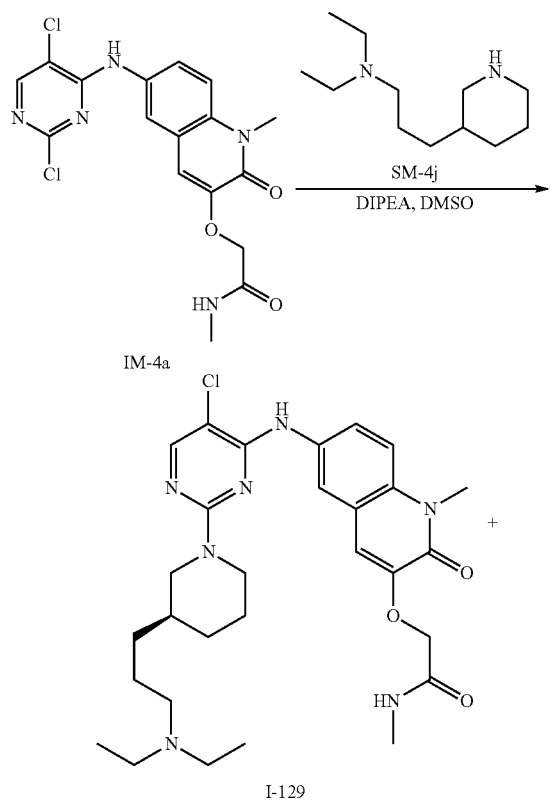

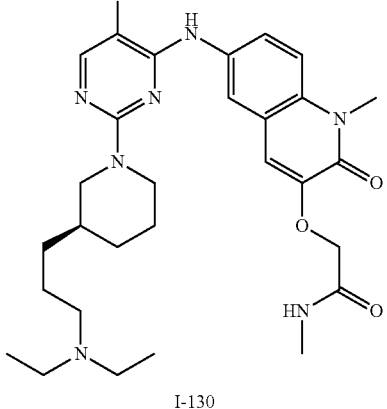

I-130

To IM-4a (300 mg; 735 μmol) and SM-4j (437 mg; 2.21 mmol) in DMSO (7.0 mL) is added DIPEA (381 μL; 2.21 mmol) and the mixture is stirred at 100° C. for 1 h. After cooling to rt the mixture is purified by preparative RP-HPLC under basic conditions to give a racemic mixture of I-129 and I-130. The enantiomers are separated by preparative chiral SFC (column: Chiralpak IA; 250×420 mm; 5 μm; total flow: 60 mL/min; backpressure: 150 bar; load/injection: 300 μL of a 10 mg/mL compound solution in MeOH/DCM=2:1) using 35% EtOH (with 20 mM $NH_3$) as co-eluent. The product containing fractions are evaporated to give 2-{[6-({5-chloro-2-[(3R)-3-[3-(diethylamino)propyl]piperidin-1-yl]pyrimidin-4-yl}amino)-1-methyl-2-oxo-1,2-dihydro-quinolin-3-yl]oxy}-N-methylacetamide (I-129) (SFC: $t_{Ret.}$=4.00 min; 90% ee) and 2-{[6-({5-chloro-2-[(3S)-3-[3-(diethylamino)propyl]piperidin-1-yl]pyrimidin-4-yl}amino)-1-methyl-2-oxo-1,2-dihydroquinolin-3-yl]oxy}-N-methylacetamide (I-130) (SFC: $t_{Ret.}$=4.95 min; 85% ee). The absolute configuration of the enantiomers is randomly assigned. Analytical SFC method to determine retention times: Agilent 1260 SFC with DAD and MS; eluent: EtOH (with 20 mM $NH_3$)/$CO_2$=35:65; column: ChiralArt Amylose SA; 250×4.6 mm; 5 μm; total flow: 4 mL/min; backpressure: 150 bar.

TABLE 5

| | Compounds I-122 to I-130 | | | |
|---|---|---|---|---|
| # | structure | $t_{Ret.}$ HPLC [min] | MS (M + H)+ | method |
| I-122 | | 0.53 | 550 | Method 2 |

TABLE 5-continued

Compounds I-122 to I-130

| # | structure | $t_{Ret.}$ HPLC [min] | MS $(M + H)^+$ | method |
|---|---|---|---|---|
| I-123 | 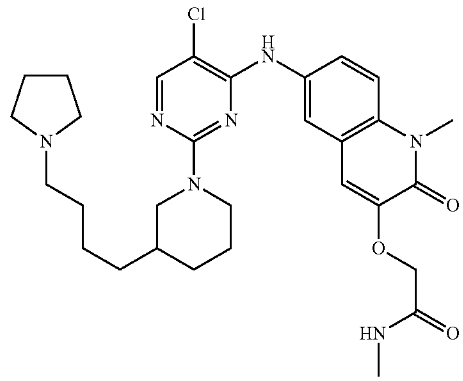 [SMILES: CNC(=O)COc1cc2cc(Nc3nc(N4CCCC(CCCCN5CCCC5)C4)ncc3Cl)ccc2n(C)c1=O] | 0.47 | 582 | Method 2 |
| I-124 | 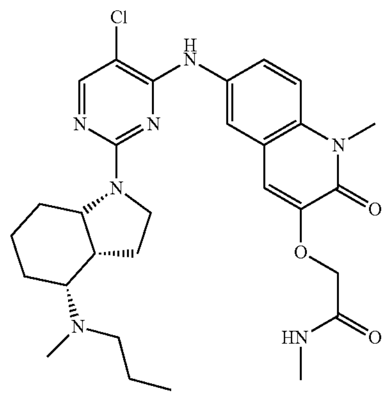 | 0.46 | 582 | Method 2 |
| I-125 | 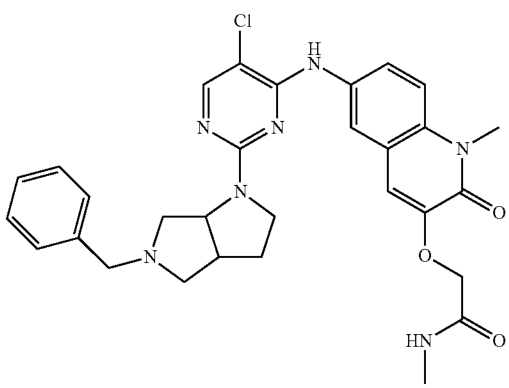 [SMILES: CNC(=O)COc1cc2cc(Nc3nc(N4CCC5CN(Cc6ccccc6)CC54)ncc3Cl)ccc2n(C)c1=O] | 0.44 | 574 | Method 2 |
| I-126 | 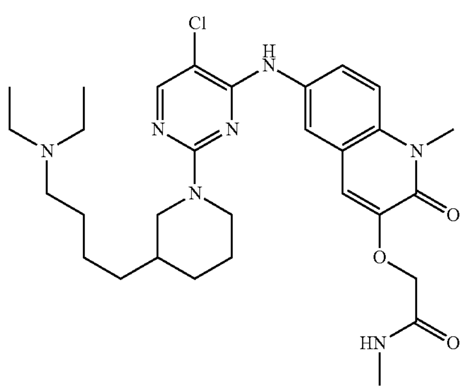 [SMILES: CCN(CC)CCCCC1CCCN(c2ncc(Cl)c(Nc3ccc4c(c3)cc(OCC(=O)NC)c(=O)n4C)n2)C1] | 0.48 | 584 | Method 2 |

TABLE 5-continued
Compounds I-122 to I-130
| # | structure | $t_{Ret.}$ HPLC [min] | MS $(M + H)^+$ | method |
|---|---|---|---|---|
| I-127 | 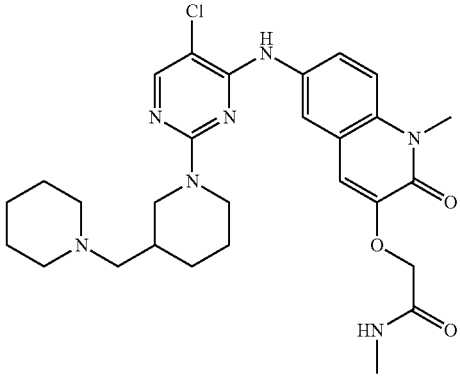 [SMILES: CNC(=O)COc1cc2cc(Nc3nc(N4CCCC(CN5CCCCC5)C4)ncc3Cl)ccc2n(C)c1=O] | 0.43 | 554 | Method 2 |
| I-128 | 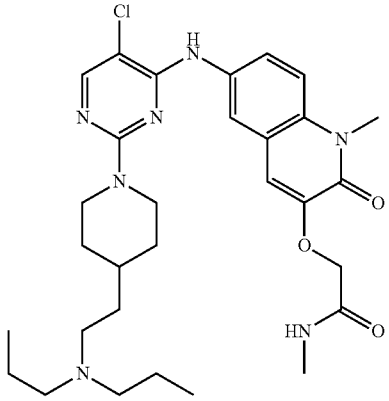 [SMILES: CCCN(CCC)CCC1CCN(c2ncc(Cl)c(Nc3ccc4c(c3)cc(OCC(=O)NC)c(=O)n4C)n2)CC1] | 0.48 | 584 | Method 2 |
| I-129 | 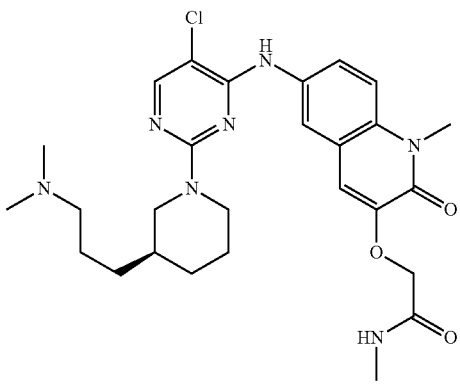 [SMILES: CNC(=O)COc1cc2cc(Nc3nc(N4CCC[C@@H](CCCN(C)C)C4)ncc3Cl)ccc2n(C)c1=O] | 0.46 | 570 | Method 2 |

TABLE 5-continued

Compounds I-122 to I-130

| # | structure | $t_{Ret.}$ HPLC [min] | MS $(M + H)^+$ | method |
|---|---|---|---|---|
| I-130 | 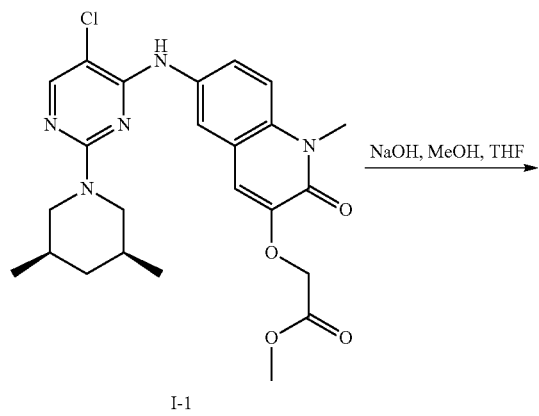 | 0.46 | 570 | Method 2 |

C.2. Experimental Procedures for the Synthesis of Compounds (I) from IM-4 with Derivatization in the Final Step C.2.1. Experimental Procedure for the Synthesis of I-131

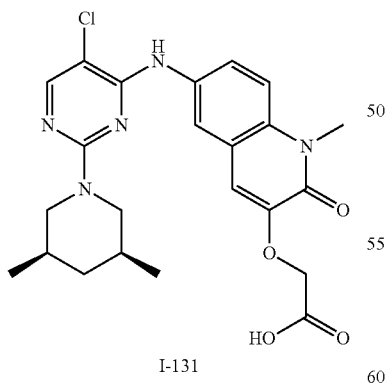

To I-1 (273 mg; 562 µmol) in THF (2.5 mL) and MeOH (2.5 mL) is added a sodium hydroxide solution (562 µL; 1.12 mmol, 2 M in H₂O) and the mixture is stirred for 30 min at rt. H₂O is added and the mixture is acidified with 4 N hydrochloric and stirring is continued. The resulting precipitate is filtered and dried in vacuo to give 2-{[6-({5-chloro-2-[cis-3,5-dimethylpiperidin-1-yl]pyrimidin-4-yl}amino)-1-methyl-2-oxo-1,2-dihydroquinolin-3-yl]oxy}-acetic acid (I-131) (HPLC-MS: $t_{Ret.}$=1.09 min; MS (M+H)⁺=472; method 1).

C.2.2. Experimental Procedure for the Synthesis of I-132

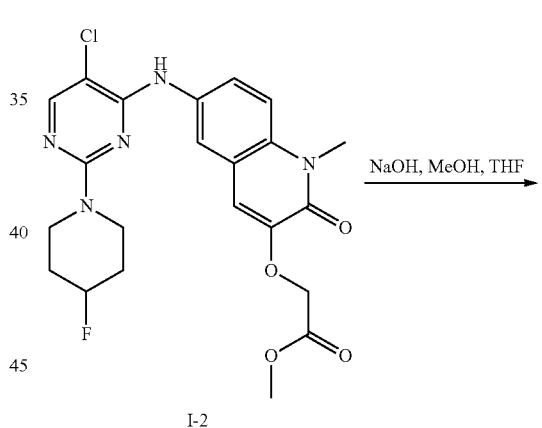

To I-2 (30.0 mg; 63.0 µmol) in THF (0.5 mL) and MeOH (0.5 mL) is added a sodium hydroxide solution (63.0 µL; 126

μmol, 2 M in H₂O) and the mixture is stirred for 30 min at rt. H₂O is added and the mixture is purified by preparative RP-HPLC under acidic conditions using a MeCN/H₂O gradient from 10:90 to 98:2 over 8 min as eluent (column: Sunfire C18; 30×50 mm; 5 μm; flow: 50 mL/min). The product containing fractions are freeze dried to give 2-[(6-{[5-chloro-2-(4-fluoropiperidin-1-yl)pyrimidin-4-yl]amino}-1-methyl-2-oxo-1,2-dihydro-quinolin-3-yl)oxy] acetic acid (I-132) (HPLC-MS: $t_{Ret.}$=0.94 min; MS (M+H)⁺=422; method 1).

C.2.3. Experimental Procedure for the Synthesis of I-133

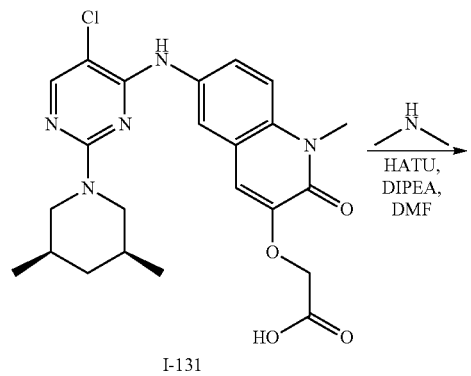

I-131

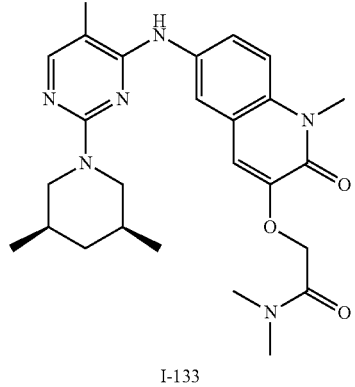

I-133

To I-131 (50.0 mg; 106 μmol) and HATU (60.4 mg; 159 μmol) in DMF (1.0 mL) is added DIPEA (72 μL; 424 μmol) and the mixture is stirred for 1 h at rt. Dimethylamine (106 μL; 212 μmol; 2M in THF) is added and stirring is continued 2 h at rt and 1 h at 45° C. After cooling to rt the mixture is purified by preparative RP-HPLC under basic conditions using a MeCN/H₂O gradient from 15:85 to 98:2 over 10 min as eluent (column: XBridge C18; 30×50 mm; flow: 50 mL/min). The product containing fractions are freeze dried to give 2-{[6-({5-chloro-2-[cis-3,5-dimethyl-piperidin-1-yl]pyrimidin-4-yl}amino)-1-methyl-2-oxo-1,2-dihydroquinolin-3-yl]oxy}-N,N-dimethylacetamide (I-133) (HPLC-MS: $t_{Ret.}$=1.38 min; MS (M+H)⁺=499; method 1).

In analogy to the procedure described under C.2.3. for the synthesis of I-133 additional amides I-134 to I-138 are prepared.

TABLE 6

Compounds I-131 to I-138

| # | structure | $t_{Ret.}$ HPLC [min] | MS (M + H)⁺ | method |
|---|---|---|---|---|
| I-131 | (structure shown) | 1.09 | 472 | Method 1 |
| I-132 | (structure shown) | 0.94 | 422 | Method 1 |

TABLE 6-continued
Compounds I-131 to I-138
| # | structure | t_{Ref.} HPLC [min] | MS (M + H)⁺ | method |
|---|---|---|---|---|
| I-133 | 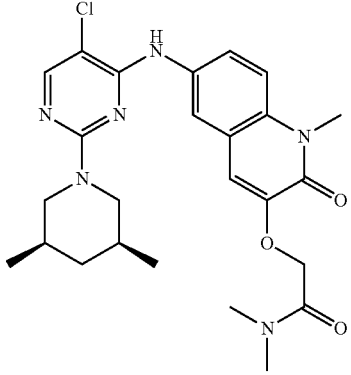 [SMILES: C[C@@H]1C[C@H](C)CN(c2ncc(Cl)c(Nc3ccc4c(c3)cc(OCC(=O)N(C)C)c(=O)n4C)n2)C1] | 1.38 | 499 | Method 1 |
| I-134 | 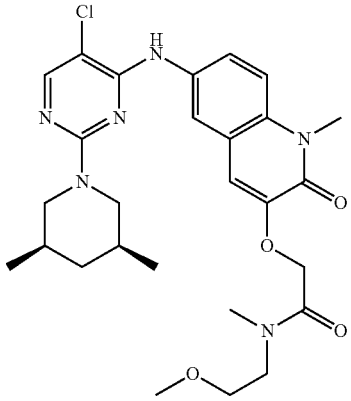 [SMILES: COCCN(C)C(=O)COc1cc2cc(Nc3nc(N4C[C@H](C)C[C@H](C)C4)ncc3Cl)ccc2n(C)c1=O] | 1.41 | 543 | Method 1 |
| I-135 | 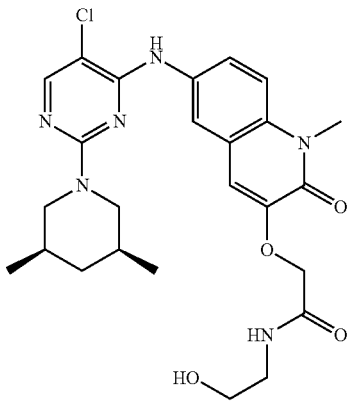 [SMILES: C[C@@H]1C[C@H](C)CN(c2ncc(Cl)c(Nc3ccc4c(c3)cc(OCC(=O)NCCO)c(=O)n4C)n2)C1] | 1.30 | 515 | Method 1 |

TABLE 6-continued

Compounds I-131 to I-138

| # | structure | $t_{Ret.}$ HPLC [min] | MS $(M + H)^+$ | method |
|---|---|---|---|---|
| I-136 | 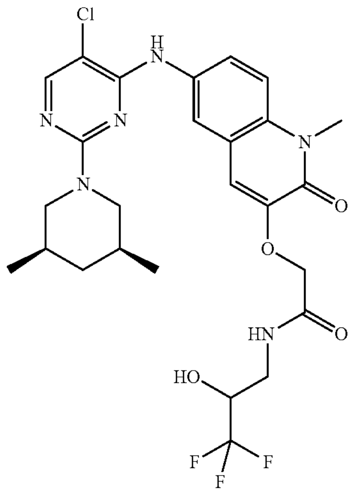 [SMILES: C[C@@H]1C[C@H](C)CN(c2ncc(Cl)c(Nc3ccc4c(c3)cc(OCC(=O)NCC(O)C(F)(F)F)c(=O)n4C)n2)C1] | 1.46 | 583 | Method 1 |
| I-137 | 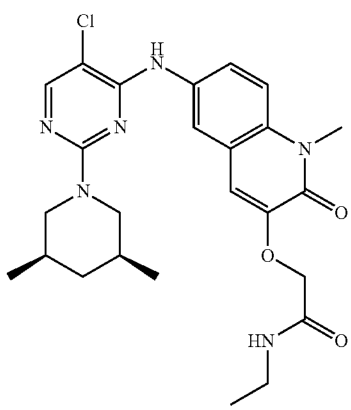 [SMILES: CCNC(=O)COc1cc2cc(Nc3nc(N4C[C@H](C)C[C@H](C)C4)ncc3Cl)ccc2n(C)c1=O] | 1.42 | 499 | Method 1 |
| I-138 | 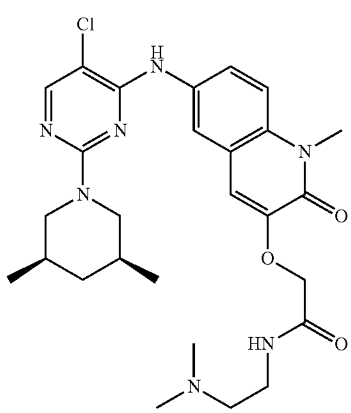 [SMILES: C[C@@H]1C[C@H](C)CN(c2ncc(Cl)c(Nc3ccc4c(c3)cc(OCC(=O)NCCN(C)C)c(=O)n4C)n2)C1] | 1.40 | 542 | Method 1 |

C.2.4. Experimental Procedure for the Synthesis of I-139

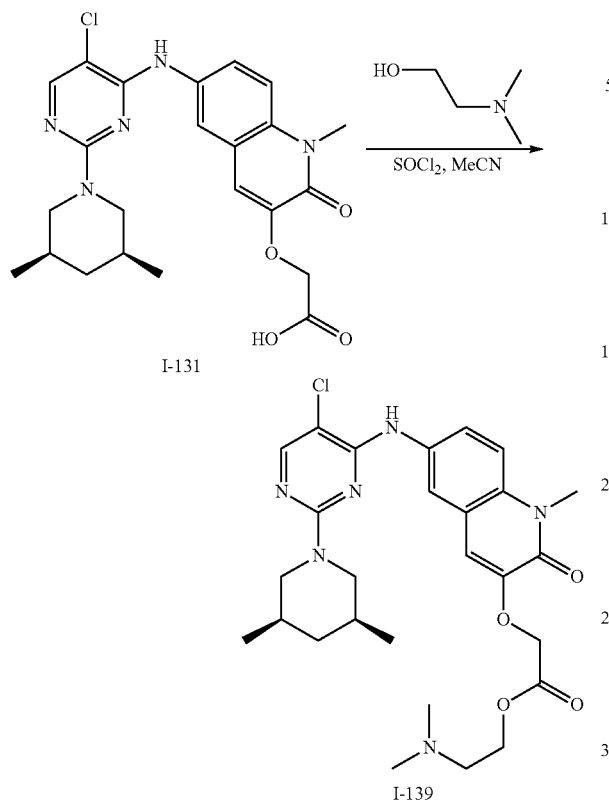

To I-131 (30.0 mg; 63.6 µmol) in MeCN (1.0 mL) is added thionylchloride (115 µL; 1.59 mmol) and the mixture is stirred for 1 h at rt to form the acid chloride. 2-(Dimethylamino)ethan-1-ol (327 µL; 3.18 mmol) is dissolved in MeCN (0.5 mL) and added dropwise to the reaction mixture. The resulting mixture is stirred for additional 30 min, quenched with $H_2O$ and directly purified by preparative RP-HPLC under basic conditions using MeCN/$H_2O$ gradients from 15:85 to 98:2 over 9 min as eluent (column: XBridge C18; 50×150 mm; 10 µm; flow: 150 mL/min). The product containing fractions are freeze dried to give 2-(dimethylamino)ethyl 2-{[6-({5-chloro-2-[cis-3,5-dimethylpiperidin-1-yl]pyrimidin-4-yl}amino)-1-methyl-2-oxo-1,2-dihydroquinolin-3-yl]oxy}acetate (I-139) (HPLC-MS: $t_{Ret.}$=1.46 min; MS (M+H)$^+$=543; method 1).

In analogy to the procedure described under C.2.4. for the synthesis of I-139 additional esters I-140 to I-142 are prepared.

TABLE 7

Compounds I-139 to I-142

| # | structure | $t_{Ret.}$ HPLC [min] | MS (M + H)$^+$ | method |
|---|---|---|---|---|
| I-139 | 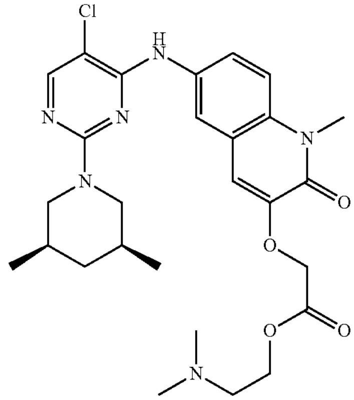 [SMILES: C[C@@H]1C[C@H](C)CN(c2ncc(Cl)c(Nc3ccc4c(c3)cc(OCC(=O)OCCN(C)C)c(=O)n4C)n2)C1] | 1.46 | 543 | Method 1 |

TABLE 7-continued
Compounds I-139 to I-142
| # | structure | t_{Ret.} HPLC [min] | MS (M + H)+ | method |
|---|---|---|---|---|
| I-140 | 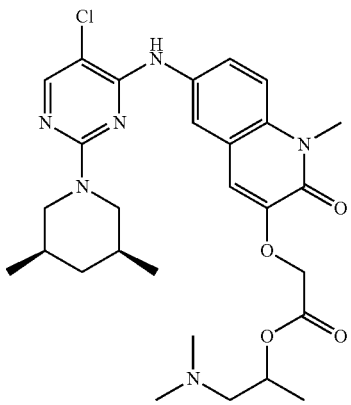 [SMILES: CC(CN(C)C)OC(=O)COc1cc2cc(Nc3nc(N4C[C@H](C)C[C@H](C)C4)ncc3Cl)ccc2n(C)c1=O] | 1.55 | 557 | Method 1 |
| I-141 | 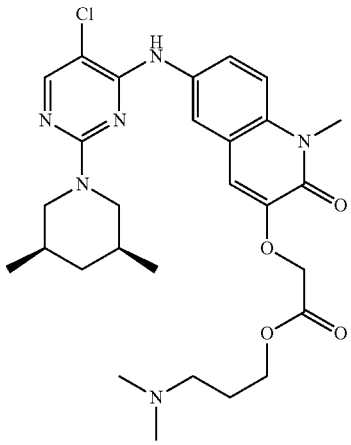 [SMILES: C[C@@H]1C[C@H](C)CN(c2ncc(Cl)c(Nc3ccc4c(c3)cc(OCC(=O)OCCCN(C)C)c(=O)n4C)n2)C1] | 1.50 | 557 | Method 1 |
| I-142 | 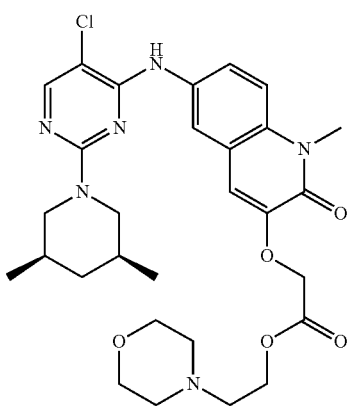 [SMILES: C[C@@H]1C[C@H](C)CN(c2ncc(Cl)c(Nc3ccc4c(c3)cc(OCC(=O)OCCN3CCOCC3)c(=O)n4C)n2)C1] | 1.41 | 585 | Method 1 |

C.2.5. Experimental Procedure for the Synthesis of I-143

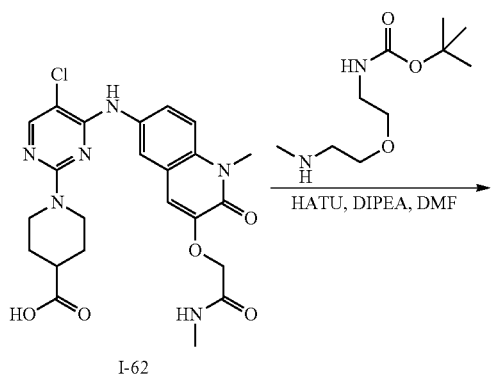

I-62

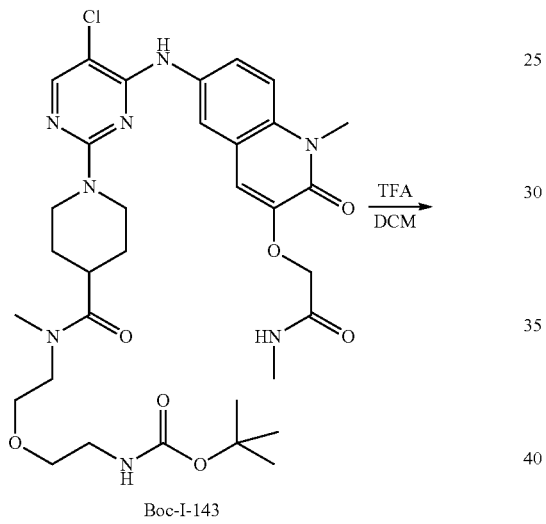

Boc-I-143

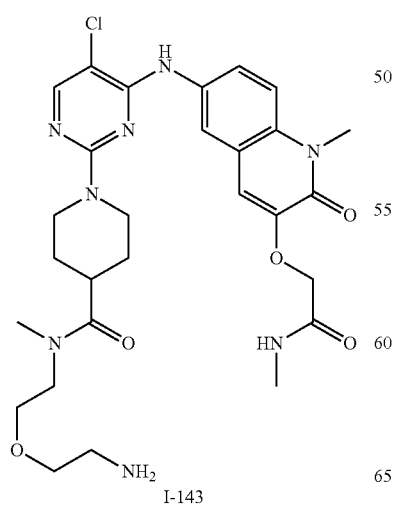

I-143

To I-62 (50.0 mg; 100 µmol) in DMF (1.0 mL) is added DIPEA (51.9 mg; 399 µmol) and HATU (56.9 mg; 150 µmol) and the mixture is stirred for 10 min at t. tert-Butyl N-{2-[2-(methylamino)ethoxy]ethyl}carbamate (40.1 mg; 150 mmol) is added and stirring is continued at rt for 2 h. The mixture is diluted with some drops of MeCN/H$_2$O, filtered through a syringe filter and purified by preparative RP-HPLC under basic conditions using a MeCN/H$_2$O gradient from 25:75 to 98:2 over 8 min as eluent (column: XBridge C18; 30×50 mm; 10 µm; flow: 150 mL/min). The product containing fractions are freeze dried to give tert-butyl N-{2-[2-({1-[5-chloro-4-({1-methyl-3-[(methylcarbamoyl)methoxy]-2-oxo-1,2-dihydro-quinolin-6-yl}-amino)pyrimidin-2-yl]piperidin-4-yl}formamido)ethoxy]ethyl}-carbamate (Boc-I-143) (HPLC-MS: $t_{Ret.}$=1.15 min; MS (M+H)$^+$=701; method 1).

To Boc-I-153 (45.0 mg; 64 µmol) in DCM (2.5 mL) is added TFA (250 µL; 3.25 mmol) and the mixture is stirred for 1 h at rt. The mixture is evaporated and the residue is taken up in saturated NaHCO$_3$ solution (1.0 mL), diluted with MeCN/H$_2$O (1.0 mL), filtered through a syringe filter and purified by preparative RP-HPLC under basic conditions using a MeCN/H$_2$O gradient from 10:90 to 70:30 over 8 min as eluent (column: XBridge C18; 30×50 mm; 10 µm; flow: 150 mL/min). The product containing fractions are freeze dried to give N-[2-(2-aminoethoxy)ethyl]-1-[5-chloro-4-({1-methyl-3-[(methylcarbamoyl)methoxy]-2-oxo-1,2-dihydroquinolin-6-yl}amino)pyrimidin-2-yl]piperidine-4-carboxamide (I-143) (HPLC-MS: $t_{Ret.}$=1.11 min; MS (M+H)$^+$=601; method 1).

In analogy to the procedures described under C.2.5. for the synthesis of I-143 additional amides I-144 to I-147 are prepared from I-62 and the corresponding Boc-protected amines.

TABLE 8

Compounds I-153 to I-147

| # | structure | $t_{Ret.}$ HPLC [min] | MS $(M + H)^+$ | method |
|---|---|---|---|---|
| I-143 | 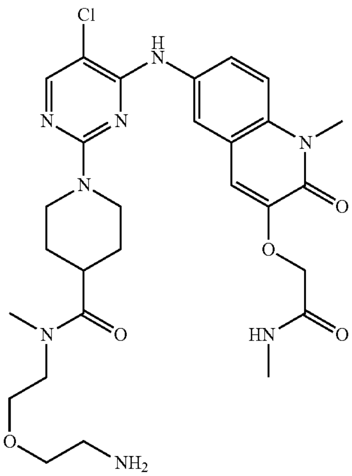 [SMILES: CNC(=O)COc1cc2cc(Nc3nc(N4CCC(C(=O)N(C)CCOCCN)CC4)ncc3Cl)ccc2n(C)c1=O] | 1.01 | 601 | Method 1 |
| I-144 | 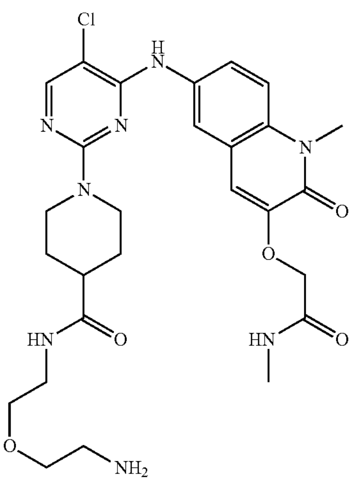 [SMILES: CNC(=O)COc1cc2cc(Nc3nc(N4CCC(C(=O)NCCOCCN)CC4)ncc3Cl)ccc2n(C)c1=O] | 0.90 | 587 | Method 1 |
| I-145 | 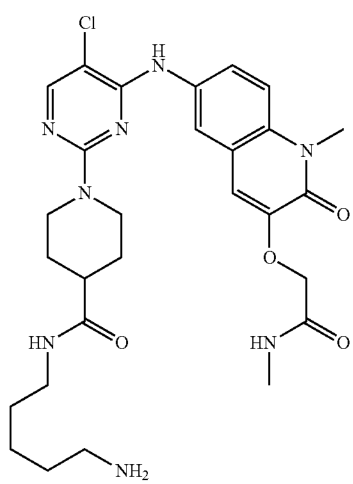 [SMILES: CNC(=O)COc1cc2cc(Nc3nc(N4CCC(C(=O)NCCCCCN)CC4)ncc3Cl)ccc2n(C)c1=O] | 0.92 | 585 | Method 1 |

TABLE 8-continued
Compounds I-153 to I-147
| # | structure | $t_{Ret.}$ HPLC [min] | MS $(M + H)^+$ | method |
|---|---|---|---|---|
| I-146 | 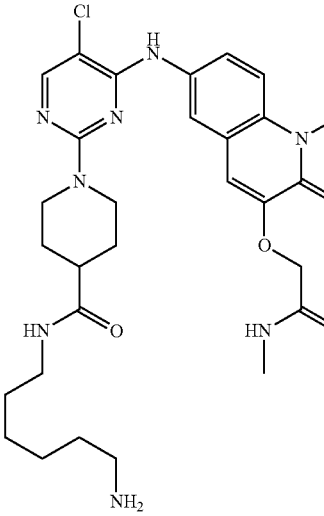 | 0.94 | 599 | Method 1 |
| I-467 | 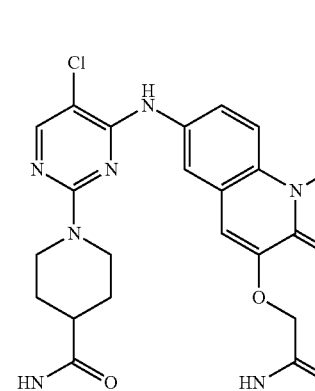 | 0.94 | 631 | Method 1 |
C.3. Experimental Procedures for the Synthesis of Compounds (I) from IM-2 and IM-3
C.3.1. Experimental Procedure for the Synthesis of I-148
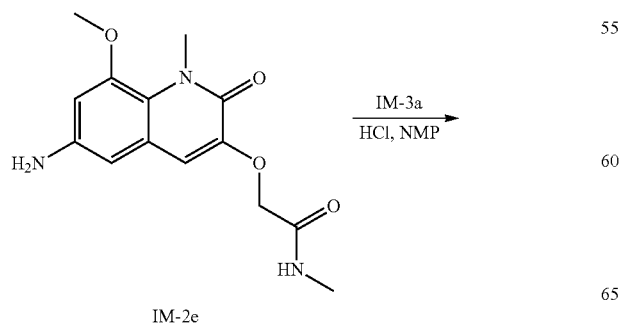
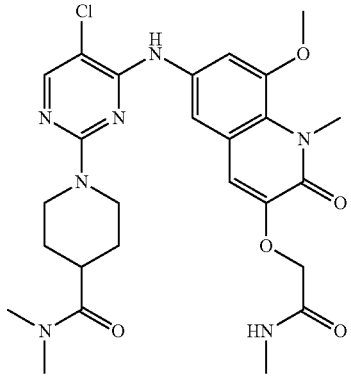 [SMILES: CNC(=O)COc1cc2cc(Nc3nc(N4CCC(C(=O)N(C)C)CC4)ncc3Cl)cc(OC)c2n(C)c1=O]
To IM-3a (208 mg; 687 µmol) and IM-2e (200 mg; 687 µmol) in NMP (5.0 mL) is added HCl (600 µL; 2.40 mmol, 4 M in 1,4-dioxane) and the mixture is stirred for 16 h at 80° C. After cooling to rt H₂O is added, the mixture is filtered and directly purified by preparative RP-HPLC under acidic conditions using a MeCN/H₂O gradient from 10:90 to 60:40 over 8 min as eluent (column: Sunfire C18; 50×150 mm; 10 μm; flow: 180 mL/min). The product containing fractions are freeze dried to give 1-[5-chloro-4-({8-methoxy-1-methyl-3-[(methylcarbamoyl)methoxy]-2-oxo-1,2-dihydroquinolin-6-yl}amino)pyrimidin-2-yl]-N,N-dimethylpiperidine-4-carboxamide (I-148) (HPLC-MS: $t_{Ret.}$=1.05 min; MS (M+H)⁺=558; method 1).

C.3.2. Experimental Procedure for the Synthesis of I-149

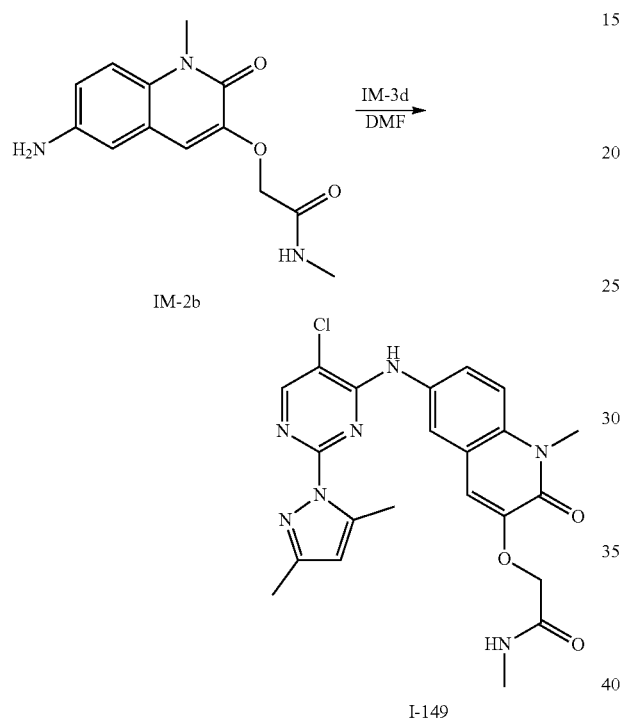

IM-2b

I-149

A mixture of IM-3d (38.2 mg; 157 μmol) and IM-2b (41.0 mg; 157 μmol) in DMF (1.0 mL) is stirred for 2 h at 70° C. After cooling to rt MeOH (6.0 mL) and H₂O (30 mL) are added and the resulting precipitate is filtered, washed with H₂O and dried in vacuo to give 2-[(6-{[5-chloro-2-(3,5-dimethyl-1H-pyrazol-1-yl)pyrimidin-4-yl]amino}-1-methyl-2-oxo-1,2-dihydroquinolin-3-yl)oxy]-N-methylacetamide (I-149) (HPLC-MS: $t_{Ret.}$=0.96 min; MS (M+H)⁺=468; method 1).

C.3.3. Experimental Procedure for the Synthesis of I-150

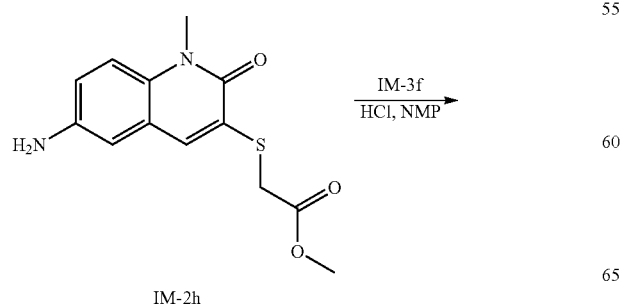

IM-2h

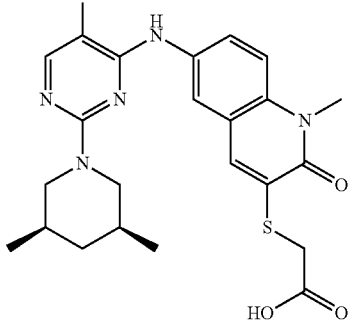

I-150

To IM-3f (72.0 mg; 277 μmol) and IM-2h (77.0 mg; 277 μmol) in NMP (2.0 mL) is added HCl (600 μL; 2.40 mmol, 4 M in 1,4-dioxane) and the mixture is stirred for 16 h at 90° C. Under the reaction conditions direct cleavage of the methyl ester occurs. After cooling to rt H₂O is added, the mixture is filtered and directly purified by preparative RP-HPLC under acidic conditions using a MeCN/H₂O gradient from 20:80 to 60:40 over 6 min as eluent (column: Triart C18; 50×150 mm; 10 μm; flow: 180 mL/min). The product containing fractions are freeze dried to give 2-{[6-({5-chloro-2-[cis-3,5-dimethylpiperidin-1-yl]pyrimidin-4-yl}amino)-1-methyl-2-oxo-1,2-dihydroquinolin-3-yl]sulfanyl}acetic acid (I-150) (HPLC-MS: $t_{Ret.}$=1.08 min; MS (M+H)⁺=488; method 1).

C.3.4. Experimental Procedure for the Synthesis of I-151

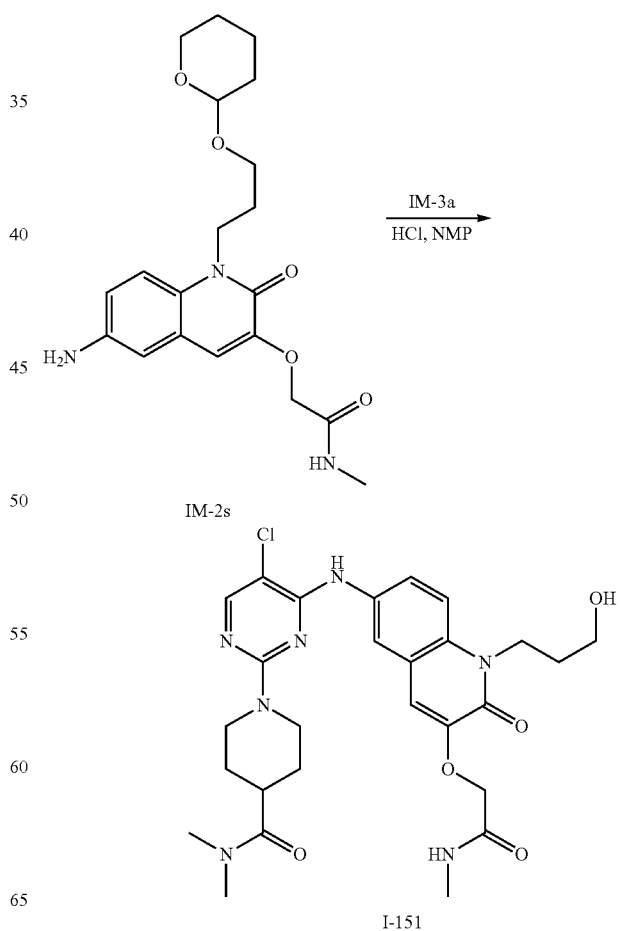

IM-2s

I-151

To IM-3a (40.0 mg; 132 µmol) and IM-2s (77.1 mg; 198 µmol) in NMP (1.0 mL) is added HCl (115 µL; 462 µmol, 4 M in 1,4-dioxane) and the mixture is stirred for 3 h at 75° C. Under the reaction conditions direct cleavage of the THP protecting group occurs. After cooling to rt MeCN/H$_2$O is added and the mixture is filtered and directly purified by preparative RP-HPLC under acidic conditions using a MeCN/H$_2$O gradient from 2:98 to 80:20 over 8 min as eluent (column: Sunfire C18; 30×50 mm; 5 µm; flow: 50 mL/min). The product containing fractions are freeze dried to give 1-(5-chloro-4-{[1-(3-hydroxypropyl)-3-[(methyl-carbamoyl)methoxy]-2-oxo-1,2-dihydroquinolin-6-yl]amino}pyrimidin-2-yl)-N,N-dimethyl-piperidine-4-carboxamide (I-151) (HPLC-MS: t$_{Ret.}$=0.94 min; MS (M+H)$^+$=572; method 1).

C.3.5. Experimental Procedure for the Synthesis of I-152

After cooling to rt MeCN/H$_2$O is added and the mixture is filtered and directly purified by preparative RP-HPLC under acidic conditions using a MeCN/H$_2$O gradient from 2:98 to 80:20 over 8 min as eluent (column: Sunfire C18; 30×50 mm; 5 µm; flow: 50 mL/min). The product containing fractions are freeze dried to give E-12 (HPLC-MS: t$_{Ret.}$=1.05 min; MS (M+H)$^+$=529; method 1).

E-12 (53.0 mg; 100 µmol) is suspended in NaOH (1.0 mL; 2 M in H$_2$O) and stirred for 1 h at 40° C. After cooling to rt the mixture is acidified with 2 N hydrochloric acid. The resulting precipitate is collected by filtration, washed with H$_2$O and dried in vacuo to give 2-{[6-({5-chloro-2-[4-(dimethylcarbamoyl)piperidin-1-yl]pyrimidin-4-yl}amino)-1-methyl-2-oxo-1,2-dihydroquinolin-3-yl]oxy}acetic acid (I-152) (HPLC-MS: t$_{Ret.}$=0.80 min; MS (M+H)$^+$=515; method 1).

C.3.6. Experimental Procedure for the Synthesis of I-153

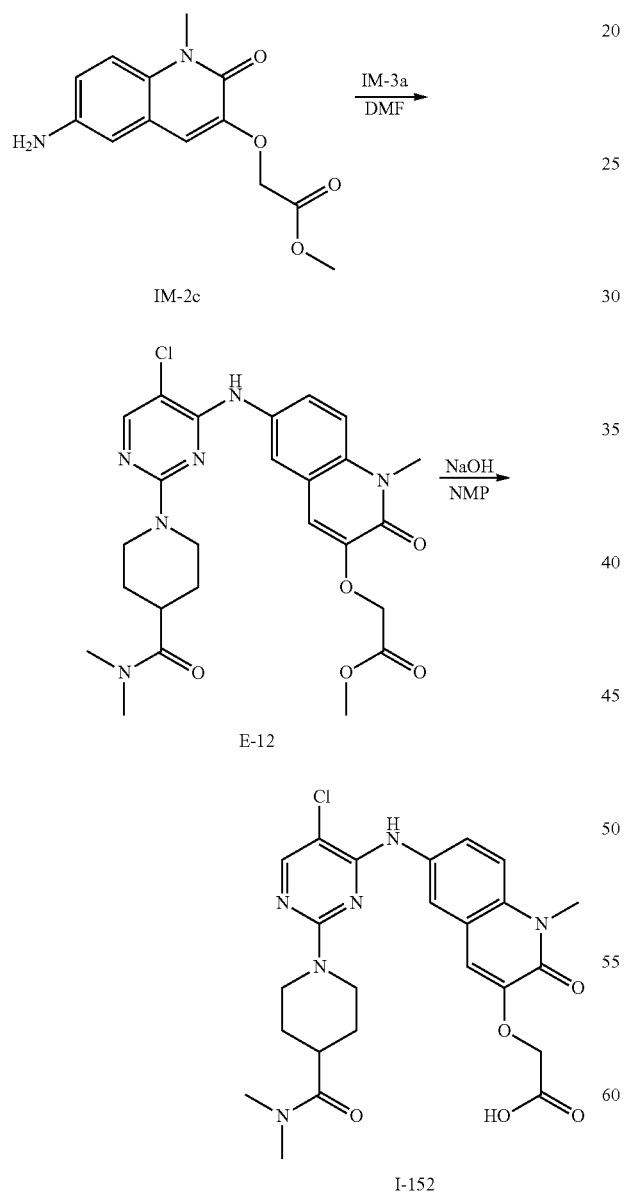

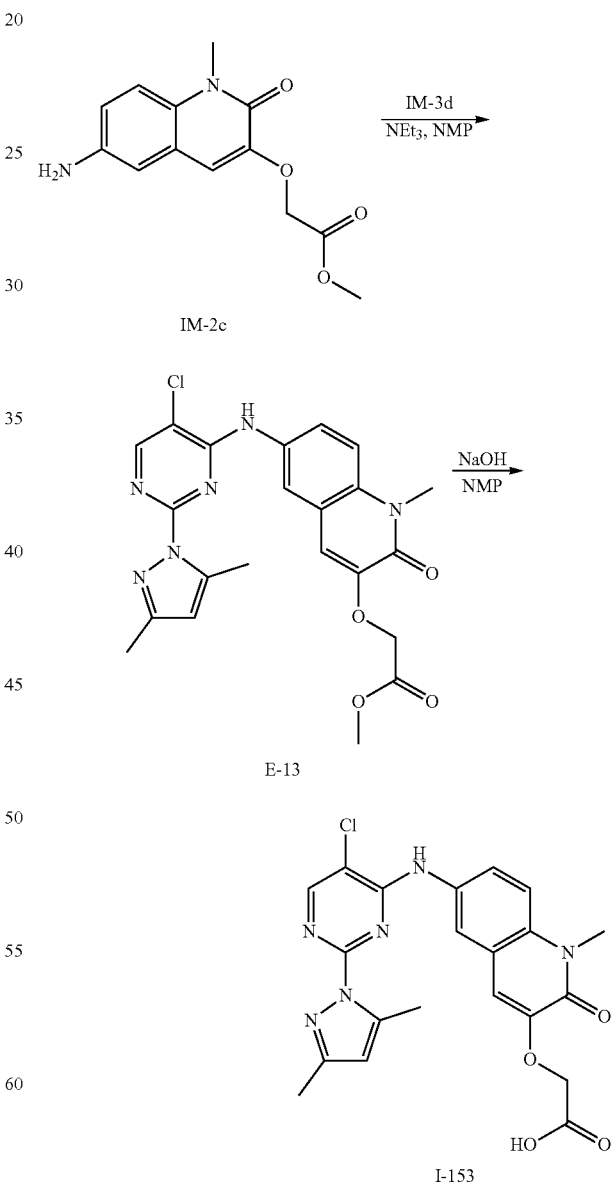

A mixture of IM-3a (139 mg; 454 µmol) and IM-2c (119 mg; 454 µmol) in DMF (1.0 mL) is stirred for 2 h at 70° C.

To IM-3d (94.9 mg; 391 µmol) and IM-2c (93.0 mg; 355 µmol) in NMP (1.0 mL) is added NEt$_3$ (73.8 µL; 533 µmol)

and the mixture is stirred for 2 h at 70° C. After cooling to rt MeCN/H₂O is added and the mixture is filtered and directly purified by preparative RP-HPLC under acidic conditions using a MeCN/H₂O gradient from 2:98 to 80:20 over 8 min as eluent (column: Triart; 30×50 mm; 5 μm). The product containing fractions are freeze dried to give E-13 (HPLC-MS: $t_{Ret.}$=1.03 min; MS (M+H)⁺=469; method 1).

E-13 (43.0 mg; 107 μmol) is suspended in NaOH (1.0 mL; 4 M in H₂O) and NMP (200 μL) and stirred for 2 h at rt. The mixture is acidified with 2 N $HCl_{aq}$ to pH 1 and H₂O (4.0 mL) is added. The resulting precipitate is collected by filtration, washed with H₂O and dried in vacuo to give 2-[(6-{[5-chloro-2-(3,5-dimethyl-1H-pyrazol-1-yl)pyrimidin-4-yl]amino}-1-methyl-2-oxo-1,2-dihydroquinolin-3-yl)oxy]acetic acid (I-153) (HPLC-MS: $t_{Ret.}$=0.77 min; MS (M+H)⁺=455; method 1).

C.3.7. Experimental Procedure for the Synthesis of I-154

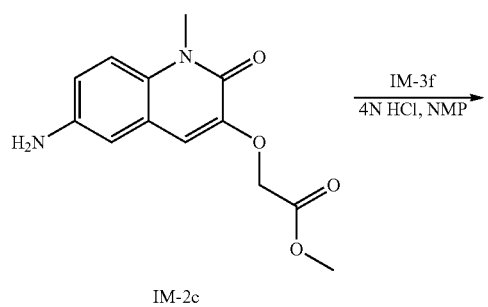

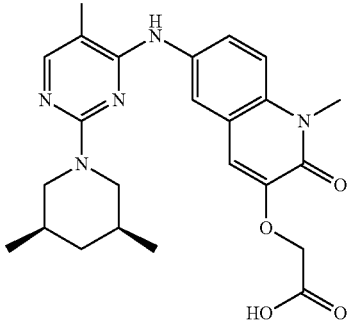

I-154

To IM-3f (56.5 mg; 217 μmol) and IM-2c (60.0 mg; 217 μmol) in NMP (1.0 mL) is added HCl (190 μL; 4 N in 1,4-dioxane) and the mixture is stirred for 3 h at 80° C. To complete ester hydrolysis additional HCl (190 μL, 4 N in 1,4-dioxane) is added and stirring is continued for 16 h at 100° C. After cooling to rt the mixture is poured into H₂O and stirred for 10 min. The resulting precipitate is collected by filtration, washed with H₂O and dried in vacuo to give 2-{[6-({5-chloro-2-[cis-3,5-dimethylpiperidin-1-yl]pyrimidin-4-yl}amino)-1-methyl-2-oxo-1,2-dihydroquinolin-3-yl]oxy}acetic acid (I-154) (HPLC-MS: $t_{Ret.}$=1.08 min; MS (M+H)⁺=486; method 1).

In analogy to the procedures described under C.3.1. to C.3.7. for the synthesis of I-148 to I-154 additional compounds I-155 to I-165 are prepared from the corresponding intermediates IM-2 and IM-3.

TABLE 9

Compounds I-148 to I-165

| # | structure | $t_{Ret.}$ HPLC [min] | MS (M + H)⁺ | method |
|---|---|---|---|---|
| I-148 | 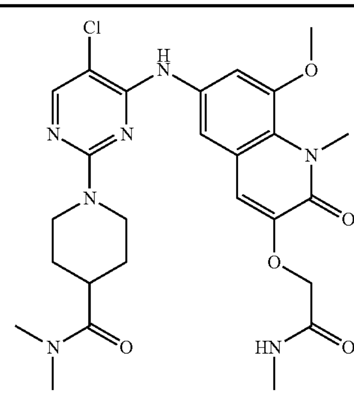 | 1.05 | 558 | Method 1 |
| I-149 | 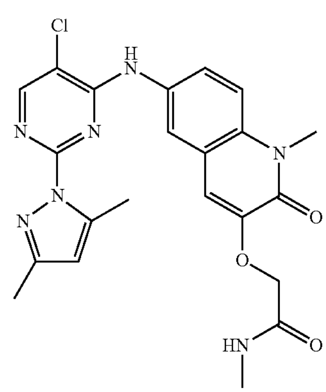 [SMILES: CNC(=O)COc1cc2cc(Nc3nc(-n4nc(C)cc4C)ncc3Cl)ccc2n(C)c1=O] | 0.96 | 468 | Method 1 |

TABLE 9-continued

Compounds I-148 to I-165

| # | structure | t<sub>Ret.</sub> HPLC [min] | MS (M + H)⁺ | method |
|---|---|---|---|---|
| I-150 | 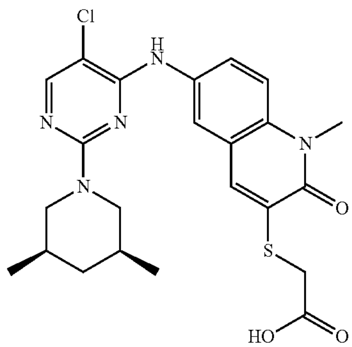 | 1.08 | 488 | Method 1 |
| I-151 | 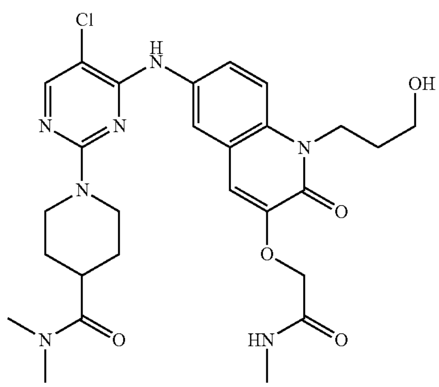 [SMILES: CNC(=O)COc1cc2cc(Nc3nc(N4CCC(C(=O)N(C)C)CC4)ncc3Cl)ccc2n(CCCO)c1=O] | 0.94 | 572 | Method 1 |
| I-152 | 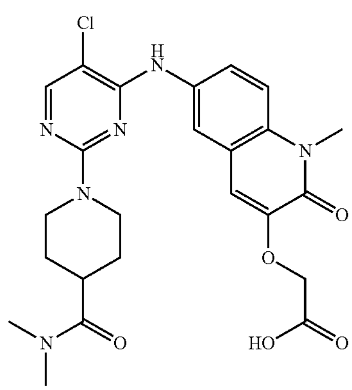 [SMILES: CN(C)C(=O)C1CCN(c2ncc(Cl)c(Nc3ccc4c(c3)cc(OCC(=O)O)c(=O)n4C)n2)CC1] | 0.80 | 515 | Method 1 |
| I-153 | 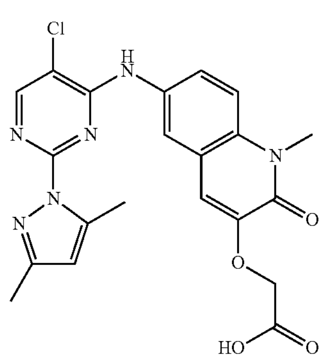 [SMILES: Cc1cc(C)n(-c2ncc(Cl)c(Nc3ccc4c(c3)cc(OCC(=O)O)c(=O)n4C)n2)n1] | 0.77 | 455 | Method 1 |

TABLE 9-continued

Compounds I-148 to I-165

| # | structure | $t_{Ret.}$ HPLC [min] | MS $(M + H)^+$ | method |
|---|---|---|---|---|
| I-154 | 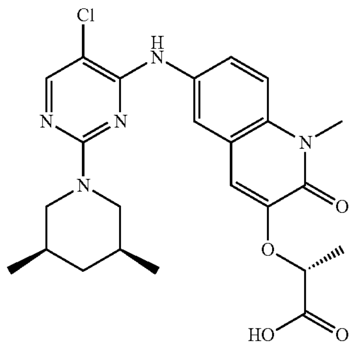 [SMILES: C[C@@H]1C[C@H](C)CN(c2ncc(Cl)c(Nc3ccc4c(c3)cc(O[C@H](C)C(=O)O)c(=O)n4C)n2)C1] | 1.08 | 486 | Method 1 |
| I-155 | 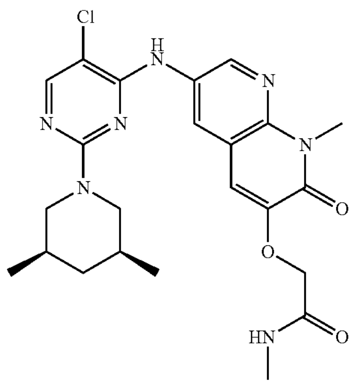 | 1.36 | 486 | Method 1 |
| I-156 | 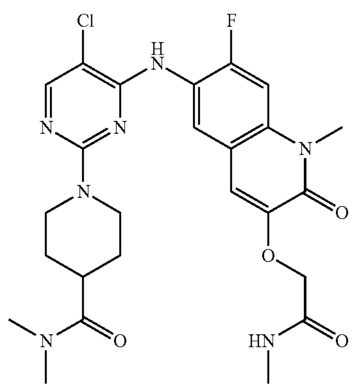 [SMILES: CNC(=O)COc1cc2cc(Nc3nc(N4CCC(C(=O)N(C)C)CC4)ncc3Cl)c(F)cc2n(C)c1=O] | 1.06 | 546 | Method 1 |
| I-157 | 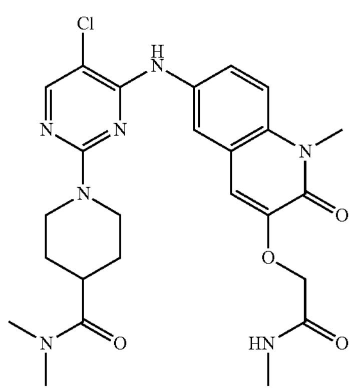 [SMILES: CNC(=O)COc1cc2cc(Nc3nc(N4CCC(C(=O)N(C)C)CC4)ncc3Cl)ccc2n(C)c1=O] | 0.98 | 528 | Method 1 |

TABLE 9-continued

Compounds I-148 to I-165

| # | structure | t_Ret. HPLC [min] | MS (M + H)+ | method |
|---|---|---|---|---|
| I-158 | 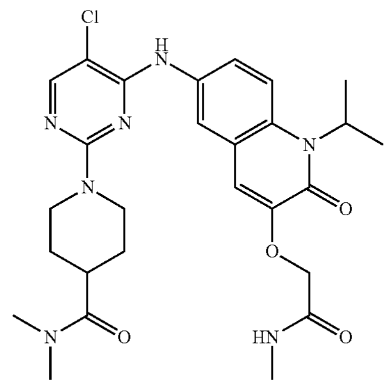 [SMILES: CNC(=O)COc1cc2cc(Nc3nc(N4CCC(C(=O)N(C)C)CC4)ncc3Cl)ccc2n(C(C)C)c1=O] | 1.10 | 556 | Method 1 |
| I-159 | 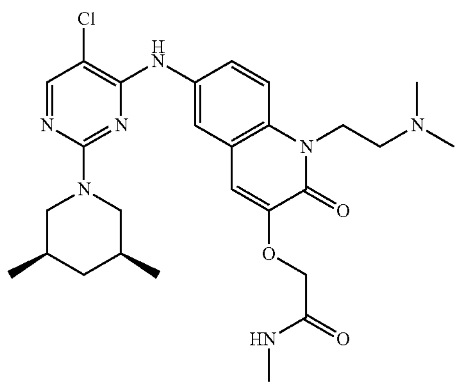 | 1.30 | 543 | Method 1 |
| I-160 | 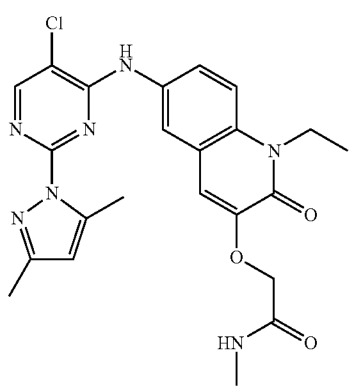 [SMILES: CCn1c(=O)c(OCC(=O)NC)cc2cc(Nc3nc(-n4nc(C)cc4C)ncc3Cl)ccc21] | 1.03 | 482 | Method 1 |
| I-161 | 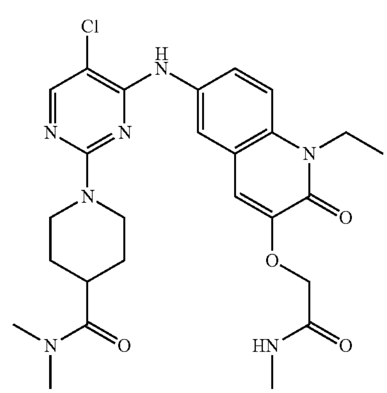 | 1.04 | 542 | Method 1 |

TABLE 9-continued

Compounds I-148 to I-165

| # | structure | $t_{Ret.}$ HPLC [min] | MS $(M + H)^+$ | method |
|---|---|---|---|---|
| I-162 | 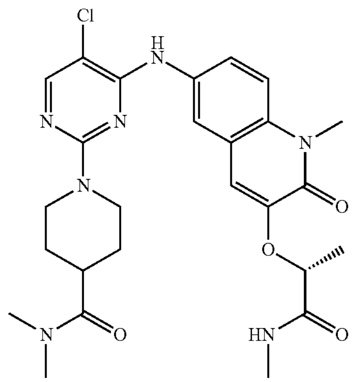 [SMILES: CNC(=O)[C@@H](C)Oc1cc2cc(Nc3nc(N4CCC(C(=O)N(C)C)CC4)ncc3Cl)ccc2n(C)c1=O] | 1.01 | 542 | Method 1 |
| I-163 | 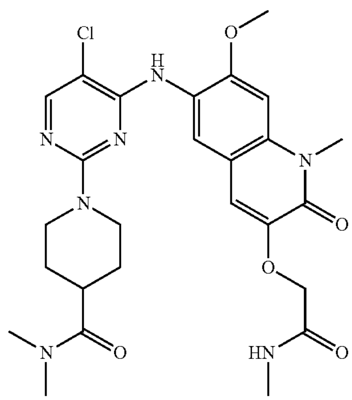 [SMILES: CNC(=O)COc1cc2cc(Nc3nc(N4CCC(C(=O)N(C)C)CC4)ncc3Cl)c(OC)cc2n(C)c1=O] | 1.13 | 558 | Method 1 |
| I-164 | 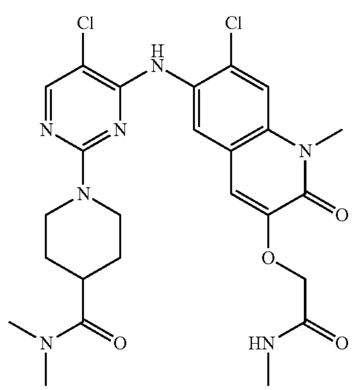 [SMILES: CNC(=O)COc1cc2cc(Nc3nc(N4CCC(C(=O)N(C)C)CC4)ncc3Cl)c(Cl)cc2n(C)c1=O] | 1.15 | 562 | Method 1 |
| I-165 | 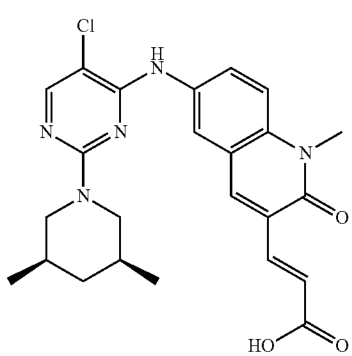 [SMILES: C[C@@H]1C[C@H](C)CN(c2ncc(Cl)c(Nc3ccc4c(c3)cc(/C=C/C(=O)O)c(=O)n4C)n2)C1] | 1.08 | 468 | Method 1 |

C.3.8. Experimental Procedure for the Synthesis of I-166

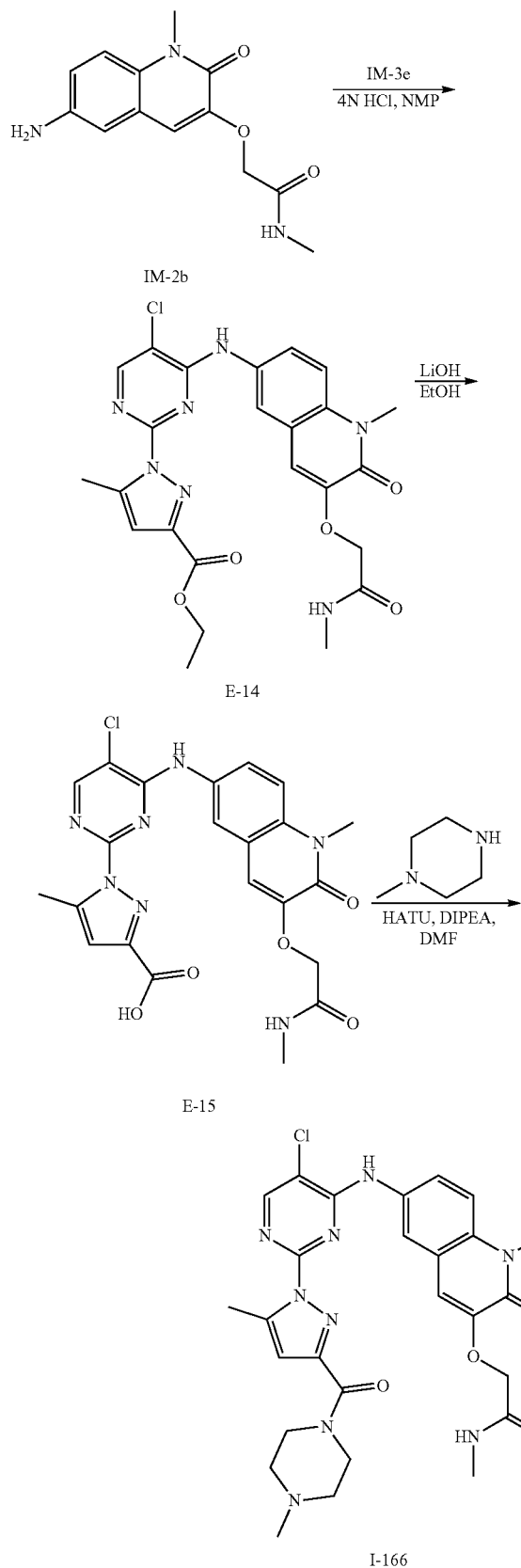

To IM-3e (500 mg; 1.66 mmol) and IM-2b (651 mg; 2.49 mmol) in NMP (10 mL) is added HCl (1.45 mL; 4 N in 1,4-dioxane) and the mixture is stirred for 3 h at 75° C. After cooling to rt the mixture is poured onto $H_2O$ and stirred for 10 min. The resulting precipitate is collected by filtration, washed with $H_2O$ and dried in vacuo to give ethyl 1-[5-chloro-4-({1-methyl-3-[(methylcarbamoyl)methoxy]-2-oxo-1,2-dihydroquinolin-6-yl}amino)pyrimidin-2-yl]-5-methyl-1H-pyrazole-3-carboxylate (E-14).

To E-14 (650 mg; 1.24 mmol) in EtOH (15 mL) is added LiOH solution (1.24 mL; 2.47 mmol, 2 M in $H_2O$) and the mixture is stirred for 5 h at rt. The reaction mixture is evaporated, taken up in $H_2O$ and acidified to pH 1 with 4 N $HCl_{aq}$. The resulting precipitate is collected by filtration, washed with MeOH and dried in vacuo to give 1-[5-chloro-4-({1-methyl-3-[(methylcarbamoyl)methoxy]-2-oxo-1,2-dihydroquinolin-6-yl}amino)-pyrimidin-2-yl]-5-methyl-1H-pyrazole-3-carboxylic acid (E-15) (HPLC-MS: $t_{Ret.}$=0.71 min; MS $(M+H)^+$=498; method 1).

To E-15 (40.0 mg; 80.3 µmol) and HATU (45.8 mg; 121 µmol) in DMF (2.0 mL) is added DIPEA (54.9 µL; 321 µmol) and the mixture is stirred at rt for 30 min. 1-Methylpiperazine (17.8 µL; 161 µmol) is added and stirring is continued for 1 h at rt. Some drops of $MeCN/H_2O$ are added and the crude material is purified by preparative RP-HPLC under acidic conditions using a $MeCN/H_2O$ gradient from 5:95 to 70:30 over 8 min as eluent (column: Sunfire C18; 30×50 mm; 5 µm; flow: 50 mL/min). The product containing fractions are freeze dried to give 2-{[6-({5-chloro-2-[5-methyl-3-(4-methylpiperazine-1-carbonyl)-1H-pyrazol-1-yl]pyrimidin-4-yl}amino)-1-methyl-2-oxo-1,2-dihydroquinolin-3-yl]oxy}-N-methylacetamide (I-166) (HPLC-MS: $t_{Ret.}$=0.92 min; MS $(M+H)^+$=580).

C.3.9. Experimental Procedure for the Synthesis of I-167 and I-168

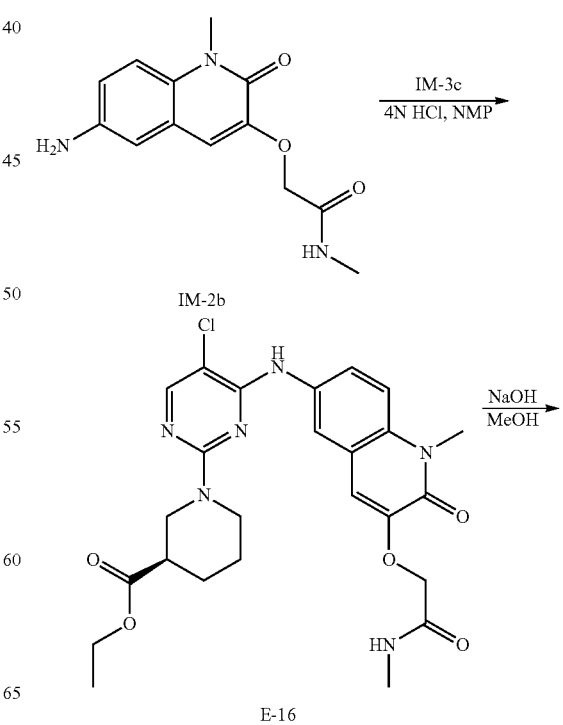

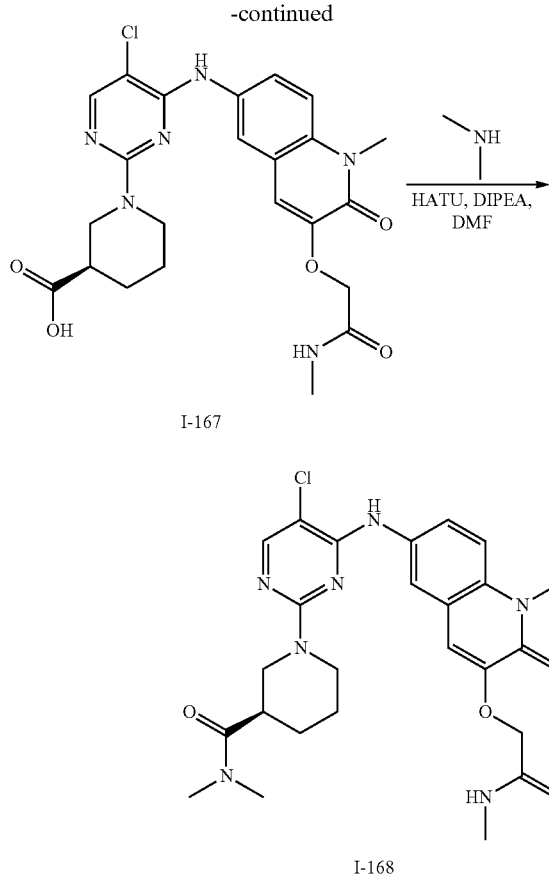

To IM-3c (450 mg; 1.48 mmol) and IM-2b (387 mg; 1.48 mmol) in NMP (5.0 mL) is added HCl (1.30 mL; 4 N in 1,4-dioxane) and the mixture is stirred for 4 h at 75° C. After cooling to rt the mixture is poured onto H$_2$O and stirred for 10 min. The resulting precipitate is collected by filtration, washed with H$_2$O and dried in vacuo to give ethyl (3R)-1-[5-chloro-4-({1-methyl-3-[(methylcarbamoyl)methoxy]-2-oxo-1,2-dihydroquinolin-6-yl}amino)pyrimidin-2-yl]-piperidine-3-carboxylate (E-16).

To E-16 (672 mg; 1.27 mmol) in MeOH (20 mL) is added NaOH solution (699 μL; 1.40 mmol, 2 M in H$_2$O) and the mixture is stirred for 2 h at 50° C. The reaction mixture is evaporated, taken up in H$_2$O and washed twice with DCM. The aqueous layer is evaporated, the residue is taken up in MeCN/H$_2$O and purified by preparative RP-HPLC under acidic conditions using a MeCN/H$_2$O gradient from 15:85 to 98:2 over 8 min as eluent (column: Sunfire C18; 50×150 mm; 10 μm; flow: 180 mL/min). The product containing fractions are freeze dried to give (3R)-1-[5-chloro-4-({1-methyl-3-[(methylcarbamoyl)methoxy]-2-oxo-1,2-dihydroquinolin-6-yl}-amino)pyrimidin-2-yl]piperidine-3-carboxylic acid (I-167) (HPLC-MS: t$_{Ret.}$=0.76 min; MS (M+H)$^+$=501; method 1).

To I-167 (45.0 mg; 89.8 μmol) and HATU (51.2 mg; 135 μmol) in DMF (1.0 mL) is added DIPEA (61.4 μL; 359 μmol) and the mixture is stirred at rt for 30 min. Dimethylamine (89.8 μL; 180 μmol, 2 M in THF) is added and stirring is continued for 1 h at rt. Some drops of MeCN/H$_2$O are added and the crude material is purified by preparative RP-HPLC under acidic conditions using a MeCN/H$_2$O gradient from 5:95 to 70:30 over 8 min as eluent (column: Sunfire C18; 30×50 mm; 5 μm; flow: 180 mL/min). The product containing fractions are freeze dried to give (3R)-1-[5-chloro-4-({1-methyl-3-[(methylcarbamoyl)methoxy]-2-oxo-1,2-dihydroquinolin-6-yl}amino)pyrimidin-2-yl]-N,N-dimethylpiperidine-3-carboxamide (I-168) (HPLC-MS: t$_{Ret.}$=1.01 min; MS (M+H)$^+$=528; method 1).

In analogy to the procedure described under C.3.8. and C.3.9 for the synthesis of I-166, I-167 and I-168 additional examples I-169 and I-170 are prepared.

TABLE 10

| # | structure | t$_{Ret.}$ HPLC [min] | MS (M + H)$^+$ | method |
|---|---|---|---|---|
| I-166 | 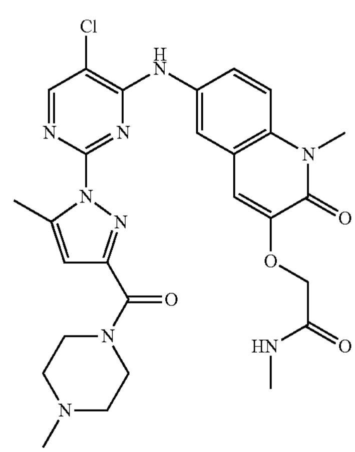 [SMILES: CNC(=O)COc1cc2cc(Nc3nc(-n4nc(C(=O)N5CCN(C)CC5)cc4C)ncc3Cl)ccc2n(C)c1=O] | 0.92 | 580 | Method 1 |

Compounds I-166 to I-170

TABLE 10-continued
Compounds I-166 to I-170
| # | structure | t_{Ret.} HPLC [min] | MS (M + H)+ | method |
|---|---|---|---|---|
| I-167 | 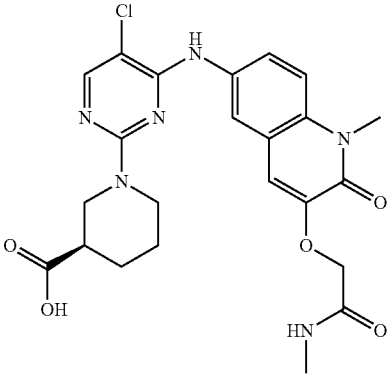 [SMILES: CNC(=O)COc1cc2cc(Nc3nc(N4CCC[C@@H](C(=O)O)C4)ncc3Cl)ccc2n(C)c1=O] | 0.76 | 501 | Method 1 |
| I-168 | 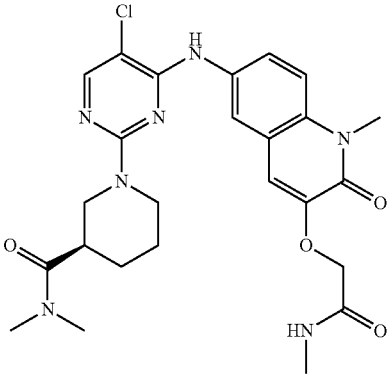 [SMILES: CNC(=O)COc1cc2cc(Nc3nc(N4CCC[C@@H](C(=O)N(C)C)C4)ncc3Cl)ccc2n(C)c1=O] | 1.01 | 528 | Method 1 |
| I-169 | 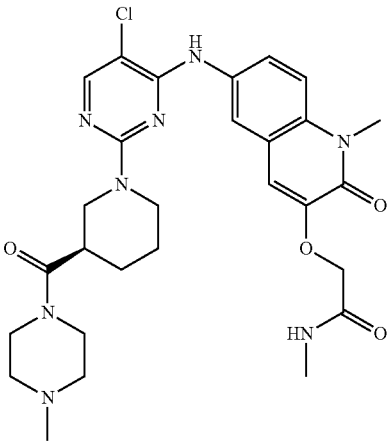 [SMILES: CNC(=O)COc1cc2cc(Nc3nc(N4CCC[C@@H](C(=O)N5CCN(C)CC5)C4)ncc3Cl)ccc2n(C)c1=O] | 1.00 | 583 | Method 1 |

TABLE 10-continued

Compounds I-166 to I-170

| # | structure | $t_{Ret.}$ HPLC [min] | MS $(M + H)^+$ | method |
|---|---|---|---|---|
| I-170 | 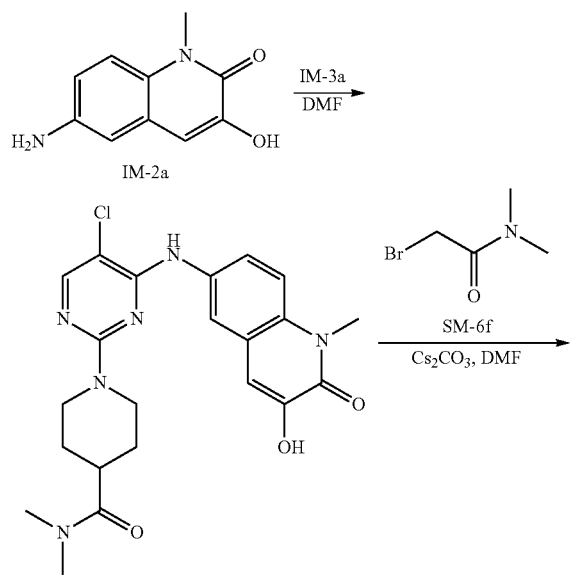 | 1.06 | 611 | Method 1 |

C.3.10. Experimental Procedure for the Synthesis of I-171

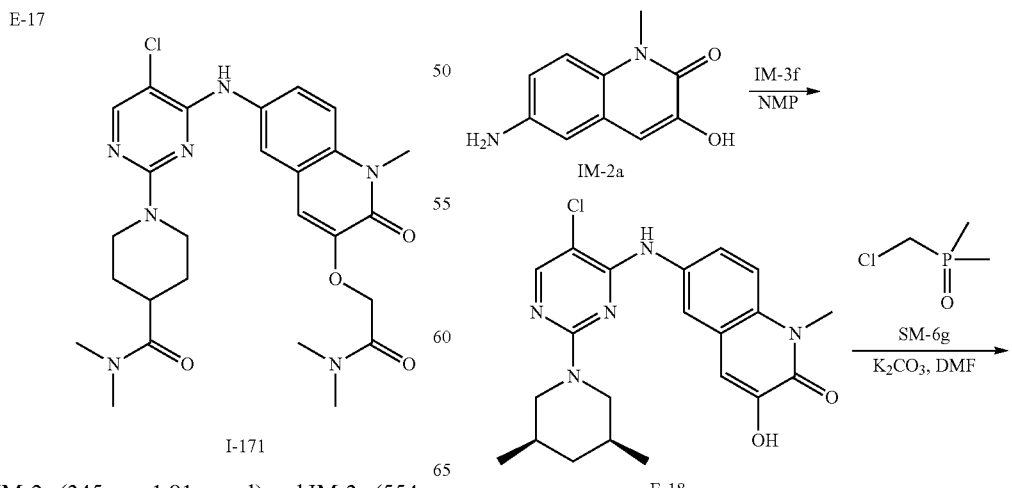

A mixture of IM-2a (345 mg; 1.81 mmol) and IM-3a (554 mg; 1.81 mmol) in DMF (4.0 mL) is stirred for 2 h at 70° C. After cooling to rt MeOH (6.0 mL) and H₂O (30 mL) are added and stirring is continued for 10 min. The resulting precipitate is collected by filtration, washed with H₂O and dried in vacuo to give 1-{5-chloro-4-[(3-hydroxy-1-methyl-2-oxo-1,2-dihydroquinolin-6-yl)amino]pyrimidin-2-yl}-N,N-dimethylpiperidine-4-carboxamide (E-17).

To E-17 (50 mg; 109 µmol) in DMF (1.0 mL) is added 2-bromo-N,N-dimethylacetamide (19.9 mg; 120 µmol) and Cs₂CO₃ (71.0 mg; 218 µmol) and the mixture is stirred for 2 h at rt. Some drops of MeCN/H₂O are added and the crude material is purified by preparative RP-HPLC under acidic conditions using a MeCN/H₂O gradient from 10:90 to 98:2 as eluent (column: Triart C18; 30×50 mm; 5 µm). The product containing fractions are freeze dried to give 1-[5-chloro-4-({1-methyl-3-[(methylcarbamoyl)methoxy]-2-oxo-1,2-dihydro-quinolin-6-yl}amino)pyrimidin-2-yl]-N,N-dimethylpiperidine-4-carboxamide (I-171) (HPLC-MS: $t_{Ret.}$=1.00 min; MS (M+H)⁺=542; method 1).

C.3.11. Experimental Procedure for the Synthesis of I-172

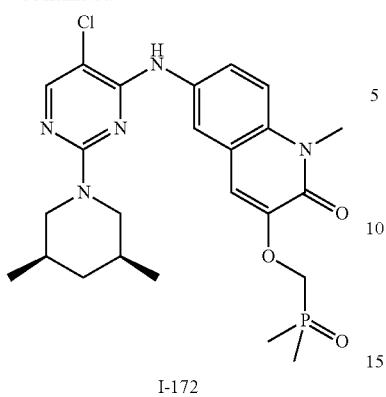

I-172

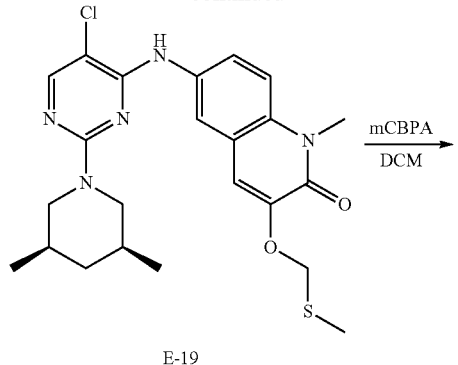

E-19

A mixture of IM-2a (230 mg; 1.21 mmol) and IM-3f (252 mg; 0.97 mmol) in NMP (2.0 mL) is stirred for 2 h at 80° C. After cooling to rt H₂O (30 mL) is added and stirring is continued for 16 h. The resulting precipitate is collected by filtration, washed with H₂O and dried in vacuo to give 6-({5-chloro-2-[cis-3,5-dimethylpiperidin-1-yl]pyrimidin-4-yl}amino)-3-hydroxy-1-methyl-1,2-dihydroquinolin-2-one (E-18) (HPLC-MS: $t_{Ret.}$=0.61 min; MS (M+H)⁺=414; method A).

To E-18 (50.0 mg; 121 μmol) in DMF (1.0 mL) is added chloro(dimethylphosphoryl)methane (22.9 mg; 181 μmol) and K₂CO₃ (25.0 mg; 181 μmol) and the mixture is stirred for 16 h at 70° C. After cooling to rt H₂O is added and the mixture is extracted with EtOAc. The combined organic layer is dried over MgSO₄, filtered and evaporated. The residue is taken up in MeCN/DMSO and purified by preparative RP-HPLC under basic conditions using a MeCN/H₂O gradient from 25:75 to 98:2 over 8 min as eluent (column: XBridge C18; 30×50 mm; 5 μm; flow: 50 mL/min). The product containing fractions are freeze dried to give 6-({5-chloro-2-[cis-3,5-dimethylpiperidin-1-yl]pyrimidin-4-yl}amino)-3-[(dimethylphosphoryl)-methoxy]-1-methyl-1,2-dihydroquinolin-2-one (I-172) (HPLC-MS: $t_{Ret.}$=1.28 min; MS (M+H)⁺=504; method 1).

C.3.12. Experimental Procedure for the Synthesis of I-173 and I-174

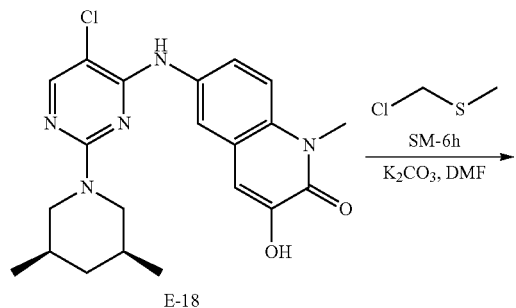

E-18

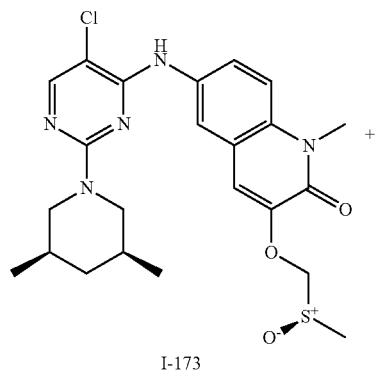

I-173

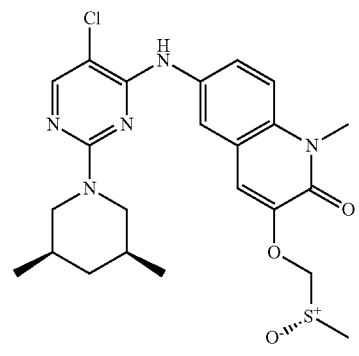

I-174

To E-18 (420 mg; 1.02 mmol) in DMF (1.0 mL) is added potassium carbonate (280 mg; 2.03 mmol) and the mixture is stirred at rt for 10 min. Chloro(methylsulfanyl)methane (96.6 mg; 1.02 mmol) is added and stirring is continued for 16 h at 50° C. After cooling to rt H₂O is added and the resulting precipitate is collected by filtration, washed with H₂O and dried in vacuo to give 6-({5-chloro-2-[cis-3,5-dimethylpiperidin-1-yl]pyrimidin-4-yl}amino)-1-methyl-3-[(methylsulfanyl)methoxy]-1,2-dihydroquinolin-2-one (E-19) (HPLC-MS: $t_{Ret.}$=1.61 min; MS (M+H)⁺=474; method 1) along with a regioisomeric side product which is separated at later stage.

To E-19 (376 mg; 793 μmol) in DCM (5.0 mL) is added mCPBA (249 mg; 793 μmol) slowly at 0° C. and the reaction mixture is stirred at this temperature for 1 h. After warming to rt the reaction mixture is directly purified by preparative RP-HPLC under acidic conditions using a MeCN/H$_2$O gradient from 25:75 to 70:30 over 6 min as eluent (column: Sunfire C18; 30×100 mm, 10 µm). The product containing fractions are freeze dried. To obtain material with higher purity the material is taken up in DCM, washed with saturated NaHCO$_3$ solution and brine, dried over MgSO$_4$, filtered and evaporated. DMF is added and the material is purified a second time by preparative RP-HPLC under basic conditions using a MeCN/H$_2$O gradient from 40:60 to 80:20 over 6 min as eluent (column: XBridge C18; 30×100 mm; 10 µm). The product containing fractions are freeze dried to give a racemic mixture of I-173 and I-174 (HPLC-MS: t$_{Ret.}$=1.29 min; MS (M+H)$^+$=490; method 1). The enantiomers are separated by preparative SFC (Method SFC1; column: Chiralpak AS; eluent MeOH/CO$_2$=30/70; total flow=50 mL/min; injection volume: 500 µL; backpressure: 200 bar). The product containing fractions are dissolved in MeCN/H$_2$O and freeze dried to give 6-({5-chloro-2 [cis 3,5 dimethylpiperidin-1-yl]pyrimidin-4-yl}amino)-3-{[(R)-methanesulfinyl]methoxy}-1-methyl-1,2-dihydroquinolin-2-one (I-173) (SFC: t$_{Ret.}$=1.88 min; 99% ee) and 6-({5-chloro-2 [cis-3,5-dimethylpiperidin-1-yl]pyrimidin-4-yl}amino)-3-{[(S)-methanesulfinyl]methoxy}-1-methyl-1,2-dihydroquinolin-2-one (I-174) (SFC: t$_{Ret.}$=2.43 min; 99% ee). The absolute configuration of the enantiomers is randomly assigned.

In analogy to the procedure described under C.3.10. to C.3.12. for the synthesis of I-171 to I-174 additional examples can be prepared.

TABLE 11

Compounds I-171 to I-175

| # | structure | t$_{Ret.}$ HPLC [min] | MS (M + H)$^+$ | method |
|---|---|---|---|---|
| I-171 | 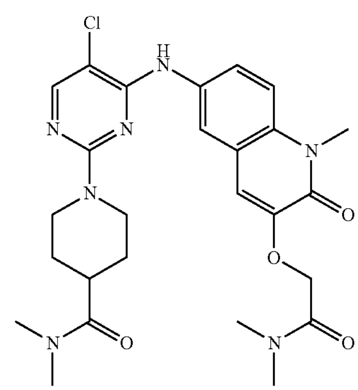 [SMILES: CN(C)C(=O)COc1cc2cc(Nc3nc(N4CCC(C(=O)N(C)C)CC4)ncc3Cl)ccc2n(C)c1=O] | 1.00 | 542 | Method 1 |
| I-172 | 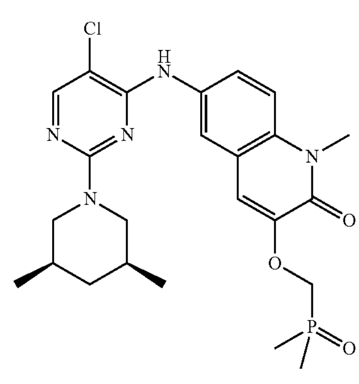 [SMILES: C[C@@H]1C[C@H](C)CN(c2ncc(Cl)c(Nc3ccc4c(c3)cc(OCP(C)(C)=O)c(=O)n4C)n2)C1] | 1.28 | 504 | Method 1 |

TABLE 11-continued

Compounds I-171 to I-175

| # | structure | t$_{Ret.}$ HPLC [min] | MS (M + H)$^+$ | method |
|---|---|---|---|---|
| I-173 | 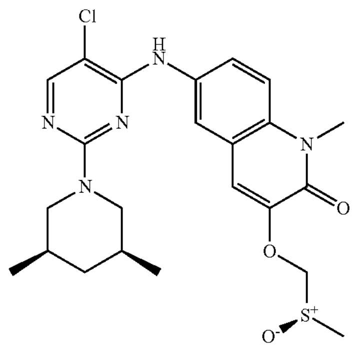 | 1.29 | 490 | Method 1 |
| I-174 | 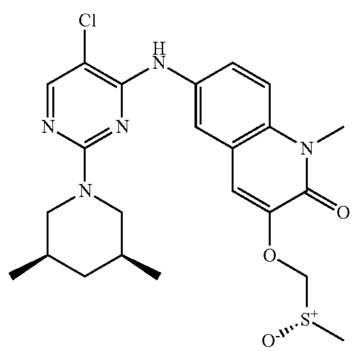 | 1.29 | 490 | Method 1 |
| I-175 | 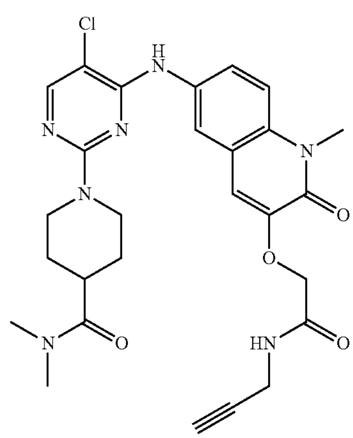 [SMILES: C#CCNC(=O)COc1cc2cc(Nc3nc(N4CCC(C(=O)N(C)C)CC4)ncc3Cl)ccc2n(C)c1=O] | 1.05 | 552 | Method 1 |

C.4. Experimental Procedures for the Synthesis of Compounds (I) from IM-3' and IM-3'

C.4.1. Experimental Procedure for the Synthesis of I-176

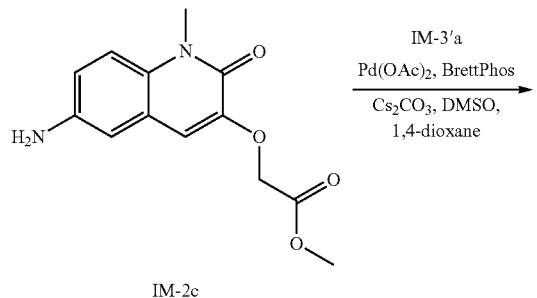

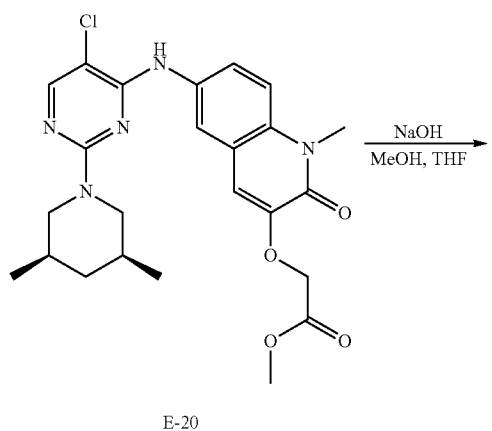

To IM-3'a (60.0 mg; 198 µmol) and IM-2c (62.3 mg; 237 µmol) in 1,4-dioxane (3.0 mL) and DMSO (300 µL) are added under an inert atmosphere (argon) Cs₂CO₃ (161 mg; 494 µmol), Pd(OAc)₂ (2.22 mg; 10.0 µmol) and 2-(dicyclohexylphosphino)3,6-dimethoxy-2',4',6'-triisopropyl-1,1'-biphenyl (BrettPhos) (10.7 mg; 20.0 µmol). The vial is sealed and heated to 100° C. under microwave irradiation for 45 min. After cooling to rt MeCN/H₂O is added, the mixture is filtered and purified by preparative RP-HPLC under acidic conditions using a MeCN/H₂O gradient from 10:90 to 98:2 over 9 min as eluent (column: Sunfire C18; 30×50 mm; 5 µm; flow: 50 mL/min). The product containing fractions are freeze dried to give methyl 2-{[6-({3-chloro-6-[cis-3,5-dimethylpiperidin-1-yl]pyridin-2-yl}amino)-1-methyl-2-oxo-1,2-dihydroquinolin-3-yl]oxy}acetate (E-20).

To E-20 (21.0 mg; 43.3 µmol) in THF (250 µL) and MeOH (250 µL) is added NaOH solution (43.3 µL; 2 M in H₂O) and the resulting mixture is stirred at rt for 30 min. The mixture is acidified with 4 N HCl$_{aq}$, MeCN/H₂O is added and the crude product is purified by preparative RP-HPLC under acidic conditions using MeCN/H₂O gradients from 15:85 to 98:2 over 9 min as eluent (column: Sunfire C18; 30×50 mm; 5 µm; flow: 50 mL/min) and a second time under basic conditions using a MeCN/H₂O gradient from 10:90 to 98:2 over 9 min as eluent (column: XBridge; 50×150 mm; 10 µm; flow: 150 mL/min). The product containing fractions are freeze dried to give 2-{[6-({3-chloro-6-[cis-3,5-dimethylpiperidin-1-yl]pyridin-2-yl}amino)-1-methyl-2-oxo-1,2-dihydroquinolin-3-yl]oxy}acetic acid (I-176) (HPLC-MS: $t_{Ret.}$=1.19 min; MS (M+H)⁺=471; method 1).

C.4.2. Experimental Procedure for the Synthesis of I-177

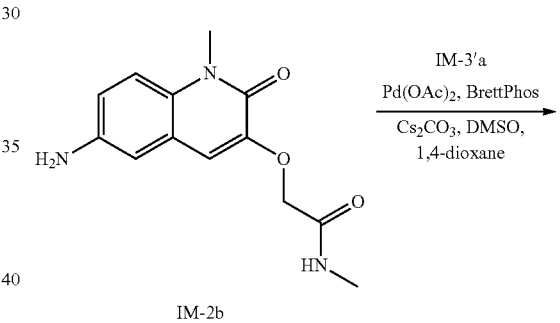

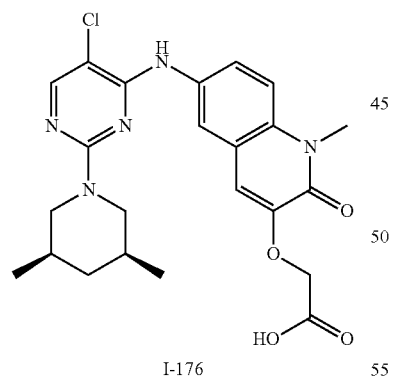

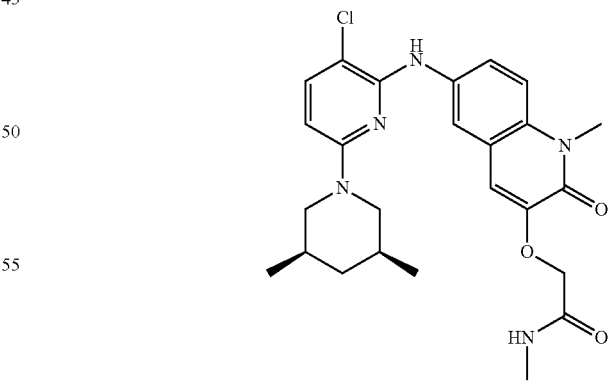

To IM-3'a (20.0 mg; 65.8 µmol) and IM-2b (20.7 mg; 79.2 µmol) in 1,4-dioxane (1.0 mL) and DMSO (100 µL) is added under an inert atmosphere (argon) Cs₂CO₃ (53.7 mg; 165 µmol), Pd(OAc)₂ (0.74 mg; 3.3 µmol) and 2-(dicyclohexylphosphino)$_{3,6}$-dimethoxy-2',4',6'-triisopropyl-1,1'-biphenyl (BrettPhos) (3.54 mg; 6.6 µmol). The vial is sealed and heated to 100° C. under microwave irradiation for 45 min. After cooling to rt MeCN/H$_2$O is added, the mixture is filtered and purified by preparative RP-HPLC under acidic conditions using a MeCN/H$_2$O gradient from 10:90 to 98:2 over 9 min as eluent (column: Sunfire C18; 30×50 mm; 5 µm; flow: 50 mL/min). The product containing fractions are freeze dried to give 2-{[6-({3-chloro-6-[cis-3,5-dimethylpiperidin-1-yl]pyridin-2-yl}amino)-1-methyl-2-oxo-1,2-dihydroquinolin-3-yl]oxy}-N-methylacetamide (I-177) (HPLC-MS: t$_{Ret.}$=1.51 min; MS (M+H)$^+$=484; method 1).

-continued

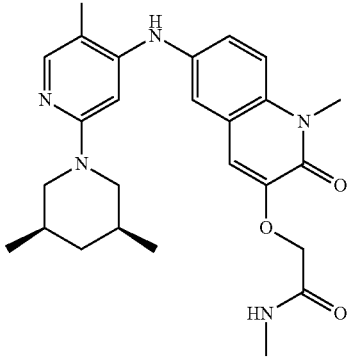

I-178

C.4.3. Experimental Procedure for the Synthesis of I-178

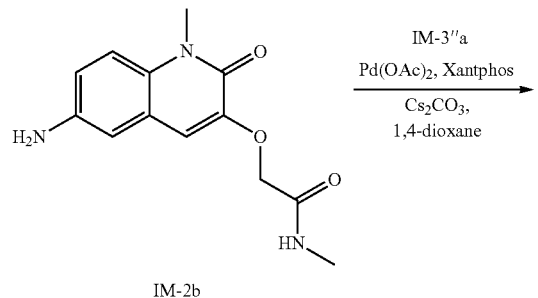

To IM-3"a (216 mg; 616 µmol) and IM-2b (183 mg; 614 µmol) in 1,4-dioxane (2.0 mL) is added under an inert atmosphere (argon) Cs$_2$CO$_3$ (402 mg; 1.23 mmol), Pd(OAc)$_2$ (5.53 mg; 24.6 µmol) and 4,5-bis(diphenylphosphino)-9,9-dimethylxanthene (Xantphos) (28.5 mg; 49.3 µmol) and the mixture is stirred for 6 h at 100° C. After cooling to rt MeCN/H$_2$O is added, the mixture is filtered and purified by preparative RP-HPLC under acidic conditions using a MeCN/H$_2$O gradient from 10:90 to 55:45 over 6 min as eluent (column: Sunfire C18; 30×100 mm; 10 µm). The product containing fractions are freeze dried to give 2-{[6-({5-chloro-2-[cis-3,5-dimethylpiperidin-1-yl]pyridin-4-yl}amino)-1-methyl-2-oxo-1,2-dihydroquinolin-3-yl]oxy}-N-methylacetamide (I-178) (HPLC-MS: t$_{Ret.}$=1.33 min; MS (M+H)$^+$=484; method 1).

TABLE 12

Compounds I-176 to I-178

| # | structure | t$_{Ret.}$ HPLC [min] | MS (M + H)$^+$ | method |
|---|---|---|---|---|
| I-176 | 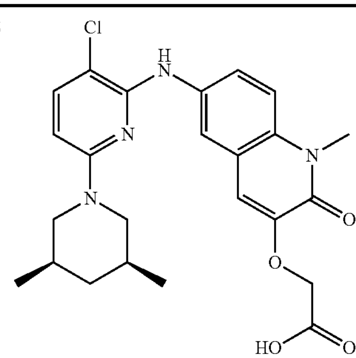 | 1.19 | 471 | Method 1 |
| I-177 | 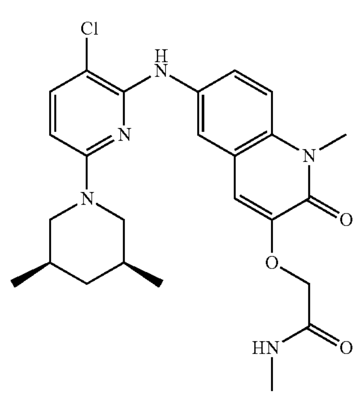 | 1.51 | 484 | Method 1 |

TABLE 12-continued

Compounds I-176 to I-178

| # | structure | $t_{Ret.}$ HPLC [min] | MS $(M + H)^+$ | method |
|---|-----------|------------------------|-----------------|--------|
| I-178 | (structure shown) | 1.33 | 484 | Method 1 |

Biological Methods

BCL6::BCOR ULight TR-FRET Assay:

Biotinylated BCL6 protein corresponding to BCL6 (amino acids 5 to 129, with the following changes to the natural protein: C8Q, C67R, C84N) is expressed in E. coli with a carboxy-terminal Avi tag (amino acid sequence GLNDIFEAQKIEWHE). The BCOR ULight peptide uses a direct carboxy-terminal ULight tag (PerkinElmer). The sequence of the peptide is CRSEIISTAPSSWVVPGP, with the amino terminus acetylated and the ULight tag attached to the cysteine. Compounds are dispensed onto assay plates (Proxiplate 384 PLUS, white, PerkinElmer) using an Access Labcyte Workstation with the Labcyte Echo 55×from a DMSO solution. For the chosen highest assay concentration of 100 µM, 150 nl of compound solution are transferred from a 10 mM DMSO compound stock solution. A series of 11 concentrations is transferred for each compound at which each concentration is fivefold lower than the previous one. DMSO is added such that every well has a total of 150 nl compound solution. 5 µL of 1 nM BCL6 protein in assay buffer (50 mM HEPES pH 7.3; 125 mM NaCl; 1 mM GSH; 0.01% Triton-X 100; 0.03% BSA) are added to the 150 nl of compounds. After 30 minutes incubation time at room temperature, 10 µL of a mix containing BCOR ULight peptide (100 nM final assay concentration) and Streptavidin-Europium (0.75 nM final assay concentration) are added. Plates are kept at room temperature. After 240 minutes incubation time the TR-FRET signal is measured in a PerkinElmer Envision HTS Multilabel Reader using the TR-FRET LANCE Ultra specs of PerkinElmer. Each plate contains negative controls (diluted DMSO instead of test compound; BCOR peptide and Streptavidin Europium mix with BCL6 protein) and positive controls (diluted DMSO instead of test compound; BCOR peptide and Streptavidin-Europium mix without BCL6 protein). Negative and positive control values are used for normalization.

LUMIER Assays

LUMIER assays are done as described (Blasche, S. & Koegl, M. Analysis of protein-protein interactions using LUMIER assays, Methods Mol. Biol 1064, 17-27 (2013); Barrios-Rodiles, M. et al., High-throughput mapping of a dynamic signaling network in mammalian cells, Science 307, 1621-1625 (2005)$_{35,36}$). In brief, proteins are transiently expressed in HEK293 cells as hybrid proteins fused to the Staphylococcus aureus protein A tag or to Renilla reniformis luciferase. BCL6 (amino acids 1-373) is fused at its amino-terminus to protein A (BCL6 1 373 nt PrA) and a peptide encompassing three repeats of the BCL6-binding sequence of NCOR1 (amino acids 1340 1355: GIT-TIKEMGRSIHEIP) is fused at its amino-terminus to Renilla luciferase (NCOR3×BID-ntRen). 4 µg of each expression construct are transfected into 500.000 HEK293 cells in 15 ml medium using 12.5 µL of lipofectamine 2000 (Invitrogen) in 2 ml OptiMEM. The next day, cells are trypsinized, resuspended in fresh medium, seeded into the well of a 96 well plate, 10.000 cells per well, and incubated overnight. The following day, Dynabeads M 280, Sheep Anti-Rabbit IgG, (Lifetechnologies #11204D, 2 mg/ml final concentration) are coated with Rabbit Anti-Mouse Antibody (Dako, 38 µL 2.1 mg/ml antibody solution per ml of coated beads), washed with PBS and suspended to 2 mg/ml. Coated Dynabeads are diluted 20 fold in lysis buffer (22 mM Tris HCl pH 7.4, 1.1% Triton, 275 mM NaCl, 11 mM EDTA, phosphatase/protease inhibitor cocktail (Thermo Scientific #1861281) (1:100), 10 mM DTT, 0.5 µL/ml Benzonase (Novagen #70746-10KU, 25 U/µL)). Compounds are added to the cells at logarithmic dose series using the HP Digital Dispenser D300 (Tecan), normalising for added DMSO. Cells are then incubated for 1 hour at 37° C. before medium is removed and cells are lysed on ice in 10 µL of ice-cold lysis buffer containing Dynabeads. Plates are briefly shaken and lysates are incubated on ice for 10 minutes. 100 µL of cold PBS are added per well, and 10% of the diluted lysate is removed to determine the luciferase activity present in each sample before washing. The rest of the sample is washed 5 times in cold PBS in a Tecan HydroSpeed plate washer and resuspended in 20 µL PBS. Luciferase activity is measured in the lysate as well as in washed beads by injection of 50 µL of renilla detection buffer (Renilla Juice, PJK 102531). Negative controls are cells co-transfected with a plasmid expressing the luciferase fusion protein and a plasmid expressing a dimer of protein A. The signal of washed beads divided by the signal of 10% of the lysate, non-washed, is calculated for both the interaction (BCL6-Protein A+NCoR1-luciferase) and the negative control (protein A dimer+NCoR1-luciferase) to generate "signals normalised for expression levels". The "signals normalised for expression levels" of the interaction test are divided by the "signals normalised for expression levels" of the negative control to derive normalised signal to background ratios.

BCL6 Degradation Assay

To quantify the effects of compounds on BCL6 degradation, SU-DHL-4 cells are collected by centrifucation and resuspended to 3 million cells per ml in RPMI (ATCC #30-2001), 10% fetal bovine serum. 300.000 cells are used per well of a 96 well plate in 100 μL medium. Compounds are added to the cells at logarithmic dose series using the HP Digital Dispenser D300 (Tecan), normalising for added DMSO. After compound addition, cells are incubated for 90 minutes at 37° C. Cells are collected by centrifugation, washed once with PBS and lysed in 25 μL lysis buffer (1% Triton, 350 mM KCl, 10 mM Tris pH 7,4, phosphatase-protease inhibitor cocktail (Thermo Scientific #1861281), 10 mM DTT, Benzonase 0.5 μL/ml (Novagen #70746 10KU, 25 U/μL). BCL6 levels are analysed using a Wes capillary electrophoresis instrument (Proteinsimple), using BCL6 antibody, (4 μg/ml, 10 μL per lane, rabbit, SIGMA #HPA0048999) and GAPDH antibody, (1 μg/ml 10 μL per lane, rabbit, Abcam #ab8245), for normalisation.

Proliferation Assays

For long-term proliferations assays, cells are inoculated at a density of 200,000 cells per ml in 1.5 ml in 24 well plates. Compounds or DMSO are added, and every 3 to 4 days cells are split to 200,000 cells per ml. Upon splitting, fresh compound is added to keep the concentration constant. Split rates are multiplied to derive proliferation factors. For routine measurement of IC50 values during compound optimization, proliferation assays are done for 12 days in semi-solid medium. Ice cold matrigel (Corning Life Sciences #354262, phenol-red free, LDEV-free, ~20 mg/ml) is added to 6667 cells/ml in ice cold medium to a concentration of 400 μg/ml, mixed by inversion and immediately pipeted into the wells of 96 well plate, 150 μL/well. Cells are grown overnight. Then 50 μL of medium are dispensed to each well and compounds are added at logarithmic dose series before returning the cells to 37° C. for 12 days. 20 μL of PrestoBlue reagent (Invitrogen, #A13261) are added per well and fluorescence was measured after 14 hours at 531 nm excitation and 595 nm emission.

The following Table shows the IC50 values of example compounds determined using the indicated assay.

| Example # | BCL6 :: BCOR ULight TR-FRET Assay IC50 (nM) |
|---|---|
| I-1 | 10 |
| I-2 | 9 |
| I-3 | 7 |
| I-4 | 3 |
| I-5 | 12 |
| I-6 | 7 |
| I-7 | 5 |
| I-8 | 21 |
| I-9 | 41 |
| I-10 | 18 |
| I-11 | 13 |
| I-12 | 7 |
| I-13 | 5 |
| I-14 | 20 |
| I-15 | 32 |
| I-16 | 10 |
| I-17 | 8 |
| I-18 | 7 |
| I-19 | 6 |
| I-20 | 6 |
| I-21 | 12 |
| I-22 | 10 |
| I-23 | 9 |
| I-24 | 13 |
| I-25 | 4 |
| I-26 | 4 |
| I-27 | 6 |
| I-28 | 12 |
| I-29 | 10 |
| I-30 | 5 |
| I-31 | 6 |
| I-32 | 5 |
| I-33 | 62 |
| I-34 | 6 |
| I-35 | 8 |
| I-36 | 5 |
| I-37 | 7 |
| I-38 | 35 |
| I-39 | n.d. |
| I-40 | 9 |
| I-41 | 8 |
| I-42 | 9 |
| I-43 | 6 |
| I-44 | 9 |
| I-45 | 7 |
| I-46 | 13 |
| I-47 | 5 |
| I-48 | 11 |
| I-49 | 11 |
| I-50 | 5 |
| I-51 | 6 |
| I-52 | 7 |
| I-53 | 6 |
| I-54 | 5 |
| I-55 | 5 |
| I-56 | 4 |
| I-57 | 6 |
| I-58 | 7 |
| I-59 | 11 |
| I-60 | 6 |
| I-61 | 4 |
| I-62 | 4 |
| I-63 | 8 |
| I-64 | 9 |
| I-65 | 23 |
| I-66 | 5 |
| I-67 | 5 |
| I-68 | 7 |
| I-69 | 23 |
| I-70 | 7 |
| I-71 | 9 |
| I-72 | 9 |
| I-73 | 4 |
| I-74 | 5 |
| I-75 | 5 |
| I-76 | 5 |
| I-77 | 8 |
| I-78 | 4 |
| I-79 | 11 |
| I-80 | 7 |
| I-81 | 7 |
| I-82 | 4 |
| I-83 | 12 |
| I-84 | 10 |
| I-85 | 9 |
| I-86 | 3 |
| I-87 | 15 |
| I-88 | 6 |
| I-89 | 8 |
| I-90 | 7 |
| I-91 | 7 |
| I-92 | 5 |
| I-93 | 4 |
| I-94 | 2 |
| I-95 | 2 |
| I-96 | 2 |
| I-97 | 4 |

| Example # | BCL6 :: BCOR ULight TR-FRET Assay IC50 (nM) |
|---|---|
| I-98 | 4 |
| I-99 | 7 |
| I-100 | 12 |
| I-101 | 10 |
| I-102 | 7 |
| I-103 | 10 |
| I-104 | 10 |
| I-105 | 114 |
| I-106 | 210 |
| I-107 | 10 |
| I-108 | 38 |
| I-109 | 21 |
| I-110 | 17 |
| I-111 | 108 |
| I-112 | 7 |
| I-113 | 7 |
| I-114 | 9 |
| I-115 | 9 |
| I-116 | 10 |
| I-117 | 11 |
| I-118 | 16 |
| I-119 | 13 |
| I-120 | 11 |
| I-121 | 10 |
| I-122 | 6 |
| I-123 | 7 |
| I-124 | 11 |
| I-125 | 10 |
| I-126 | 7 |
| I-127 | 9 |
| I-128 | 7 |
| I-129 | 7 |
| I-130 | 9 |
| I-131 | 5 |
| I-132 | 5 |
| I-133 | 29 |
| I-134 | 77 |
| I-135 | 16 |
| I-136 | 269 |
| I-137 | 21 |
| I-138 | 529 |
| I-139 | 6 |
| I-140 | 5 |
| I-141 | 9 |
| I-142 | 5 |
| I-143 | 6 |
| I-144 | 22 |
| I-145 | 6 |
| I-146 | 6 |
| I-147 | 5 |
| I-148 | 3 |
| I-149 | 12 |
| I-150 | 85 |
| I-151 | 6 |
| I-152 | 5 |
| I-153 | 11 |
| I-154 | 82 |
| I-155 | 9 |
| I-156 | 19 |
| I-157 | 5 |
| I-158 | 6 |
| I-159 | 85 |
| I-160 | 7 |
| I-161 | 5 |
| I-162 | 98 |
| I-163 | 60 |
| I-164 | 281 |
| I-165 | 22 |
| I-166 | 16 |
| I-167 | 4 |
| I-168 | 6 |
| I-169 | 6 |
| I-170 | 8 |
| I-171 | 39 |
| I-172 | 187 |
| I-173 | 37 |
| I-174 | 16 |
| I-175 | 10 |
| I-176 | 106 |
| I-177 | 87 |
| I-178 | 22 |

Therapeutic Use

Due to their biological properties the compounds of the invention, their tautomers, racemates, enantiomers, diastereomers, mixtures thereof and the salts of all the above-mentioned forms may be suitable for treating diseases characterised by excessive or abnormal cell proliferation such as cancer.

For example, the following cancers, tumors and other proliferative diseases may be treated with compounds of the invention, without being restricted thereto:

Cancers/tumors/carcinomas of the head and neck: e.g. tumors/carcinomas/cancers of the nasal cavity, paranasal sinuses, nasopharynx, oral cavity (including lip, gum, alveolar ridge, retromolar trigone, floor of mouth, tongue, hard palate, buccal mucosa), oropharynx (including base of tongue, tonsil, tonsillar pilar, soft palate, tonsillar fossa, pharyngeal wall), middle ear, larynx (including supraglottis, glottis, subglottis, vocal cords), hypopharynx, salivary glands (including minor salivary glands);

cancers/tumors/carcinomas of the lung: e.g. non-small cell lung cancer (NSCLC) (squamous cell carcinoma, spindle cell carcinoma, adenocarcinoma, large cell carcinoma, clear cell carcinoma, bronchioalveolar), small cell lung cancer (SCLC) (oat cell cancer, intermediate cell cancer, combined oat cell cancer);

neoplasms of the mediastinum: e.g. neurogenic tumors (including neurofibroma, neurilemoma, malignant schwannoma, neurosarcoma, ganglioneuroblastoma, ganglioneuroma, neuroblastoma, pheochromocytoma, paraganglioma), germ cell tumors (including seminoma, teratoma, non-seminoma), thymic tumors (including thymoma, thymolipoma, thymic carcinoma, thymic carcinoid), mesenchymal tumors (including fibroma, fibrosarcoma, lipoma, liposarcoma, myxoma, mesothelioma, leiomyoma, leiomyosarcoma, rhabdomyosarcoma, xanthogranuloma, mesenchymoma, hemangioma, hemangioendothelioma, hemangiopericytoma, lymphangioma, lymphangiopericytoma, lymphangiomyoma);

cancers/tumors/carcinomas of the gastrointestinal (GI) tract: e.g. tumors/carcinomas/cancers of the esophagus, stomach (gastric cancer), pancreas, liver and biliary tree (including hepatocellular carcinoma (HCC), e.g. childhood HCC, fibrolamellar HCC, combined HCC, spindle cell HCC, clear cell HCC, giant cell HCC, carcinosarcoma HCC, sclerosing HCC; hepatoblastoma; cholangiocarcinoma; cholangiocellular carcinoma; hepatic cystadenocarcinoma; angiosarcoma, hemangioendothelioma, leiomyosarcoma, malignant schwannoma, fibrosarcoma, Klatskin tumor), gall bladder, extrahepatic bile ducts, small intestine (including duodenum, jejunum, ileum), large intestine (including cecum, colon, rectum, anus; colorectal cancer, gastrointestinal stroma tumor (GIST)), genitourinary system (including kidney, e.g. renal pelvis, renal cell carcinoma (RCC), nephroblastoma (Wilms' tumor), hypernephroma, Grawitz tumor; ureter; urinary bladder, e.g. urachal cancer, urothelial cancer; urethra, e.g. distal, bulbomembranous, prostatic; prostate (androgen dependent, androgen independent, castration resistant, hormone independent, hormone refractory), penis);

cancers/tumors/carcinomas of the testis: e.g. seminomas, non-seminomas, Gynecologic cancers/tumors/carcinomas: e.g. tumors/carcinomas/cancers of the ovary, fallopian tube, peritoneum, cervix, vulva, vagina, uterine body (including endometrium, fundus);

cancers/tumors/carcinomas of the breast: e.g. mammary carcinoma (infiltrating ductal, colloid, lobular invasive, tubular, adenocystic, papillary, medullary, mucinous), hormone receptor positive breast cancer (estrogen receptor positive breast cancer, progesterone receptor positive breast cancer), Her2 positive breast cancer, triple negative breast cancer, Paget's disease of the breast;

cancers/tumors/carcinomas of the endocrine system: e.g. tumors/carcinomas/cancers of the endocrine glands, thyroid gland (thyroid carcinomas/tumors; papillary, follicular, anaplastic, medullary), parathyroid gland (parathyroid carcinoma/tumor), adrenal cortex (adrenal cortical carcinoma/tumors), pituitary gland (including prolactinoma, craniopharyngioma), thymus, adrenal glands, pineal gland, carotid body, islet cell tumors, paraganglion, pancreatic endocrine tumors (PET; non-functional PET, PPoma, gastrinoma, insulinoma, VIPoma, glucagonoma, somatostatinoma, GRFoma, ACTHoma), carcinoid tumors;

sarcomas of the soft tissues: e.g. fibrosarcoma, fibrous histiocytoma, liposarcoma, leiomyosarcoma, rhabdomyosarcoma, angiosarcoma, lymphangiosarcoma, Kaposi's sarcoma, glomus tumor, hemangiopericytoma, synovial sarcoma, giant cell tumor of tendon sheath, solitary fibrous tumor of pleura and peritoneum, diffuse mesothelioma, malignant peripheral nerve sheath tumor (MPNST), granular cell tumor, clear cell sarcoma, melanocytic schwannoma, plexosarcoma, neuroblastoma, ganglioneuroblastoma, neuroepithelioma, extraskeletal Ewing's sarcoma, paraganglioma, extraskeletal chondrosarcoma, extraskeletal osteosarcoma, mesenchymoma, alveolar soft part sarcoma, epithelioid sarcoma, extrarenal rhabdoid tumor, desmoplastic small cell tumor;

sarcomas of the bone: e.g. myeloma, reticulum cell sarcoma, chondrosarcoma (including central, peripheral, clear cell, mesenchymal chondrosarcoma), osteosarcoma (including parosteal, periosteal, high-grade surface, small cell, radiation-induced osteosarcoma, Paget's sarcoma), Ewing's tumor, malignant giant cell tumor, adamantinoma, (fibrous) histiocytoma, fibrosarcoma, chordoma, small round cell sarcoma, hemangioendothelioma, hemangiopericytoma, osteochondroma, osteoid osteoma, osteoblastoma, eosinophilic granuloma, chondroblastoma;

mesothelioma: e.g. pleural mesothelioma, peritoneal mesothelioma;

cancers of the skin: e.g. basal cell carcinoma, squamous cell carcinoma, Merkel's cell carcinoma, melanoma (including cutaneous, superficial spreading, lentigo maligna, acral lentiginous, nodular, intraocular melanoma), actinic keratosis, eyelid cancer;

neoplasms of the central nervous system and brain: e.g. astrocytoma (cerebral, cerebellar, diffuse, fibrillary, anaplastic, pilocytic, protoplasmic, gemistocytary), glioblastoma, gliomas, oligodendrogliomas, oligoastrocytomas, ependymomas, ependymoblastomas, choroid plexus tumors, medulloblastomas, meningiomas, schwannomas, hemangioblastomas, hemangiomas, hemangiopericytomas, neuromas, ganglioneuromas, neuroblastomas, retinoblastomas, neurinomas (e.g. acoustic), spinal axis tumors;

lymphomas and leukemias: e.g. B-cell non-Hodgkin lymphomas (NHL) (including small lymphocytic lymphoma (SLL), lymphoplasmacytoid lymphoma (LPL), mantle cell lymphoma (MCL), follicular lymphoma (FL), diffuse large B-cell lymphoma (DLBCL), Burkitt's lymphoma (BL)), T-cell non-Hodgkin lymphomas (including anaplastic large cell lymphoma (ALCL), adult T-cell leukemia/lymphoma (ATLL), cutaneous T-cell lymphoma (CTCL), peripheral T-cell lymphoma (PTCL)), lymphoblastic T-cell lymphoma (T-LBL), adult T-cell lymphoma, lymphoblastic B-cell lymphoma (B-LBL), immunocytoma, chronic B-cell lymphocytic leukemia (B-CLL), chronic T-cell lymphocytic leukemia (T-CLL) B-cell small lymphocytic lymphoma (B-SLL), cutaneous T-cell lymphoma (CTLC), primary central nervous system lymphoma (PCNSL), immunoblastoma, Hodgkin's disease (HD) (including nodular lymphocyte predominance HD (NLPHD), nodular sclerosis HD (NSHD), mixed-cellularity HD (MCHD), lymphocyte-rich classic HD, lymphocyte-depleted HD (LDHD)), large granular lymphocyte leukemia (LGL), chronic myelogenous leukemia (CML), acute myelogenous/myeloid leukemia (AML), acute lymphatic/lymphoblastic leukemia (ALL), acute promyelocytic leukemia (APL), chronic lymphocytic/lymphatic leukemia (CLL), prolymphocytic leukemia (PLL), hairy cell leukemia, chronic myelogenous/myeloid leukemia (CML), myeloma, plasmacytoma, multiple myeloma (MM), plasmacytoma, myelodysplastic syndromes (MDS), chronic myelomonocytic leukemia (CMML);

cancers of unknown primary site (CUP);

All cancers/tumors/carcinomas mentioned above which are characterized by their specific location/origin in the body are meant to include both the primary tumors and the metastatic tumors derived therefrom.

All cancers/tumors/carcinomas mentioned above may be further differentiated by their histopathological classification:

Epithelial cancers, e.g. squamous cell carcinoma (SCC) (carcinoma in situ, superficially invasive, verrucous carcinoma, pseudosarcoma, anaplastic, transitional cell, lymphoepithelial), adenocarcinoma (AC) (well-differentiated, mucinous, papillary, pleomorphic giant cell, ductal, small cell, signet-ring cell, spindle cell, clear cell, oat cell, colloid, adenosquamous, mucoepidermoid, adenoid cystic), mucinous cystadenocarcinoma, acinar cell carcinoma, large cell carcinoma, small cell carcinoma, neuroendocrine tumors (small cell carcinoma, paraganglioma, carcinoid); oncocytic carcinoma;

Nonepithilial cancers, e.g. sarcomas (fibrosarcoma, chondrosarcoma, rhabdomyosarcoma, leiomyosarcoma, hemangiosarcoma, giant cell sarcoma, lymphosarcoma, fibrous histiocytoma, liposarcoma, angiosarcoma, lymphangiosarcoma, neurofibrosarcoma), lymphoma, melanoma, germ cell tumors, hematological neoplasms, mixed and undifferentiated carcinomas;

The compounds of the invention may be used in therapeutic regimens in the context of first line, second line, or any further line treatments.

The compounds of the invention may be used for the prevention, short-term or long-term treatment of the above-mentioned diseases, optionally also in combination with radiotherapy and/or surgery.

Of course, the above also includes the use of the compounds of the invention in various methods of treating the above diseases by administering a therapeutically effective dose to a patient in need thereof, as well as the use of these compounds for the manufacture of medicaments for the treatment of such diseases, as well as pharmaceutical compositions including such compounds of the invention, as well as the preparation and/or manufacture of medicaments including such compounds of the invention, and the like.

Combinations with Other Active Substances

The compounds of the invention may be used on their own or in combination with one or several other pharmacologically active substances such as state-of-the-art or standard-of-care compounds, such as e.g. cell proliferation inhibitors, anti-angiogenic substances, steroids or immune modulators/checkpoint inhibitors, and the like.

Therapeutic agents (=cytostatic and/or cytotoxic active substances) which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors and/or of their corresponding receptors (growth factors such as for example platelet derived growth factor (PDGF), fibroblast growth factor (FGF), vascular endothelial growth factor (VEGF), epidermal growth factor (EGF), insuline-like growth factors (IGF), human epidermal growth factor (HER, e.g. HER2, HER3, HER4) and hepatocyte growth factor (HGF) and/or their corresponding receptors), inhibitors are for example (anti-)growth factor antibodies, (anti-)growth factor receptor antibodies and tyrosine kinase inhibitors, such as for example cetuximab, gefitinib, afatinib, nintedanib, imatinib, lapatinib, bosutinib, bevacizumab and trastuzumab); antimetabolites (e.g. antifolates such as methotrexate, raltitrexed, pyrimidine analogues such as 5-fluorouracil (5-FU), ribonucleoside and deoxyribonucleoside analogues, capecitabine and gemcitabine, purine and adenosine analogues such as mercaptopurine, thioguanine, cladribine and pentostatin, cytarabine (ara C), fludarabine); antitumour antibiotics (e.g. anthracyclins such as doxorubicin, doxil (pegylated liposomal doxorubicin hydrochloride, myocet (non-pegylated liposomal doxorubicin), daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); angiogenesis inhibitors (e.g. tasquinimod), tubuline inhibitors; DNA synthesis inhibitors, PARP inhibitors, topoisomerase inhibitors (e.g. epipodophyllotoxins such as for example etoposide and etopophos, teniposide, amsacrin, topotecan, irinotecan, mitoxantrone), serine/threonine kinase inhibitors (e.g. PDK 1 inhibitors, Raf inhibitors, A-Raf inhibitors, B-Raf inhibitors, C-Raf inhibitors, mTOR inhibitors, mTORC1/2 inhibitors, PI3K inhibitors, PI3Kα inhibitors, dual mTOR/PI3K inhibitors, STK 33 inhibitors, AKT inhibitors, PLK 1 inhibitors, inhibitors of CDKs, Aurora kinase inhibitors), tyrosine kinase inhibitors (e.g. PTK2/FAK inhibitors), protein protein interaction inhibitors (e.g. IAP activator, Mcl-1, MDM2/MDMX), MEK inhibitors, ERK inhibitors, FLT3 inhibitors, BRD4 inhibitors, IGF-1R inhibitors, TRAILR2 agonists, Bcl-xL inhibitors, Bcl-2 inhibitors, Bcl-2/Bcl-xL inhibitors, ErbB receptor inhibitors, BCR-ABL inhibitors, ABL inhibitors, Src inhibitors, rapamycin analogs (e.g. everolimus, temsirolimus, ridaforolimus, sirolimus), androgen synthesis inhibitors, androgen receptor inhibitors, DNMT inhibitors, HDAC inhibitors, ANG1/2 inhibitors, CYP17 inhibitors, radiopharmaceuticals, proteasome inhibitors, immunotherapeutic agents such as immune checkpont inhibitors (e.g. CTLA4, PD1, PD-L1, PD-L2, LAG3, and TIM3 binding molecules/immunoglobulins, such as e.g. ipilimumab, nivolumab, pembrolizumab), ADCC (antibody-dependent cell-mediated cytotoxicity) enhancers (e.g. anti-CD33 antibodies, anti-CD37 antibodies, anti-CD20 antibodies), t-cell engagers (e.g. bi-specific T-cell engagers (BiTEs®) like e.g. CD3×BCMA, CD3×CD33, CD3×CD19), PSMA×CD3), tumor vaccines and various chemotherapeutic agents such as amifostin, anagrelid, clodronat, filgrastin, interferon, interferon alpha, leucovorin, procarbazine, levamisole, mesna, mitotane, pamidronate and porfimer.

Most preferred are combinations with IAP activators, proteasome inhibitors, immunotherapeutic agents such as immune checkpoint inhibitors (e.g. CTLA4, PD1, PD-L1, PD-L2, LAG3, and TIM3 binding molecules/immunoglobulins, such as e.g. ipilimumab, nivolumab, pembrolizumab), ADCC (antibody-dependent cell-mediated cytotoxicity) enhancers (e.g. anti-CD33 antibodies, anti-CD37 antibodies, anti-CD20 antibodies), T-cell engagers (e.g. bi-specific T-cell engagers (BiTEs®) like e.g. CD3×BCMA, CD3×CD33, CD3×CD19, PSMA×CD3) and tumor vaccines.

When two or more substances or principles are to be used as part of a combined treatment regimen, they can be administered via the same route of administration or via different routes of administration, at essentially the same time (i.e. simultaneously, concurrently) or at different times (e.g. sequentially, successively, alternately, consecutively, or according to any other sort of alternating regime).

When the substances or principles are to be administered simultaneously via the same route of administration, they may be administered as different pharmaceutical formulations or compositions or as part of a combined pharmaceutical formulation or composition. Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmacological or therapeutic effect.

Of course, the above includes the preparation and methods of preparing, the compounds of the invention for the combined use with the above combination partners. Also included are the preparation, and methods of preparing, the above-mentioned combination partners for the combined use with the compounds of the invention.

Furthermore, the invention also encompasses kits comprising at least one compound of the invention and one or more other components selected from the group consisting of other drugs used for the treatment of the diseases and disorders as described above, and devices as described below.

Formulations

Suitable preparations for administering the compounds of the invention will be apparent to those with ordinary skill in the art and include for example tablets, pills, capsules, suppositories, lozenges, troches, solutions—particularly solutions for injection (s.c., i.v., i.m.) and infusion (injectables)—elixirs, syrups, sachets, emulsions, inhalatives or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) of the invention with known excipients, for example inert diluents, carriers, disintegrants, adjuvants, surfactants, binders and/or lubricants. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may of course contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage range of the compounds of formula (I) applicable per day is usually from 1 mg to 2000 mg, preferably from 1 to 1000 mg.

The dosage for intravenous use is from 1 mg to 1000 mg with different infusion rates, preferably between 5 mg and 500 mg with different infusion rates.

However, it may sometimes be necessary to depart from the amounts specified, depending on the body weight, age, the route of administration, severity of the disease, the individual response to the drug, the nature of its formulation and the time or interval over which the drug is administered (continuous or intermittent treatment with one or multiple doses per day). Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples of Pharmaceutical Formulations

| A) Tablets | per tablet |
|---|---|
| active substance according to formulae (I) | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| active substance according to formulae (I) | 80 mg |
| lactose | 55 mg |
| corn starch | 190 mg |
| microcrystalline cellulose | 35 mg |
| polyvinylpyrrolidone | 15 mg |
| sodiumcarboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) Tablets | per tablet |
|---|---|
| active substance according to formulae (I) | 25 mg |
| lactose | 50 mg |
| microcrystalline cellulose | 24 mg |
| magnesium stearate | 1 mg |
| | 100 mg |

The active substance, lactose and cellulose are mixed together. The mixture is screened, then either moistened with water, kneaded, wet-granulated and dried or dry-granulated or directly final blend with the magnesium stearate and compressed to tablets of suitable shape and size. When wet-granulated, additional lactose or cellulose and magnesium stearate is added and the mixture is compressed to produce tablets of suitable shape and size.

| D) Ampoule solution | |
|---|---|
| active substance according to formulae (I) | 50 mg |
| sodium chloride | 50 mg |
| water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:
1. A compound of formula (I), or a pharmaceutically acceptable salt thereof,

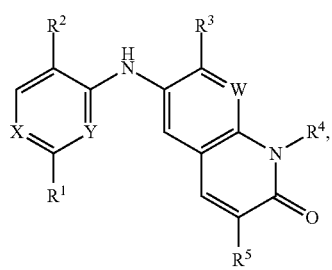

(I)

wherein
$R^1$ is selected from the group consisting of 4-12 membered heterocyclyl and 5-12 membered heteroaryl, wherein said heterocyclyl or said heteroaryl contains at least one nitrogen atom and is linked via nitrogen, and wherein the heterocylyl group is optionally and independently substituted by one or more, identical or different groups independently selected from $R^7$, and the heteroaryl group is optionally and independently substituted by one or more, identical or different group independently selected from $R^8$;
$R^7$ is selected from the group consisting of =O, —CN, —CCH, —OH, —COOH, halogen, —O—$C_{1-6}$alkyl,
—$C_{1-6}$haloalkyl, 5 or 6 membered heteroaryl, phenyl, —N($R^9R^{10}$), —C(O)—$R^{11}$, —C(O)N($R^{12}R^{13}$) and 5-8 membered heterocyclyl, which heterocyclyl is optionally substituted with one group selected from —$C_{1-6}$alkyl;
or $R^7$ is —$C_{1-6}$alkyl optionally substituted with —COOH, —OH, —COO($C_{1-6}$alkyl), —CON($C_{1-3}$alkyl)$_2$, —O—$C_{1-6}$alkyl, —N($C_{1-3}$alkyl)$_2$, phenyl or 5 or 6 membered heterocyclyl, which heterocyclyl is optionally substituted with one group selected from —$C_{1-6}$alkyl;
$R^9$ is selected from hydrogen or —$C_{1-4}$alkyl;
$R^{10}$ is selected from the group consisting of hydrogen, —$C_{1-4}$alkyl, —$C_{1-4}$haloalkyl, 6 membered heterocyclyl and 6 membered heteroaryl;
$R^{11}$ is selected from the group consisting of —$C_{1-3}$alkyl-N($C_{1-3}$alkyl)$_2$ and 5 or 6 membered heterocyclyl, which heterocyclyl is optionally substituted with one group selected from —$C_{1-3}$alkyl;
$R^{12}$ is selected from hydrogen or —$C_{1-3}$alkyl;
$R^{13}$ is selected from —$C_{1-6}$alkyl optionally substituted with —NH$_2$, —O—$C_{1-6}$alkyl, —O—$C_{1-6}$alkyl-NH$_2$ or —O—$C_{1-6}$alkyl—O—$C_{1-6}$alkyl-NH$_2$;
or $R^{13}$ is a 6 membered heterocyclyl optionally substituted with —$C_{1-3}$alkyl;
$R^8$ is selected from —COOH, —$C_{1-6}$alkyl, —C(O)—$R^{19}$, or —C(O)N($R^{20}R^{21}$);
$R^{19}$ is a 6 membered heterocyclyl optionally substituted with —$C_{1-3}$alkyl;
$R^{20}$ and $R^{21}$ are independently selected from hydrogen or —$C_{1-3}$alkyl;
$R^2$ is selected from the group consisting of chlorine and fluorine;
$R^3$ is selected from the group consisting of hydrogen, —$C_{1-4}$alkyl, —O—$C_{1-4}$alkyl and halogen;
$R^4$ is selected from the group consisting of hydrogen, —$C_{3-6}$cycloalkyl, and 4 to 7 membered heterocyclyl, wherein each group is optionally substituted by one group selected from —$C_{1-3}$alkyl, or
$R^4$ is —$C_{1-6}$alkyl optionally substituted with one group selected from —OH, —NH$_2$, —O—$C_{1-4}$alkyl, —NH—$C_{1-4}$alkyl, —N($C_{1-4}$alkyl)$_2$, —$C_{3-6}$cycloalkyl or 4 to 7 membered heterocyclyl, wherein each cycloalkyl and heterocyclyl group is optionally and independently substituted by one group selected from —$C_{1-3}$alkyl;
$R^5$ is —$L_1$—C($R^{14}R^{15}$)—$R^{16}$ or —CH=CH—$R^{16}$
wherein
$L_1$ is —O— or —S—;
$R^{14}$ is hydrogen or $C_{1-4}$alkyl;
$R^{15}$ is hydrogen or $C_{1-4}$alkyl;
or $R^{14}$ and $R^{15}$ taken together form a —$C_{3-5}$cycloalkyl;
$R^{16}$ is —COOH, —CONH$_2$, —C(O)$R^{17}$, —C(O)O$R^{17}$, —C(O)N$R^{17}R^{18}$, —S(O)—$C_{1-6}$alkyl, —S(O)$_2$—$C_{1-6}$alkyl, —P(O)—($C_{1-6}$alkyl)$_2$, or —C(NH)NH$_2$;
$R^{17}$ is a 3-6 membered heterocyclyl or —$C_{1-4}$alkyl optionally substituted by one or more, identical or different groups selected from —OH, —CF$_3$, —N($C_{1-4}$alkyl)$_2$, —$C_{3-6}$cycloalkyl, 3-6 membered heterocyclyl, —$C_{2-4}$alkenyl, or —$C_{2-4}$alkynyl;
$R^{18}$ is hydrogen or $C_{1-4}$alkyl;
W is nitrogen or C$R^6$;
X is nitrogen or CH;
Y is nitrogen or CH;
wherein at least one of X and Y is nitrogen;
$R^6$ is selected from the group consisting of hydrogen, —$C_{1-4}$alkyl, —O—$C_{1-4}$alkyl, —O—$C_{1-4}$haloalkyl, —$C_{1-4}$haloalkyl and halogen.

2. The compound according to claim 1, or a pharmaceutically acceptable salt thereof, wherein $R^3$ is selected from the group consisting of hydrogen, halogen and —O—CH$_3$.

3. The compound according to claim 1, or a pharmaceutically acceptable salt thereof, wherein $R^4$ is —C$_{1-4}$alkyl, optionally substituted with one group selected from —OH, —C$_{3-6}$cycloalkyl or —N(C$_{1-4}$ alkyl)$_2$.

4. The compound according to claim 3, or a pharmaceutically acceptable salt thereof, wherein $R^4$ is selected from the group consisting of —CH$_3$, —CH$_2$CH$_3$, —CH$_2$CH$_2$CH$_3$, —CH(CH$_3$)$_2$, —(CH$_2$)$_3$OH, —(CH$_2$)$_2$(CH$_3$)$_2$, —CH$_2$—cyclopropyl and —(CH$_2$)$_2$N(CH$_3$)$_2$.

5. The compound according to claim 1, or a pharmaceutically acceptable salt thereof, wherein
W is CR$^6$ and
$R^6$ is selected from the group consisting of hydrogen, C$_{1-4}$alkyl, —O—C$_{1-4}$alkyl, —O—C$_{1-4}$ haloalkyl, and halogen.

6. The compound according to claim 5, or a pharmaceutically acceptable salt thereof, wherein
$R^6$ is selected from the group consisting of hydrogen, and —O—CH$_3$.

7. The compound according to claim 1, or a pharmaceutically acceptable salt thereof, wherein $R^1$ is a heterocyclyl selected from the group consisting of 5 to 7 membered heterocyclyl,

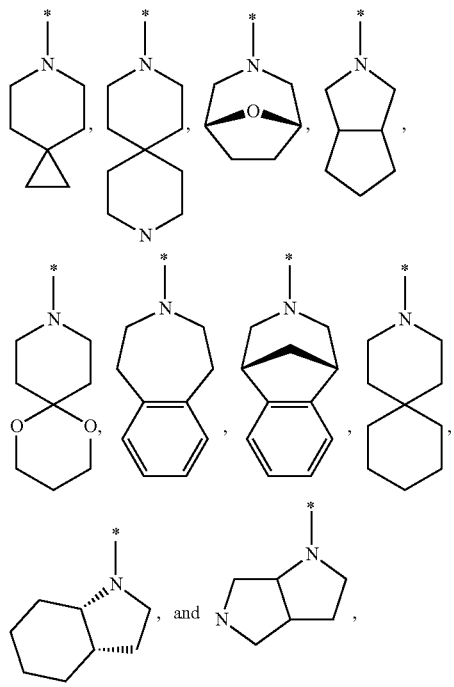

or $R_1$ is a heteroaryl selected from the group consisting of 5 to 7 membered heteroaryl,

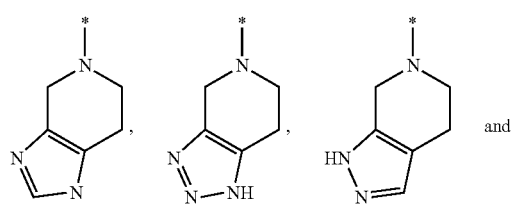

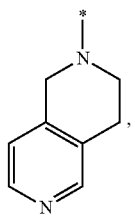

wherein said heterocyclyl or said heteroaryl contains at least one nitrogen atom and is linked via nitrogen, and the heterocylyl group is optionally and independently substituted by one or more, identical or different groups independently selected from $R^7$, and the heteroaryl group is optionally and independently substituted by one or more, identical or different group independently selected from $R^8$, wherein $R^7$ is selected from the group consisting of =O, —CN, —CCH, —OH, —COOH, halogen, —O—C$_{1-6}$alkyl, —C$_{1-6}$haloalkyl, 5 or 6 membered heteroaryl, phenyl, —N(R$^9$R$^{10}$), —C(O)—R$^{11}$, —C(O)N(R$^{12}$R$^{13}$) and 5-8 membered heterocyclyl, which heterocyclyl is optionally substituted with one group selected from —C$_{1-6}$alkyl;

or $R^7$ is —C$_{1-6}$alkyl optionally substituted with —COOH, —OH, —COO(C$_{1-6}$alkyl), —CON(C$_{1-3}$alkyl)$_2$, —O—C$_{1-6}$alkyl, —N(C$_{1-3}$alkyl)$_2$, phenyl or 5 or 6 membered heterocyclyl, which heterocyclyl is optionally substituted with one group selected from —C$_{1-6}$alkyl;

$R^9$ is selected from hydrogen or —C$_{1-4}$alkyl;

$R^{10}$ is selected from the group consisting of hydrogen, —C$_{1-4}$alkyl, —C$_{1-4}$haloalkyl, 6 membered heterocyclyl and 6 membered heteroaryl;

$R^{11}$ is selected from the group consisting of —C$_{1-3}$alkyl—N(C$_{1-3}$alkyl)$_2$ and 5 or 6 membered heterocyclyl, which heterocyclyl is optionally substituted with one group selected from —C$_{1-3}$alkyl, $R^{12}$ is selected from hydrogen or —C$_{1-3}$alkyl;

$R^{13}$ is selected from —C$_{1-6}$alkyl optionally substituted with —NH$_2$, —O—C$_{1-6}$alkyl, —O—C$_{1-6}$alkyl-NH$_2$ or —O—C$_{1-6}$alkyl —O—C$_{1-6}$alkyl —NH$_2$;

or $R^{13}$ is a 6 membered heterocyclyl optionally substituted with —C$_{1-3}$alkyl;

$R^8$ is selected from —COOH, —C$_{1-6}$alkyl, —C(O)—R$^{19}$, or —C(O)N(R$^{20}$R$^{21}$);

$R^{19}$ is a 6 membered heterocyclyl optionally substituted with —C$_{1-3}$alkyl;

$R^{20}$ and $R^{21}$ are independently selected from hydrogen or —C$_{1-3}$alkyl.

8. The compound according to claim 1, or a pharmaceutically acceptable salt thereof, wherein
$R^1$ is a heterocyclyl selected from among

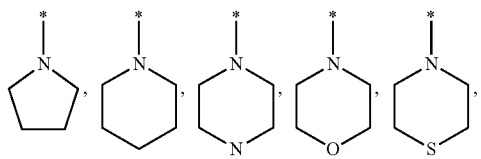

-continued

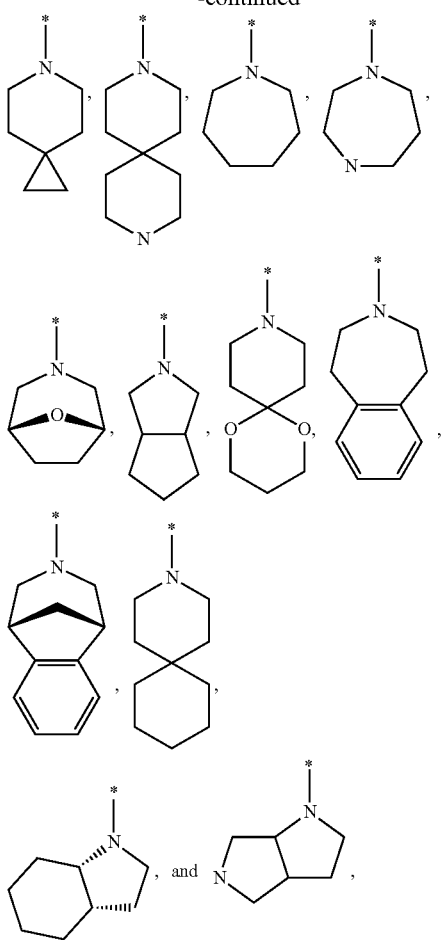

which heterocyclyl is optionally and independently substituted with one, two, three or four substituents independently selected from the group R$^7$ and when R$^1$ is substituted with three or four substituents independently selected from the group R$^7$ at least two of them are independently selected from the group —C$_{1-3}$alkyl; or R$^1$ is a heteroaryl selected from the group consisting of

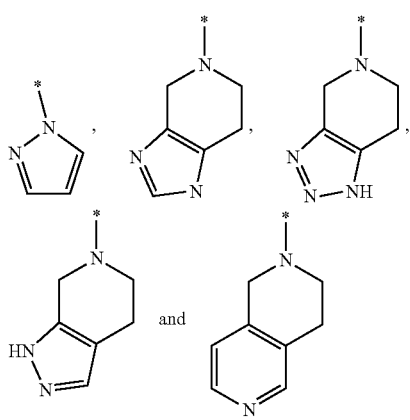

which heteroaryl is optionally and independently substituted with one or two substituents independently selected from the group R$^8$, wherein R$^7$ is selected from the group consisting of =O, —CCH, —CN, —OH, —COOH, halogen, —O—C$_{1-6}$alkyl, —C$_{1-6}$haloalkyl, 5 or 6 membered heteroaryl, phenyl, —N(R$^9$R$^{10}$), —C(O)—R$^{11}$, —C(O)N(R$^{12}$R$^{13}$) and 5-8 membered heterocyclyl, which heterocyclyl is optionally substituted with one group selected from —C$_{1-3}$ alkyl;

or R$^7$ is —C$_{1-6}$alkyl optionally substituted with —COOH, —OH, —COO(C$_{1-6}$alkyl), —CON(C$_{1-3}$alkyl)$_2$, —O—C$_{1-6}$alkyl, —N(C$_{1-3}$alkyl)$_2$, phenyl or 5 or 6 membered heterocyclyl, which heterocyclyl is optionally substituted with one group selected from —C$_{1-3}$ alkyl;

R$^9$ is selected from hydrogen or —C$_{1-4}$alkyl;

R$^{10}$ is selected from the group consisting of hydrogen, —C$_{1-4}$alkyl, —C$_{1-4}$haloalkyl, 5 or 6 membered heterocyclyl and 6 membered heteroaryl;

R$^{11}$ is selected from the group consisting of —C$_{1-3}$alkyl —N(C$_{1-3}$alkyl)$_2$ and 5 or 6 membered heterocyclyl, which heterocyclyl is optionally substituted with one group selected from —C$_{1-3}$alkyl;

R$^{12}$ is selected from hydrogen or —C$_{1-3}$alkyl;

R$^{13}$ is selected from —C$_{1-6}$alkyl, optionally substituted with —NH$_2$, —O—C$_{1-6}$alkyl, —O—C$_{1-6}$alkyl-NH$_2$ or —O—C$_{1-6}$alkyl—NH$_2$;

or R$^{13}$ is a 6 membered heterocyclyl optionally substituted with —C$_{1-3}$alkyl; and wherein R$^8$ is selected from —COOH, —C$_{1-6}$alkyl, —C(O)—R$^{19}$, or —C(O)N(R$^{20}$R$^{21}$);

R$^{19}$ is a 6 membered heterocyclyl optionally substituted with —C$_{1-3}$alkyl; and R$^{20}$ and R$^{21}$ are independently selected from hydrogen or —C$_{1-3}$alkyl.

9. The compound according to claim 1, or a pharmaceutically acceptable salt thereof, wherein
R$^1$ is

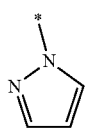

optionally substituted with one or two groups independently selected from R$^8$, or R$^1$ is selected from the group consisting of

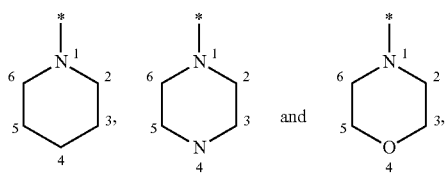 [SMILES: *N1CCCCC1 ; *N1CCNCC1 ; *N1CCOCC1]

wherein the piperidinly and piperazinyl groups can be optionally and independently substituted in 3, 4, and/or 5 position and the morpholinyl group can be optionally and independently substituted in 3 and/or 5 position with one, two, three or four substituents independently selected from the group R$^7$ and wherein when R$^1$ is substituted with three or four substituents independently selected from the group R$^7$ and at least two of those substituents are —C$_{1-3}$alkyl, wherein $R^7$ is selected from the group consisting of =O, —CCH, —CN, —OH, —COOH, halogen, —O—$C_{1-6}$alkyl, —$C_{1-6}$haloalkyl, 5 or 6 membered heteroaryl, phenyl, —N($R^9R^{10}$), —C(O)—$R^{11}$, —C(O)N($R^{12}R^{13}$) and 5-8 membered heterocyclyl, which heterocyclyl is optionally substituted with one group selected from —$C_{1-3}$alkyl;

or $R^7$ is —$C_{1-6}$alkyl optionally substituted with —COOH, —OH, —COO($C_{1-6}$alkyl), —CON($C_{1-3}$alkyl)$_2$, —O—$C_{1-6}$alkyl, —N($C_{1-3}$alkyl)$_2$, phenyl or 5 or 6 membered heterocyclyl, which heterocyclyl is optionally substituted with one group selected from —$C_{1-3}$alkyl;

$R^9$ is selected from hydrogen or —$C_{1-4}$alkyl;

$R^{10}$ is selected from the group consisting of hydrogen, —$C_{1-4}$alkyl, —$C_{1-4}$haloalkyl, 6 membered heterocyclyl and 6 membered heteroaryl;

$R^{11}$ is selected from the group consisting of —$C_{1-3}$alkyl-N($C_{1-3}$alkyl)$_2$ and 5 or 6 membered heterocyclyl, which heterocyclyl is optionally substituted with —$C_{1-3}$alkyl;

$R^{12}$ is selected from hydrogen or —$C_{1-3}$alkyl;

$R^{13}$ is selected from —$C_{1-6}$alkyl, optionally substituted with —NH$_2$, —O—$C_{1-6}$alkyl, —O—$C_{1-6}$alkyl —NH$_2$ or —O—$C_{1-6}$ alkyl—O—$C_{1-6}$alkyl —NH$_2$;

or $R^{13}$ is a 6 membered heterocyclyl optionally substituted with —$C_{1-3}$alkyl;

and wherein $R^8$ is selected from —COOH, —$C_{1-6}$alkyl, —C(O)—$R^{19}$, or —C(O)N($R^{20}R^{21}$);

$R^{19}$ is a 6 membered heterocyclyl optionally substituted with —$C_{1-3}$ alkyl;

$R^{20}$ and $R^{21}$ are independently selected from hydrogen or —$C_{1-3}$alkyl.

10. The compound according to claim 1, or a pharmaceutically acceptable salt thereof, wherein $R^1$ is selected from among

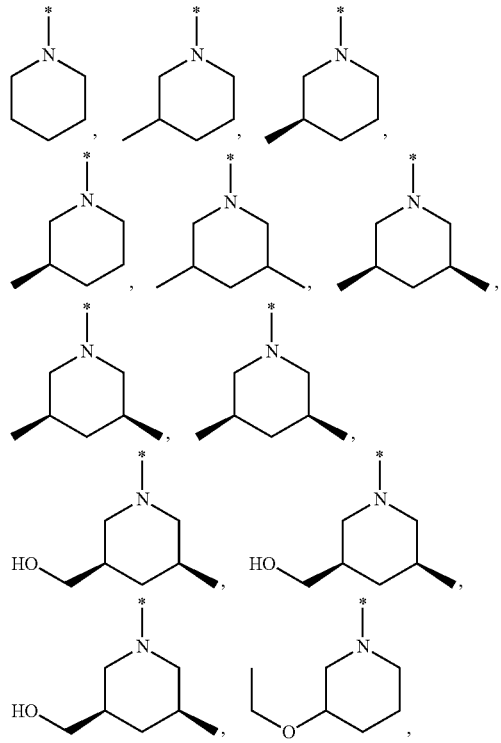

-continued

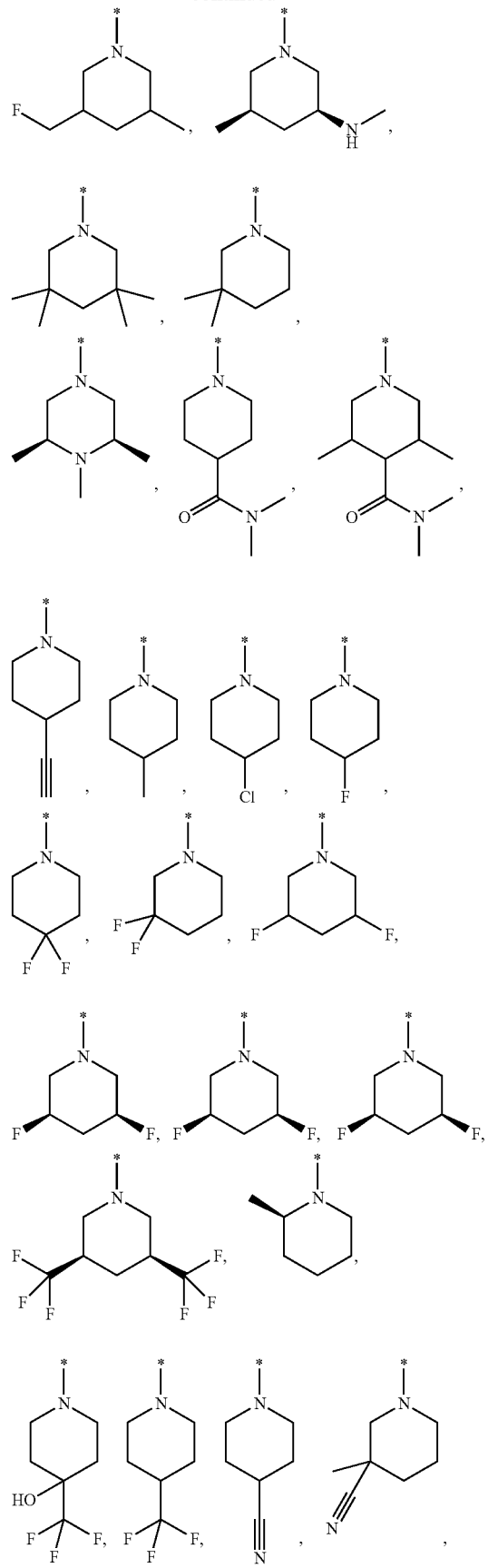

265
-continued
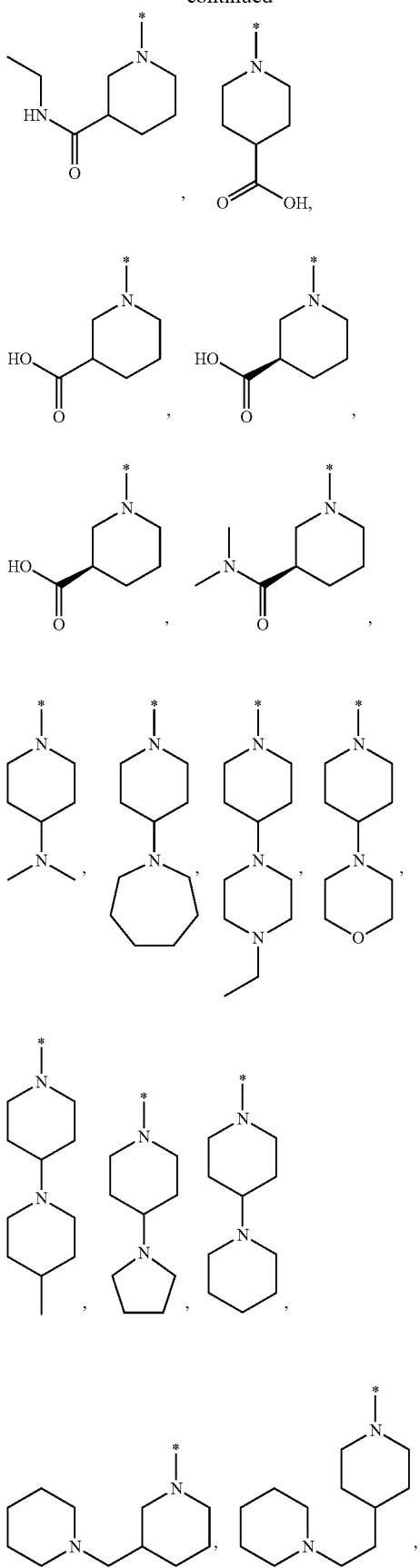
266
-continued
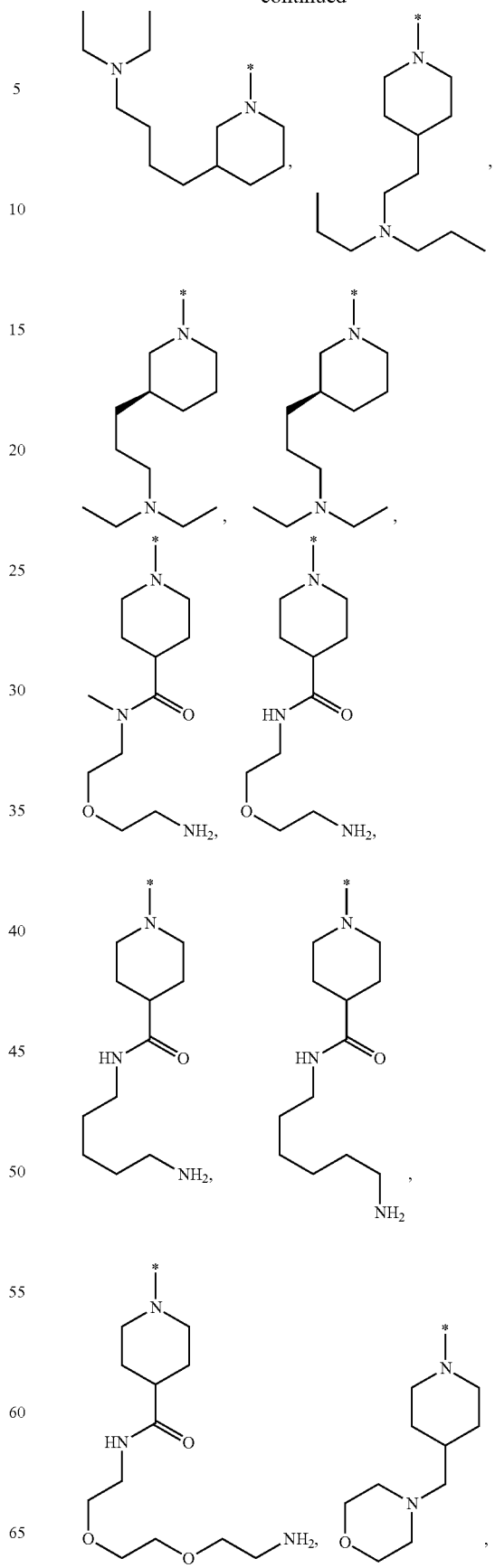

267
-continued
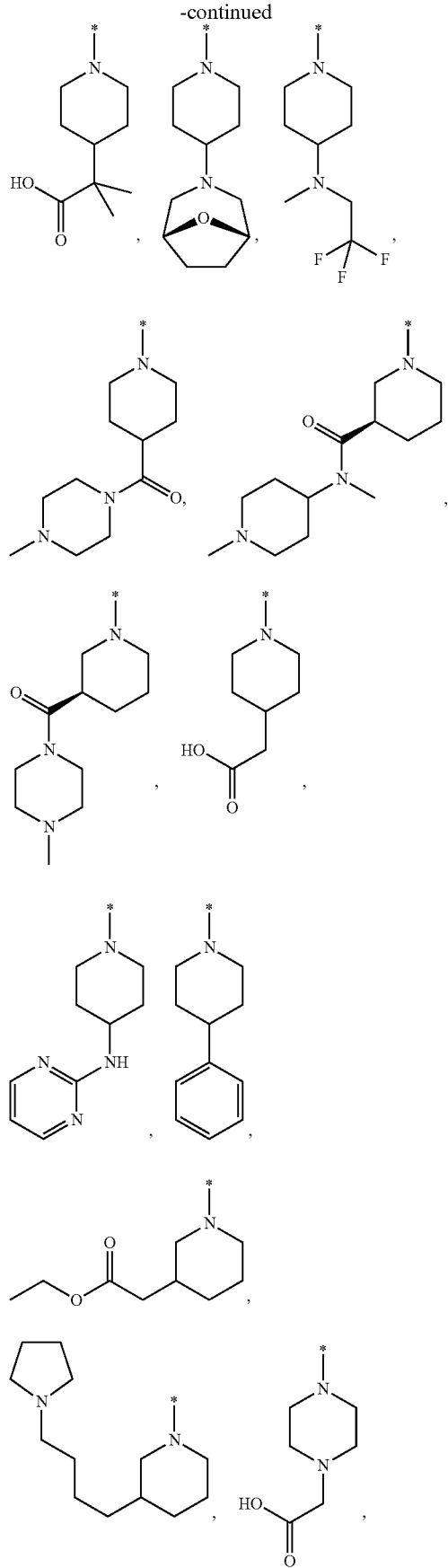
268
-continued
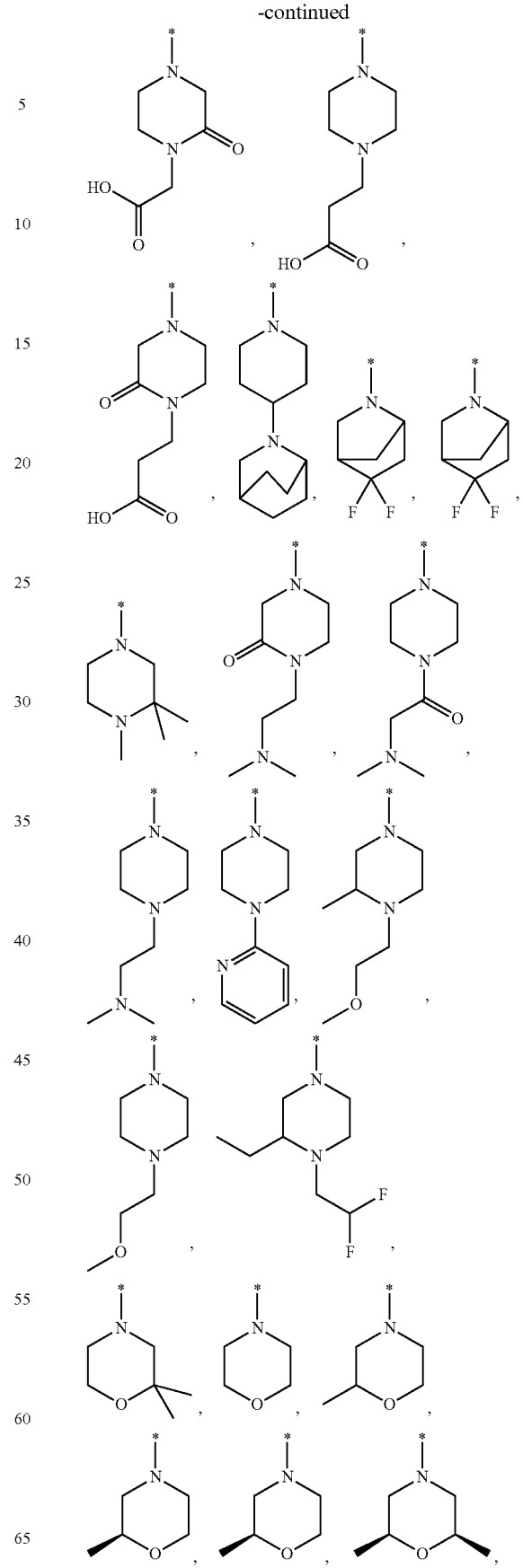

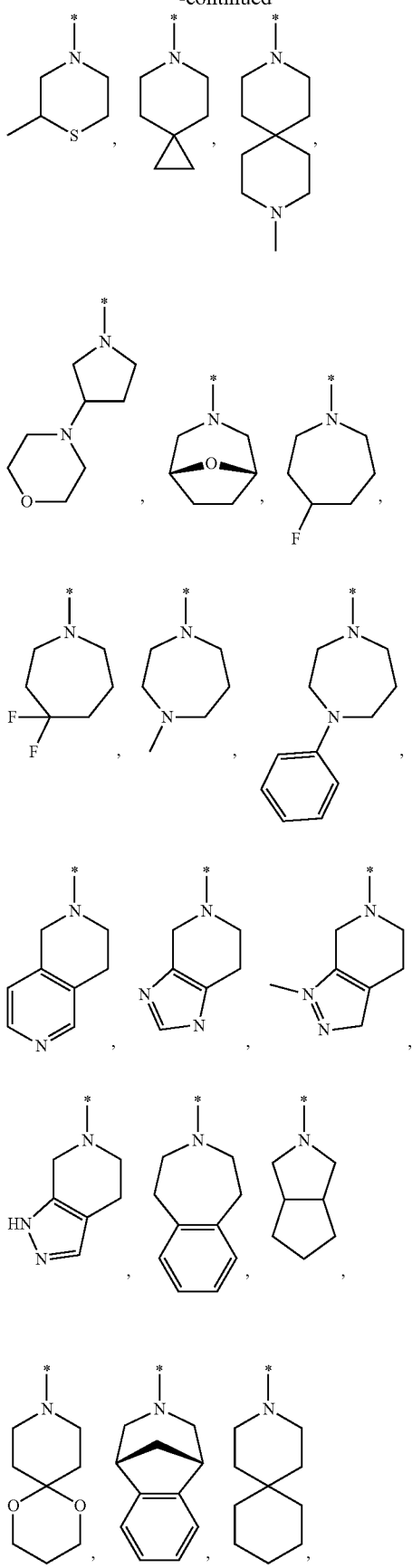
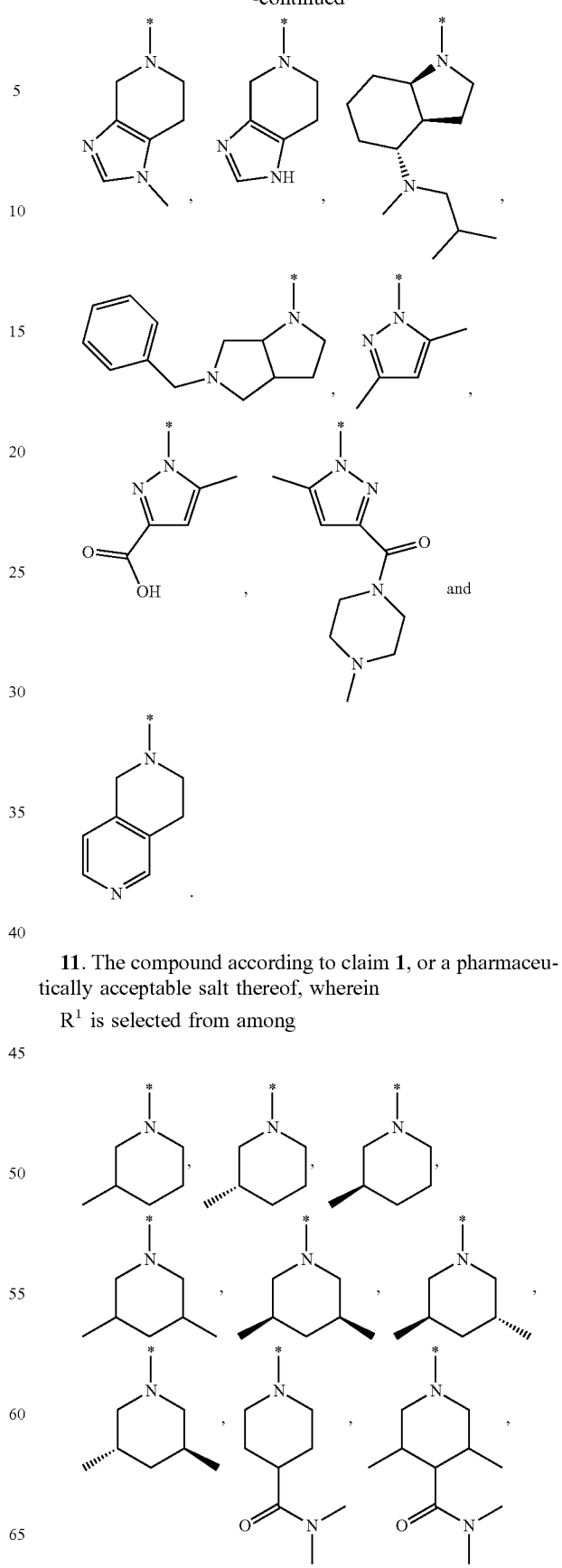
11. The compound according to claim 1, or a pharmaceutically acceptable salt thereof, wherein
R¹ is selected from among 271
-continued
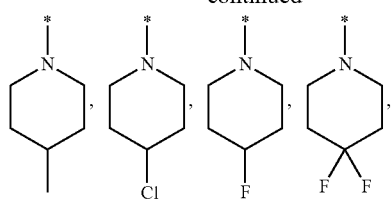
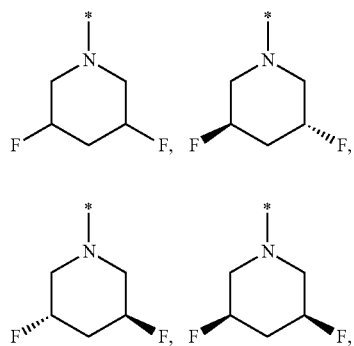
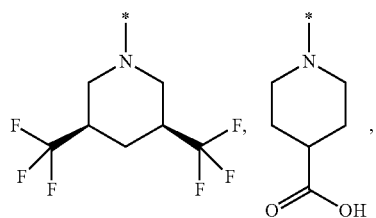
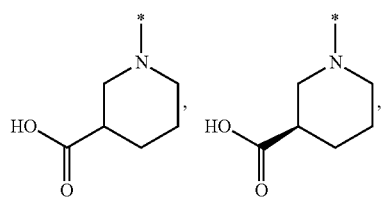
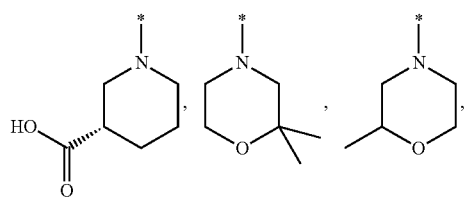
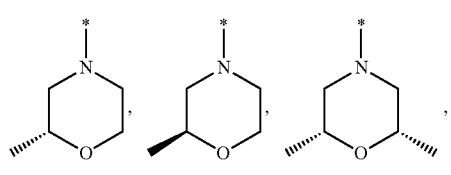
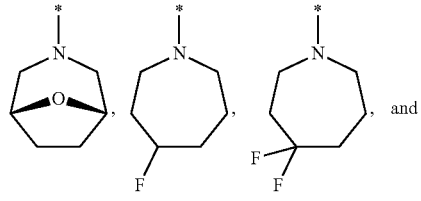
272
-continued
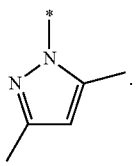
12. The compound according to claim 1, or a pharmaceutically acceptable salt thereof, wherein
R⁵ is selected from the group consisting of
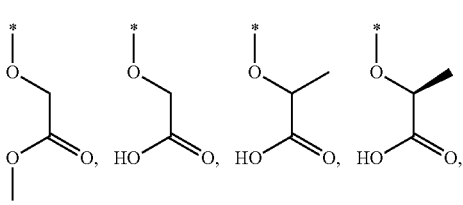
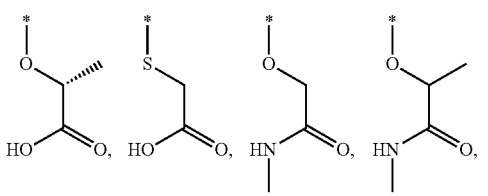
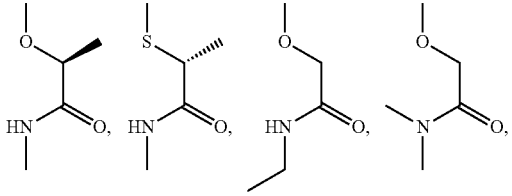
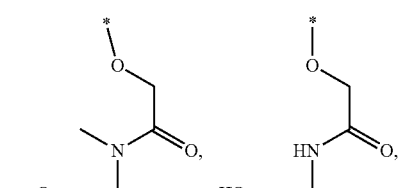
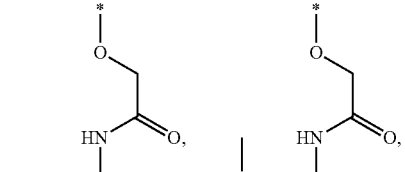
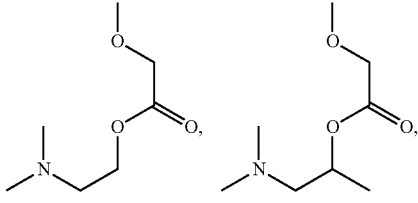

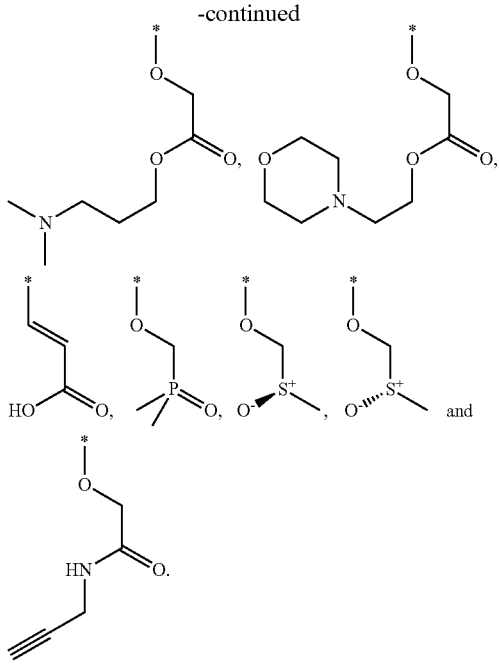
13. The compound according to claim 12, or a pharmaceutically acceptable salt thereof, wherein
$R^5$ is selected from the group consisting of
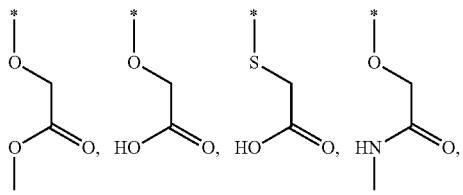
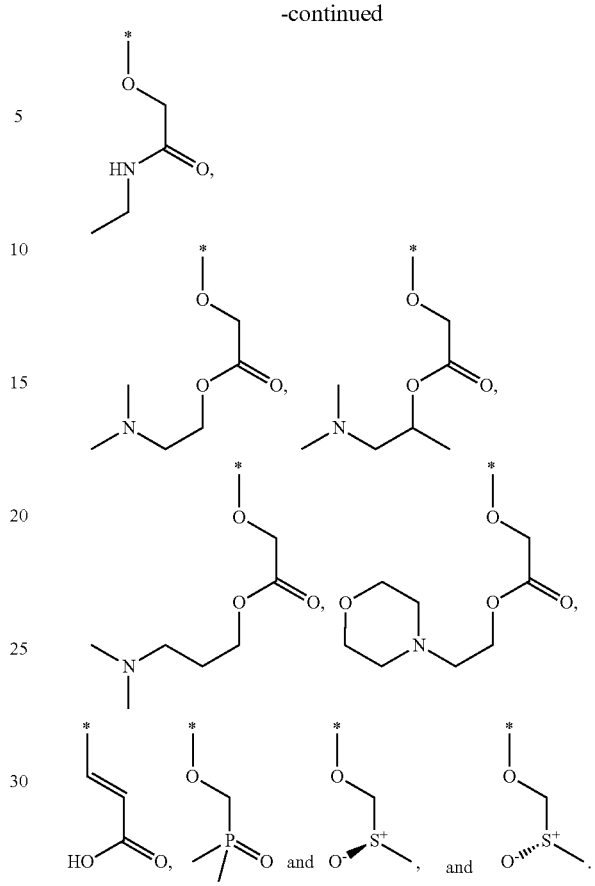
14. A pharmaceutical composition comprising a therapeutically effective amount of the compound according to claim 1, or a pharmaceutically acceptable salt thereof, and a pharmaceutically acceptable carrier.
\* \* \* \* \*